(12) United States Patent
Parham et al.

(10) Patent No.: US 11,581,497 B2
(45) Date of Patent: Feb. 14, 2023

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Christian Ehrenreich, Darmstadt (DE); Christian Eickhoff, Mannheim (DE); Jens Kaiser, Ludwigshafen (DE)

(73) Assignee: MERCK PATENT GMBH, Darmstadt (DE)

( * ) Notice: Subject to any disclaimer, the term of this patent is extended or adjusted under 35 U.S.C. 154(b) by 175 days.

(21) Appl. No.: 17/258,787

(22) PCT Filed: Jul. 8, 2019

(86) PCT No.: PCT/EP2019/068195
§ 371 (c)(1),
(2) Date: Jan. 8, 2021

(87) PCT Pub. No.: WO2020/011686
PCT Pub. Date: Jan. 16, 2020

(65) Prior Publication Data
US 2021/0320264 A1    Oct. 14, 2021

(30) Foreign Application Priority Data

Jul. 9, 2018 (EP) ...................................... 8182473

(51) Int. Cl.
| | | |
|---|---|---|
| *H01L 51/00* | (2006.01) | |
| *C07D 471/04* | (2006.01) | |
| *C07D 471/14* | (2006.01) | |
| *C09K 11/02* | (2006.01) | |
| *C09K 11/08* | (2006.01) | |
| *H01L 51/50* | (2006.01) | |

(52) U.S. Cl.
CPC ........ *H01L 51/0072* (2013.01); *C07D 471/04* (2013.01); *C07D 471/14* (2013.01); *C09K 11/02* (2013.01); *C09K 11/08* (2013.01); *H01L 51/0067* (2013.01); *H01L 51/0073* (2013.01); *C09K 2211/1007* (2013.01); *C09K 2211/1029* (2013.01); *C09K 2211/185* (2013.01); *H01L 51/5016* (2013.01); *H01L 51/5056* (2013.01); *H01L 51/5072* (2013.01); *H01L 51/5096* (2013.01)

(58) Field of Classification Search
CPC ....................................................... H01L 51/00
See application file for complete search history.

(56) References Cited

U.S. PATENT DOCUMENTS

2020/0358005 A1    11/2020    Parham et al.

FOREIGN PATENT DOCUMENTS

| | | |
|---|---|---|
| KR | 10-2010-0097797 A | 9/2010 |
| KR | 10-2015-0064500 A | 6/2015 |
| WO | 2015/125986 A1 | 8/2015 |
| WO | 2019/081391 A1 | 5/2019 |
| WO | 2019/107739 A1 | 6/2019 |

OTHER PUBLICATIONS

International Preliminary Report on Patentability received for PCT Patent Application No. PCT/EP2019/068195, dated Jan. 21, 2021, 13 pages. (7 pages of English Translation and 6 pages of Original Document).
International Search Report and Written Opinion received for PCT Patent Application No. PCT/EP2019/068195, dated Aug. 28, 2019, 15 pages (7 pages of English Translation and 8 pages of Original Document).

*Primary Examiner* — Khanh T Nguyen
(74) *Attorney, Agent, or Firm* — Faegre Drinker Biddle & Reath LLP

(57) ABSTRACT

The present invention relates to compounds, which are suitable for use in electronic devices, and to electronic devices, in particular organic electroluminescent devices, containing said compounds.

17 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2019/068195, filed Jul. 8, 2019, which claims benefit of European Application No. 18182473.1, filed Jul. 9, 2018, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties.

The problem addressed by the present invention is that of providing compounds suitable for use in an OLED, especially as matrix material for phosphorescent emitters, but also as electron transport materials or hole blocker materials. A further problem addressed by the present invention is that of providing further organic semiconductors for organic electroluminescent devices, in order thus to enable the person skilled in the art to have a greater possible choice of materials for the production of OLEDs.

It has been found that, surprisingly, particular compounds described in detail hereinafter solve this problem and are of good suitability for use in OLEDs. These OLEDs especially have a long lifetime, high efficiency and low operating voltage. The present invention therefore provides these compounds and electronic devices, especially organic electroluminescent devices, comprising such compounds.

The present invention provides a compound of formula (1)

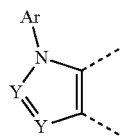

Formula (1)

where the symbols used are as follows:
X two adjacent X are a group of the following formula (2) or (3), and the remaining X are the same or different at each instance and are CR or N;

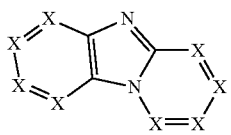

Formula (2)

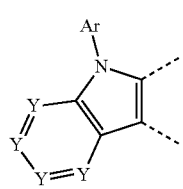

Formula (3)

where the dotted bonds indicate the linkage of this group in the formula (1);

Y is the same or different at each instance and is CR' or N;

Ar is the same or different at each instance and is an aromatic or heteroaromatic ring system which has 5 to 40 aromatic ring atoms and may be substituted by one or more R radicals;

R, R' is the same or different at each instance and is H, D, F, Cl, Br, I, N(Ar')$_2$, N(R$^1$)$_2$, OAr', SAr', CN, NO$_2$, OR$^1$, SR$^1$, COOR$^1$, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R$^1$ radicals, where one or more nonadjacent CH$_2$ groups may be replaced by Si(R$^1$)$_2$, C=O, NR$^1$, O, S or CONR$^1$, or an aromatic or heteroaromatic ring system which has 5 to 60 aromatic ring atoms, preferably 5 to 40 aromatic ring atoms, and may be substituted in each case by one or more R$^1$ radicals; at the same time, two R radicals together may also form an aliphatic or heteroaliphatic ring system; in addition, two R' radicals together may also form an aliphatic, heteroaliphatic, aromatic or heteroaromatic ring system;

Ar' is the same or different at each instance and is an aromatic or heteroaromatic ring system which has 5 to 40 aromatic ring atoms and may be substituted by one or more R$^1$ radicals;

R$^1$ is the same or different at each instance and is H, D, F, Cl, Br, I, N(R$^2$)$_2$, CN, NO$_2$, OR$^2$, SR$^2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more R$^2$ radicals, where one or more nonadjacent CH$_2$ groups may be replaced by Si(R$^2$)$_2$, C=O, NR$^2$, O, S or CONR$^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more R$^2$ radicals; at the same time, two or more R$^1$ radicals together may form an aliphatic ring system;

R$^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. Here, an aryl group or heteroaryl group is understood to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group $OR^1$ having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group $SR^1$ having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, more preferably F or CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

The wording that two or more radicals together may form an aliphatic ring, in the context of the present description, should be understood to mean, inter alia, that the two radicals are joined to one another by a chemical bond with formal elimination of two hydrogen atoms. This is illustrated by the following scheme:

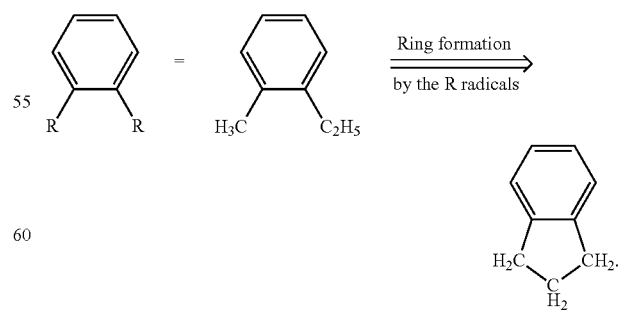

In addition, however, the abovementioned wording shall also be understood to mean that, if one of the two radicals is hydrogen, the second radical binds to the position to which the hydrogen atom was bonded, forming a ring. This shall be illustrated by the following scheme:

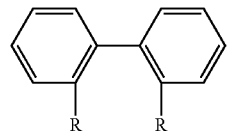

=

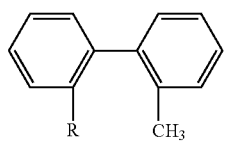

Ring formation by the R radicals ⟶

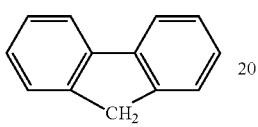

According to the position of the bond of the group of the formula (2) or (3), different isomers arise. These are shown hereinafter by the formulae (4) to (15) for the group of the formula (2), and corresponding structures arise analogously for the group of the formula (3), Formula (4)

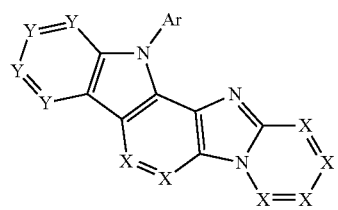

Formula (5)

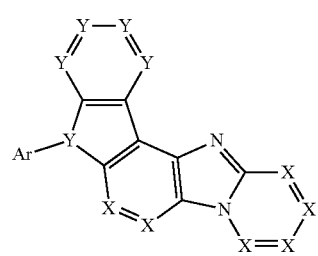

Formula (6)

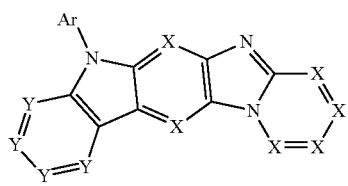

Formula (7)

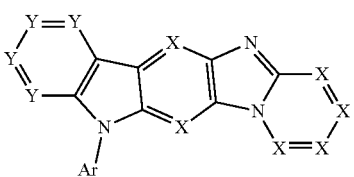

Formula (8)

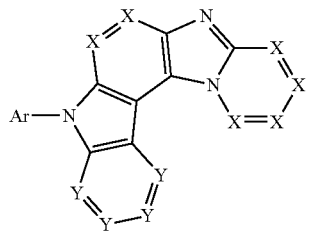

Formula (9)

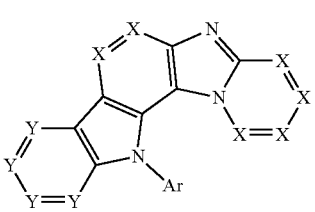

Formula (10)

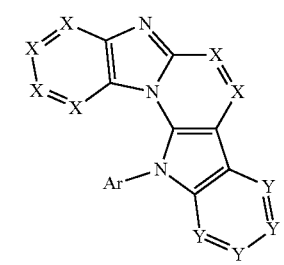

Formula (11)

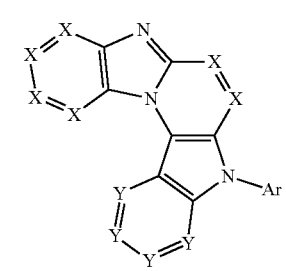

Formula (12)

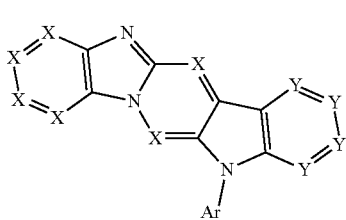

-continued

Formula (13)

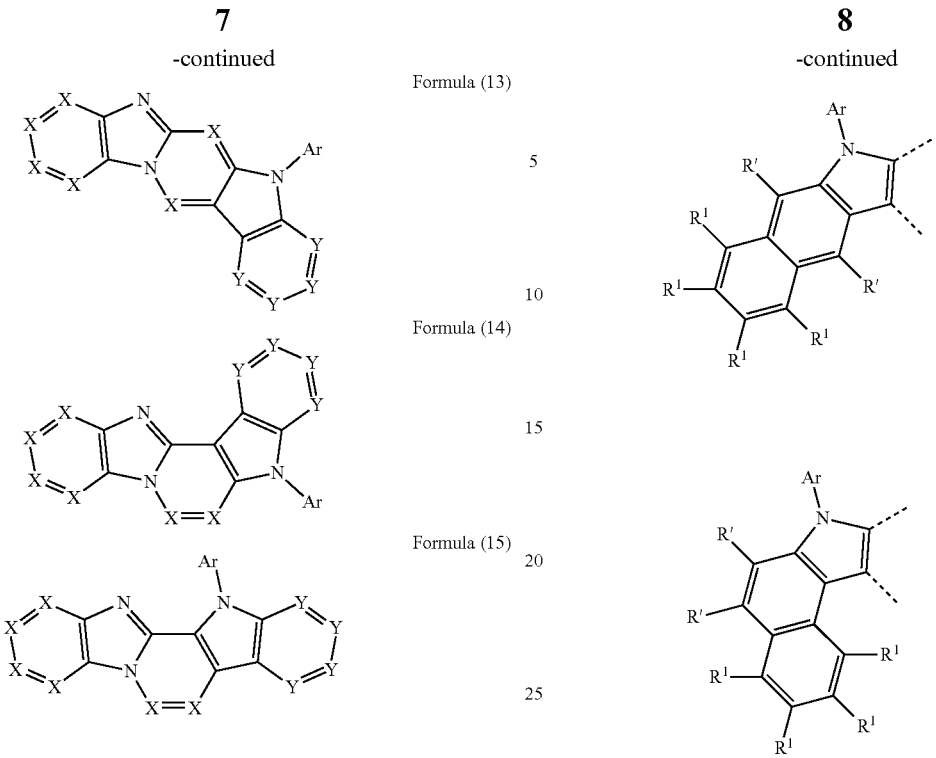

Formula (14)

Formula (15)

where the symbols used have the definitions given above.

In a preferred embodiment of the invention, the compound of the formula (1) contains a group of the formula (2).

In a further preferred embodiment of the invention, in the group of the formula (2) or (3), not more than one symbol Y is N, and the other symbols Y are the same or different and are CR'. More preferably, all symbols Y in formula (2) and (3) are CR'.

In one embodiment of the invention, the R' radicals on Y do not form an aromatic or heteroaromatic ring system with one another. In that case, the groups of the formulae (2) and (3) are selected from the groups of the formulae (2a) and (3a) below. In a further embodiment of the invention, the R' radicals on Y form an aromatic or heteroaromatic ring system with one another, preferably an aromatic ring system. If adjacent R' radicals on Y form an aromatic ring system with one another, the group of the formula (2) is preferably a group of one of the following formulae (2b) to (2e):

Formula (2a)

Formula (2b)

-continued

Formula (2c)

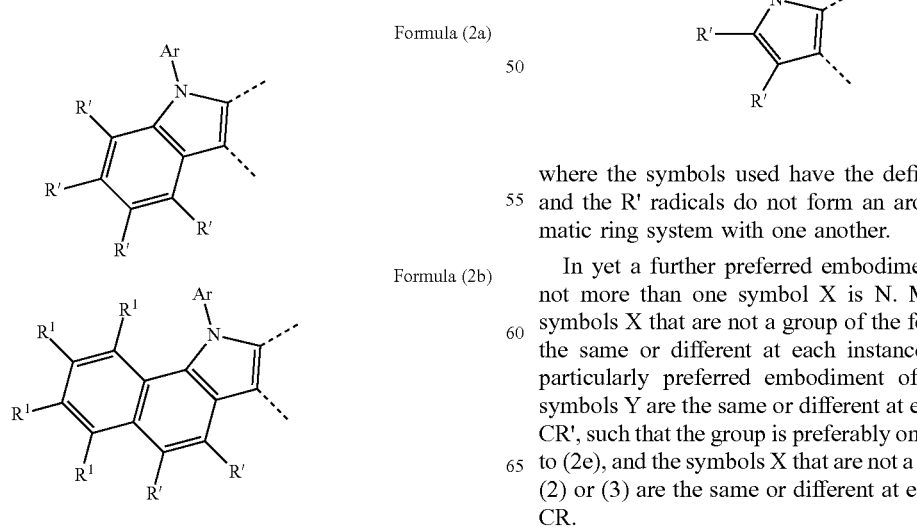

Formula (2d)

Formula (2e)

Formula (3a)

where the symbols used have the definitions given above and the R' radicals do not form an aromatic or heteroaromatic ring system with one another.

In yet a further preferred embodiment of the invention, not more than one symbol X is N. More preferably, the symbols X that are not a group of the formula (2) or (3) are the same or different at each instance and are CR. In a particularly preferred embodiment of the invention, the symbols Y are the same or different at each instance and are CR', such that the group is preferably one of the formula (2a) to (2e), and the symbols X that are not a group of the formula (2) or (3) are the same or different at each instance and are CR.

Preference is thus given to the structures of the following formulae (4a) to (15a):
Formula (4a)
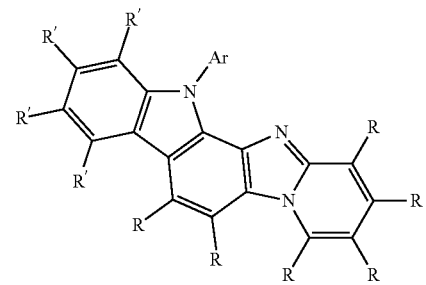
Formula (5a)
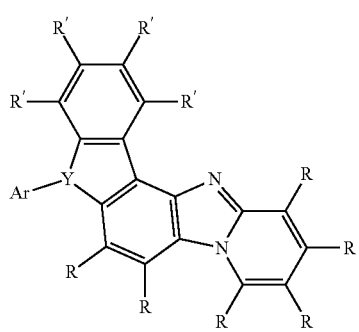
Formula (6a)
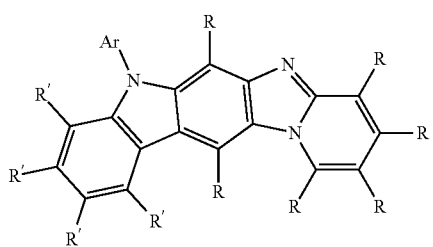
Formula (7a)
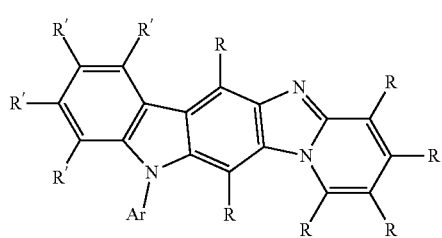
Formula (8a)
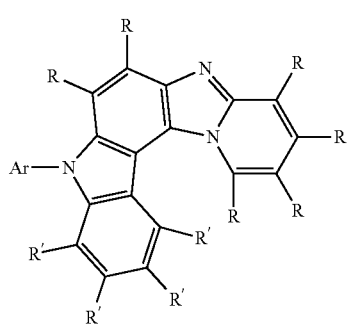
Formula (9a)
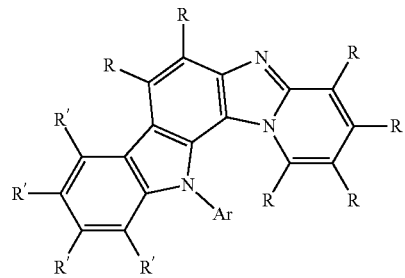
Formula (10a)
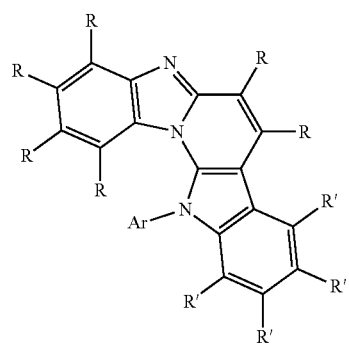
Formula (11a)
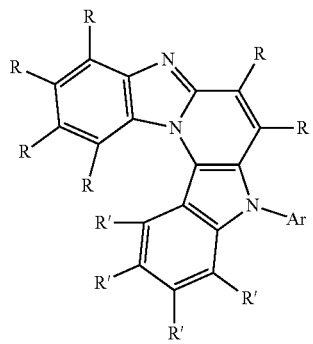
Formula (12a)
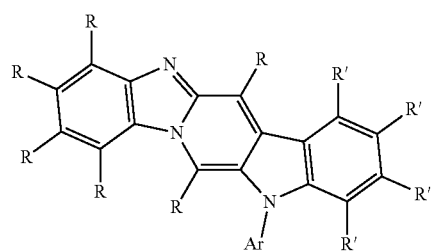
Formula (13a)
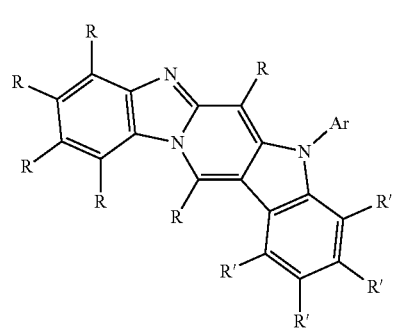

Formula (14a)

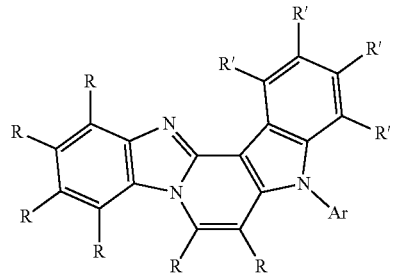

Formula (15a)

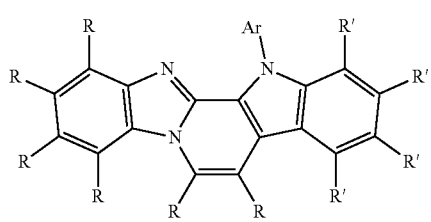

where the symbols used have the definitions given above.

In a preferred embodiment of the invention, not more than three R and R' radicals in total, more preferably not more than two R and R' radicals and most preferably not more than one R or R' radical in the compound of the formula (1) or the preferred structures detailed above are/is a group other than hydrogen. When two R' radicals together form an aromatic or heteroaromatic ring system, it is preferable when, apart from these two R' radicals, not more than two further R and/or R' radicals, especially not more than one further R and/or R' radical, are/is a group other than hydrogen.

Particular preference is given to the structures of the following formulae (4b) to (15c):

Formula (4b)

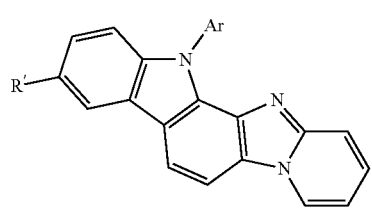

Formula (5b)

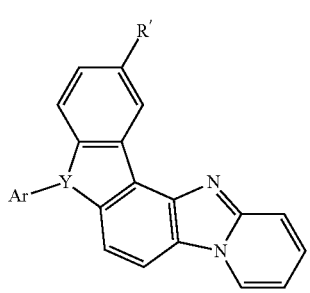

Formula (6b)

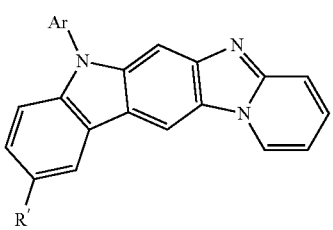

Formula (7b)

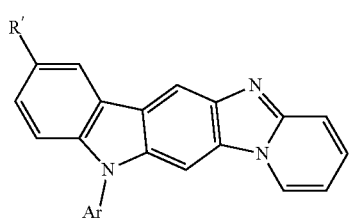

Formula (8b)

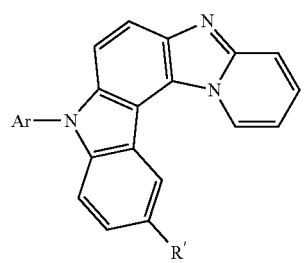

Formula (9b)

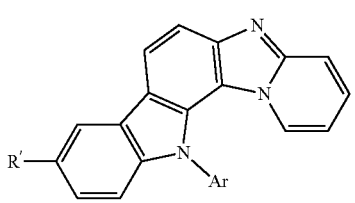

Formula (10b)

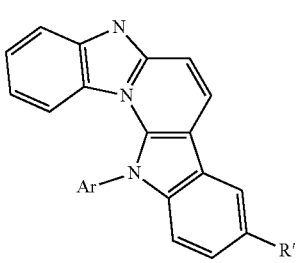

Formula (10c)

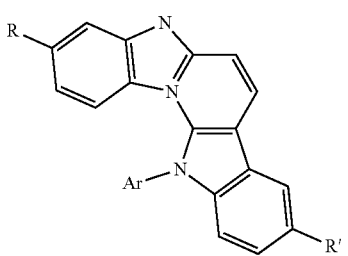

Formula (11b)

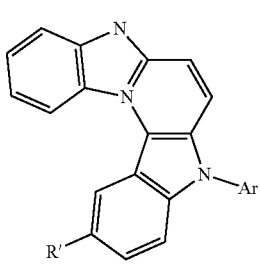

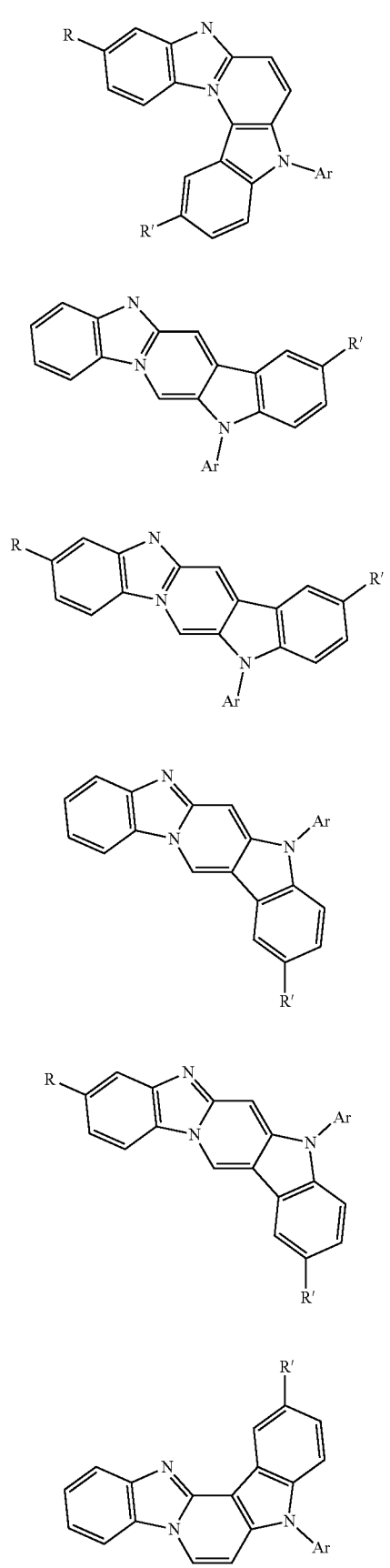

where the symbols used have the definitions given above.

There follows a description of preferred substituents Ar, R, R', Ar', $R^1$ and $R^2$ in the compounds of the invention. In a particularly preferred embodiment of the invention, the preferences specified hereinafter for Ar, R, R', Ar', $R^1$ and $R^2$ occur simultaneously and are applicable to the structures of the formula (1) and to all preferred embodiments detailed above.

In a preferred embodiment of the invention, Ar is the same or different at each instance and is an aromatic or heteroaromatic ring system which has 6 to 30 aromatic ring atoms and may be substituted by one or more R radicals. More preferably, Ar is the same or different at each instance and is an aromatic or heteroaromatic ring system which has 6 to 24 aromatic ring atoms, especially 6 to 12 aromatic ring atoms, and may be substituted by one or more, preferably nonaromatic, R radicals. When Ar is a heteroaryl group, especially triazine, pyrimidine, quinazoline or carbazole, preference may also be given to aromatic or heteroaromatic substituents R on this heteroaryl group. It may further be preferable when Ar is substituted by an $N(Ar')_2$ group, such that the Ar substituent constitutes a triarylamine or triheteroarylamine group overall.

Suitable aromatic or heteroaromatic ring systems Ar are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals, preferably nonaromatic R radicals. When Ar is a heteroaryl group, especially triazine, pyrimidine, quinazoline or carbazole, preference may also be given to aromatic or heteroaromatic R radicals on this heteroaryl group.
Ar here is preferably the same or different at each instance and is selected from the groups of the following formulae Ar-1 to Ar-83:
Ar-1
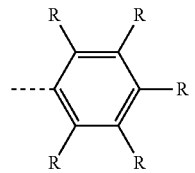
Ar-2
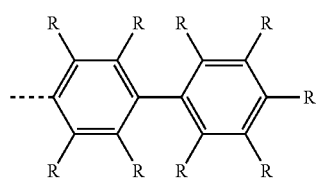
Ar-3
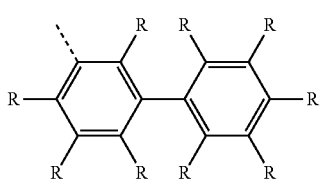
Ar-4
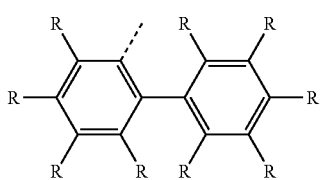
Ar-5
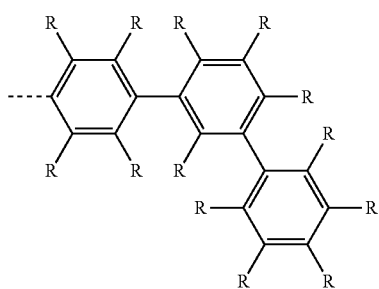
-continued
Ar-6
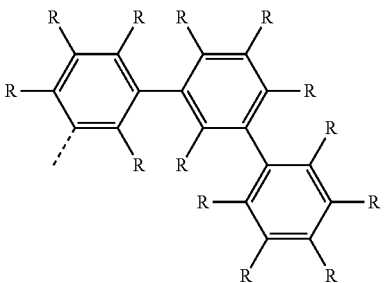
Ar-7
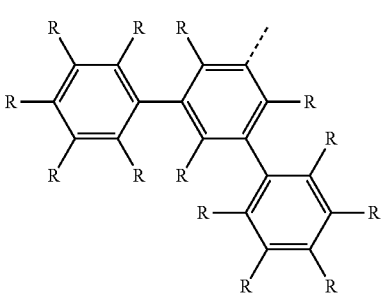
Ar-8
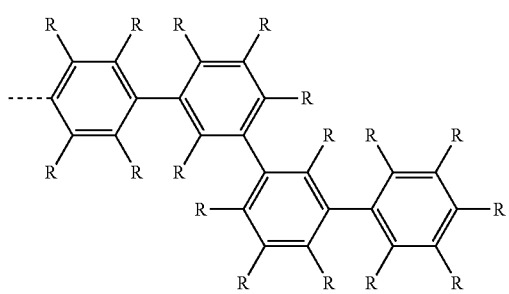
Ar-9
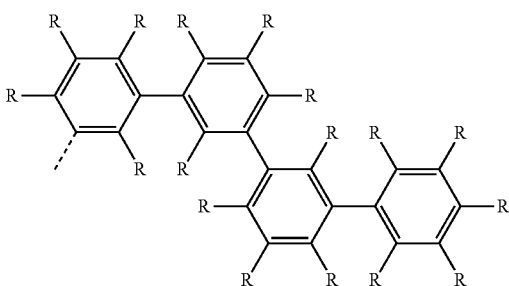
Ar-10
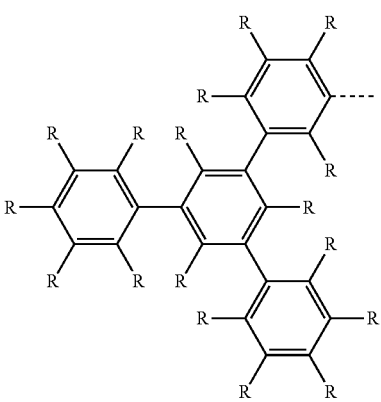

Ar-11
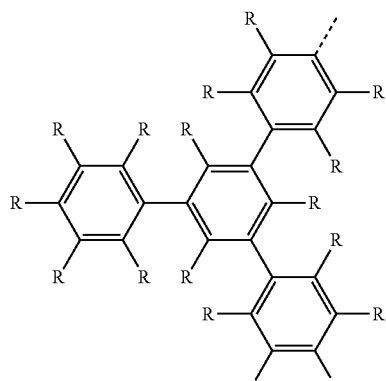
Ar-12
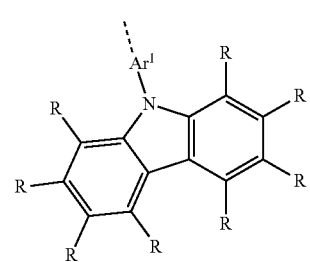
Ar-13
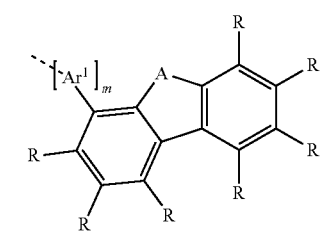
Ar-14
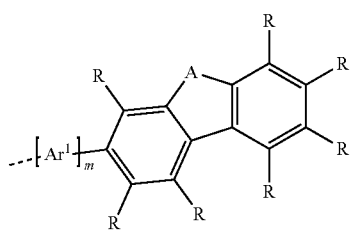
Ar-15
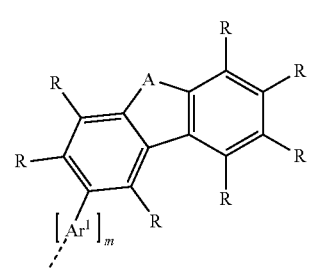
Ar-16
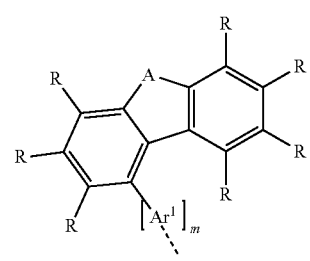
Ar-17
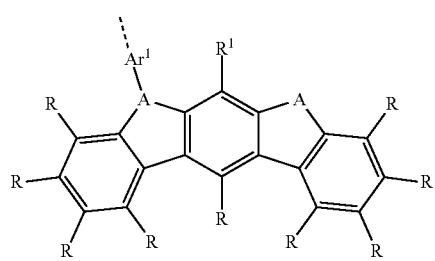
Ar-18
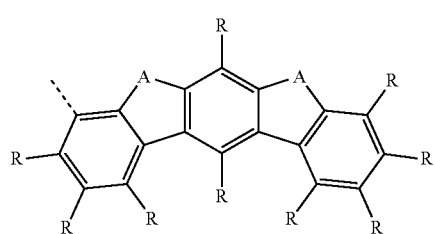
Ar-19
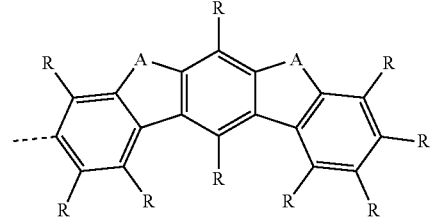
Ar-20
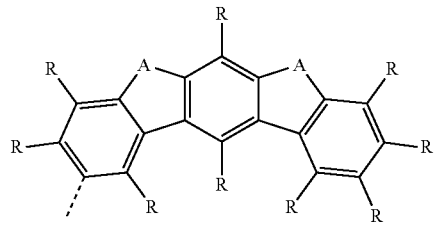
Ar-21
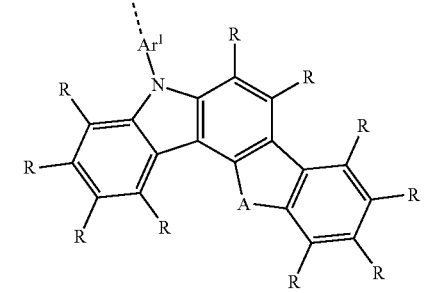

-continued
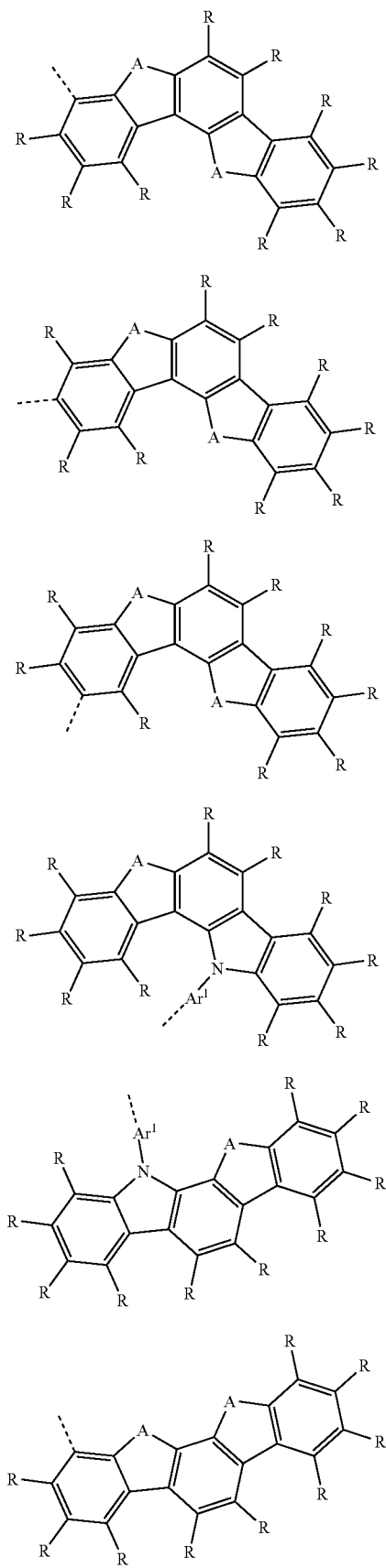
Ar-22
Ar-23
Ar-24
Ar-25
Ar-26
Ar-27
-continued
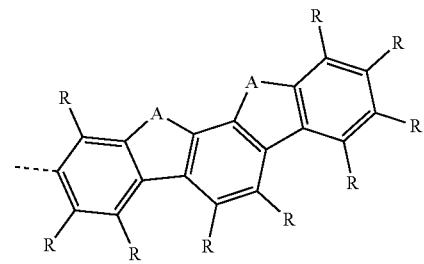
Ar-28
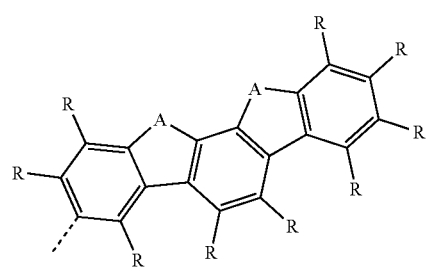
Ar-29
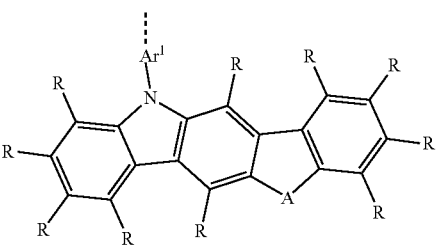
Ar-30
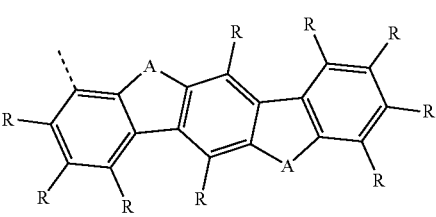
Ar-31
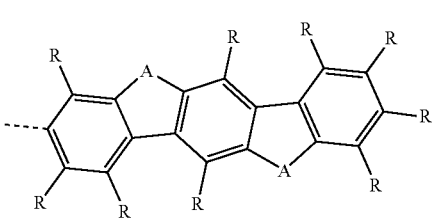
Ar-32
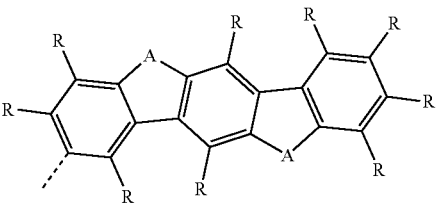
Ar-33

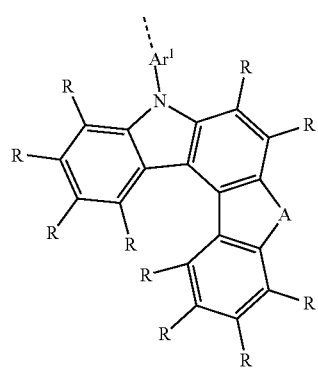
Ar-34
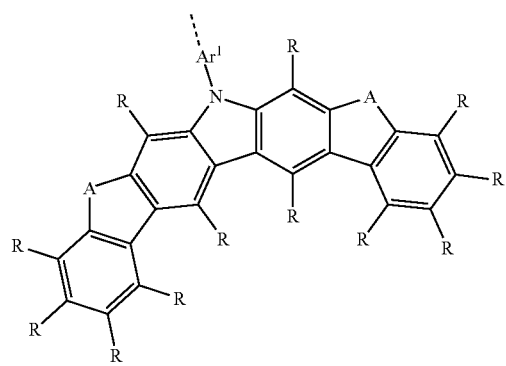
Ar-38
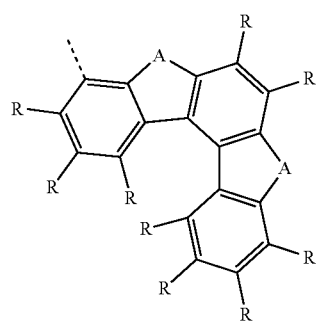
Ar-35
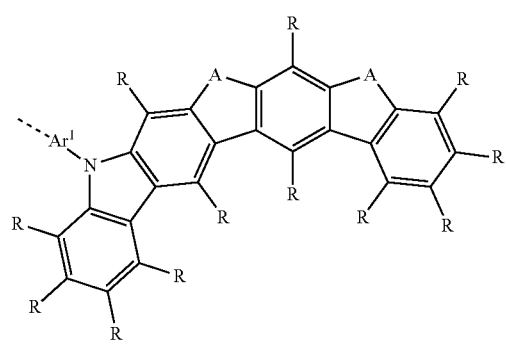
Ar-39
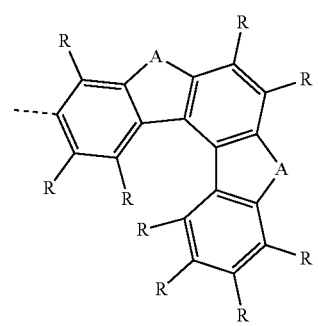
Ar-36
Ar-40
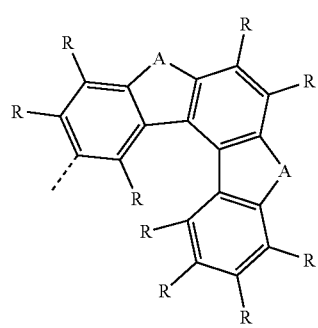
Ar-37
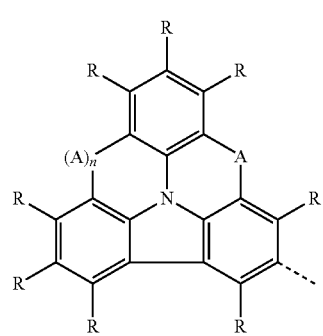
Ar-41

-continued
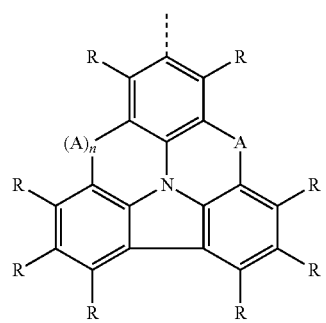
Ar-42
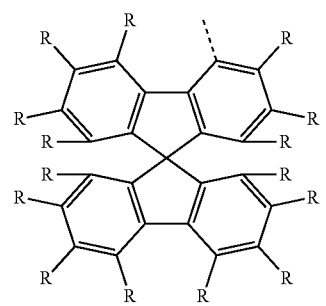
Ar-43
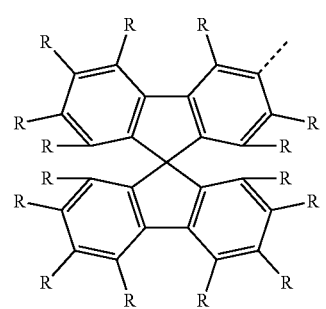
Ar-44
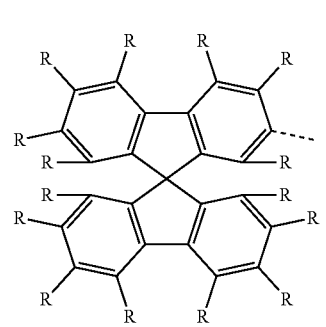
Ar-45
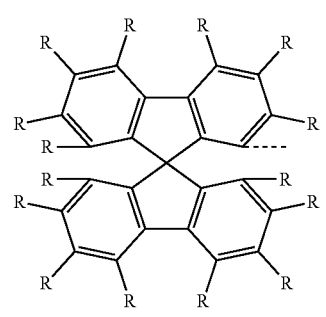
Ar-46
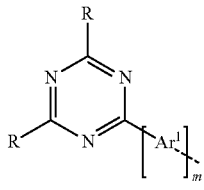
Ar-47
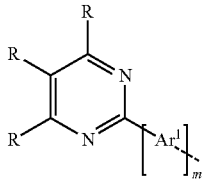
Ar-48
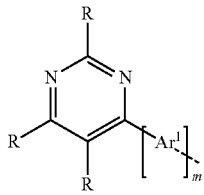
Ar-49
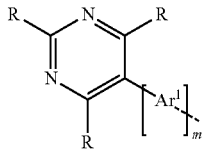
Ar-50
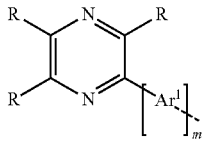
Ar-51
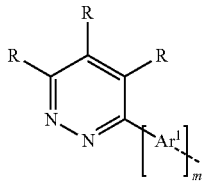
Ar-52
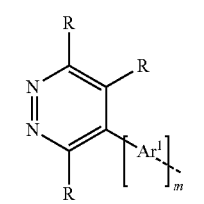
Ar-53
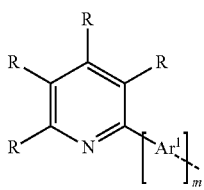
Ar-54

-continued
Ar-55
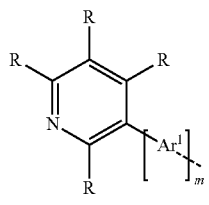
Ar-56
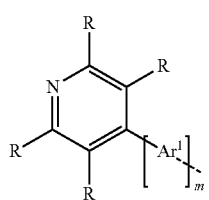
Ar-57
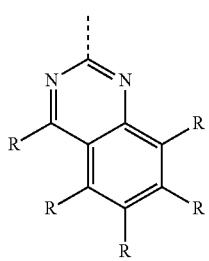
Ar-58
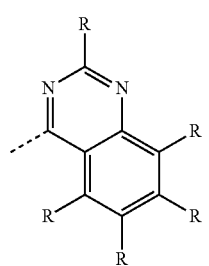
Ar-59
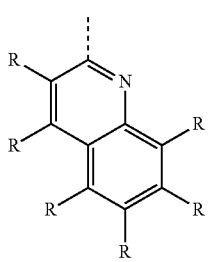
Ar-60
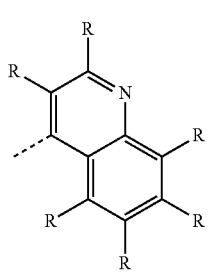
Ar-61
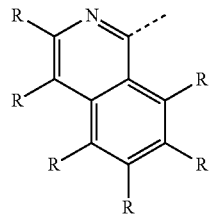
Ar-62
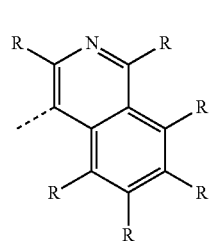
Ar-63
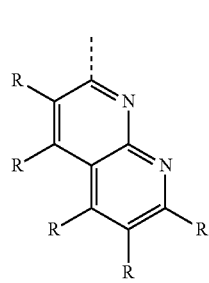
Ar-64
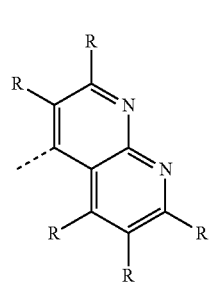
Ar-65
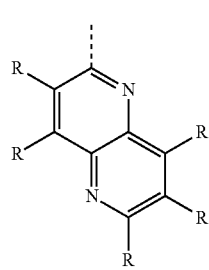
Ar-66
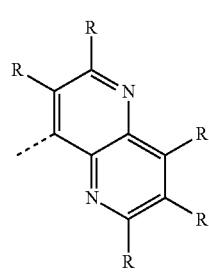

Ar-67 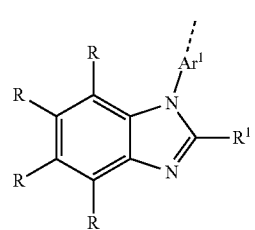
Ar-68 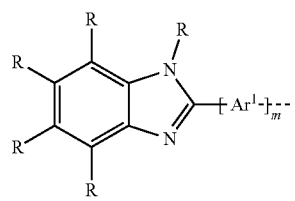
Ar-69 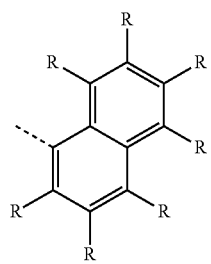
Ar-70 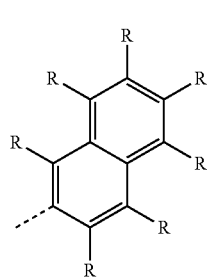
Ar-71 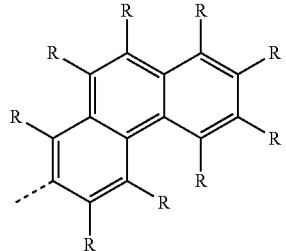
Ar-72 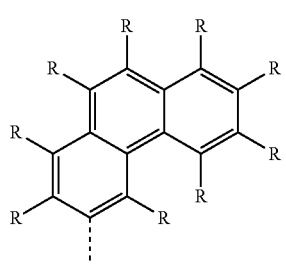
Ar-73 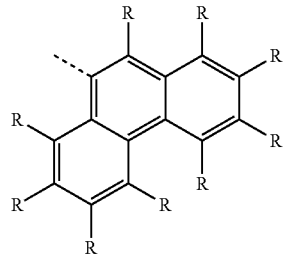
Ar-74 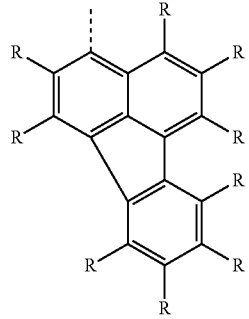
Ar-75 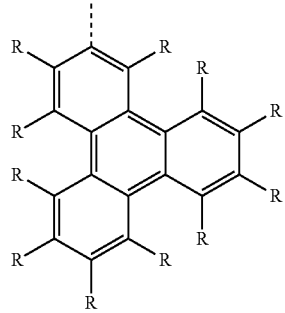
Ar-76 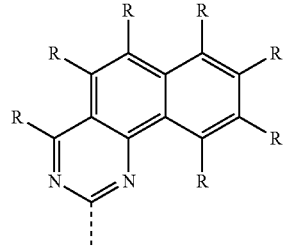
Ar-77 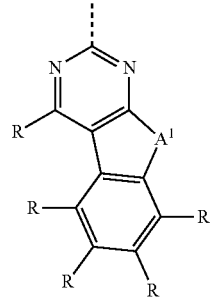

Ar-78 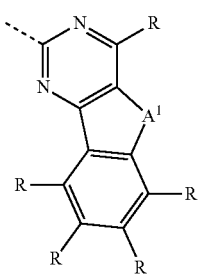

Ar-79 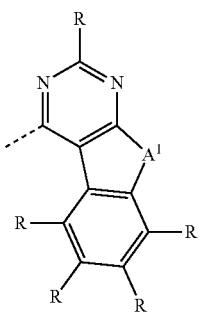

Ar-80 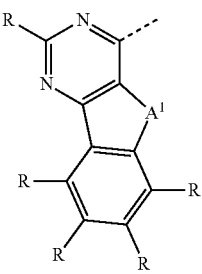

Ar-81 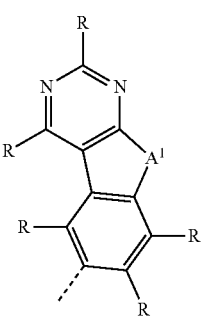

Ar-82 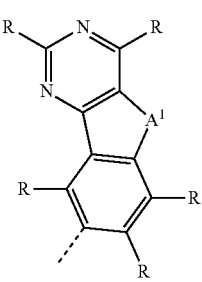

Ar-83 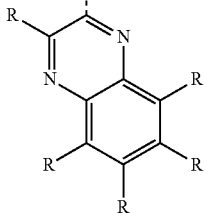

where R is as defined above, the dotted bond represents the bond to the nitrogen atom and, in addition:

$Ar^1$ is the same or different at each instance and is a bivalent aromatic or heteroaromatic ring system which has 6 to 18 aromatic ring atoms and may be substituted in each case by one or more R radicals;

A is the same or different at each instance and is $C(R)_2$, NR, O or S;

n is 0 or 1, where n=0 means that no A group is bonded at this position and R radicals are bonded to the corresponding carbon atoms instead;

m is 0 or 1, where m=0 means that the $Ar^1$ group is absent and that the corresponding aromatic or heteroaromatic group is bonded directly to the nitrogen atom.

In a preferred embodiment of the invention, R and R' are the same or different at each instance and are selected from the group consisting of H, D, F, $N(Ar')_2$, CN, $OR^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, but is preferably unsubstituted, and where one or more nonadjacent $CH_2$ groups may be replaced by O, or an aromatic or heteroaromatic ring system which has 6 to 30 aromatic ring atoms and may be substituted in each case by one or more $R^1$ radicals; at the same time, two R radicals together may also form an aliphatic ring system; in addition, two R' radicals together may also form an aliphatic or aromatic ring system. More preferably, R and R' are the same or different at each instance and are selected from the group consisting of H, $N(Ar')_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms and may be substituted in each case by one or more $R^1$ radicals, preferably nonaromatic $R^1$ radicals. Most preferably, R and R' are the same or different at each instance and are selected from the group consisting of H or an aromatic or heteroaromatic ring system which has 6 to 24 aromatic ring atoms and may be substituted in each case by one or more $R^1$ radicals, preferably nonaromatic $R^1$ radicals. It may additionally be preferable when R or R' is a triaryl-or-heteroarylamine group which may be substituted by one or more $R^1$ radicals. This group is one embodiment of an aromatic or heteroaromatic ring system, in which case two or more aryl or heteroaryl groups are joined to one another by a nitrogen atom. When R or R' is a triaryl-or-heteroarylamine group, this group preferably has 18 to 30 aromatic ring atoms and may be substituted by one or more R¹ radicals, preferably nonaromatic R¹ radicals.

In a further preferred embodiment of the invention, Ar' is an aromatic or heteroaromatic ring system which has 6 to 30 aromatic ring atoms and may be substituted by one or more R¹ radicals. In a particularly preferred embodiment of the invention, Ar' is an aromatic or heteroaromatic ring system which has 6 to 24 aromatic ring atoms, especially 6 to 13 aromatic ring atoms, and may be substituted by one or more, preferably nonaromatic, R¹ radicals.

In a further preferred embodiment of the invention, R¹ is the same or different at each instance and is selected from the group consisting of H, D, F, CN, OR², a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more R² radicals, and where one or more nonadjacent CH₂ groups may be replaced by O, or an aromatic or heteroaromatic ring system which has 6 to 30 aromatic ring atoms and may be substituted in each case by one or more R² radicals; at the same time, two or more R¹ radicals together may form an aliphatic ring system. In a particularly preferred embodiment of the invention, R¹ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more R² radicals, but is preferably unsubstituted, or an aromatic or heteroaromatic ring system which has 6 to 24 aromatic ring atoms and may be substituted in each case by one or more R² radicals, but is preferably unsubstituted.

In a further preferred embodiment of the invention, R² is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

Suitable aromatic or heteroaromatic ring systems R, R' or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R¹ radicals. When R or Ar' is a heteroaryl group, especially triazine, pyrimidine, quinazoline or carbazole, preference may also be given to aromatic or heteroaromatic R¹ radicals on this heteroaryl group.

The R or R' groups here, when they are an aromatic or heteroaromatic ring system, or Ar' are preferably selected from the groups of the following formulae R-1 to R-83:

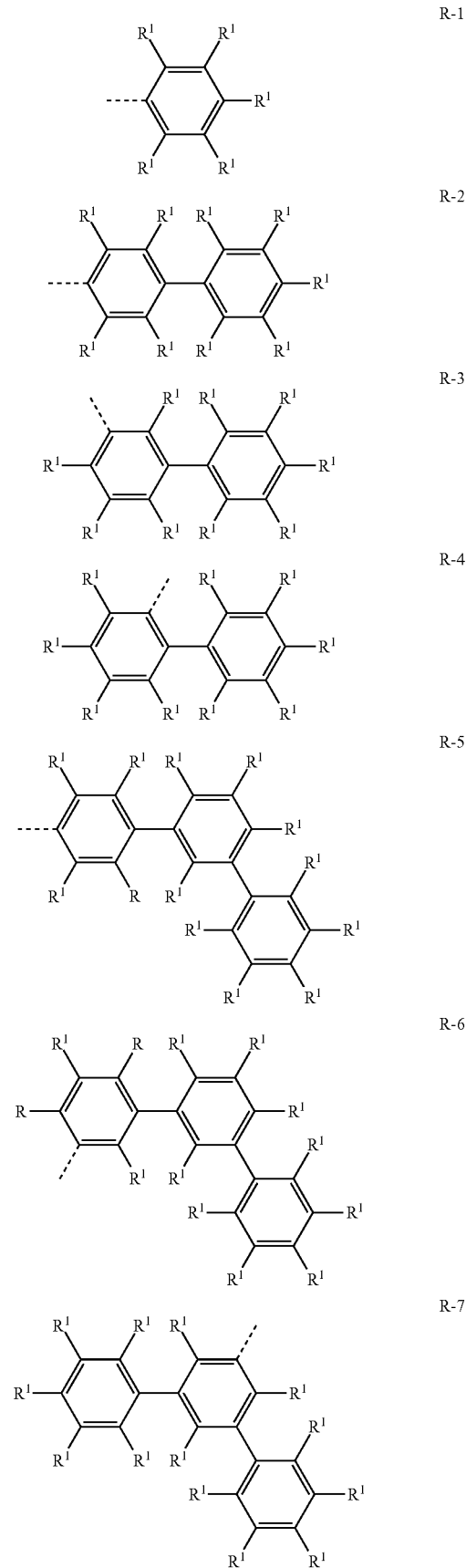

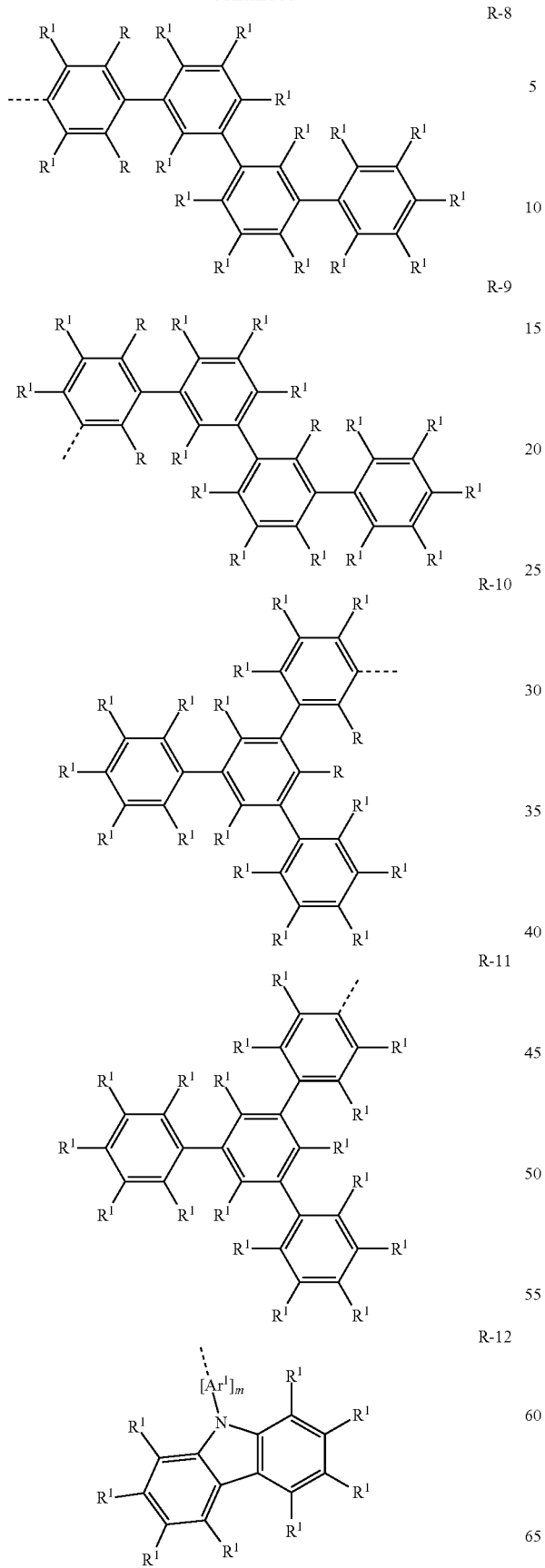
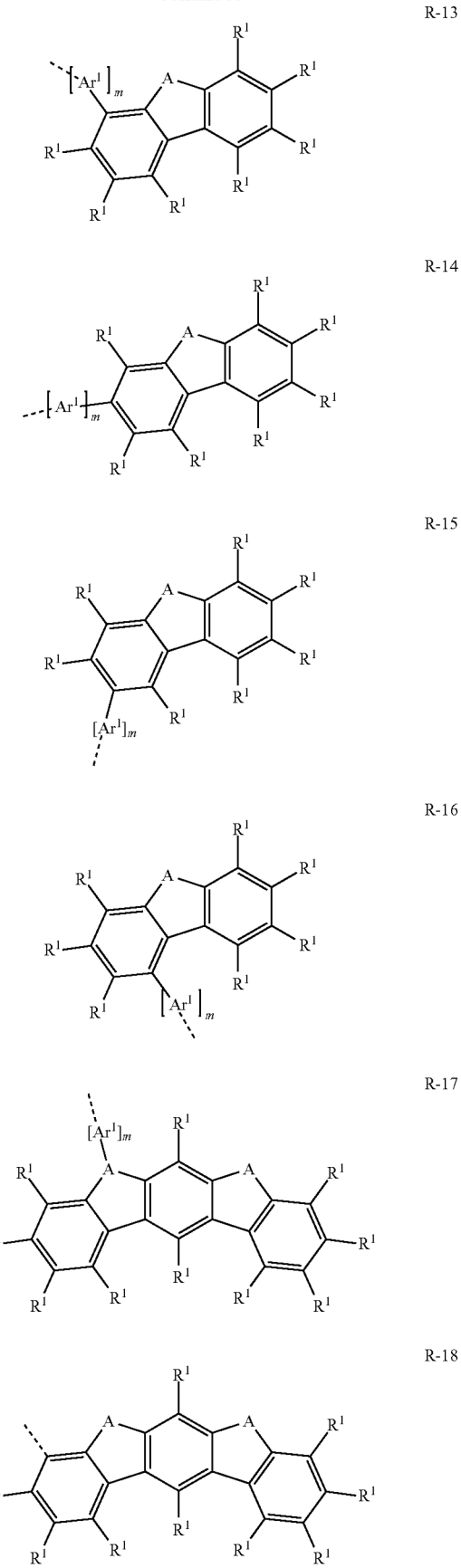

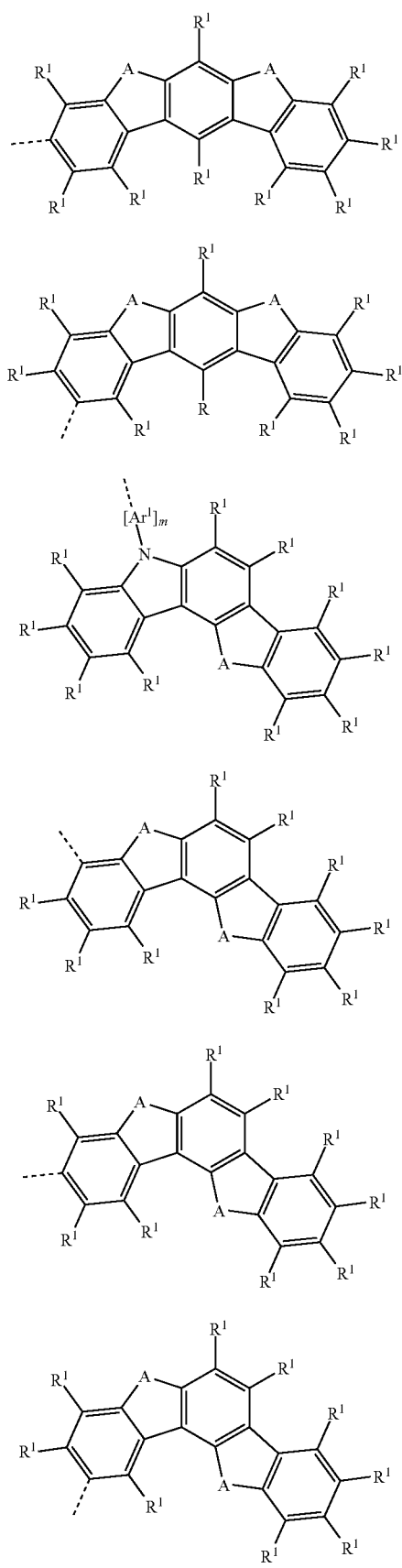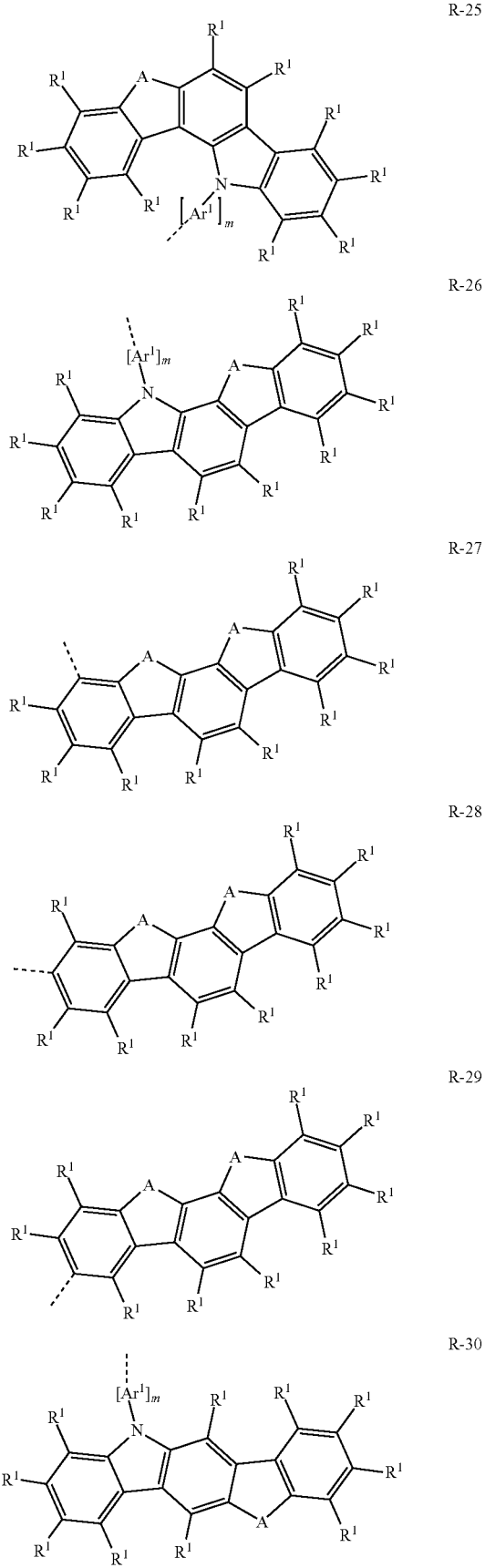

-continued
R-31
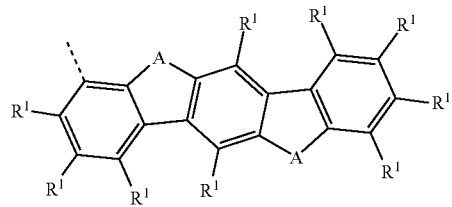
R-32
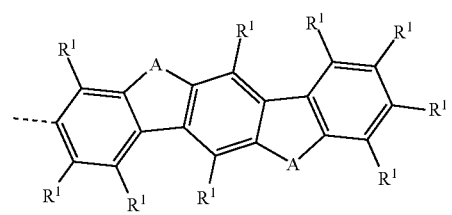
R-33
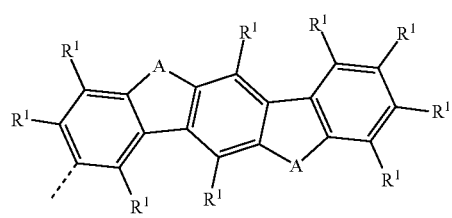
R-34
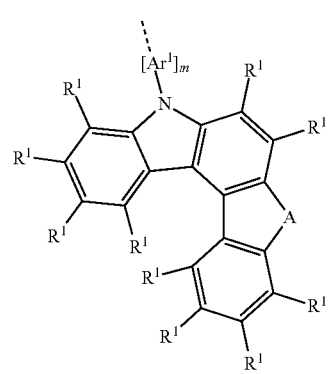
R-35
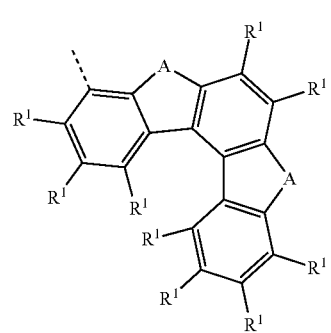
-continued
R-36
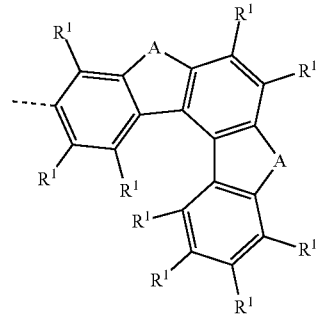
R-37
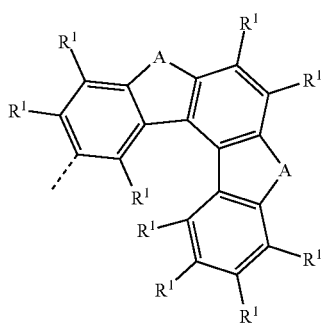
R-38
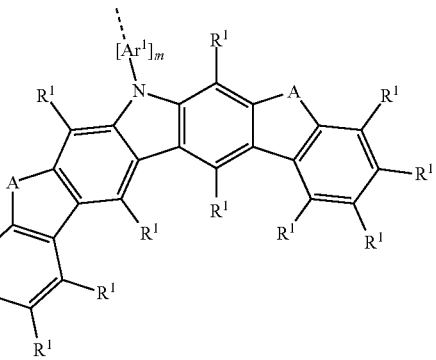
R-39
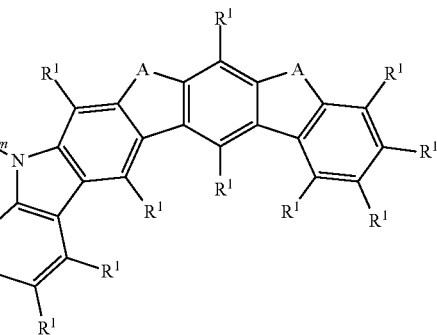

-continued
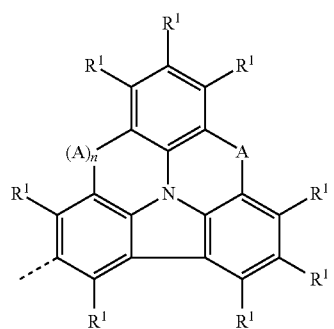
R-40
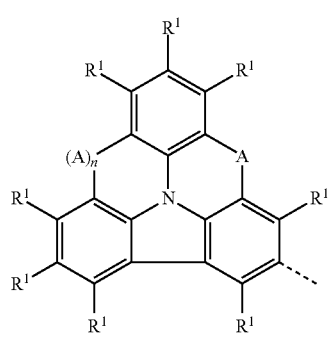
R-41
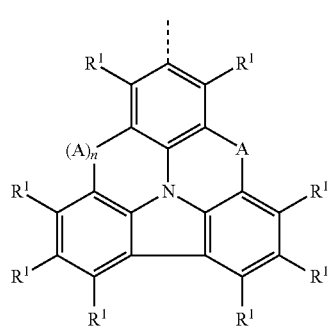
R-42
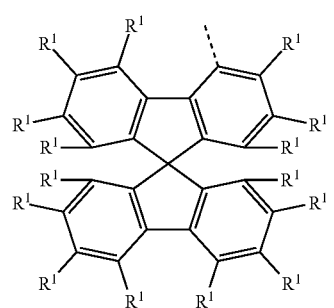
R-43
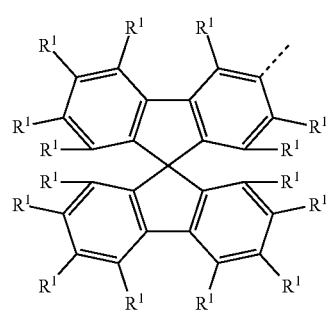
R-44
-continued
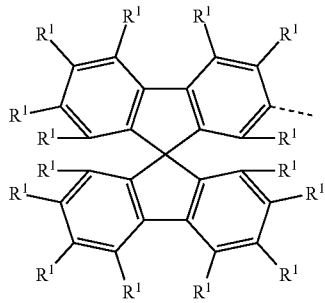
R-45
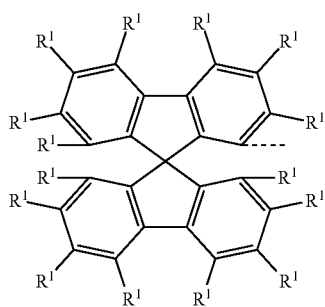
R-46
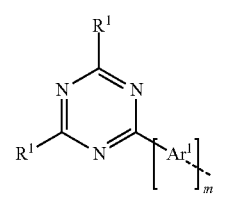
R-47
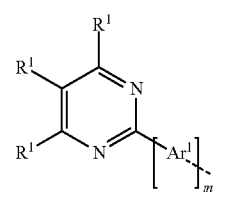
R-48
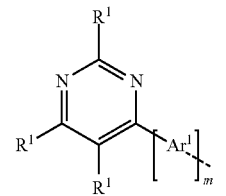
R-49
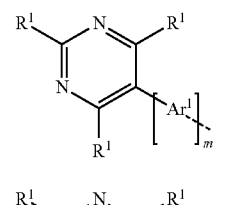
R-50
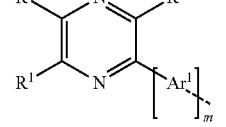
R-51

R-52 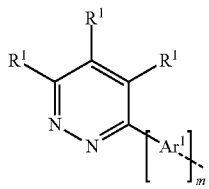
R-53 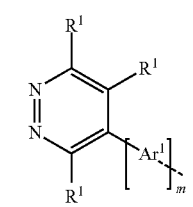
R-54 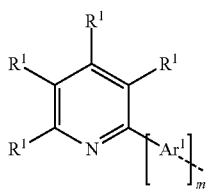
R-55 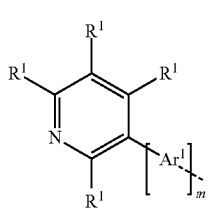
R-56 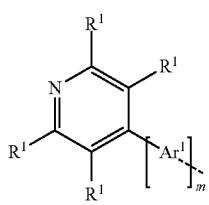
R-57 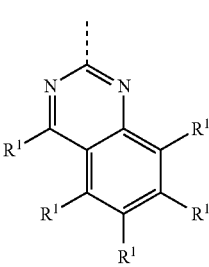
R-58 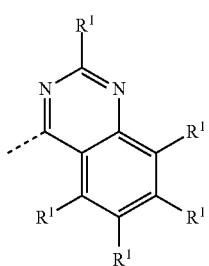
R-59 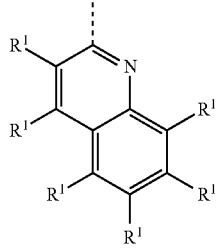
R-60 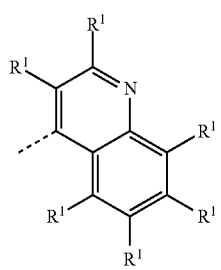
R-61 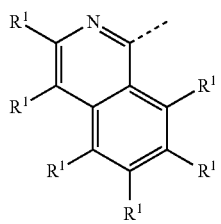
R-62 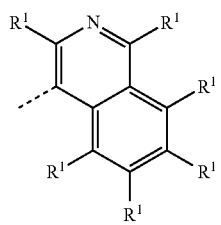
R-63 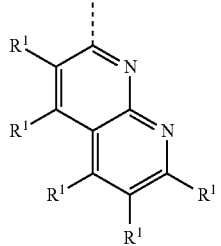
R-64 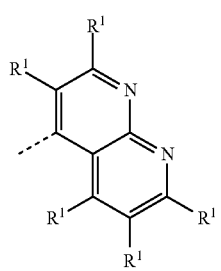

R-65
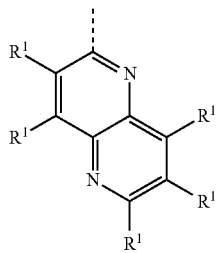
R-66
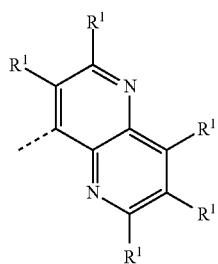
R-67
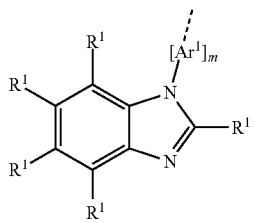
R-68
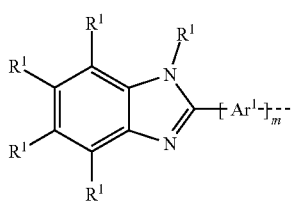
R-69
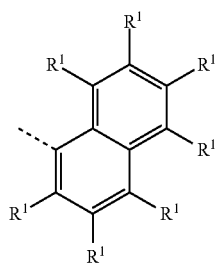
R-70
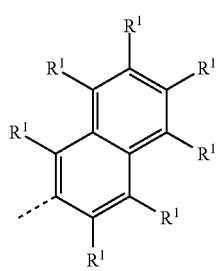
R-71
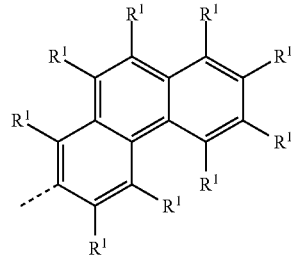
R-72
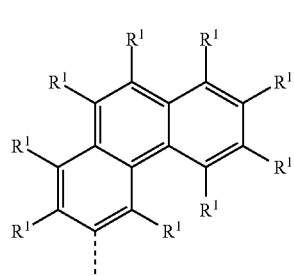
R-73
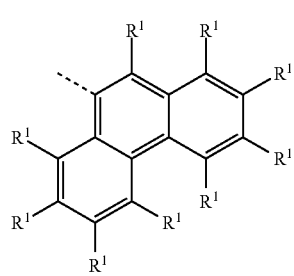
R-74
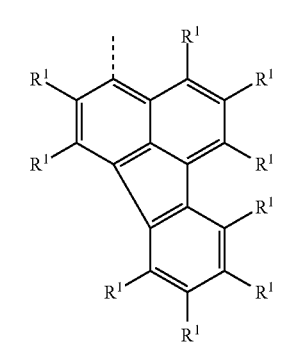
R-75
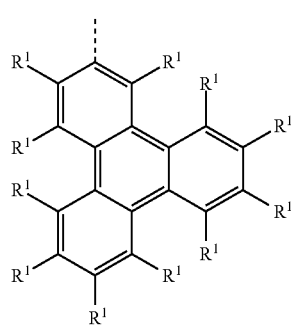

-continued

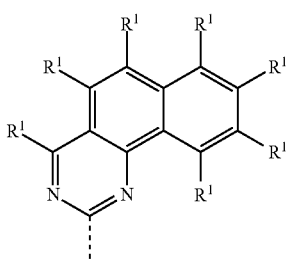
R-76

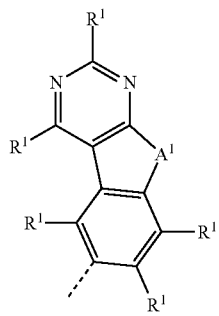
R-81

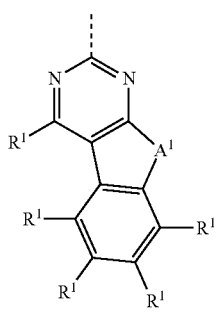
R-77

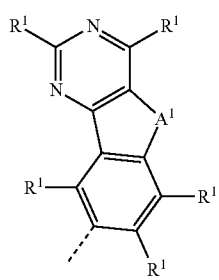
R-82

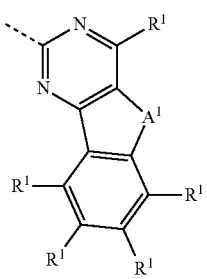
R-78

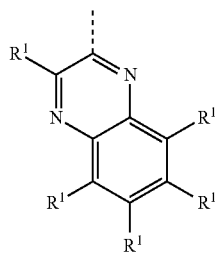
R-83

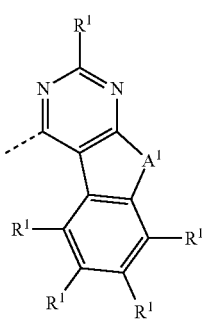
R-79

R-80 where $R^1$ has the definitions given above, the dotted bond represents the bond to a carbon atom of the base skeleton in formulae (1), (2) and (3) or in the preferred embodiments or to the nitrogen atom in the $N(Ar')_2$ group and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

n is 0 or 1, where n=0 means that no A group is bonded at this position and $R^1$ radicals are bonded to the corresponding carbon atoms instead;

m is 0 or 1, where m=0 means that the $Ar^1$ group is absent and that the corresponding aromatic or heteroaromatic group is bonded directly to a carbon atom of the base skeleton in formula (1) or in the preferred embodiments, or to the nitrogen atom in the $N(Ar')_2$ group; with the proviso that m=1 for the structures (R-12), (R-17), (R-21), (R-25), (R-26), (R-30), (R-34), (R-38) and (R-39) when these groups are embodiments of Ar'.

When the abovementioned Ar-1 to Ar-83 groups for Ar or R-1 to R-83 groups for R, R' or Ar' have two or more A groups, possible options for these include all combinations from the definition of A. Preferred embodiments in that case are those in which one A group is NR or $NR^1$ and the other A group is $C(R)_2$ or $C(R^1)_2$ or in which both A groups are NR or $NR^1$ or in which both A groups are O. In a particularly preferred embodiment of the invention, in Ar, R or Ar' groups having two or more A groups, at least one A group is $C(R)_2$ or $C(R^1)_2$ or is NR or $NR^1$.

When A is NR or $NR^1$, the substituent R or $R^1$ bonded to the nitrogen atom is preferably an aromatic or heteroaromatic ring system which has 5 to 24 aromatic ring atoms and may also be substituted by one or more $R^1$ or $R^2$ radicals. In a particularly preferred embodiment, this R or $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^1$ or $R^2$ radicals. Particular preference is given to phenyl, biphenyl, terphenyl and quaterphenyl having bonding patterns as listed above for Ar-1 to Ar-11 or R-1 to R-11, where these structures may be substituted by one or more $R^1$ or $R^2$ radicals, but are preferably unsubstituted.

When A is $C(R)_2$ or $C(R^1)_2$, the substituents R or $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more $R^1$ or $R^2$ radicals. Most preferably, R or $R^1$ is a methyl group or a phenyl group. In this case, the R or $R^1$ radicals together may also form a ring system, which leads to a spiro system.

Further suitable Ar, R, R' or Ar' groups are groups of the formula —$Ar^4$—$N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. Ar results in such a group when the Ar group is substituted by an $N(Ar')_2$ group. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another via a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, especially 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group. This is especially true when $Ar^4$ is bonded to $Ar^2$ via a single bond.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more $R^1$ radicals. More preferably, $Ar^2$ and $Ar^3$ are the same or different at each instance and are an aromatic ring system which has 6 to 24 aromatic ring atoms and may be substituted by one or more $R^1$ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, the alkyl groups in compounds of the invention which are processed by vacuum evaporation preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the Ar, R, R', Ar', $R^1$ and $R^2$ radicals do not contain any fused aryl or heteroaryl groups in which two or more six-membered rings are fused directly to one another. An exception to this is formed by phenanthrene and triphenylene which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

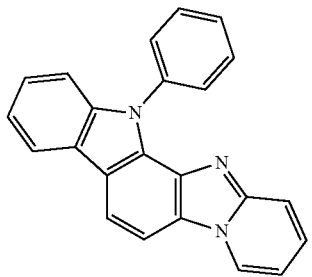 [SMILES: c1ccc(-n2c3ccccc3c3ccc4c(nc5ccccn54)c32)cc1]
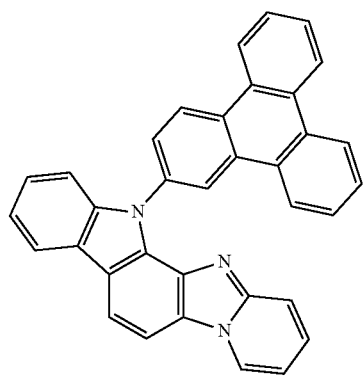 [SMILES: c1ccc2c(c1)c1ccccc1c1cc(-n3c4ccccc4c4ccc5c(nc6ccccn65)c43)ccc21]
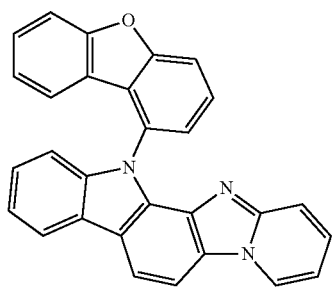 [SMILES: c1ccc2c(c1)oc1cccc(-n3c4ccccc4c4ccc5c(nc6ccccn65)c43)c12]
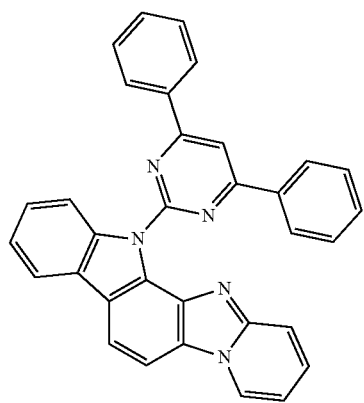 [SMILES: c1ccc(-c2cc(-c3ccccc3)nc(-n3c4ccccc4c4ccc5c(nc6ccccn65)c43)n2)cc1]

-continued
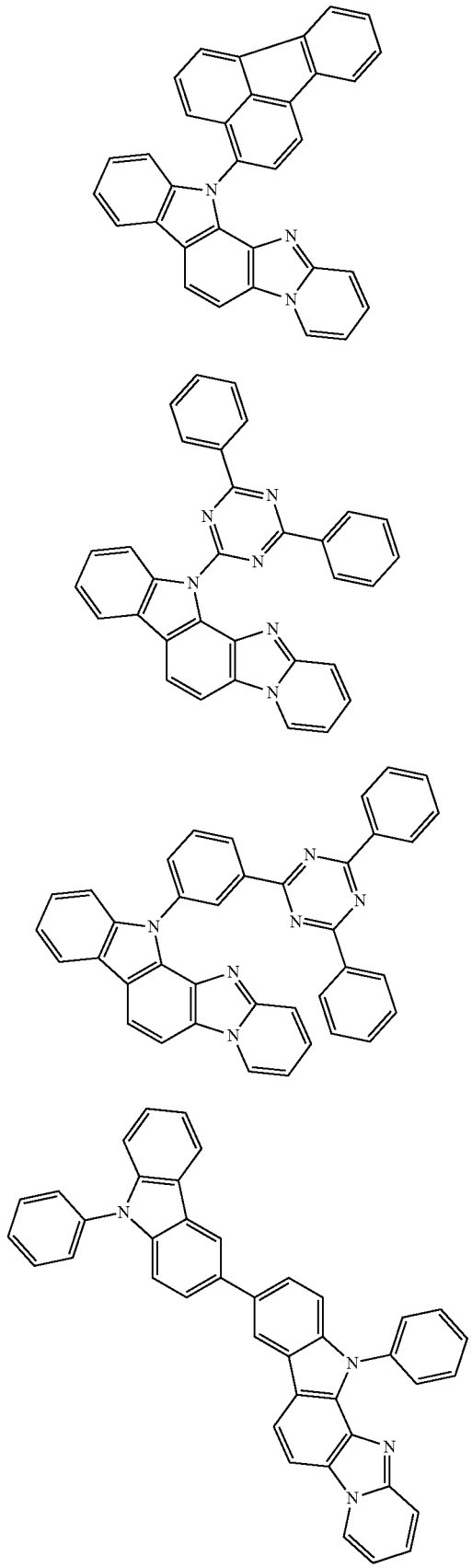

-continued
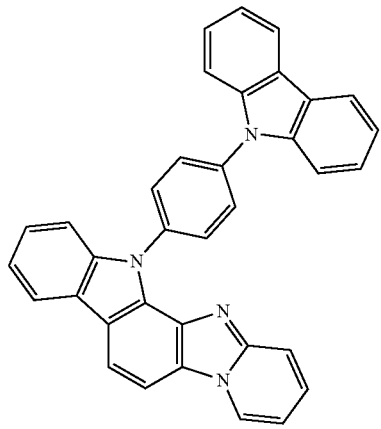 [SMILES: c1ccc2c(c1)c1ccccc1n2-c1ccc(-n2c3ccccc3c3ccc4c(nc5ccccn54)c32)cc1]
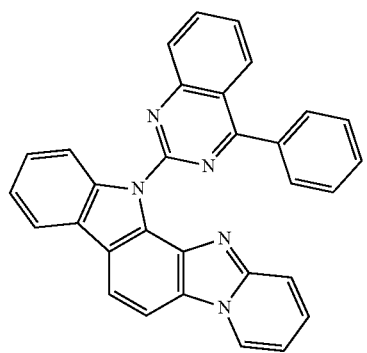 [SMILES: c1ccc(-c2nc(-n3c4ccccc4c4ccc5c(nc6ccccn65)c43)nc3ccccc23)cc1]
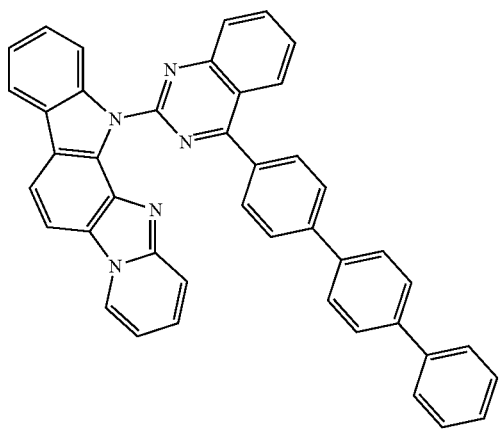 [SMILES: c1ccc(-c2ccc(-c3ccc(-c4nc(-n5c6ccccc6c6ccc7c(nc8ccccn87)c65)nc5ccccc45)cc3)cc2)cc1]
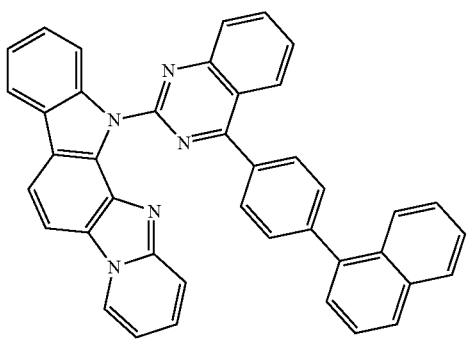 [SMILES: c1ccc2c(-c3ccc(-c4nc(-n5c6ccccc6c6ccc7c(nc8ccccn87)c65)nc5ccccc45)cc3)cccc2c1]

-continued
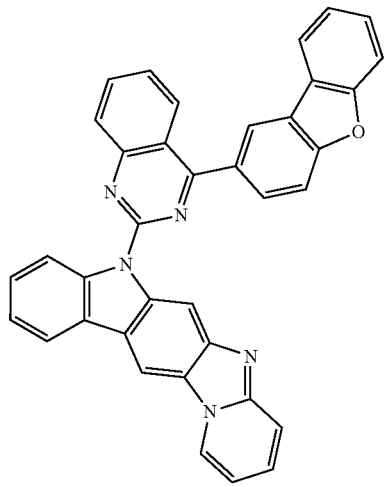 [SMILES: c1ccc2c(-c3ccc4oc5ccccc5c4c3)nc(-n3c4ccccc4c4cc5c(cc43)nc3ccccn35)nc2c1]
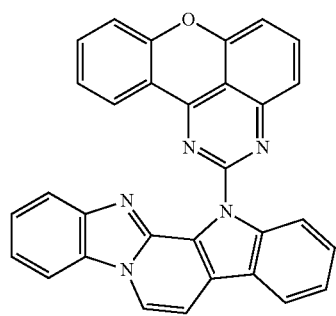 [SMILES: c1ccc2c(c1)Oc1cccc3nc(-n4c5ccccc5c5ccn6c7ccccc7nc6c54)nc-2c13]
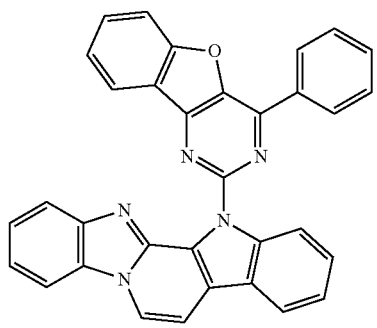 [SMILES: c1ccc(-c2nc(-n3c4ccccc4c4ccn5c6ccccc6nc5c43)nc3c2oc2ccccc23)cc1]
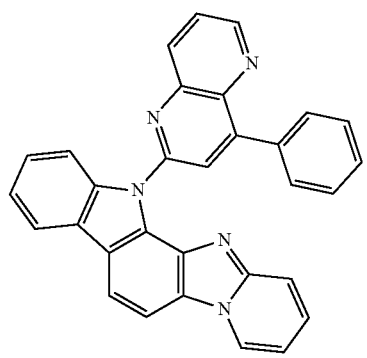 [SMILES: c1ccc(-c2cc(-n3c4ccccc4c4ccc5c(nc6ccccn65)c43)nc3cccnc23)cc1]

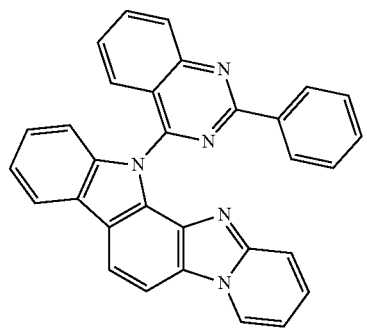 [SMILES: c1ccc(-c2nc(-n3c4ccccc4c4ccc5c(nc6ccccn65)c43)c3ccccc3n2)cc1]
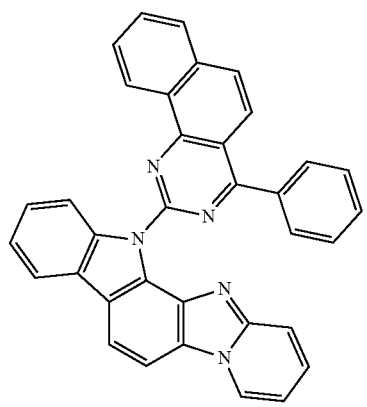 [SMILES: c1ccc(-c2nc(-n3c4ccccc4c4ccc5c(nc6ccccn65)c43)nc3c2ccc2ccccc23)cc1]
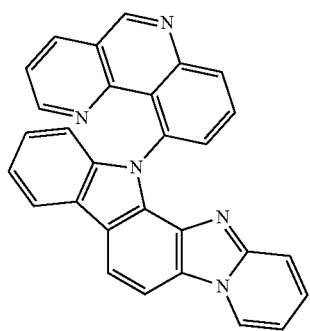 [SMILES: c1cnc2c(c1)cnc1cccc(-n3c4ccccc4c4ccc5c(nc6ccccn65)c43)c12]
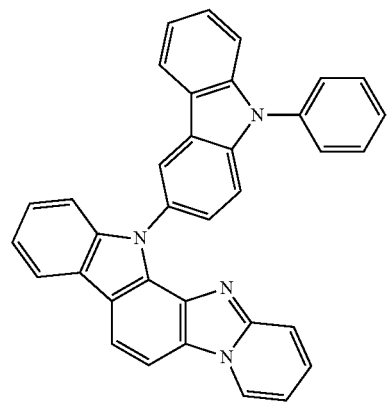 [SMILES: c1ccc(-n2c3ccccc3c3cc(-n4c5ccccc5c5ccc6c(nc7ccccn76)c54)ccc32)cc1]

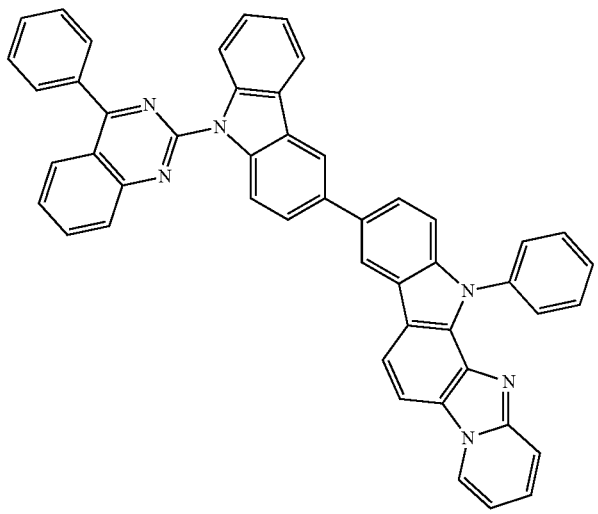 [SMILES: c1ccc(-c2nc(-n3c4ccccc4c4cc(-c5ccc6c(c5)c5ccc7c(nc8ccccn87)c5n6-c5ccccc5)ccc43)nc3ccccc23)cc1]
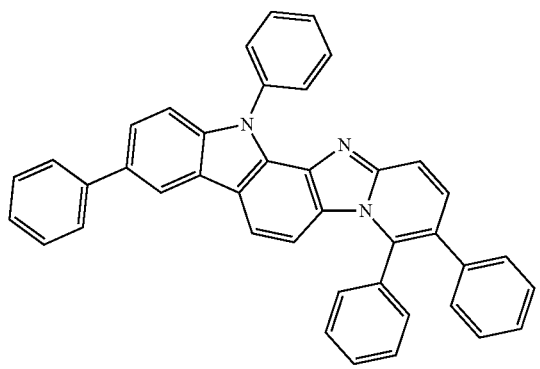 [SMILES: c1ccc(-c2ccc3c(c2)c2ccc4c(nc5ccc(-c6ccccc6)c(-c6ccccc6)n54)c2n3-c2ccccc2)cc1]
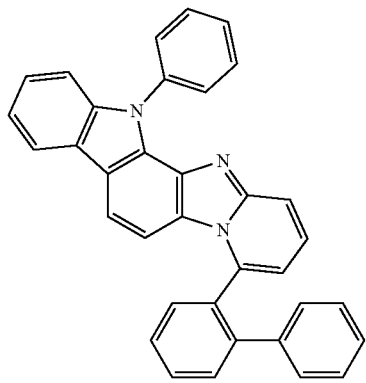 [SMILES: c1ccc(-c2ccccc2-c2cccc3nc4c5c(ccc4n23)c2ccccc2n5-c2ccccc2)cc1]
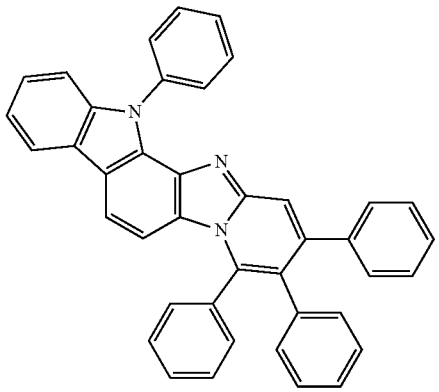 [SMILES: c1ccc(-c2cc3nc4c5c(ccc4n3c(-c3ccccc3)c2-c2ccccc2)c2ccccc2n5-c2ccccc2)cc1]

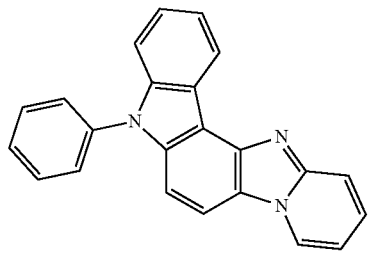 [SMILES: c1ccc(-n2c3ccccc3c3c4nc5ccccn5c4ccc32)cc1]
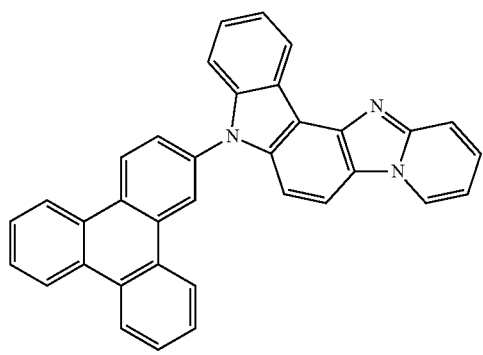 [SMILES: c1ccc2c(c1)c1ccccc1c1cc(-n3c4ccccc4c4c5nc6ccccn6c5ccc43)ccc21]
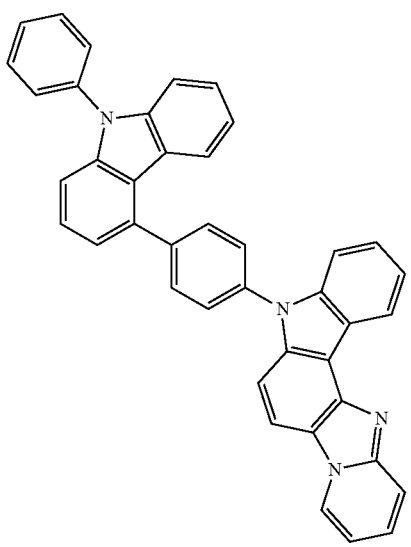 [SMILES: c1ccc(-n2c3ccccc3c3c(-c4ccc(-n5c6ccccc6c6c7nc8ccccn8c7ccc65)cc4)cccc32)cc1]
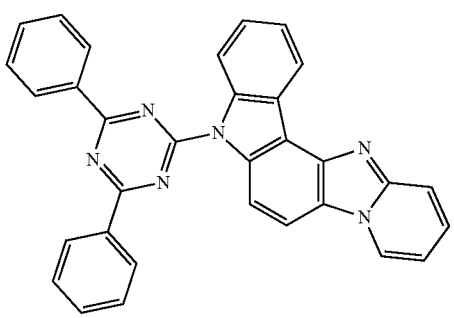 [SMILES: c1ccc(-c2nc(-c3ccccc3)nc(-n3c4ccccc4c4c5nc6ccccn6c5ccc43)n2)cc1]

-continued
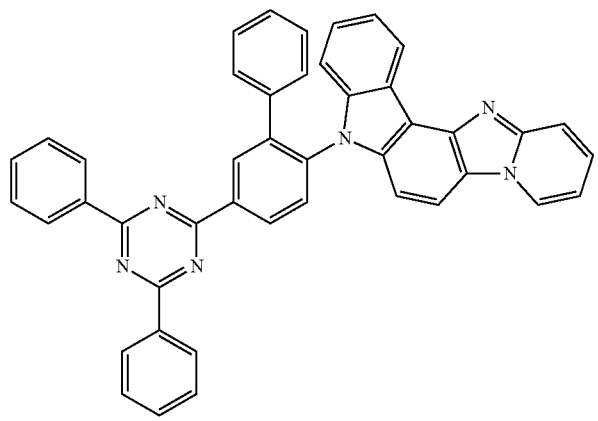 [SMILES: c1ccc(-c2nc(-c3ccccc3)nc(-c3ccc(-n4c5ccccc5c5c6nc7ccccn7c6ccc54)c(-c4ccccc4)c3)n2)cc1]
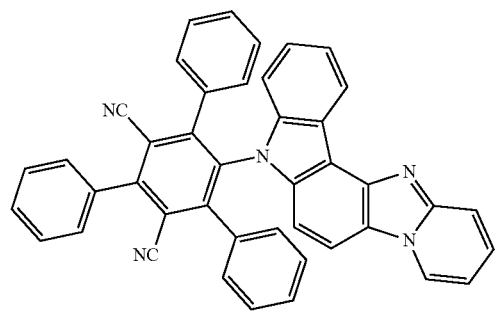 [SMILES: N#Cc1c(-c2ccccc2)c(C#N)c(-c2ccccc2)c(-n2c3ccccc3c3c4nc5ccccn5c4ccc32)c1-c1ccccc1]
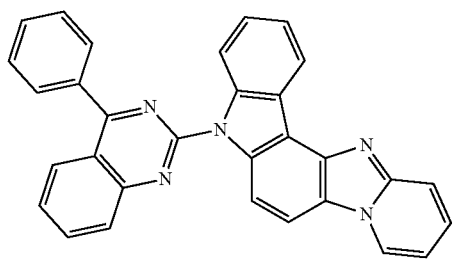 [SMILES: c1ccc(-c2nc(-n3c4ccccc4c4c5nc6ccccn6c5ccc43)nc3ccccc23)cc1]
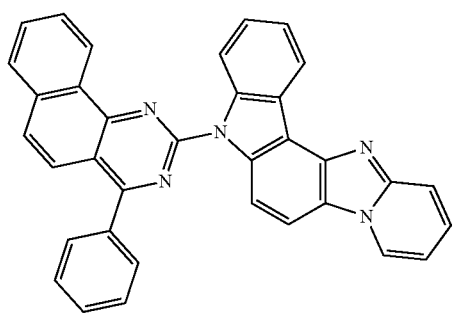 [SMILES: c1ccc(-c2nc(-n3c4ccccc4c4c5nc6ccccn6c5ccc43)nc3c2ccc2ccccc23)cc1]

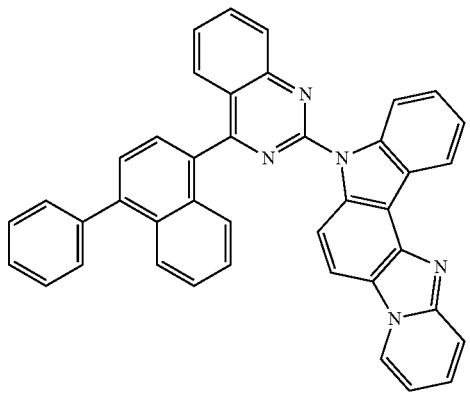 [SMILES: c1ccc(-c2ccc(-c3nc(-n4c5ccccc5c5c6nc7ccccn7c6ccc54)nc4ccccc34)c3ccccc23)cc1]
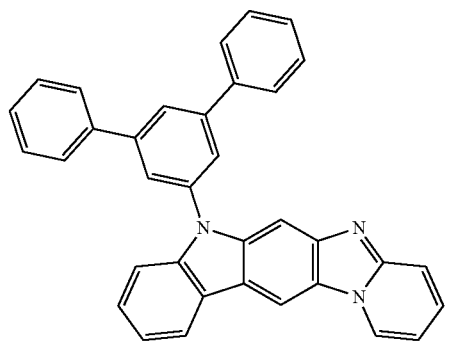 [SMILES: c1ccc(-c2cc(-c3ccccc3)cc(-n3c4ccccc4c4cc5c(cc43)nc3ccccn35)c2)cc1]
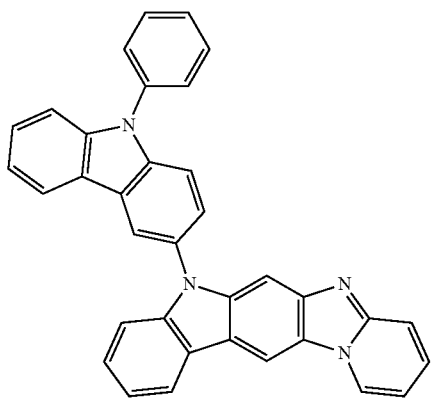 [SMILES: c1ccc(-n2c3ccccc3c3cc(-n4c5ccccc5c5cc6c(cc54)nc4ccccn46)ccc32)cc1]
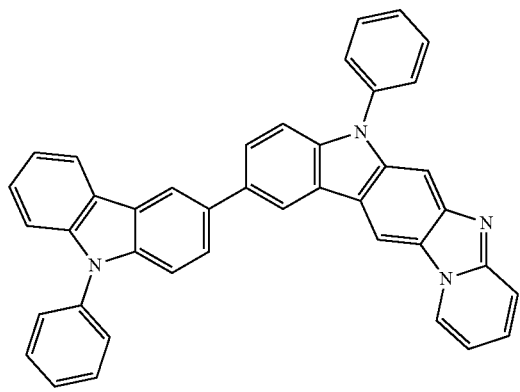 [SMILES: c1ccc(-n2c3ccccc3c3cc(-c4ccc5c(c4)c4cc6c(cc4n5-c4ccccc4)nc4ccccn46)ccc32)cc1]

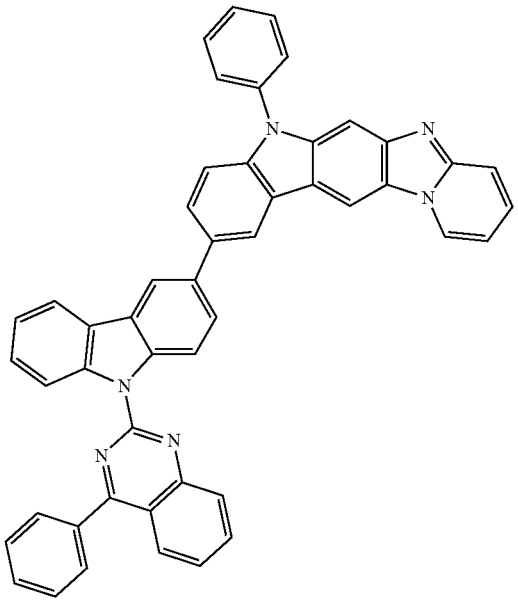 [SMILES: c1ccc(-c2nc(-n3c4ccccc4c4cc(-c5ccc6c(c5)c5cc7c(cc5n6-c5ccccc5)nc5ccccn57)ccc43)nc3ccccc23)cc1]
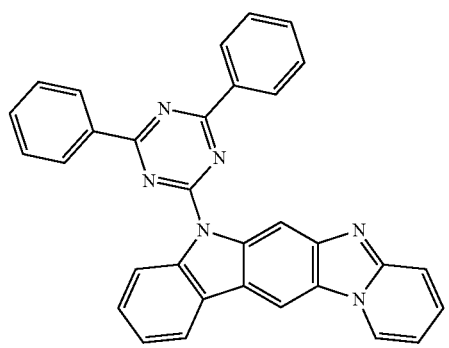 [SMILES: c1ccc(-c2nc(-c3ccccc3)nc(-n3c4ccccc4c4cc5c(cc43)nc3ccccn35)n2)cc1]
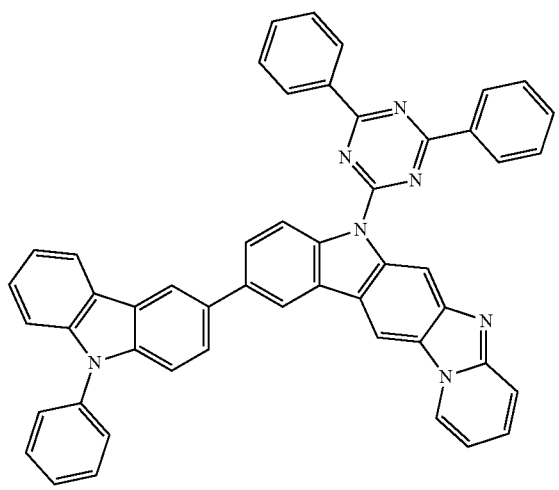 [SMILES: c1ccc(-c2nc(-c3ccccc3)nc(-n3c4ccc(-c5ccc6c(c5)c5ccccc5n6-c5ccccc5)cc4c4cc5c(cc43)nc3ccccn35)n2)cc1]

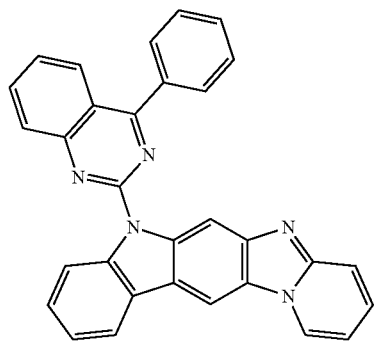 [SMILES: c1ccc(-c2nc(-n3c4ccccc4c4cc5c(cc43)nc3ccccn35)nc3ccccc23)cc1]
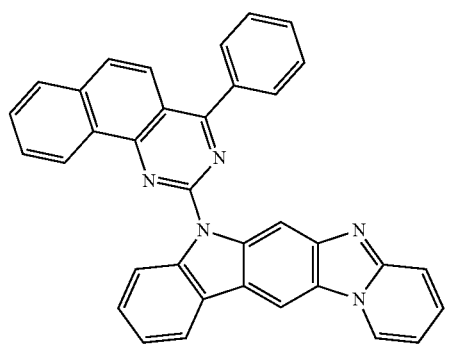 [SMILES: c1ccc(-c2nc(-n3c4ccccc4c4cc5c(cc43)nc3ccccn35)nc3c2ccc2ccccc23)cc1]
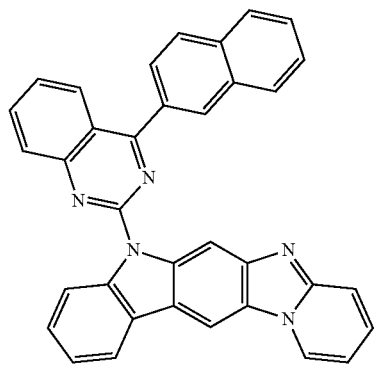 [SMILES: c1ccc2cc(-c3nc(-n4c5ccccc5c5cc6c(cc54)nc4ccccn46)nc4ccccc34)ccc2c1]
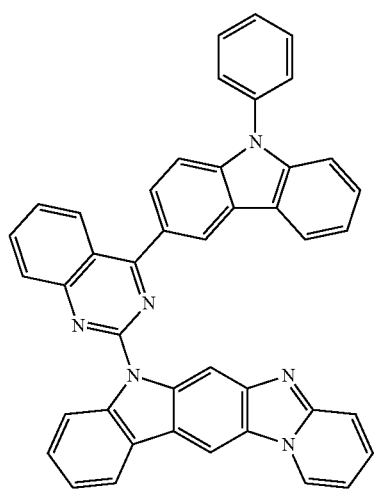 [SMILES: c1ccc(-n2c3ccccc3c3cc(-c4nc(-n5c6ccccc6c6cc7c(cc65)nc5ccccn57)nc5ccccc45)ccc32)cc1]

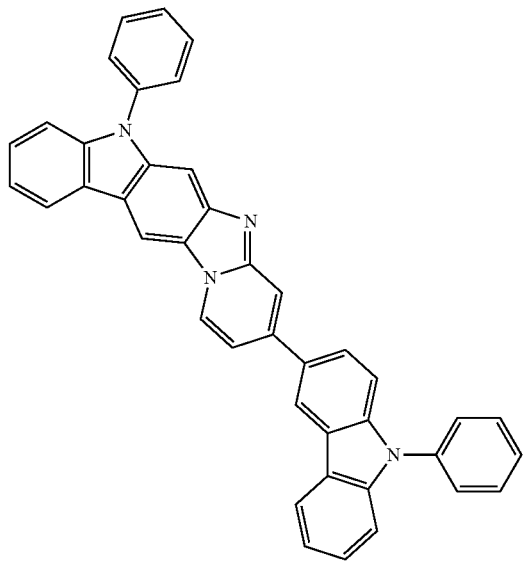 [SMILES: c1ccc(-n2c3ccccc3c3cc(-c4ccn5c(c4)nc4cc6c(cc45)c4ccccc4n6-c4ccccc4)ccc32)cc1]
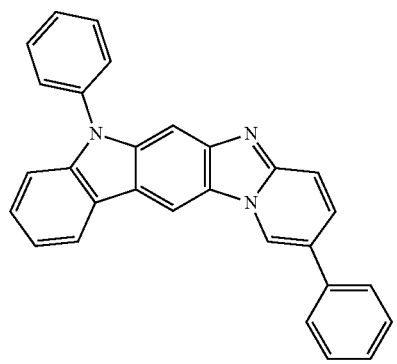 [SMILES: c1ccc(-c2ccc3nc4cc5c(cc4n3c2)c2ccccc2n5-c2ccccc2)cc1]
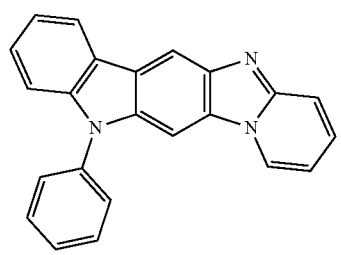 [SMILES: c1ccc(-n2c3ccccc3c3cc4nc5ccccn5c4cc32)cc1]
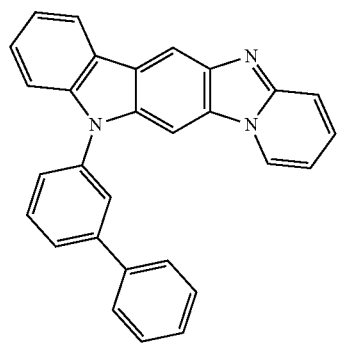 [SMILES: c1ccc(-c2cccc(-n3c4ccccc4c4cc5nc6ccccn6c5cc43)c2)cc1]

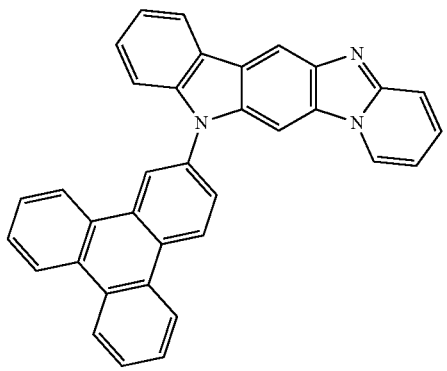 [SMILES: c1ccc2c(c1)c1ccccc1c1cc(-n3c4ccccc4c4cc5nc6ccccn6c5cc43)ccc21]
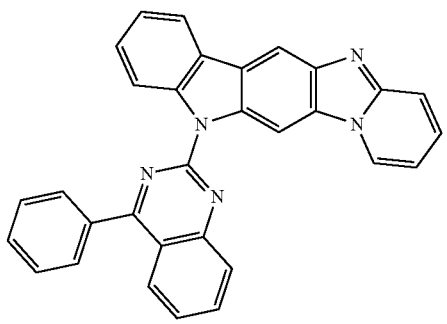 [SMILES: c1ccc(-c2nc(-n3c4ccccc4c4cc5nc6ccccn6c5cc43)nc3ccccc23)cc1]
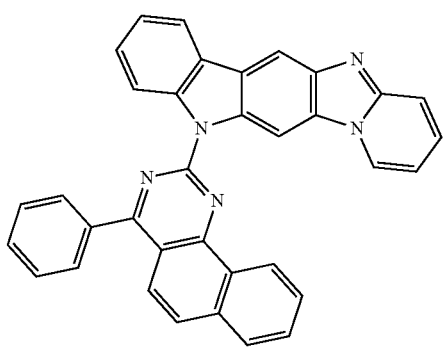 [SMILES: c1ccc(-c2nc(-n3c4ccccc4c4cc5nc6ccccn6c5cc43)nc3c2ccc2ccccc23)cc1]
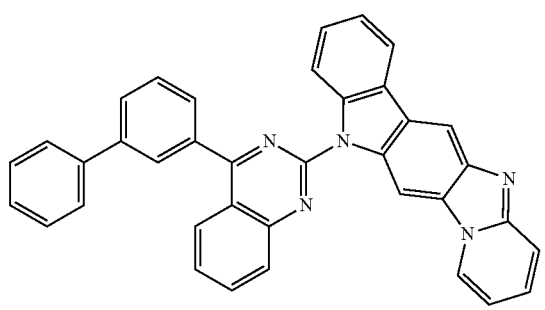 [SMILES: c1ccc(-c2cccc(-c3nc(-n4c5ccccc5c5cc6nc7ccccn7c6cc54)nc4ccccc34)c2)cc1]

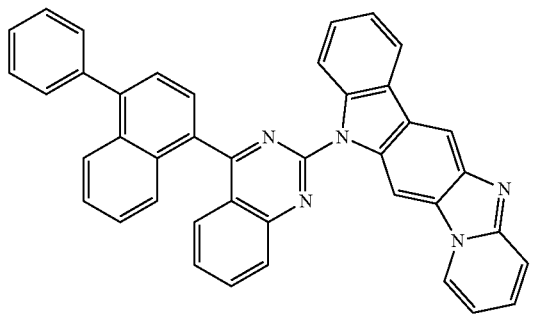 [SMILES: c1ccc(-c2ccc(-c3nc(-n4c5ccccc5c5cc6nc7ccccn7c6cc54)nc4ccccc34)c3ccccc23)cc1]
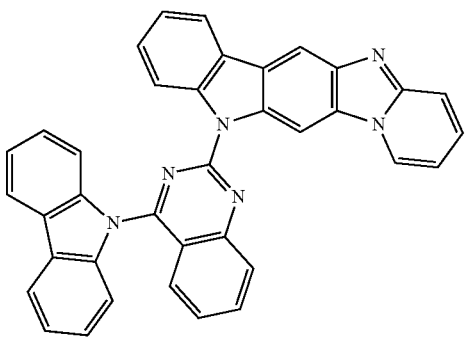 [SMILES: c1ccc2c(-n3c4ccccc4c4ccccc43)nc(-n3c4ccccc4c4cc5nc6ccccn6c5cc43)nc2c1]
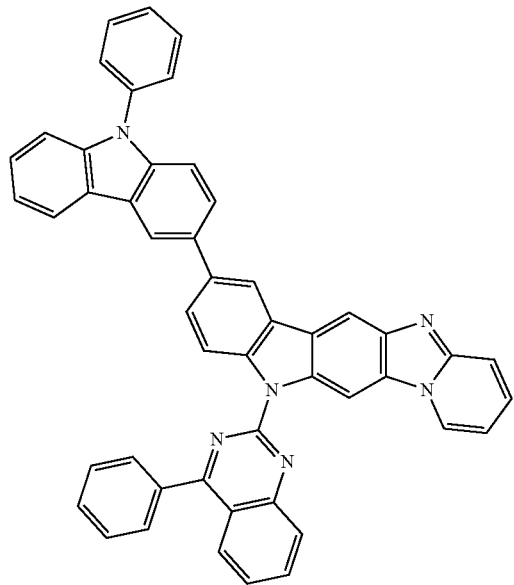 [SMILES: c1ccc(-c2nc(-n3c4ccc(-c5ccc6c(c5)c5ccccc5n6-c5ccccc5)cc4c4cc5nc6ccccn6c5cc43)nc3ccccc23)cc1]
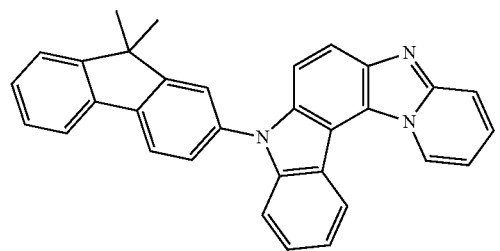 [SMILES: CC1(C)c2ccccc2-c2ccc(-n3c4ccccc4c4c3ccc3nc5ccccn5c34)cc21]

-continued
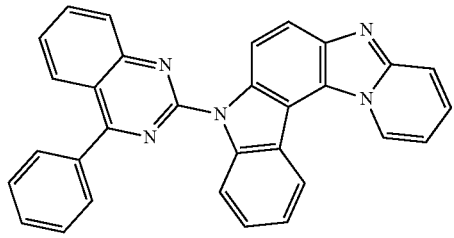 [SMILES: c1ccc(-c2nc(-n3c4ccccc4c4c3ccc3nc5ccccn5c34)nc3ccccc23)cc1]
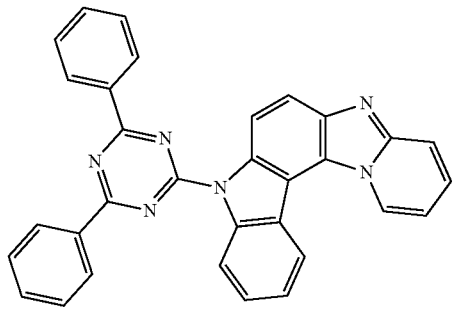 [SMILES: c1ccc(-c2nc(-c3ccccc3)nc(-n3c4ccccc4c4c3ccc3nc5ccccn5c34)n2)cc1]
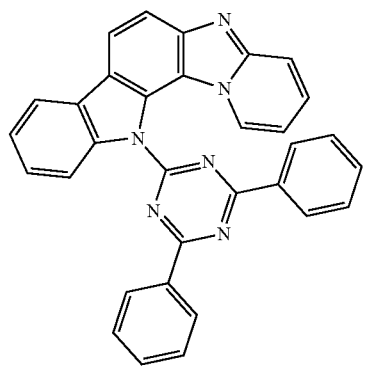 [SMILES: c1ccc(-c2nc(-c3ccccc3)nc(-n3c4ccccc4c4ccc5nc6ccccn6c5c43)n2)cc1]
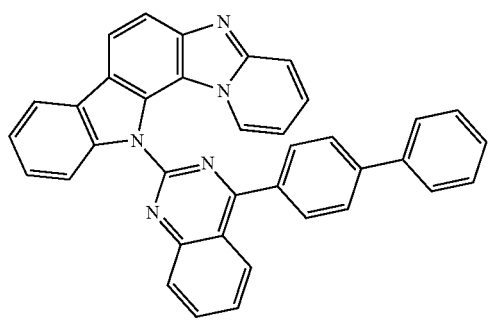 [SMILES: c1ccc(-c2ccc(-c3nc(-n4c5ccccc5c5ccc6nc7ccccn7c6c54)nc4ccccc34)cc2)cc1]
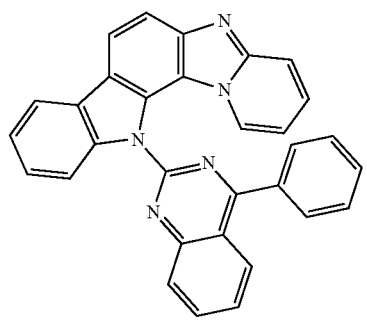 [SMILES: c1ccc(-c2nc(-n3c4ccccc4c4ccc5nc6ccccn6c5c43)nc3ccccc23)cc1]

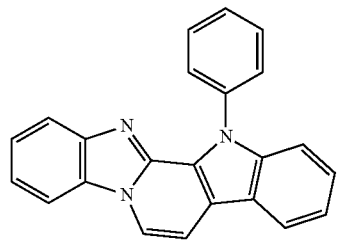 [SMILES: c1ccc(-n2c3ccccc3c3ccn4c5ccccc5nc4c32)cc1]
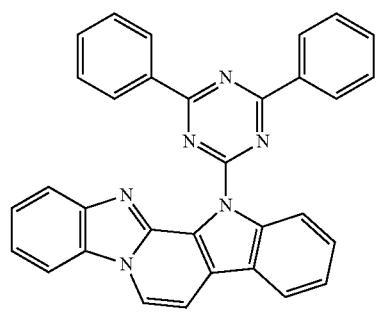 [SMILES: c1ccc(-c2nc(-c3ccccc3)nc(-n3c4ccccc4c4ccn5c6ccccc6nc5c43)n2)cc1]
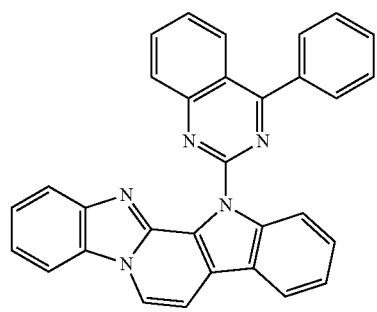 [SMILES: c1ccc(-c2nc(-n3c4ccccc4c4ccn5c6ccccc6nc5c43)nc3ccccc23)cc1]
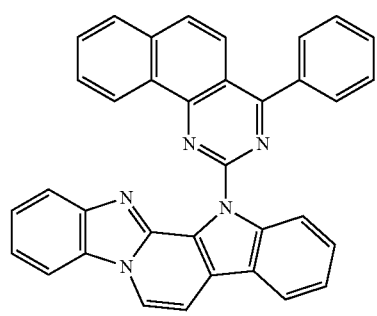 [SMILES: c1ccc(-c2nc(-n3c4ccccc4c4ccn5c6ccccc6nc5c43)nc3c2ccc2ccccc23)cc1]

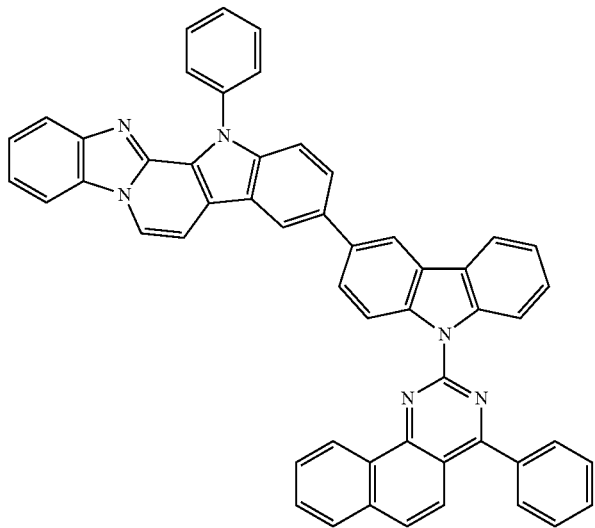 [SMILES: c1ccc(-c2nc(-n3c4ccccc4c4cc(-c5ccc6c(c5)c5ccn7c8ccccc8nc7c5n6-c5ccccc5)ccc43)nc3c2ccc2ccccc23)cc1]
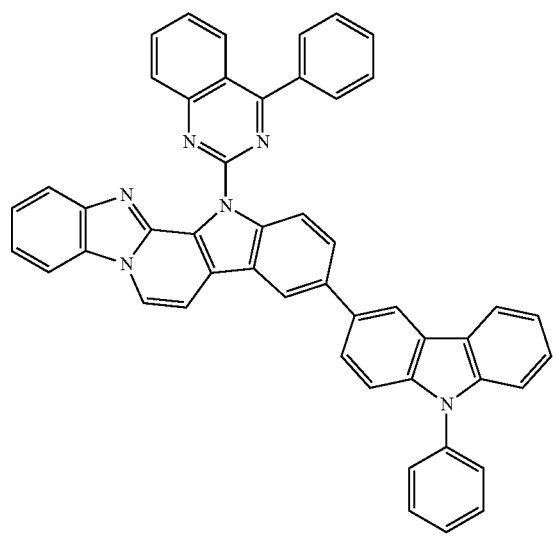 [SMILES: c1ccc(-c2nc(-n3c4ccc(-c5ccc6c(c5)c5ccccc5n6-c5ccccc5)cc4c4ccn5c6ccccc6nc5c43)nc3ccccc23)cc1]
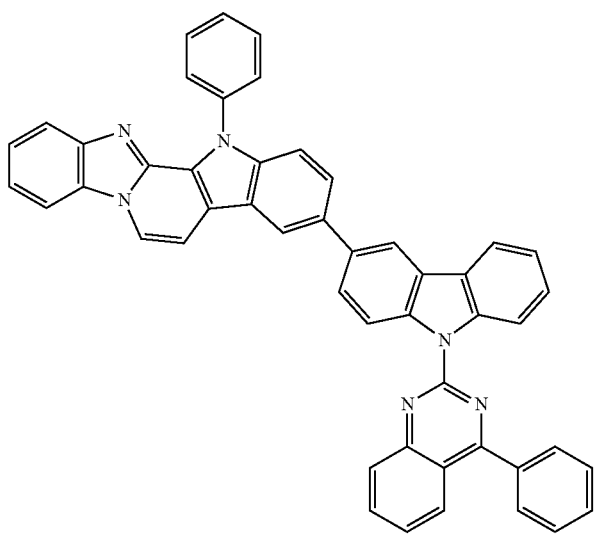 [SMILES: c1ccc(-c2nc(-n3c4ccccc4c4cc(-c5ccc6c(c5)c5ccn7c8ccccc8nc7c5n6-c5ccccc5)ccc43)nc3ccccc23)cc1]

-continued
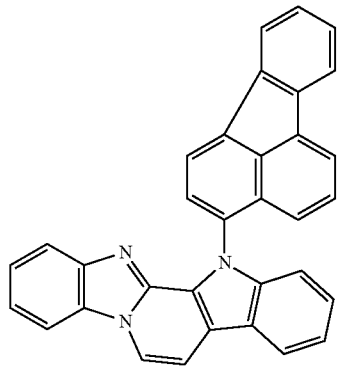 [SMILES: c1ccc2c(c1)-c1cccc3c(-n4c5ccccc5c5ccn6c7ccccc7nc6c54)ccc-2c13]
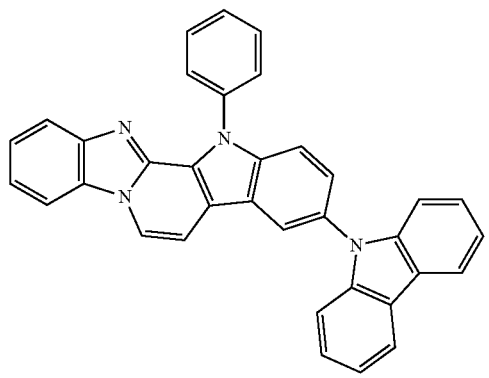 [SMILES: c1ccc(-n2c3ccc(-n4c5ccccc5c5ccccc54)cc3c3ccn4c5ccccc5nc4c32)cc1]
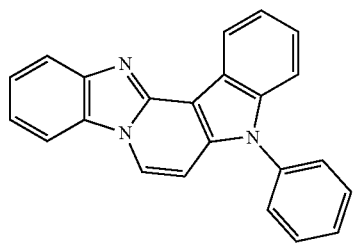 [SMILES: c1ccc(-n2c3ccccc3c3c2ccn2c4ccccc4nc32)cc1]
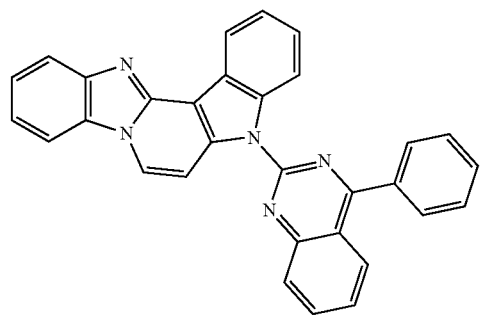 [SMILES: c1ccc(-c2nc(-n3c4ccccc4c4c3ccn3c5ccccc5nc43)nc3ccccc23)cc1]

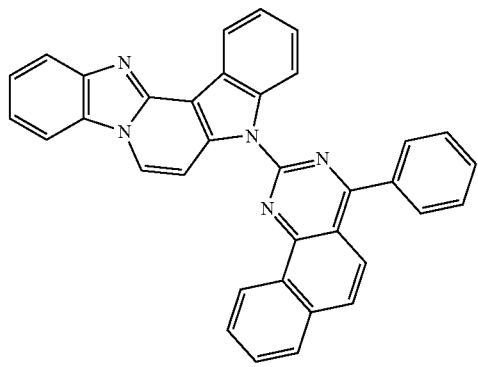 [SMILES: c1ccc(-c2nc(-n3c4ccccc4c4c3ccn3c5ccccc5nc43)nc3c2ccc2ccccc23)cc1]
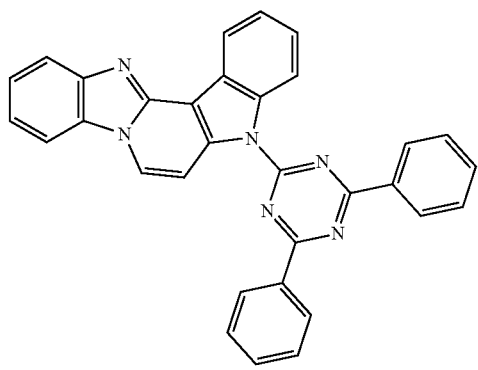 [SMILES: c1ccc(-c2nc(-c3ccccc3)nc(-n3c4ccccc4c4c3ccn3c5ccccc5nc43)n2)cc1]
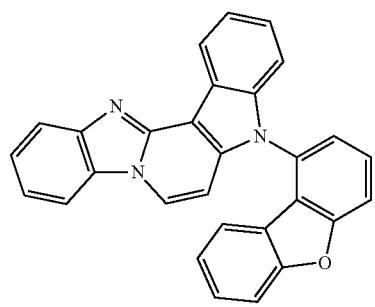 [SMILES: c1ccc2c(c1)nc1c3c4ccccc4n(-c4cccc5oc6ccccc6c45)c3ccn21]
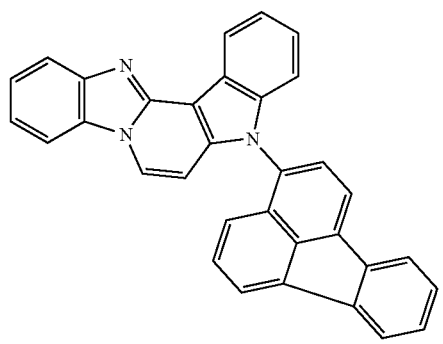 [SMILES: c1ccc2c(c1)-c1cccc3c(-n4c5ccccc5c5c4ccn4c6ccccc6nc54)ccc-2c13]

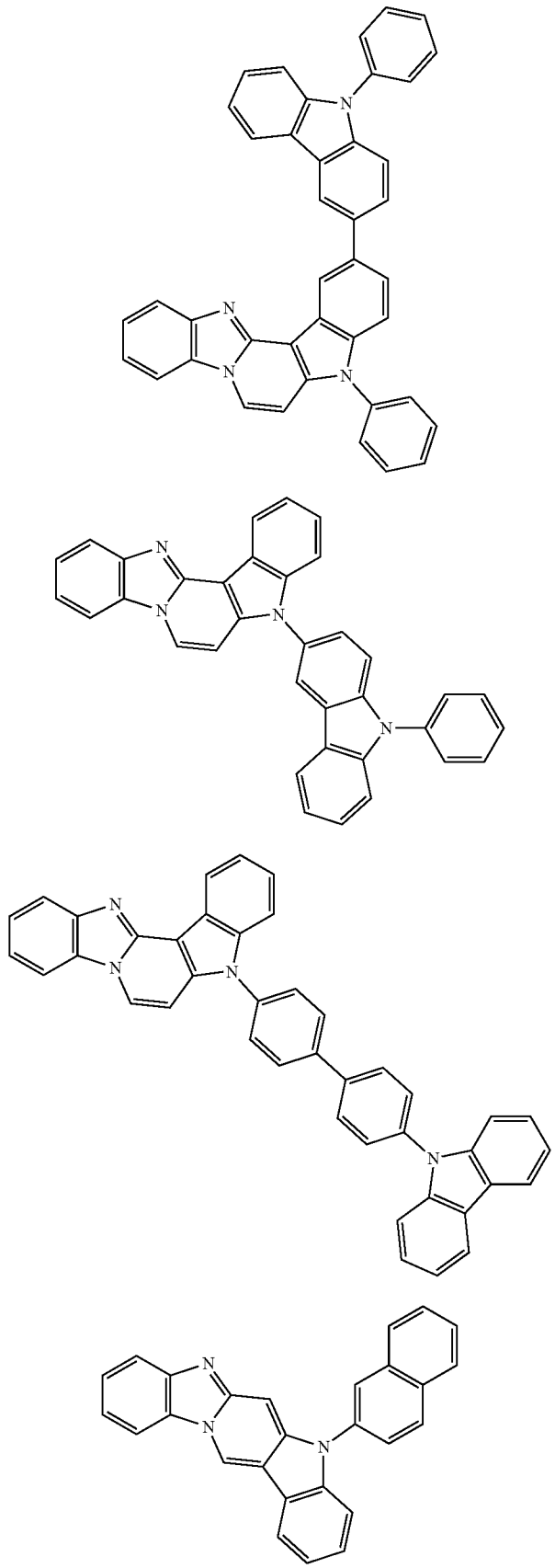

-continued
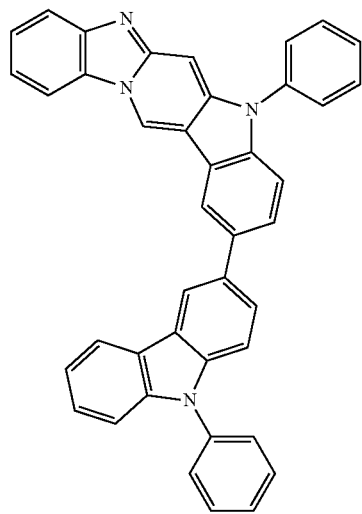 [SMILES: c1ccc(-n2c3ccccc3c3cc(-c4ccc5c(c4)c4cn6c(cc4n5-c4ccccc4)nc4ccccc46)ccc32)cc1]
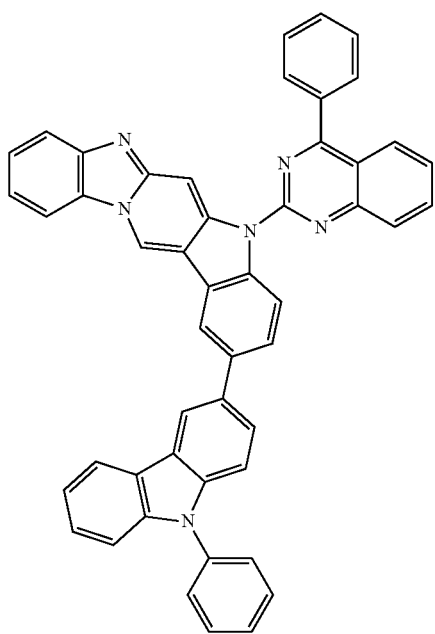 [SMILES: c1ccc(-c2nc(-n3c4ccc(-c5ccc6c(c5)c5ccccc5n6-c5ccccc5)cc4c4cn5c(cc43)nc3ccccc35)nc3ccccc23)cc1]

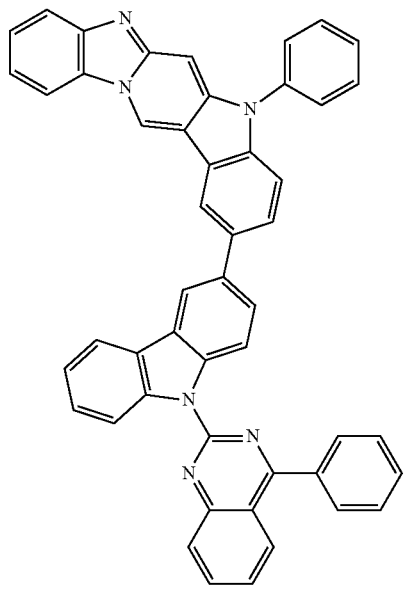 [SMILES: c1ccc(-c2nc(-n3c4ccccc4c4cc(-c5ccc6c(c5)c5cn7c(cc5n6-c5ccccc5)nc5ccccc57)ccc43)nc3ccccc23)cc1]
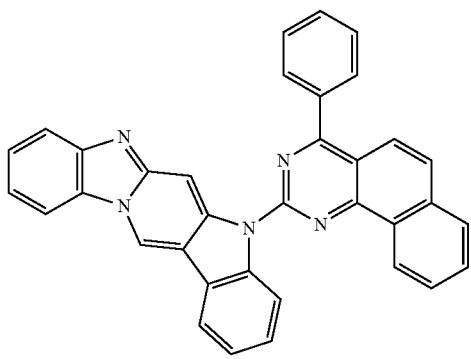 [SMILES: c1ccc(-c2nc(-n3c4ccccc4c4cn5c(cc43)nc3ccccc35)nc3c2ccc2ccccc23)cc1]
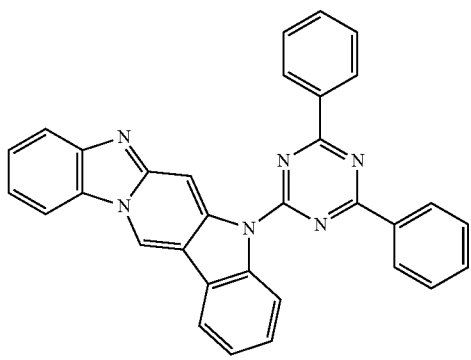 [SMILES: c1ccc(-c2nc(-c3ccccc3)nc(-n3c4ccccc4c4cn5c(cc43)nc3ccccc35)n2)cc1]
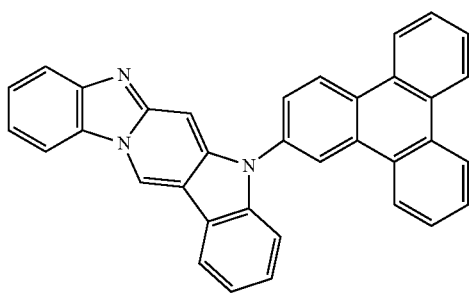 [SMILES: c1ccc2c(c1)nc1cc3c(cn12)c1ccccc1n3-c1ccc2c3ccccc3c3ccccc3c2c1]

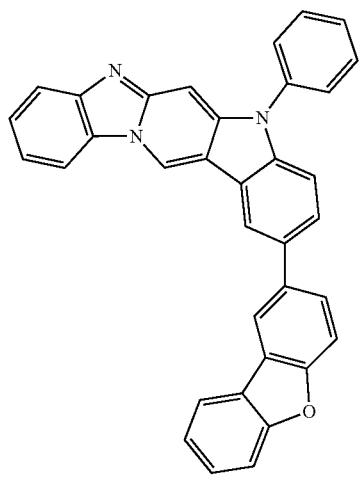 [SMILES: c1ccc(-n2c3ccc(-c4ccc5oc6ccccc6c5c4)cc3c3cn4c(cc32)nc2ccccc24)cc1]
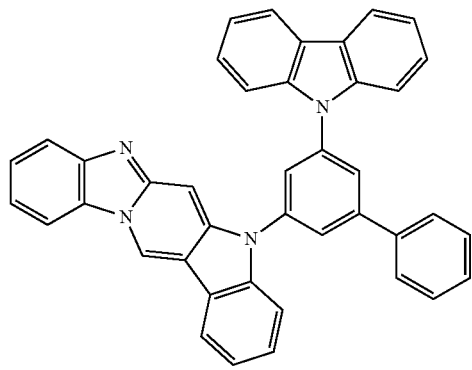 [SMILES: c1ccc(-c2cc(-n3c4ccccc4c4ccccc43)cc(-n3c4ccccc4c4cn5c(cc43)nc3ccccc35)c2)cc1]
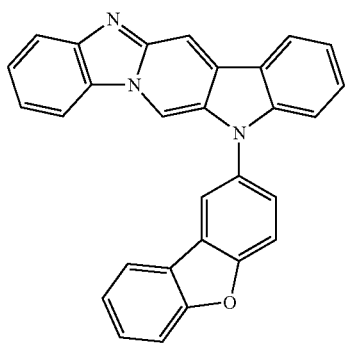 [SMILES: c1ccc2c(c1)nc1cc3c4ccccc4n(-c4ccc5oc6ccccc6c5c4)c3cn12]
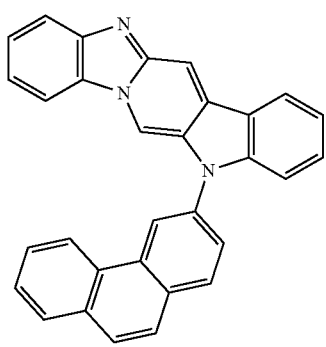 [SMILES: c1ccc2c(c1)ccc1ccc(-n3c4ccccc4c4cc5nc6ccccc6n5cc43)cc12]

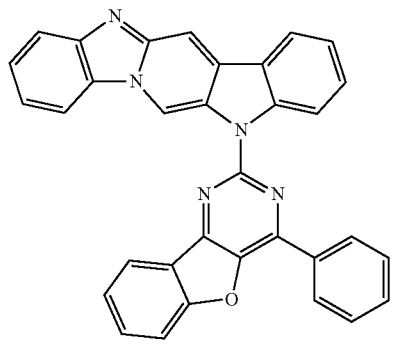 [SMILES: c1ccc(-c2nc(-n3c4ccccc4c4cc5nc6ccccc6n5cc43)nc3c2oc2ccccc23)cc1]
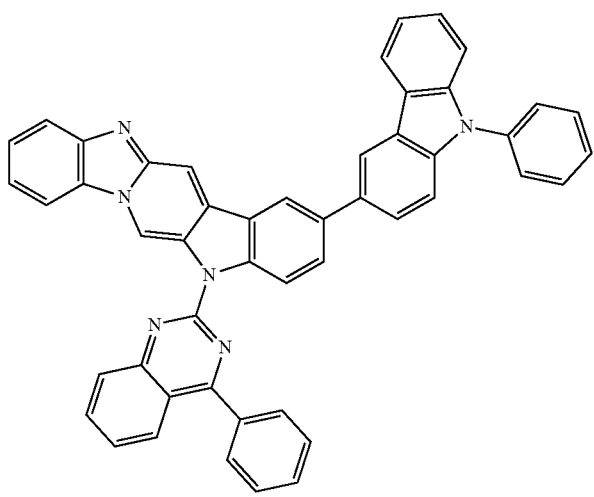 [SMILES: c1ccc(-c2nc(-n3c4ccc(-c5ccc6c(c5)c5ccccc5n6-c5ccccc5)cc4c4cc5nc6ccccc6n5cc43)nc3ccccc23)cc1]
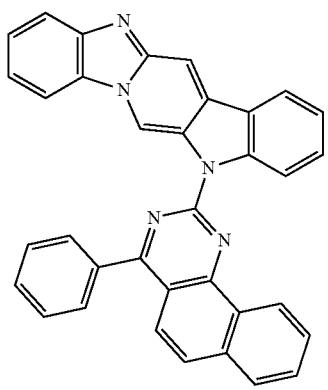 [SMILES: c1ccc(-c2nc(-n3c4ccccc4c4cc5nc6ccccc6n5cc43)nc3c2ccc2ccccc23)cc1]
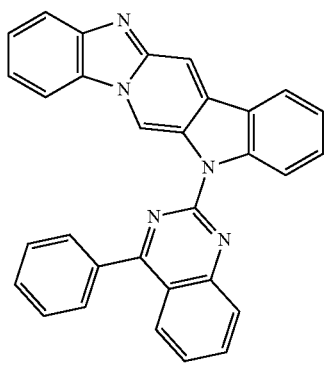 [SMILES: c1ccc(-c2nc(-n3c4ccccc4c4cc5nc6ccccc6n5cc43)nc3ccccc23)cc1]

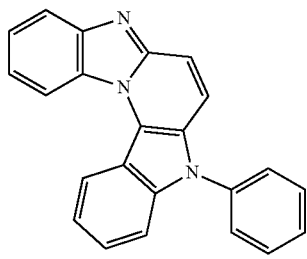 [SMILES: c1ccc(-n2c3ccccc3c3c2ccc2nc4ccccc4n23)cc1]
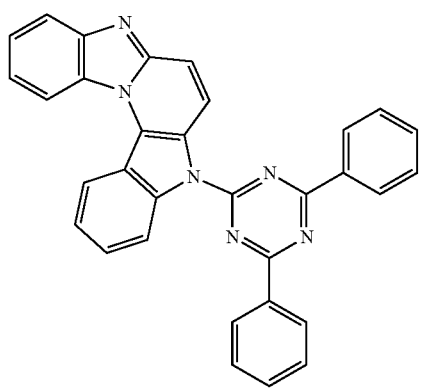 [SMILES: c1ccc(-c2nc(-c3ccccc3)nc(-n3c4ccccc4c4c3ccc3nc5ccccc5n34)n2)cc1]
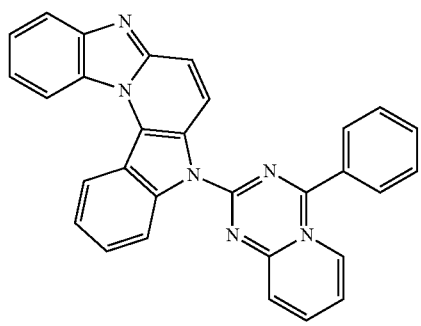
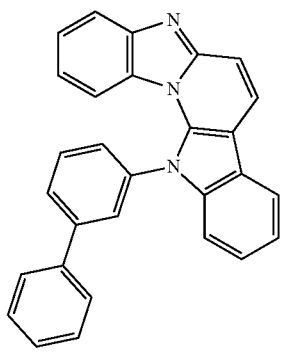 [SMILES: c1ccc(-c2cccc(-n3c4ccccc4c4ccc5nc6ccccc6n5c43)c2)cc1]

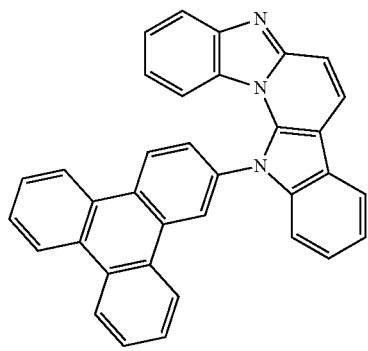 [SMILES: c1ccc2c(c1)nc1ccc3c4ccccc4n(-c4ccc5c6ccccc6c6ccccc6c5c4)c3n12]
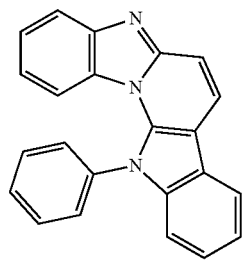 [SMILES: c1ccc(-n2c3ccccc3c3ccc4nc5ccccc5n4c32)cc1]
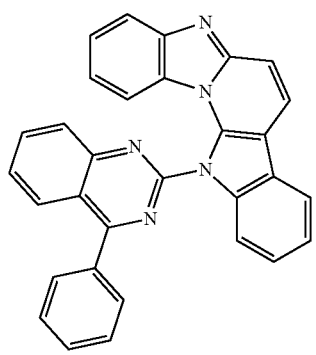 [SMILES: c1ccc(-c2nc(-n3c4ccccc4c4ccc5nc6ccccc6n5c43)nc3ccccc23)cc1]
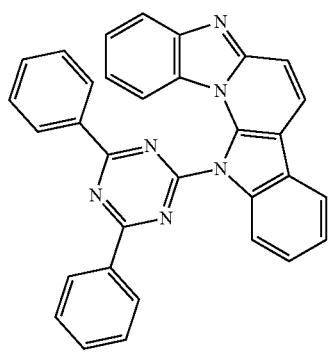 [SMILES: c1ccc(-c2nc(-c3ccccc3)nc(-n3c4ccccc4c4ccc5nc6ccccc6n5c43)n2)cc1]

-continued
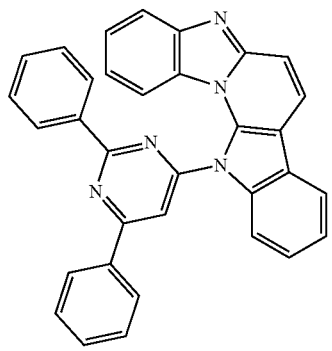 [SMILES: c1ccc(-c2cc(-n3c4ccccc4c4ccc5nc6ccccc6n5c43)nc(-c3ccccc3)n2)cc1]
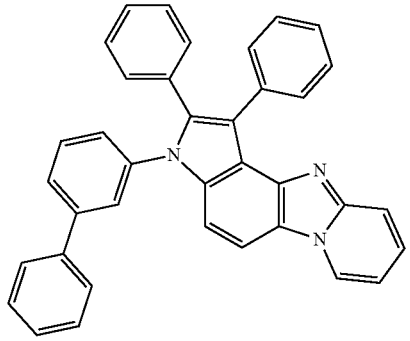 [SMILES: c1ccc(-c2cccc(-n3c(-c4ccccc4)c(-c4ccccc4)c4c5nc6ccccn6c5ccc43)c2)cc1]
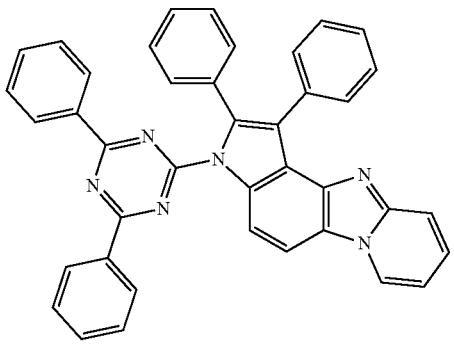 [SMILES: c1ccc(-c2nc(-c3ccccc3)nc(-n3c(-c4ccccc4)c(-c4ccccc4)c4c5nc6ccccn6c5ccc43)n2)cc1]
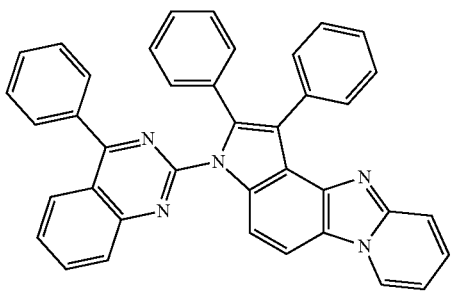 [SMILES: c1ccc(-c2nc(-n3c(-c4ccccc4)c(-c4ccccc4)c4c5nc6ccccn6c5ccc43)nc3ccccc23)cc1]
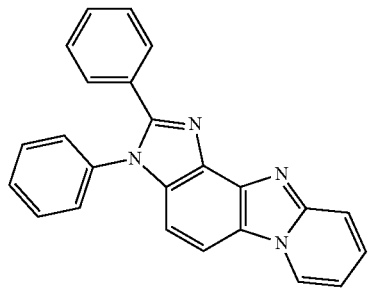 [SMILES: c1ccc(-c2nc3c4nc5ccccn5c4ccc3n2-c2ccccc2)cc1]

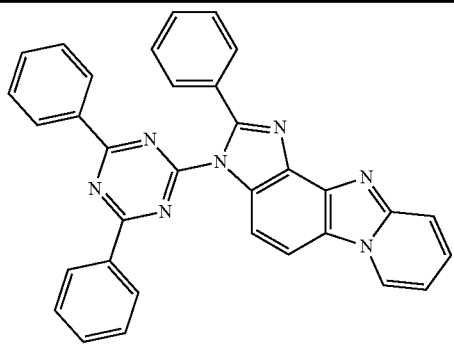
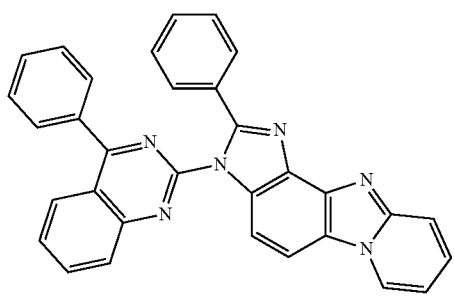 [SMILES: c1ccc(-c2nc(-n3c(-c4ccccc4)nc4c5nc6ccccn6c5ccc43)nc3ccccc23)cc1]
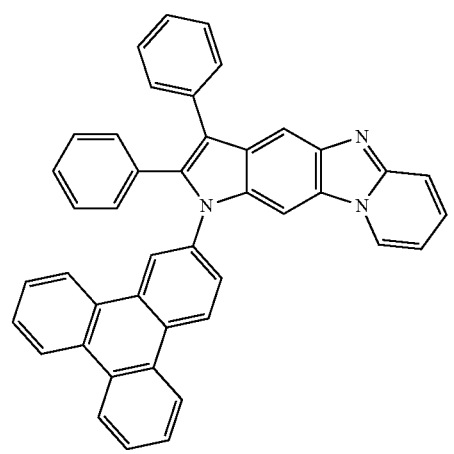 [SMILES: c1ccc(-c2c(-c3ccccc3)n(-c3ccc4c5ccccc5c5ccccc5c4c3)c3cc4c(cc23)nc2ccccn24)cc1]
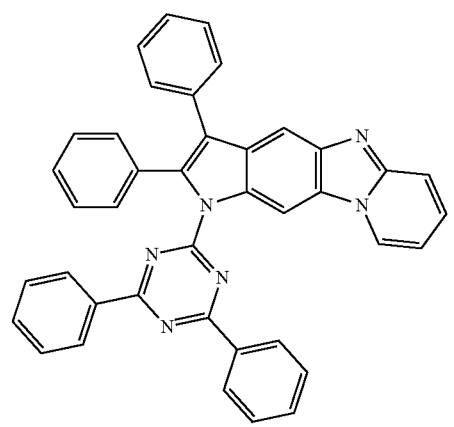 [SMILES: c1ccc(-c2nc(-c3ccccc3)nc(-n3c(-c4ccccc4)c(-c4ccccc4)c4cc5nc6ccccn6c5cc43)n2)cc1]

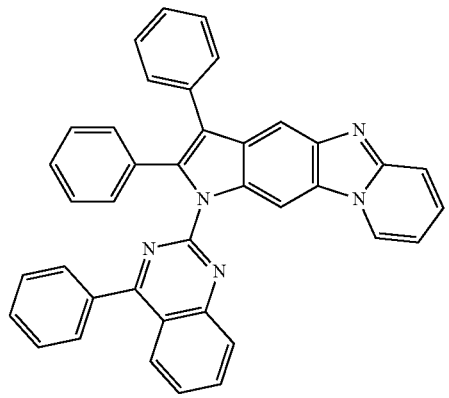 [SMILES: c1ccc(-c2nc(-n3c(-c4ccccc4)c(-c4ccccc4)c4cc5nc6ccccn6c5cc43)nc3ccccc23)cc1]
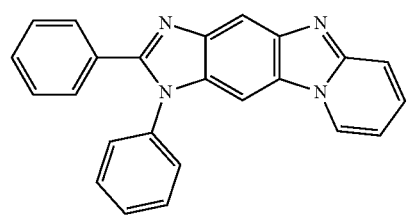 [SMILES: c1ccc(-c2nc3cc4nc5ccccn5c4cc3n2-c2ccccc2)cc1]
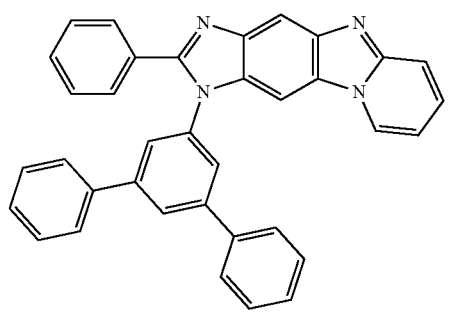 [SMILES: c1ccc(-c2cc(-c3ccccc3)cc(-n3c(-c4ccccc4)nc4cc5nc6ccccn6c5cc43)c2)cc1]
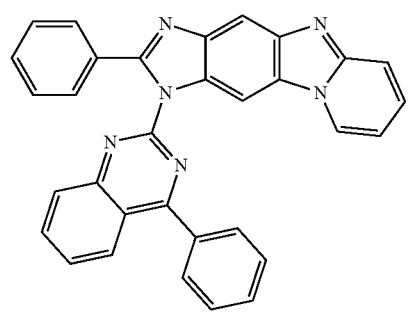 [SMILES: c1ccc(-c2nc(-n3c(-c4ccccc4)nc4cc5nc6ccccn6c5cc43)nc3ccccc23)cc1]
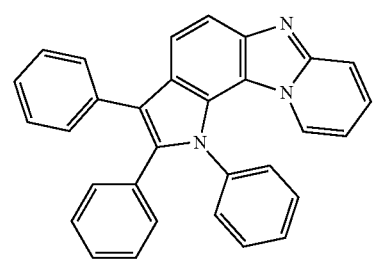 [SMILES: c1ccc(-c2c(-c3ccccc3)n(-c3ccccc3)c3c2ccc2nc4ccccn4c23)cc1]

-continued
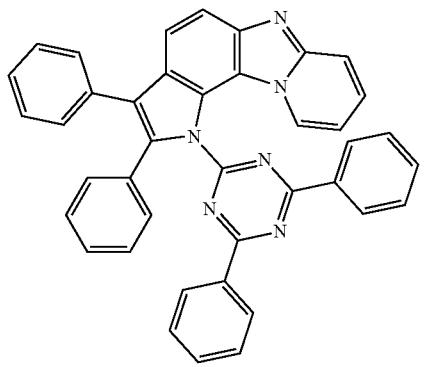 [SMILES: c1ccc(-c2nc(-c3ccccc3)nc(-n3c(-c4ccccc4)c(-c4ccccc4)c4ccc5nc6ccccn6c5c43)n2)cc1]
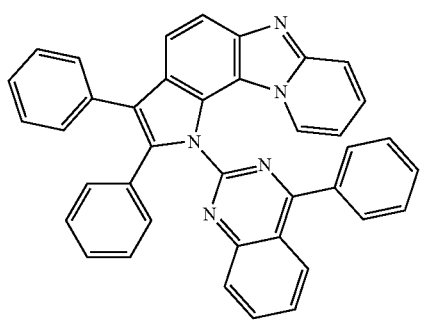 [SMILES: c1ccc(-c2nc(-n3c(-c4ccccc4)c(-c4ccccc4)c4ccc5nc6ccccn6c5c43)nc3ccccc23)cc1]
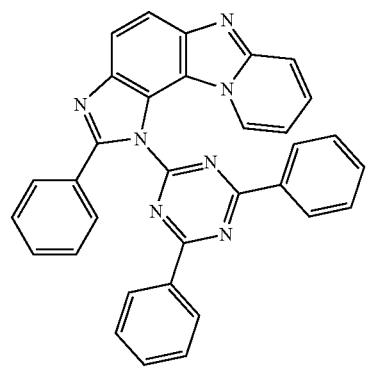 [SMILES: c1ccc(-c2nc(-c3ccccc3)nc(-n3c(-c4ccccc4)nc4ccc5nc6ccccn6c5c43)n2)cc1]
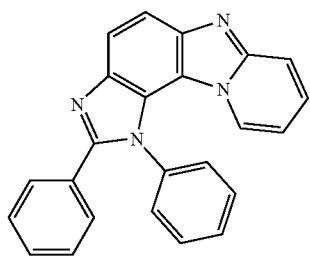 [SMILES: c1ccc(-c2nc3ccc4nc5ccccn5c4c3n2-c2ccccc2)cc1]
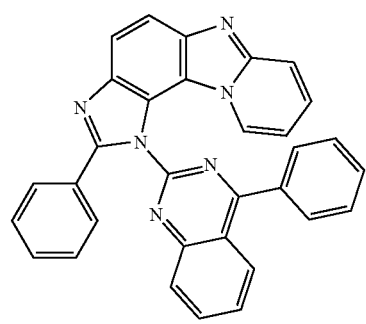 [SMILES: c1ccc(-c2nc(-n3c(-c4ccccc4)nc4ccc5nc6ccccn6c5c43)nc3ccccc23)cc1]

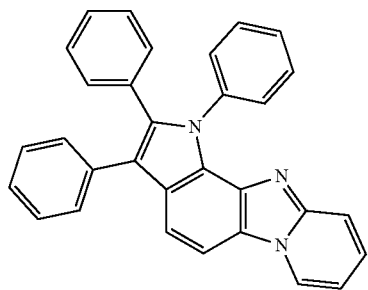 [SMILES: c1ccc(-c2c(-c3ccccc3)n(-c3ccccc3)c3c2ccc2c3nc3ccccn32)cc1]
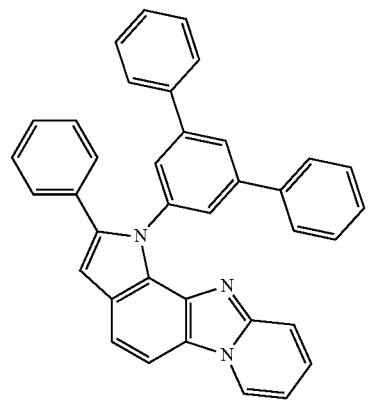 [SMILES: c1ccc(-c2cc(-c3ccccc3)cc(-n3c(-c4ccccc4)cc4ccc5c(nc6ccccn65)c43)c2)cc1]
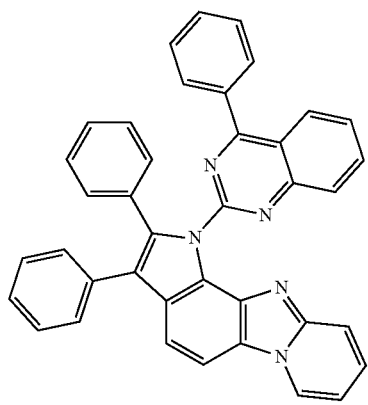 [SMILES: c1ccc(-c2nc(-n3c(-c4ccccc4)c(-c4ccccc4)c4ccc5c(nc6ccccn65)c43)nc3ccccc23)cc1]
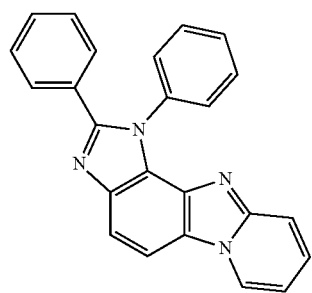 [SMILES: c1ccc(-c2nc3ccc4c(nc5ccccn54)c3n2-c2ccccc2)cc1]

-continued
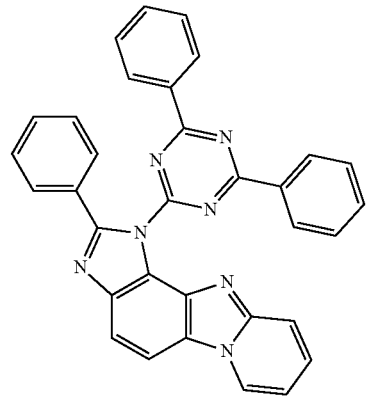 [SMILES: c1ccc(-c2nc(-c3ccccc3)nc(-n3c(-c4ccccc4)nc4ccc5c(nc6ccccn65)c43)n2)cc1]
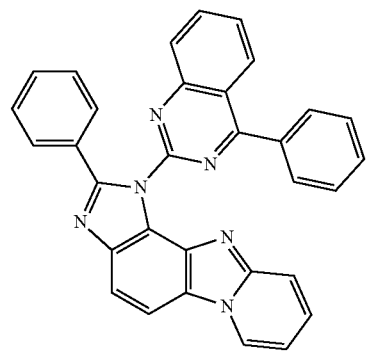 [SMILES: c1ccc(-c2nc(-n3c(-c4ccccc4)nc4ccc5c(nc6ccccn65)c43)nc3ccccc23)cc1]
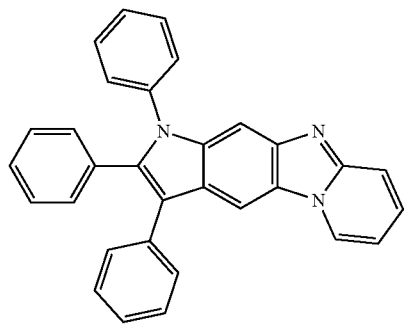 [SMILES: c1ccc(-c2c(-c3ccccc3)n(-c3ccccc3)c3cc4nc5ccccn5c4cc23)cc1]
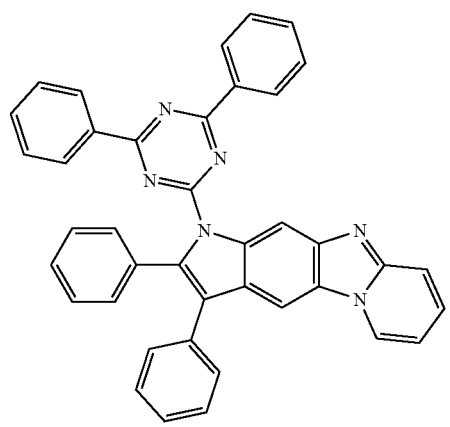 [SMILES: c1ccc(-c2nc(-c3ccccc3)nc(-n3c(-c4ccccc4)c(-c4ccccc4)c4cc5c(cc43)nc3ccccn35)n2)cc1]

-continued
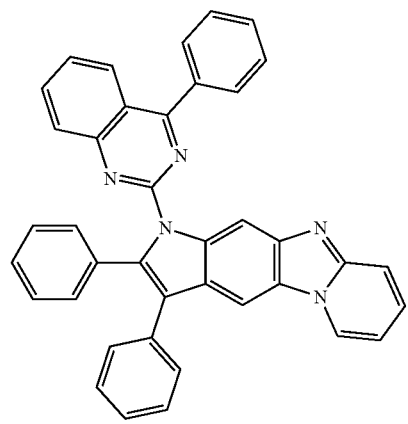 [SMILES: c1ccc(-c2nc(-n3c(-c4ccccc4)c(-c4ccccc4)c4cc5c(cc43)nc3ccccn35)nc3ccccc23)cc1]
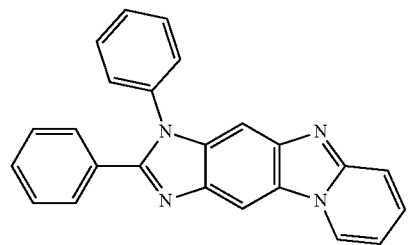 [SMILES: c1ccc(-c2nc3cc4c(cc3n2-c2ccccc2)nc2ccccn24)cc1]
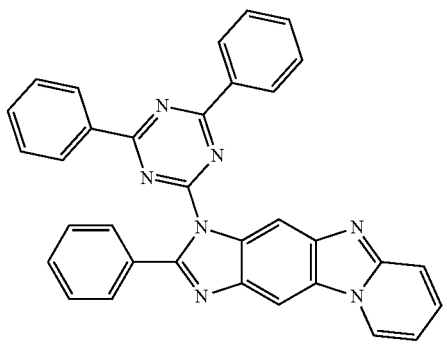 [SMILES: c1ccc(-c2nc(-c3ccccc3)nc(-n3c(-c4ccccc4)nc4cc5c(cc43)nc3ccccn35)n2)cc1]
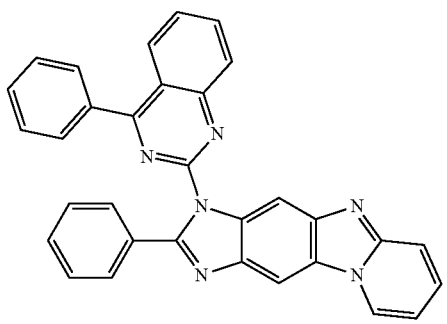 [SMILES: c1ccc(-c2nc(-n3c(-c4ccccc4)nc4cc5c(cc43)nc3ccccn35)nc3ccccc23)cc1]
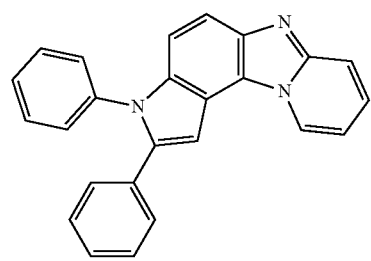 [SMILES: c1ccc(-c2cc3c(ccc4nc5ccccn5c43)n2-c2ccccc2)cc1]

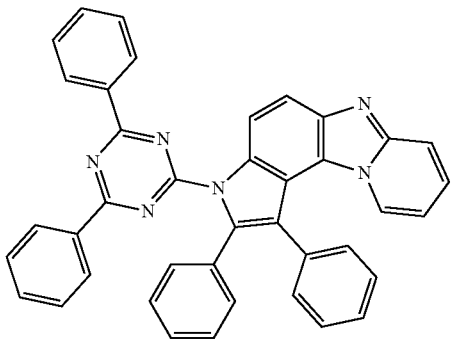 [SMILES: c1ccc(-c2nc(-c3ccccc3)nc(-n3c(-c4ccccc4)c(-c4ccccc4)c4c3ccc3nc5ccccn5c34)n2)cc1]
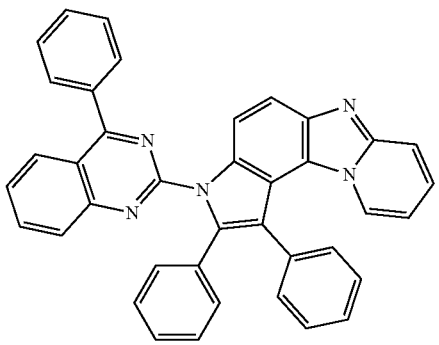 [SMILES: c1ccc(-c2nc(-n3c(-c4ccccc4)c(-c4ccccc4)c4c3ccc3nc5ccccn5c34)nc3ccccc23)cc1]
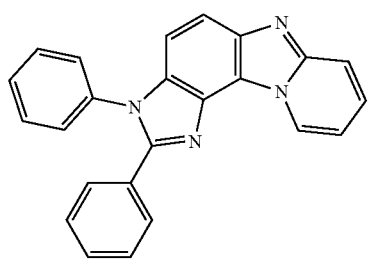 [SMILES: c1ccc(-c2nc3c(ccc4nc5ccccn5c43)n2-c2ccccc2)cc1]
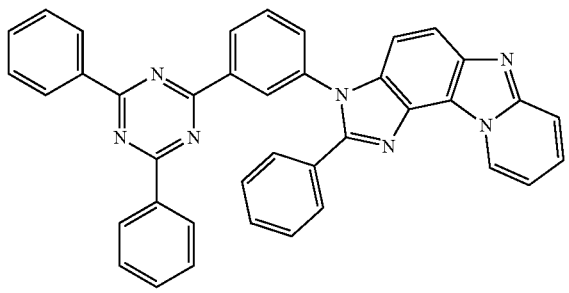 [SMILES: c1ccc(-c2nc(-c3ccccc3)nc(-c3cccc(-n4c(-c5ccccc5)nc5c4ccc4nc6ccccn6c45)c3)n2)cc1]
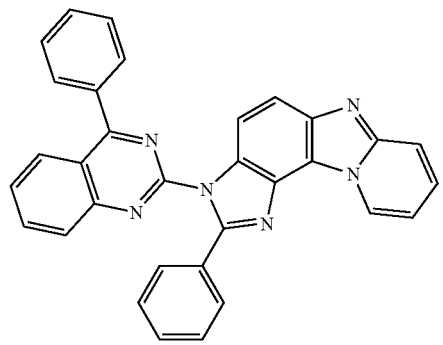 [SMILES: c1ccc(-c2nc(-n3c(-c4ccccc4)nc4c3ccc3nc5ccccn5c34)nc3ccccc23)cc1]

-continued
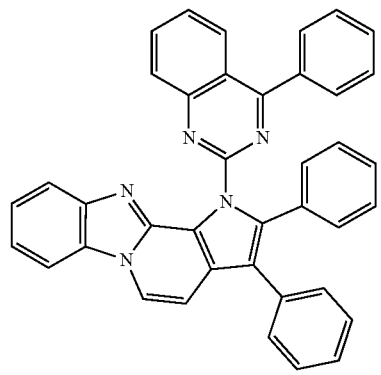 [SMILES: c1ccc(-c2nc(-n3c(-c4ccccc4)c(-c4ccccc4)c4ccn5c6ccccc6nc5c43)nc3ccccc23)cc1]
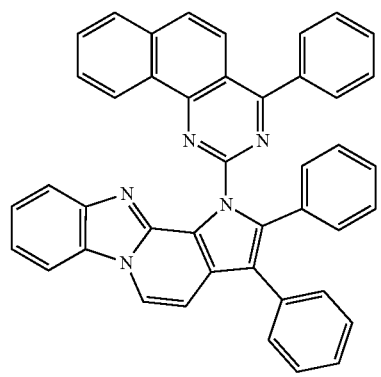 [SMILES: c1ccc(-c2nc(-n3c(-c4ccccc4)c(-c4ccccc4)c4ccn5c6ccccc6nc5c43)nc3c2ccc2ccccc23)cc1]
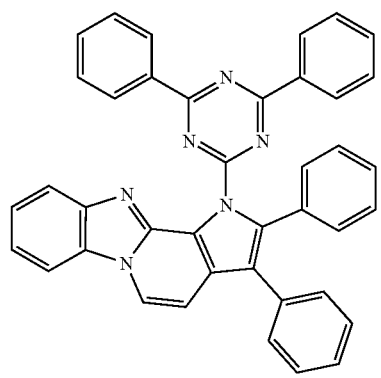 [SMILES: c1ccc(-c2nc(-c3ccccc3)nc(-n3c(-c4ccccc4)c(-c4ccccc4)c4ccn5c6ccccc6nc5c43)n2)cc1]
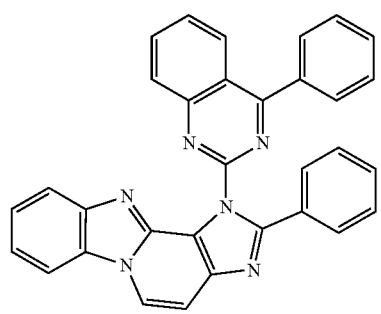 [SMILES: c1ccc(-c2nc(-n3c(-c4ccccc4)nc4ccn5c6ccccc6nc5c43)nc3ccccc23)cc1]

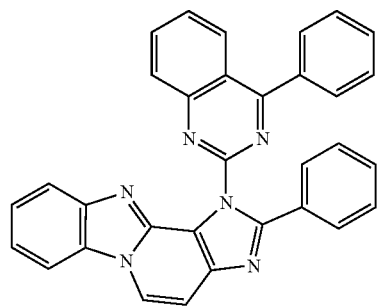 [SMILES: c1ccc(-c2nc(-n3c(-c4ccccc4)nc4ccn5c6ccccc6nc5c43)nc3ccccc23)cc1]
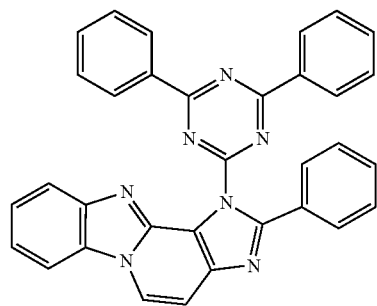 [SMILES: c1ccc(-c2nc(-c3ccccc3)nc(-n3c(-c4ccccc4)nc4ccn5c6ccccc6nc5c43)n2)cc1]
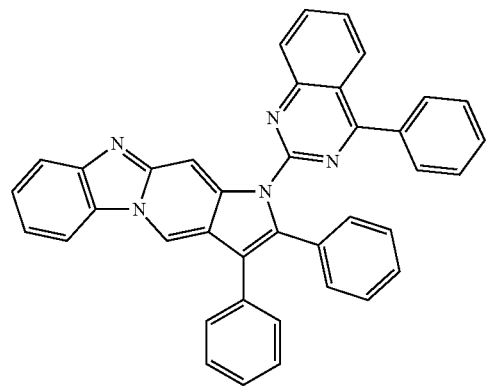 [SMILES: c1ccc(-c2nc(-n3c(-c4ccccc4)c(-c4ccccc4)c4cn5c(cc43)nc3ccccc35)nc3ccccc23)cc1]
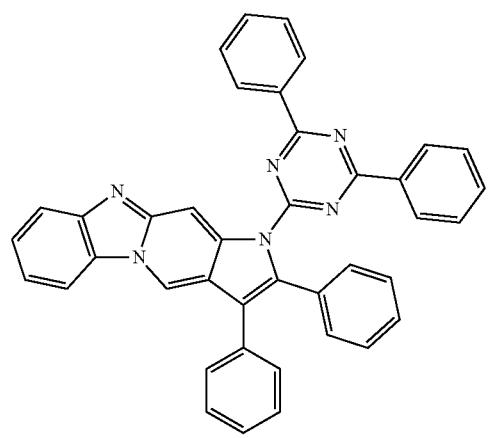 [SMILES: c1ccc(-c2nc(-c3ccccc3)nc(-n3c(-c4ccccc4)c(-c4ccccc4)c4cn5c(cc43)nc3ccccc35)n2)cc1]

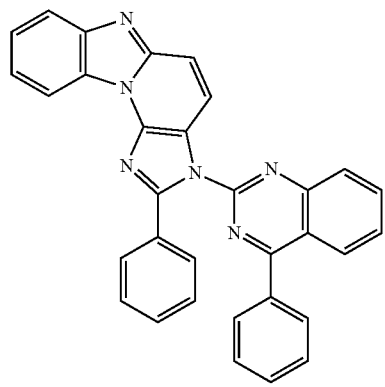 [SMILES: c1ccc(-c2nc(-n3c(-c4ccccc4)nc4c3ccc3nc5ccccc5n34)nc3ccccc23)cc1]
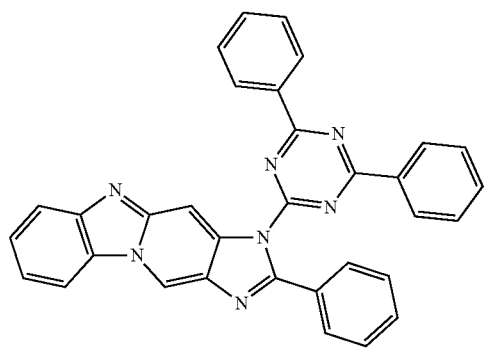 [SMILES: c1ccc(-c2nc(-c3ccccc3)nc(-n3c(-c4ccccc4)nc4cn5c(cc43)nc3ccccc35)n2)cc1]
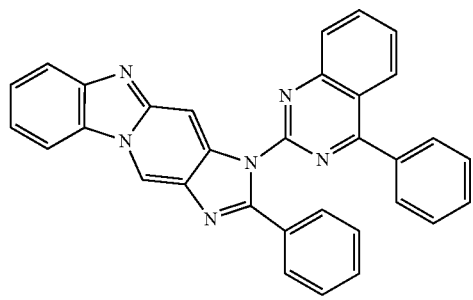 [SMILES: c1ccc(-c2nc(-n3c(-c4ccccc4)nc4cn5c(cc43)nc3ccccc35)nc3ccccc23)cc1]
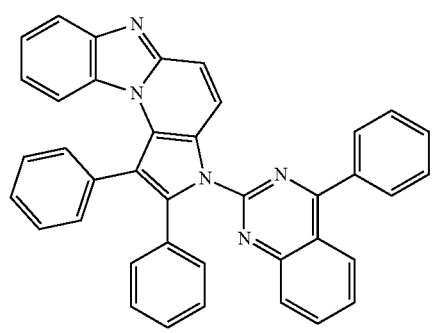 [SMILES: c1ccc(-c2nc(-n3c(-c4ccccc4)c(-c4ccccc4)c4c3ccc3nc5ccccc5n34)nc3ccccc23)cc1]

-continued
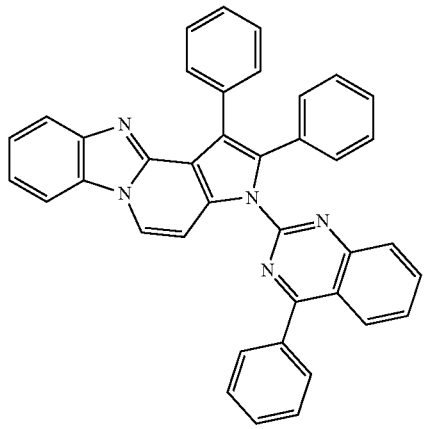 [SMILES: c1ccc(-c2nc(-n3c(-c4ccccc4)c(-c4ccccc4)c4c3ccn3c5ccccc5nc43)nc3ccccc23)cc1]
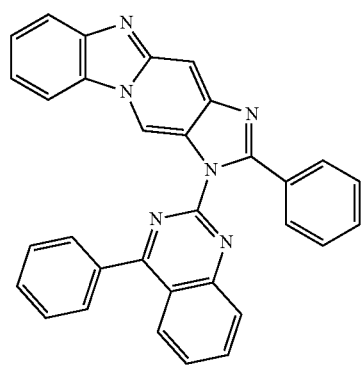 [SMILES: c1ccc(-c2nc(-n3c(-c4ccccc4)nc4cc5nc6ccccc6n5cc43)nc3ccccc23)cc1]
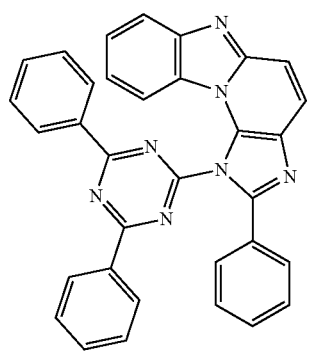 [SMILES: c1ccc(-c2nc(-c3ccccc3)nc(-n3c(-c4ccccc4)nc4ccc5nc6ccccc6n5c43)n2)cc1]
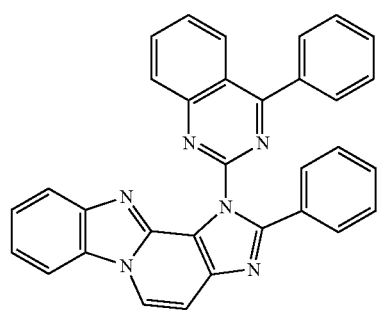 [SMILES: c1ccc(-c2nc(-n3c(-c4ccccc4)nc4ccn5c6ccccc6nc5c43)nc3ccccc23)cc1]

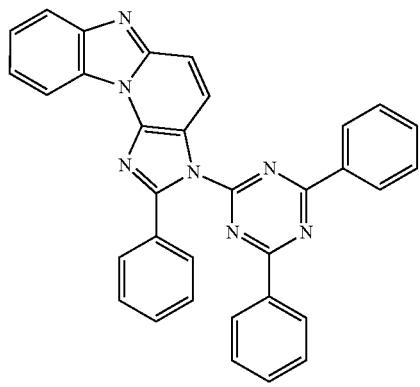 [SMILES: c1ccc(-c2nc(-c3ccccc3)nc(-n3c(-c4ccccc4)nc4c3ccc3nc5ccccc5n34)n2)cc1]
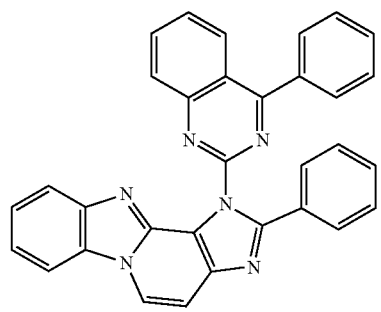 [SMILES: c1ccc(-c2nc(-n3c(-c4ccccc4)nc4ccn5c6ccccc6nc5c43)nc3ccccc23)cc1]
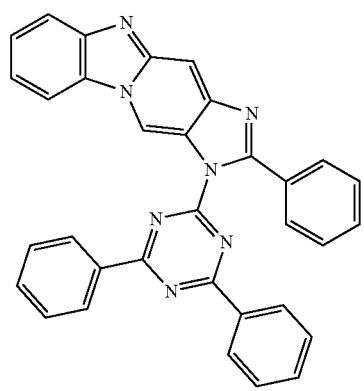 [SMILES: c1ccc(-c2nc(-c3ccccc3)nc(-n3c(-c4ccccc4)nc4cc5nc6ccccc6n5cc43)n2)cc1]
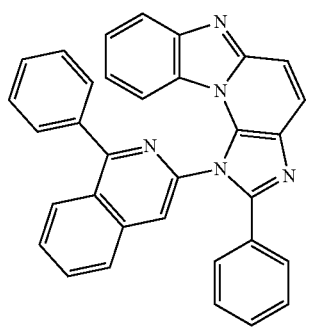 [SMILES: c1ccc(-c2nc(-n3c(-c4ccccc4)nc4ccc5nc6ccccc6n5c43)cc3ccccc23)cc1]

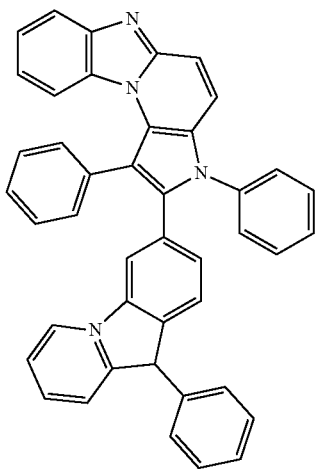
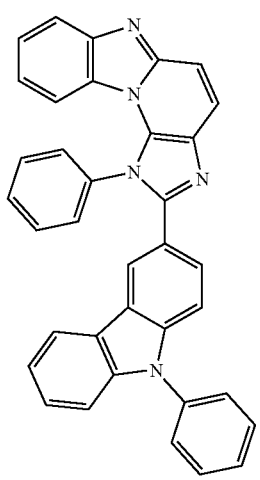 [SMILES: c1ccc(-n2c(-c3ccc4c(c3)c3ccccc3n4-c3ccccc3)nc3ccc4nc5ccccc5n4c32)cc1]
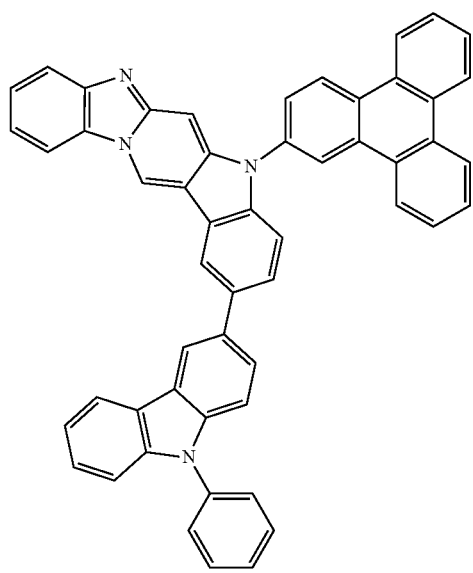 [SMILES: c1ccc(-n2c3ccccc3c3cc(-c4ccc5c(c4)c4cn6c(cc4n5-c4ccc5c7ccccc7c7ccccc7c5c4)nc4ccccc46)ccc32)cc1]

-continued
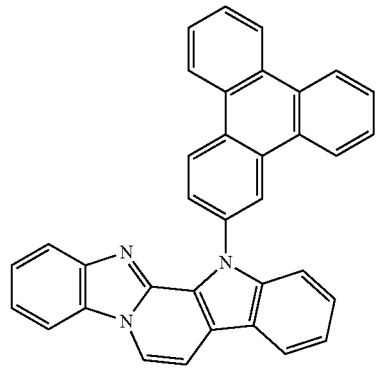 [SMILES: c1ccc2c(c1)nc1c3c(ccn21)c1ccccc1n3-c1ccc2c3ccccc3c3ccccc3c2c1]
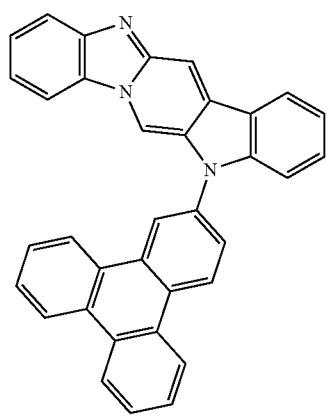 [SMILES: c1ccc2c(c1)nc1cc3c4ccccc4n(-c4ccc5c6ccccc6c6ccccc6c5c4)c3cn12]
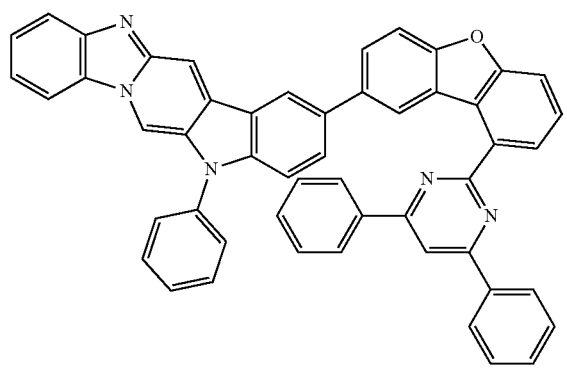 [SMILES: c1ccc(-c2cc(-c3ccccc3)nc(-c3cccc4oc5ccc(-c6ccc7c(c6)c6cc8nc9ccccc9n8cc6n7-c6ccccc6)cc5c34)n2)cc1]
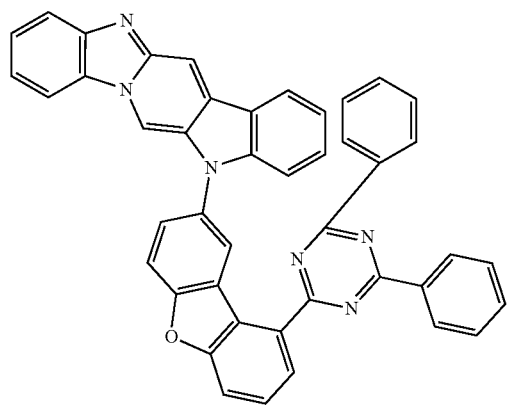 [SMILES: c1ccc(-c2nc(-c3ccccc3)nc(-c3cccc4oc5ccc(-n6c7ccccc7c7cc8nc9ccccc9n8cc76)cc5c34)n2)cc1]

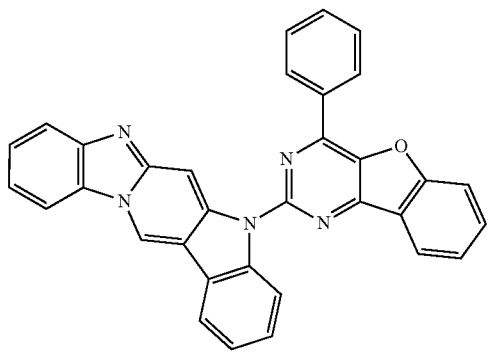 [SMILES: c1ccc(-c2nc(-n3c4ccccc4c4cn5c(cc43)nc3ccccc35)nc3c2oc2ccccc23)cc1]
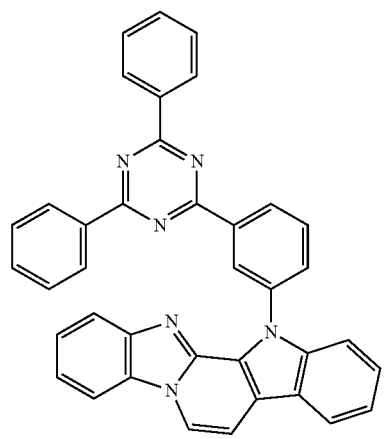 [SMILES: c1ccc(-c2nc(-c3ccccc3)nc(-c3cccc(-n4c5ccccc5c5ccn6c7ccccc7nc6c54)c3)n2)cc1]
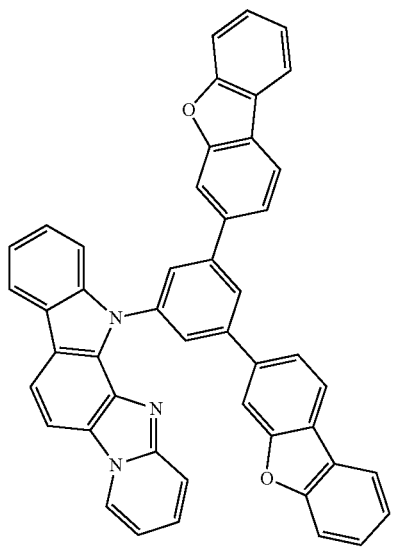 [SMILES: c1ccc2c(c1)oc1cc(-c3cc(-c4ccc5c(c4)oc4ccccc45)cc(-n4c5ccccc5c5ccc6c(nc7ccccn76)c54)c3)ccc12]

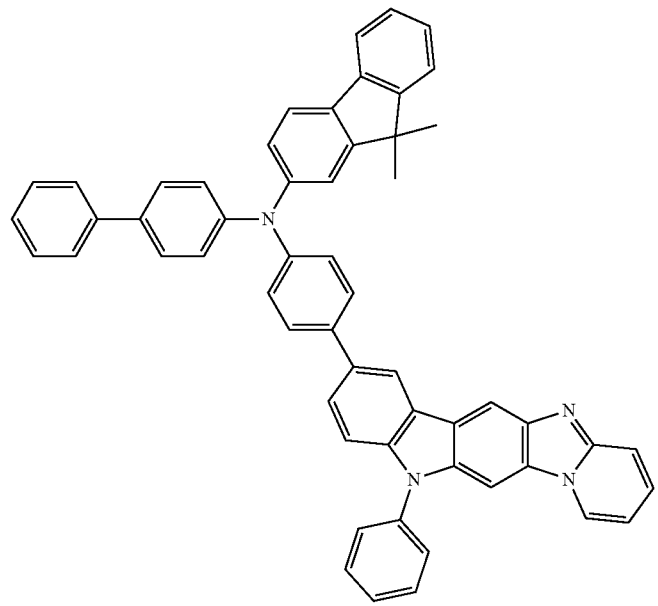 [SMILES: CC1(C)c2ccccc2-c2ccc(N(c3ccc(-c4ccccc4)cc3)c3ccc(-c4ccc5c(c4)c4cc6nc7ccccn7c6cc4n5-c4ccccc4)cc3)cc21]
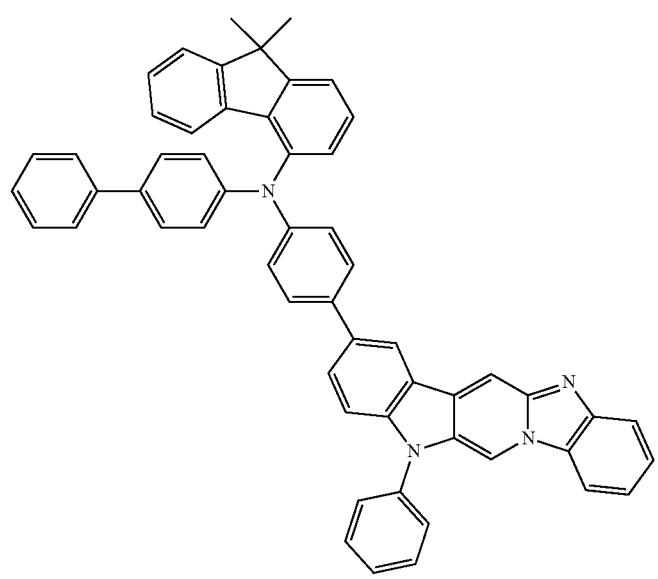 [SMILES: CC1(C)c2ccccc2-c2c(N(c3ccc(-c4ccccc4)cc3)c3ccc(-c4ccc5c(c4)c4cc6nc7ccccc7n6cc4n5-c4ccccc4)cc3)cccc21]
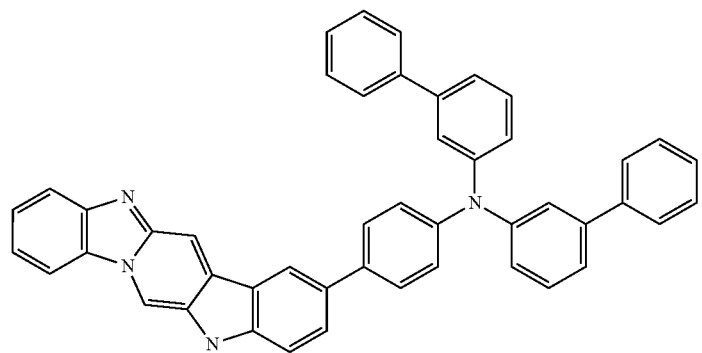 [SMILES: c1ccc(-c2cccc(N(c3ccc(-c4ccc5[nH]c6cn7c(cc6c5c4)nc4ccccc47)cc3)c3cccc(-c4ccccc4)c3)c2)cc1]

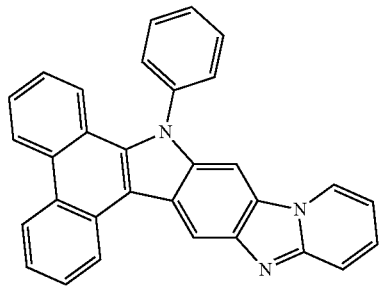 [SMILES: c1ccc(-n2c3cc4c(cc3c3c5ccccc5c5ccccc5c32)nc2ccccn24)cc1]
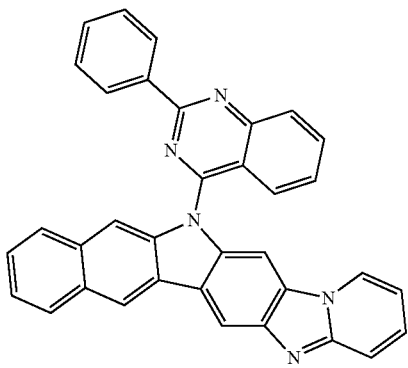 [SMILES: c1ccc(-c2nc(-n3c4cc5ccccc5cc4c4cc5nc6ccccn6c5cc43)c3ccccc3n2)cc1]
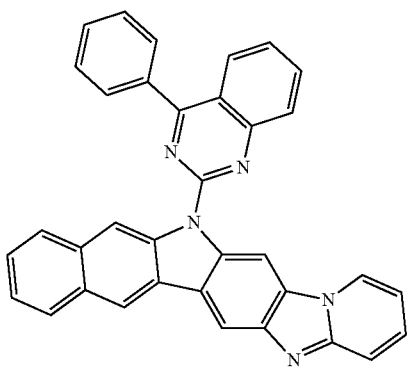 [SMILES: c1ccc(-c2nc(-n3c4cc5ccccc5cc4c4cc5nc6ccccn6c5cc43)nc3ccccc23)cc1]
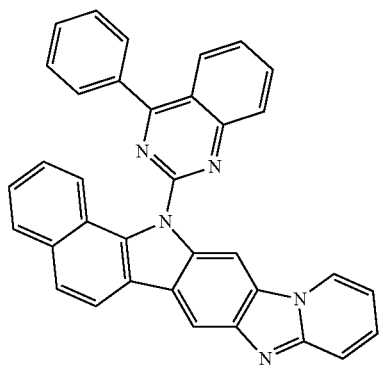 [SMILES: c1ccc(-c2nc(-n3c4cc5c(cc4c4ccc6ccccc6c43)nc3ccccn35)nc3ccccc23)cc1]

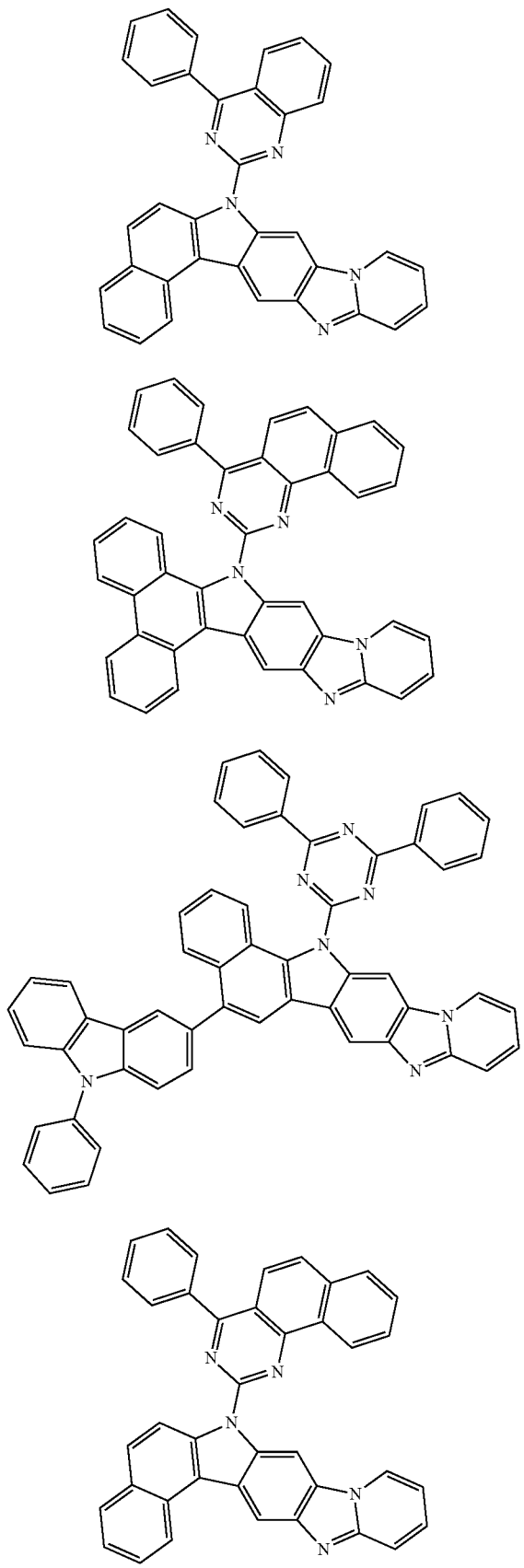

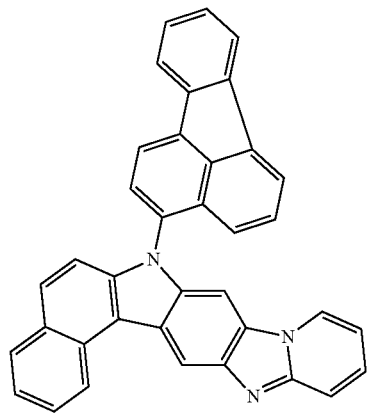 [SMILES: c1ccc2c(c1)-c1cccc3c(-n4c5cc6c(cc5c5c7ccccc7ccc54)nc4ccccn46)ccc-2c13]
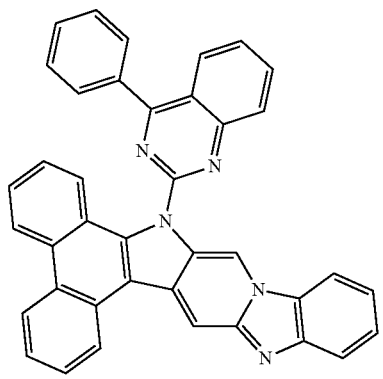 [SMILES: c1ccc(-c2nc(-n3c4cn5c(cc4c4c6ccccc6c6ccccc6c43)nc3ccccc35)nc3ccccc23)cc1]
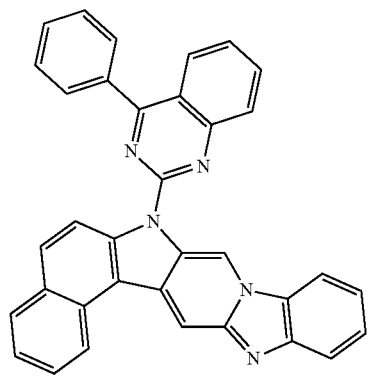 [SMILES: c1ccc(-c2nc(-n3c4cn5c(cc4c4c6ccccc6ccc43)nc3ccccc35)nc3ccccc23)cc1]
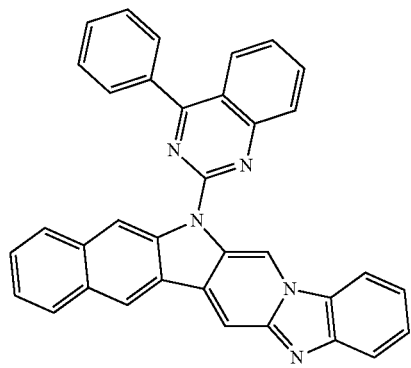 [SMILES: c1ccc(-c2nc(-n3c4cc5ccccc5cc4c4cc5nc6ccccc6n5cc43)nc3ccccc23)cc1]

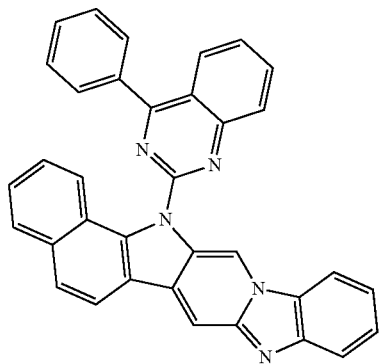 [SMILES: c1ccc(-c2nc(-n3c4cn5c(cc4c4ccc6ccccc6c43)nc3ccccc35)nc3ccccc23)cc1]
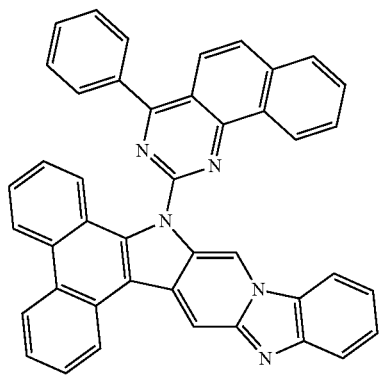 [SMILES: c1ccc(-c2nc(-n3c4cn5c(cc4c4c6ccccc6c6ccccc6c43)nc3ccccc35)nc3c2ccc2ccccc23)cc1]
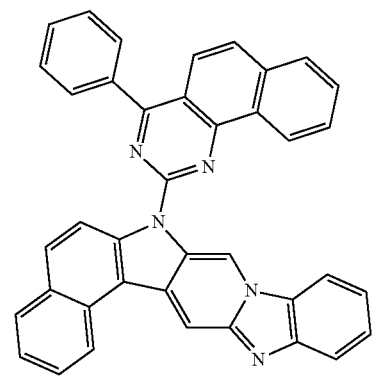 [SMILES: c1ccc(-c2nc(-n3c4cn5c(cc4c4c6ccccc6ccc43)nc3ccccc35)nc3c2ccc2ccccc23)cc1]
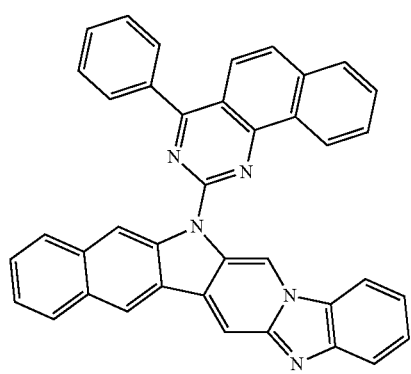 [SMILES: c1ccc(-c2nc(-n3c4cc5ccccc5cc4c4cc5nc6ccccc6n5cc43)nc3c2ccc2ccccc23)cc1]

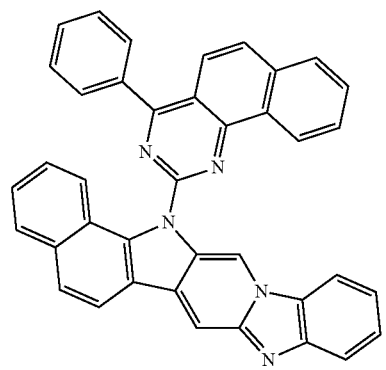 [SMILES: c1ccc(-c2nc(-n3c4cn5c(cc4c4ccc6ccccc6c43)nc3ccccc35)nc3c2ccc2ccccc23)cc1]
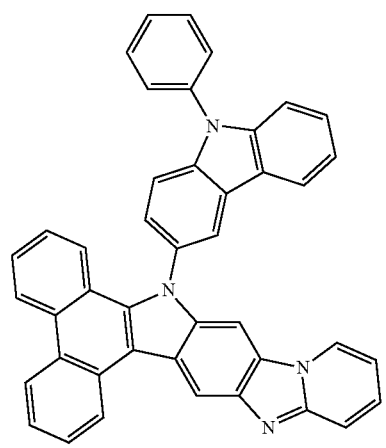 [SMILES: c1ccc(-n2c3ccccc3c3cc(-n4c5cc6c(cc5c5c7ccccc7c7ccccc7c54)nc4ccccn46)ccc32)cc1]
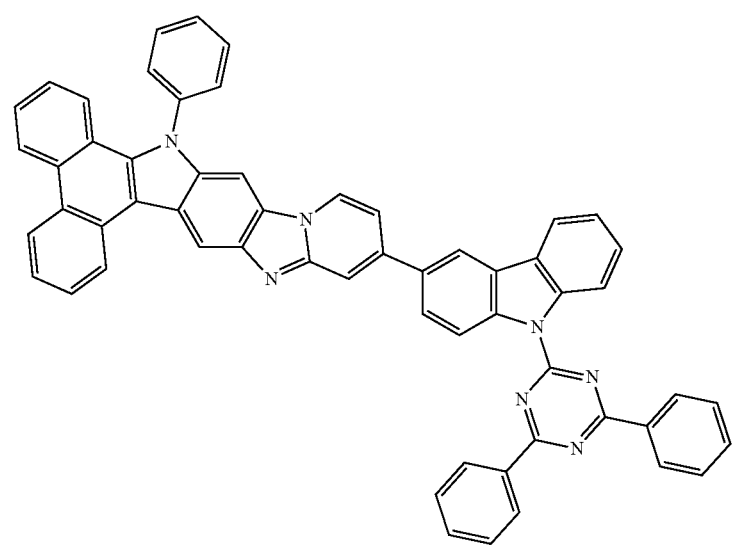 [SMILES: c1ccc(-c2nc(-c3ccccc3)nc(-n3c4ccccc4c4cc(-c5ccn6c(c5)nc5cc7c8c9ccccc9c9ccccc9c8n(-c8ccccc8)c7cc56)ccc43)n2)cc1]

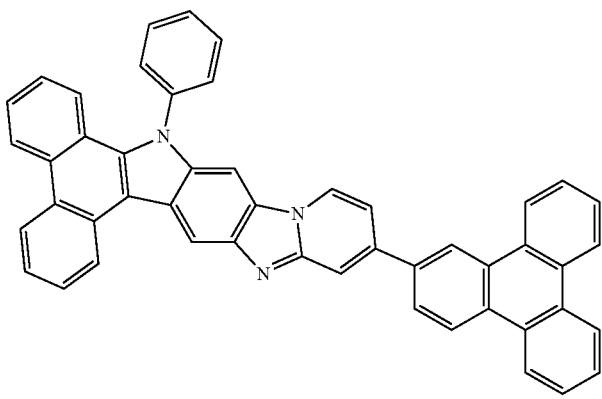 [SMILES: c1ccc(-n2c3cc4c(cc3c3c5ccccc5c5ccccc5c32)nc2cc(-c3ccc5c6ccccc6c6ccccc6c5c3)ccn24)cc1]
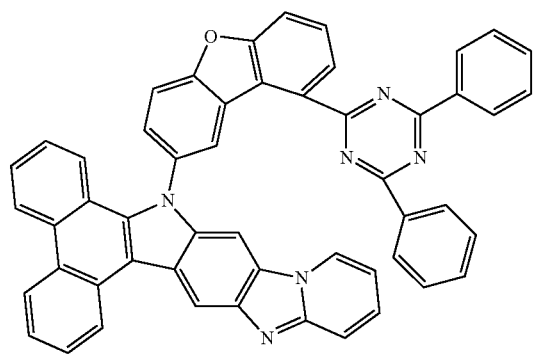 [SMILES: c1ccc(-c2nc(-c3ccccc3)nc(-c3cccc4oc5ccc(-n6c7cc8c(cc7c7c9ccccc9c9ccccc9c76)nc6ccccn68)cc5c34)n2)cc1]
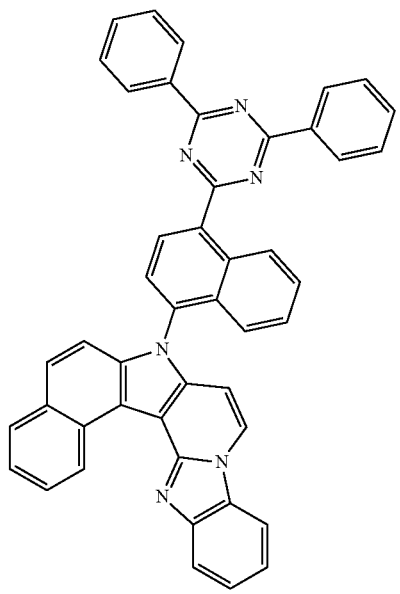 [SMILES: c1ccc(-c2nc(-c3ccccc3)nc(-c3ccc(-n4c5ccc6ccccc6c5c5c4ccn4c6ccccc6nc54)c4ccccc34)n2)cc1]

-continued
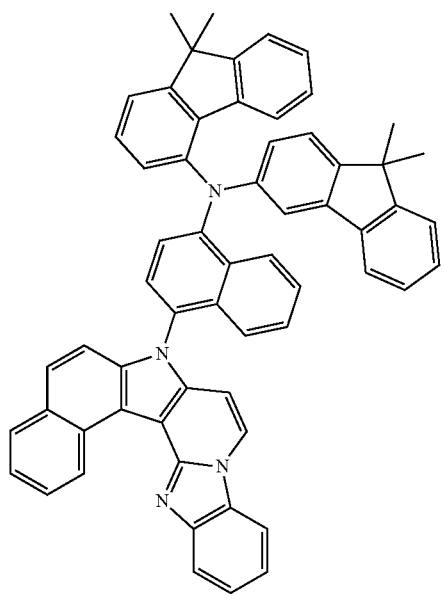 [SMILES: CC1(C)c2ccccc2-c2cc(N(c3cccc4c3-c3ccccc3C4(C)C)c3ccc(-n4c5ccc6ccccc6c5c5c4ccn4c6ccccc6nc54)c4ccccc34)ccc21]
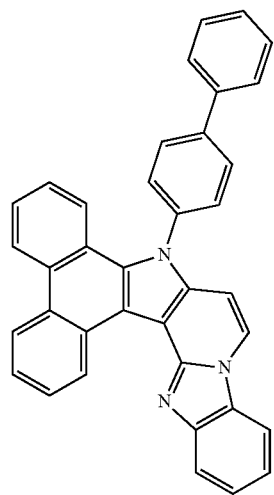 [SMILES: c1ccc(-c2ccc(-n3c4ccn5c6ccccc6nc5c4c4c5ccccc5c5ccccc5c43)cc2)cc1]
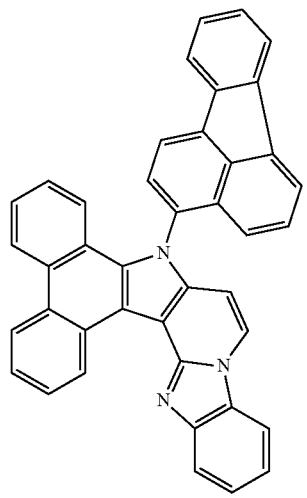 [SMILES: c1ccc2c(c1)-c1cccc3c(-n4c5ccn6c7ccccc7nc6c5c5c6ccccc6c6ccccc6c54)ccc-2c13]

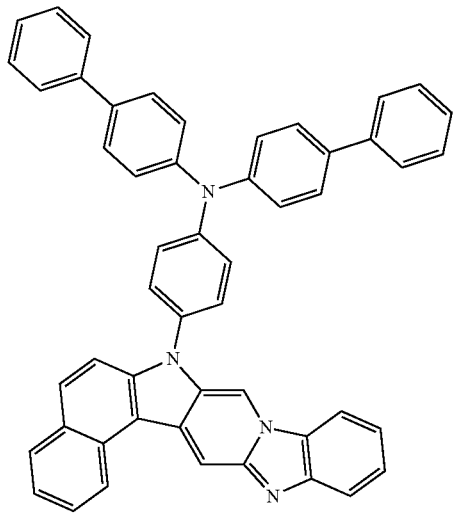 [SMILES: c1ccc(-c2ccc(N(c3ccc(-c4ccccc4)cc3)c3ccc(-n4c5cn6c(cc5c5c7ccccc7ccc54)nc4ccccc46)cc3)cc2)cc1]
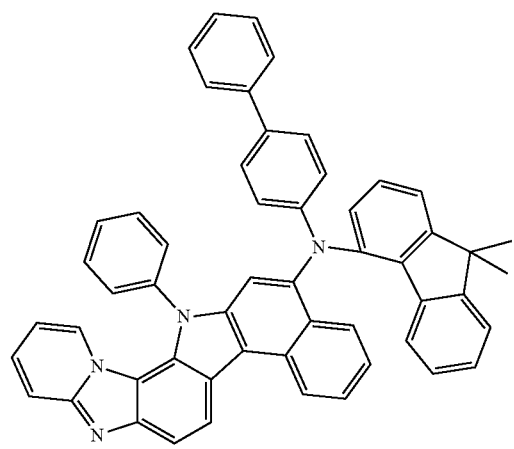 [SMILES: CC1(C)c2ccccc2-c2c(N(c3ccc(-c4ccccc4)cc3)c3cc4c(c5ccccc35)c3ccc5nc6ccccn6c5c3n4-c3ccccc3)cccc21]
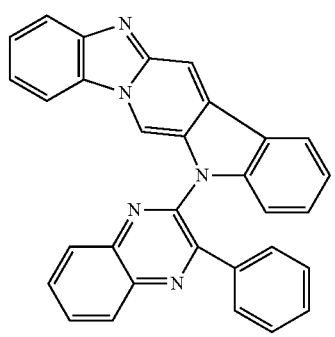 [SMILES: c1ccc(-c2nc3ccccc3nc2-n2c3ccccc3c3cc4nc5ccccc5n4cc32)cc1]
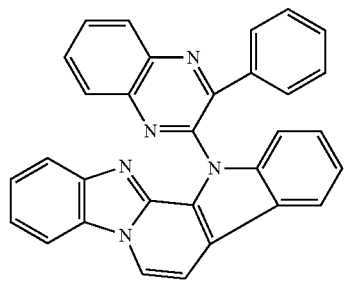 [SMILES: c1ccc(-c2nc3ccccc3nc2-n2c3ccccc3c3ccn4c5ccccc5nc4c32)cc1]

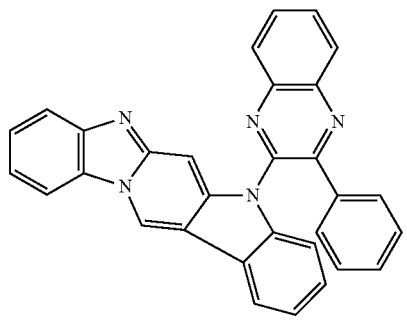 [SMILES: c1ccc(-c2nc3ccccc3nc2-n2c3ccccc3c3cn4c(cc32)nc2ccccc24)cc1]
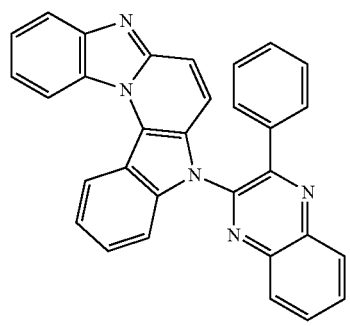 [SMILES: c1ccc(-c2nc3ccccc3nc2-n2c3ccccc3c3c2ccc2nc4ccccc4n23)cc1]
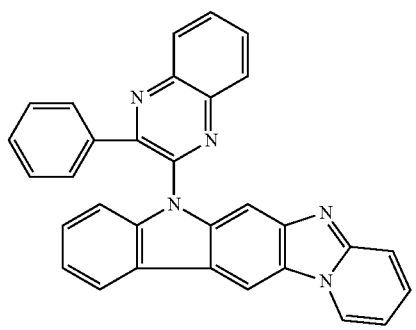 [SMILES: c1ccc(-c2nc3ccccc3nc2-n2c3ccccc3c3cc4c(cc32)nc2ccccn24)cc1]
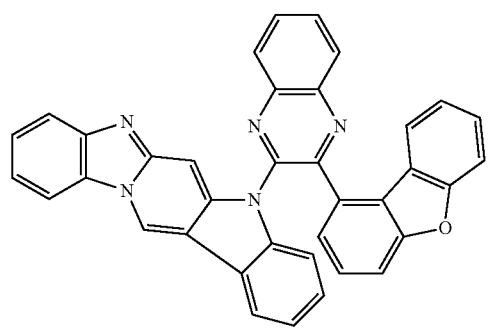 [SMILES: c1ccc2nc(-n3c4ccccc4c4cn5c(cc43)nc3ccccc35)c(-c3cccc4oc5ccccc5c34)nc2c1]

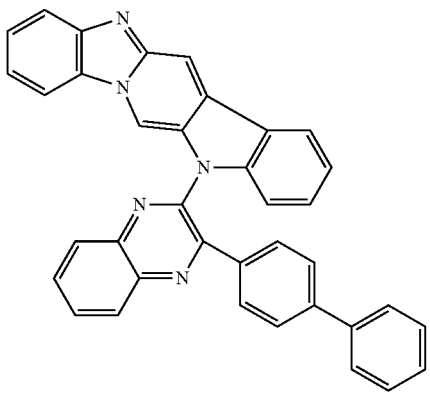 [SMILES: c1ccc(-c2ccc(-c3nc4ccccc4nc3-n3c4ccccc4c4cc5nc6ccccc6n5cc43)cc2)cc1]

The base structure of the compounds of the invention can be prepared by the route outlined in schemes 1 to 3. Scheme 1 shows the reaction of the pyridobenzimidazoles known from the literature with 2-chloroaniline in a palladium-catalyzed amination. Scheme 2 shows the CH-activating cyclization of these products to give the corresponding indolopyridobenzimidazole base structures. The functionalized base structures may subsequently be obtained by means of a further palladium-catalyzed amination (scheme 3), for example Buchwald or Ullmann coupling, with a suitable aryl halide. These structures may also be further halogenated, especially in the para position to the nitrogen on the indole ring, and converted to further derivatives, for example by a Buchwald coupling or a Suzuki coupling.

Scheme 1

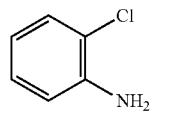

+

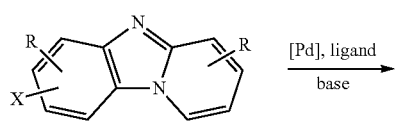

or

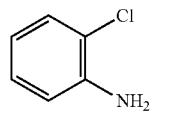

+

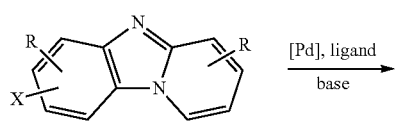

Scheme 2

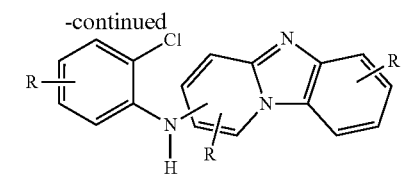

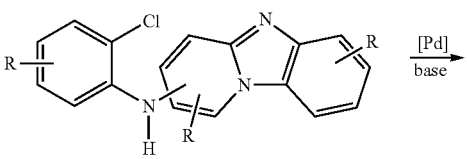

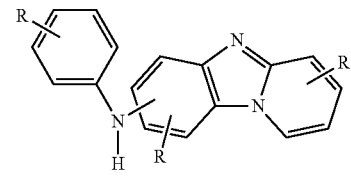

isomer mixture or

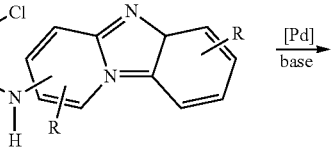

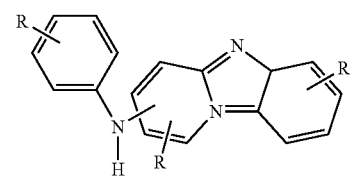

isomer mixture

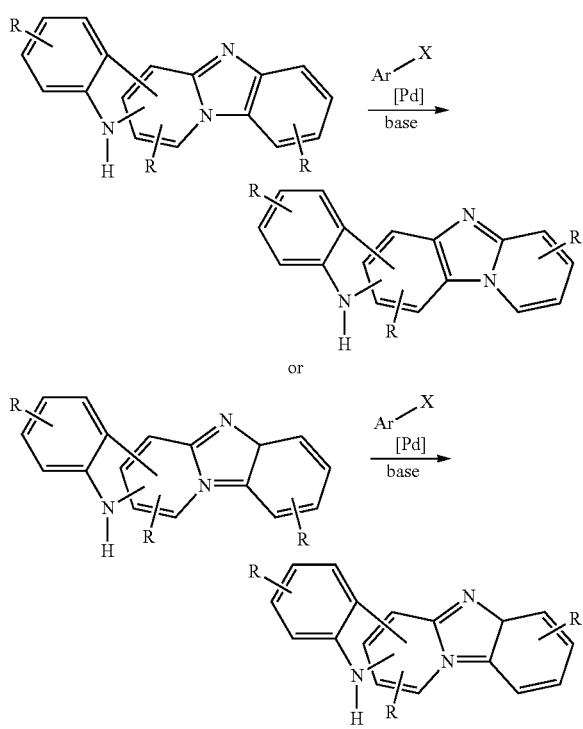

or

The present invention therefore further provides a process for preparing the compounds of the invention, wherein the base skeleton that still does not contain an Ar group is first synthesized and, in a next step, the Ar group is introduced, for example by a C—N coupling reaction.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2006/130598, WO 2009/021126, WO 2009/124627 and WO 2010/006680.

In a preferred embodiment of the invention, the materials are used in combination with a further matrix material. Preferred co-matrix materials are selected from the group of the biscarbazoles, the bridged carbazoles, the triarylamines, the dibenzofuran-carbazole derivatives or dibenzofuranamine derivatives, and the carbazoleamines.

Preferred biscarbazoles are the structures of the following formulae (16) and (17):

Formula (16)

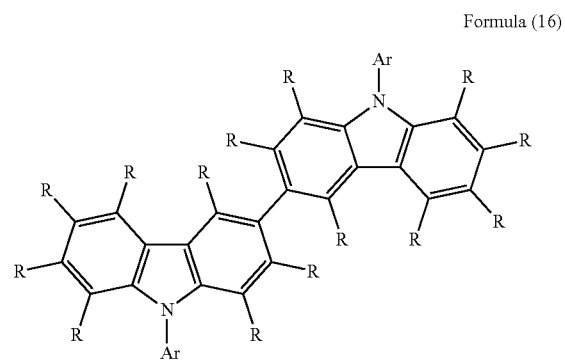

Formula (17)

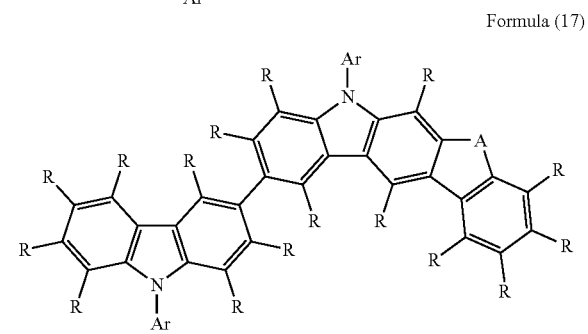

where Ar and A have the definitions given above and R has the definitions given above, but R radicals here may also together form an aromatic or heteroaromatic ring system. In a preferred embodiment of the invention, A is $CR_2$.

Preferred embodiments of the compounds of the formulae (16) and (17) are the compounds of the following formulae (16a) and (17a):

Formula (16a)

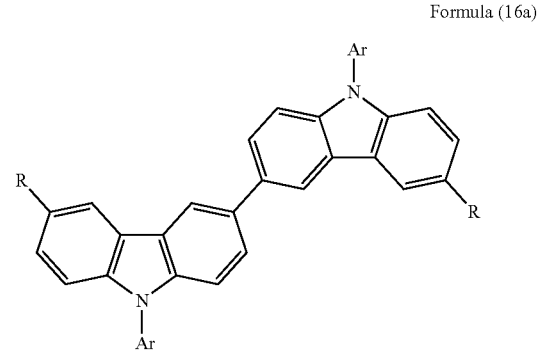

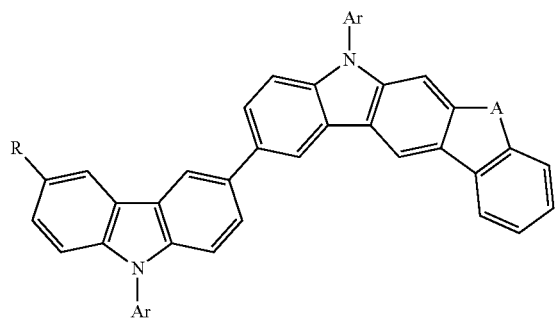
Formula (17a)
where the symbols used have the definitions given above.
Examples of suitable compounds of formulae (16) and (17) are the compounds depicted below:
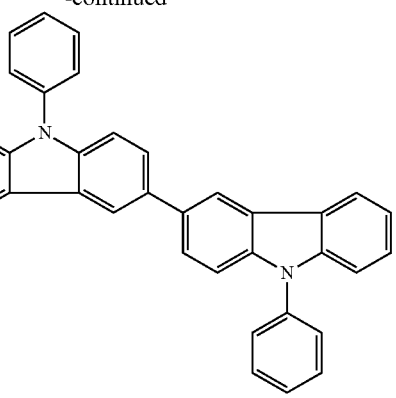
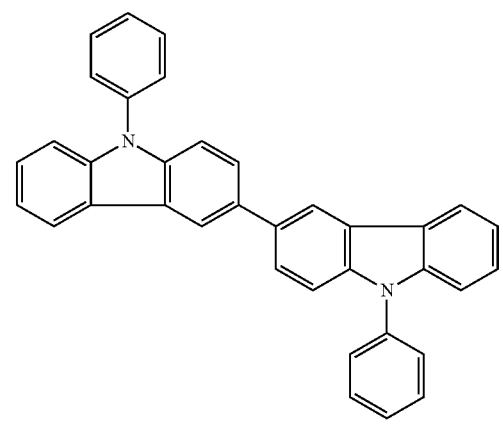
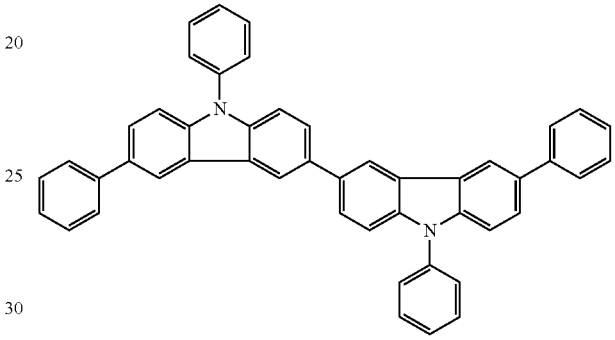
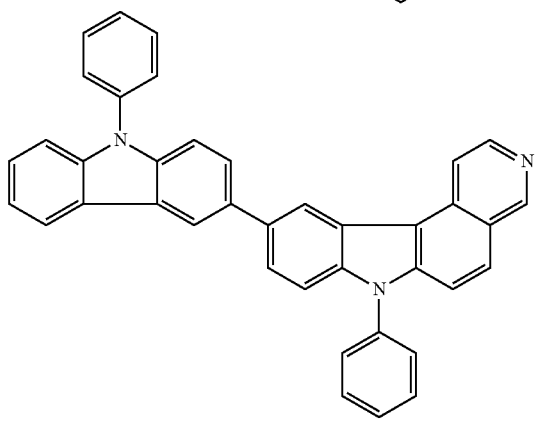
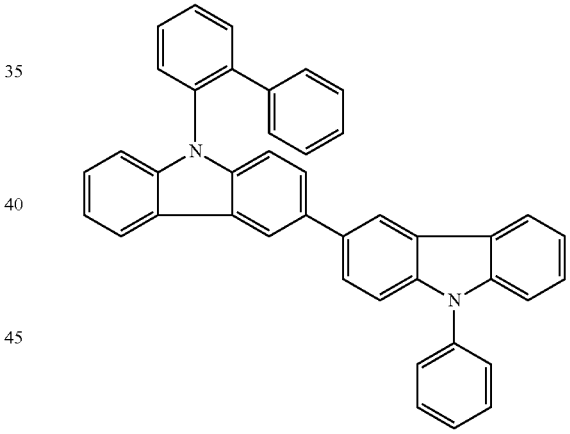
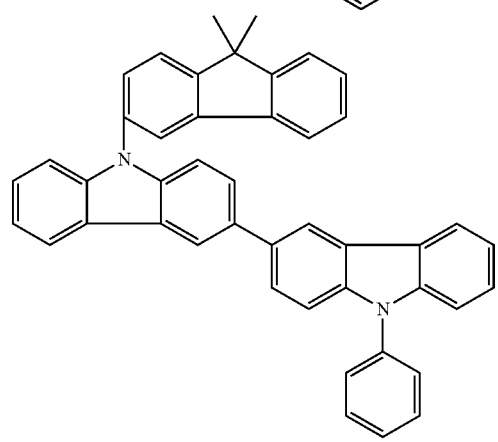
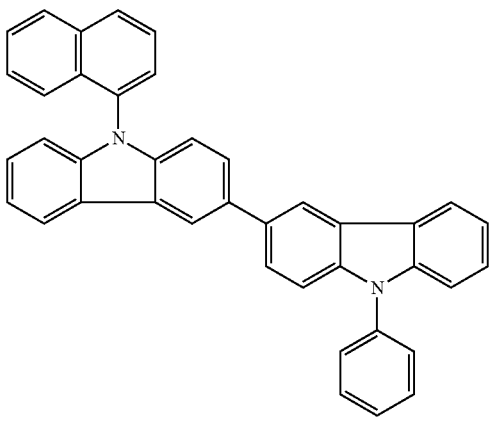

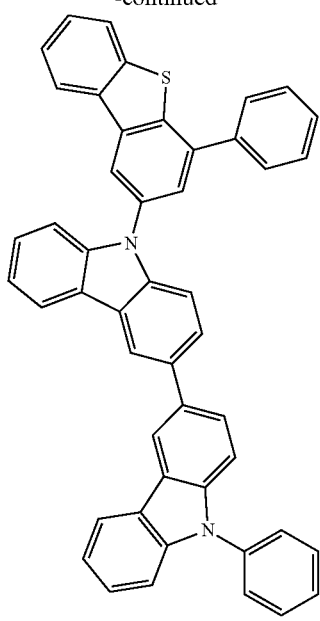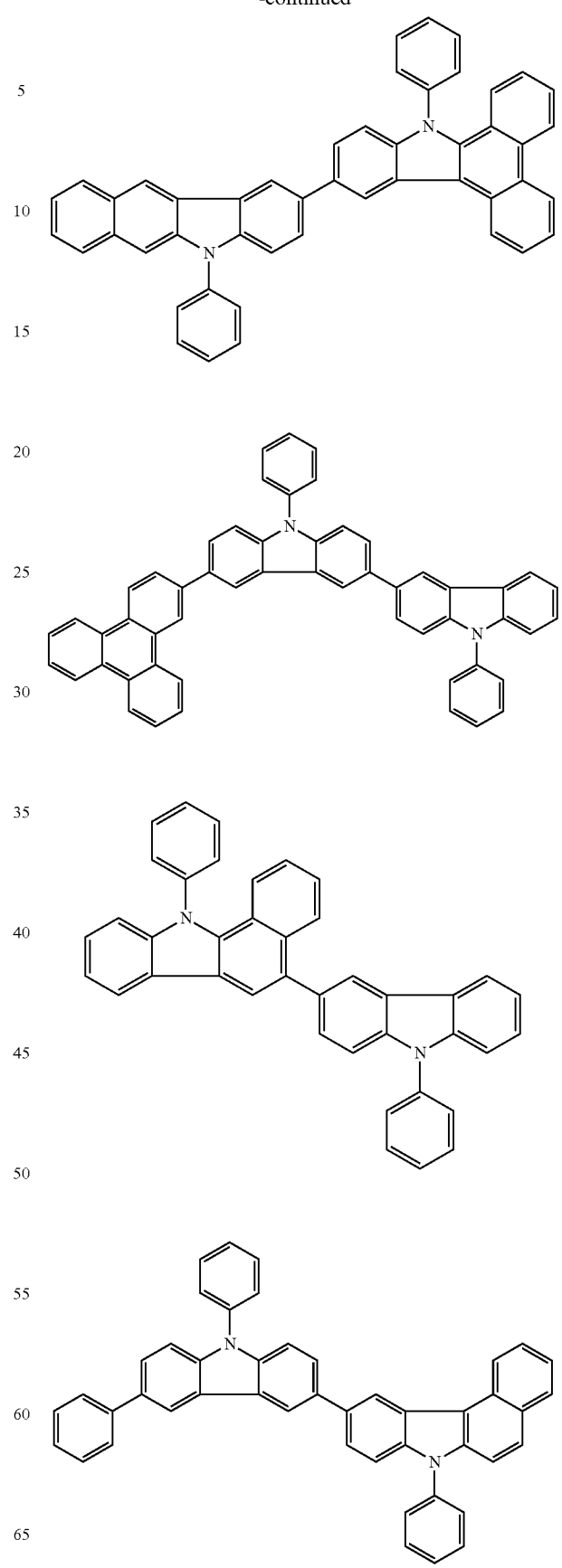

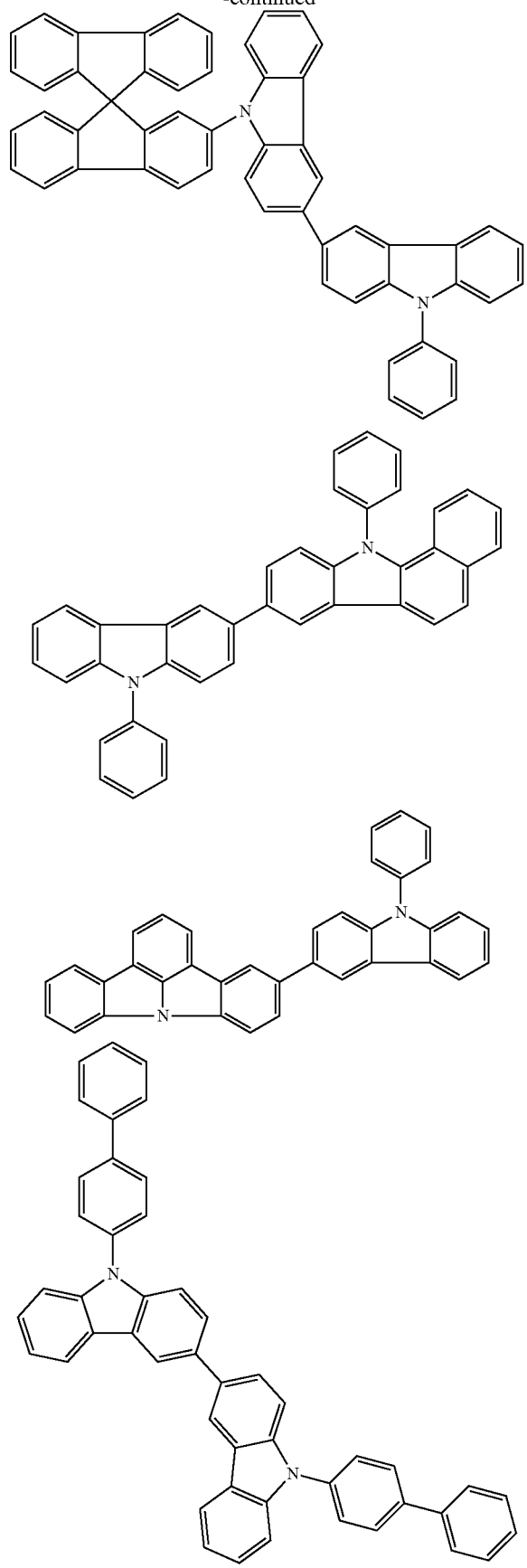
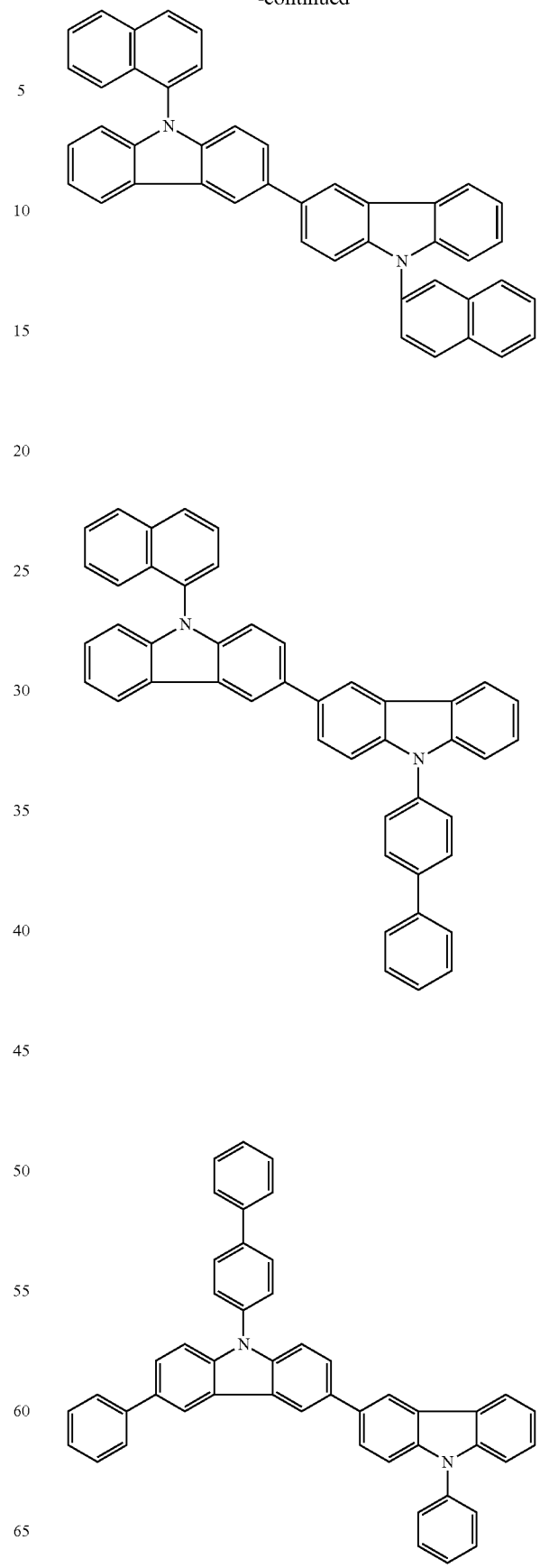

-continued
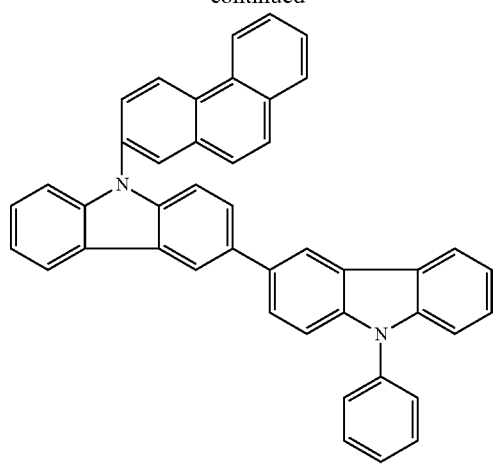
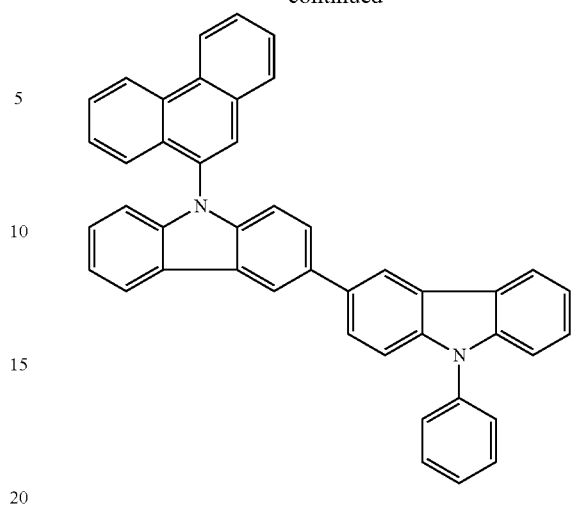
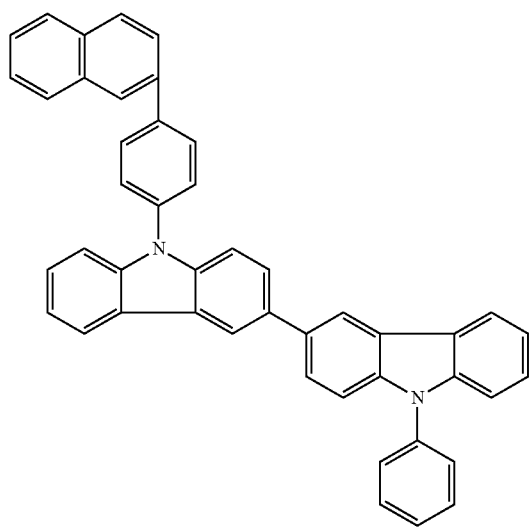
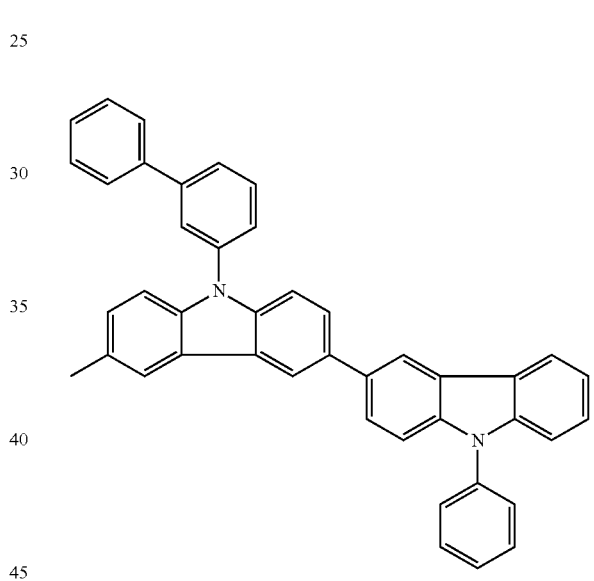
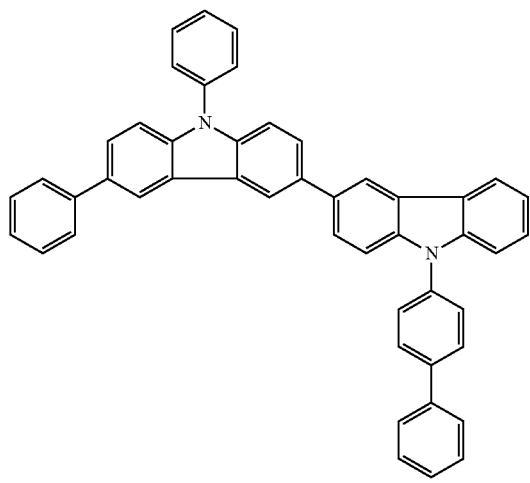
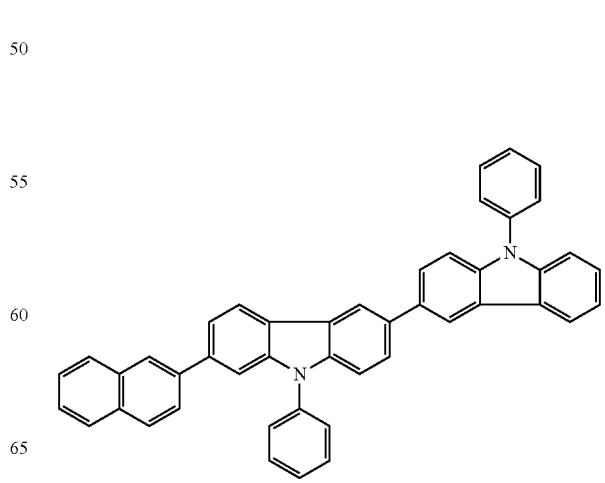

167
-continued
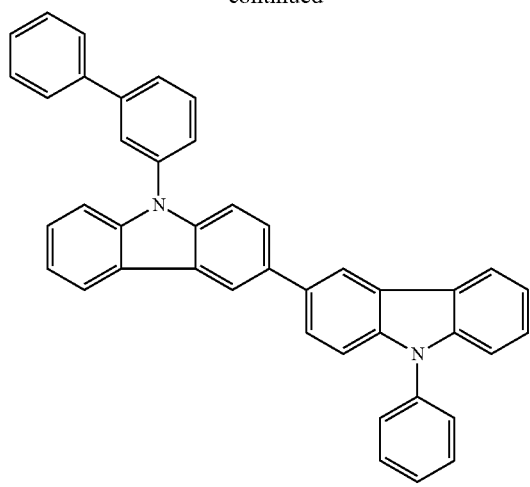
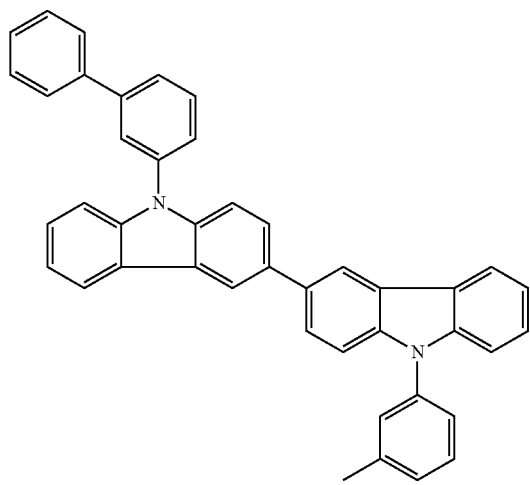
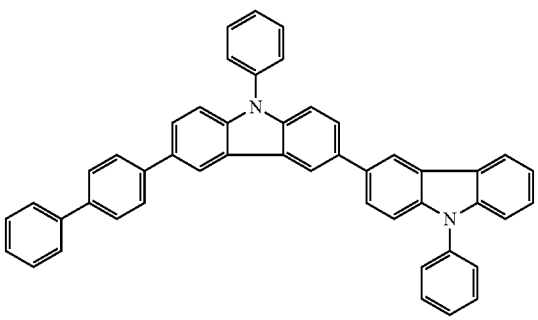
168
-continued
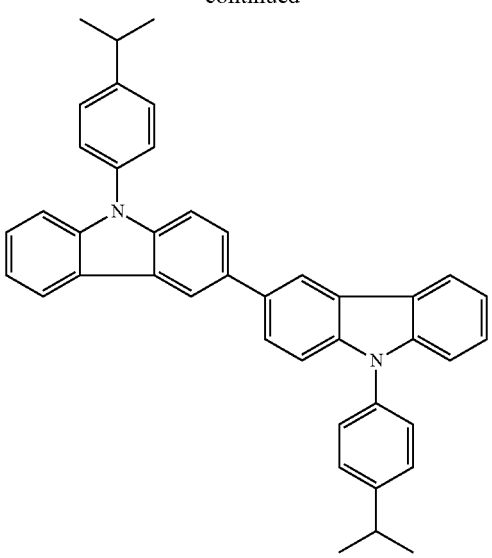
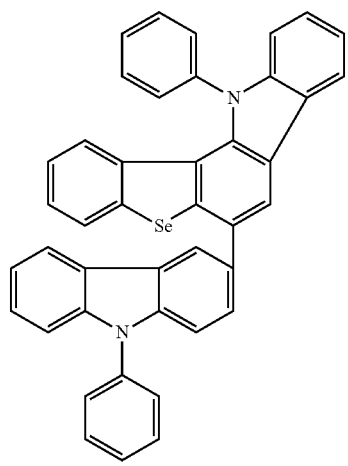
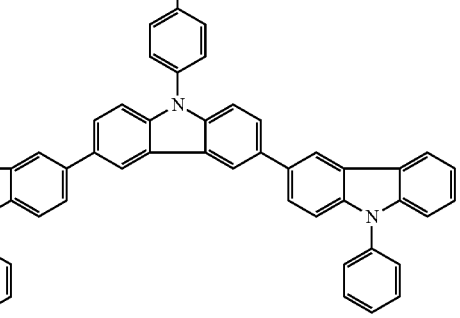

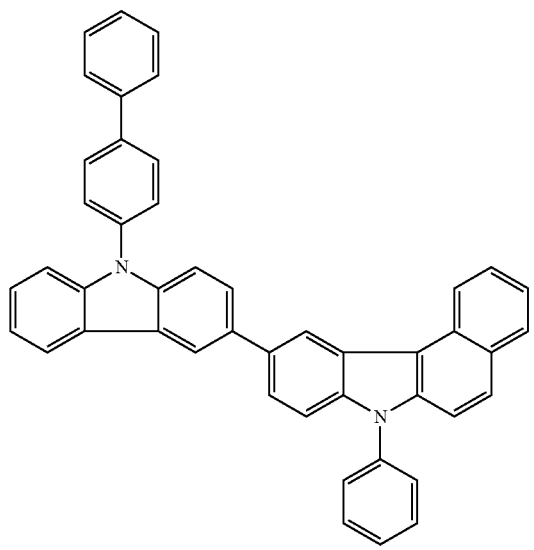
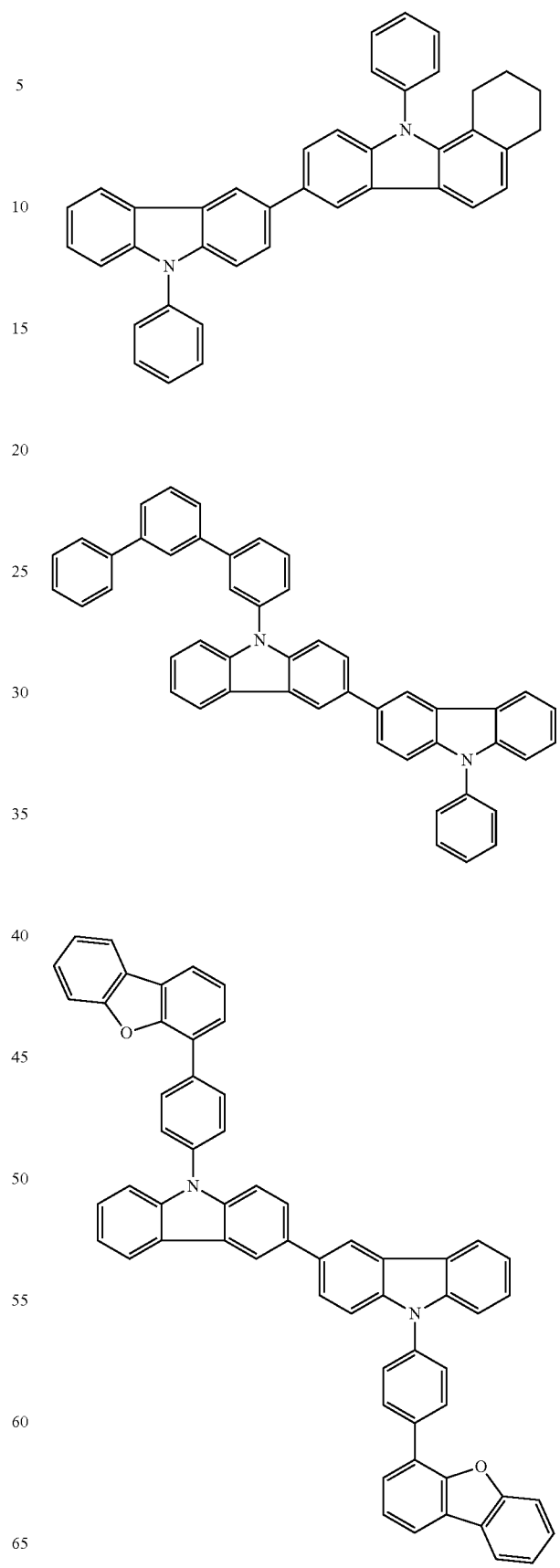

171
-continued
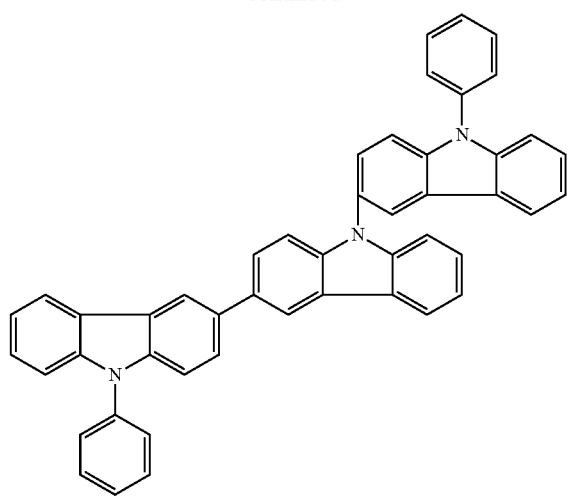
172
-continued
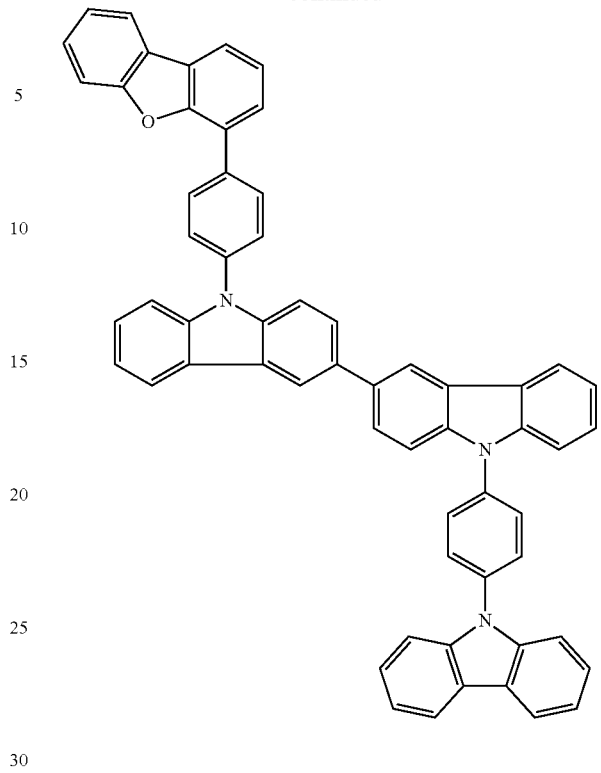
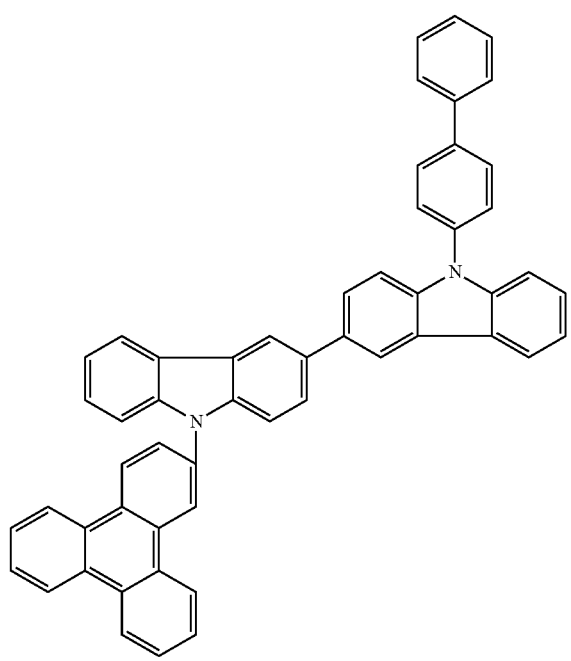
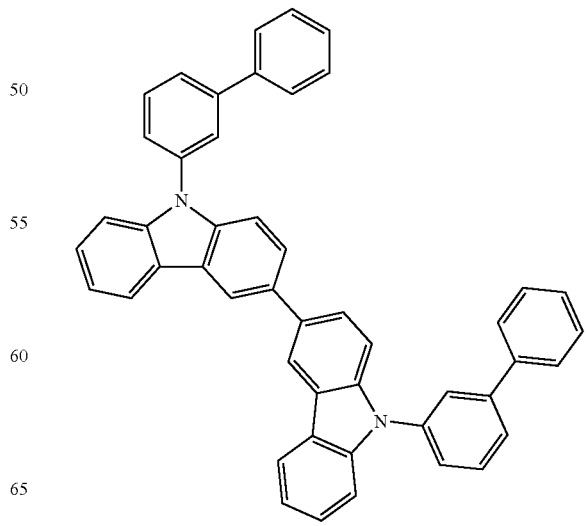

173
-continued
174
-continued
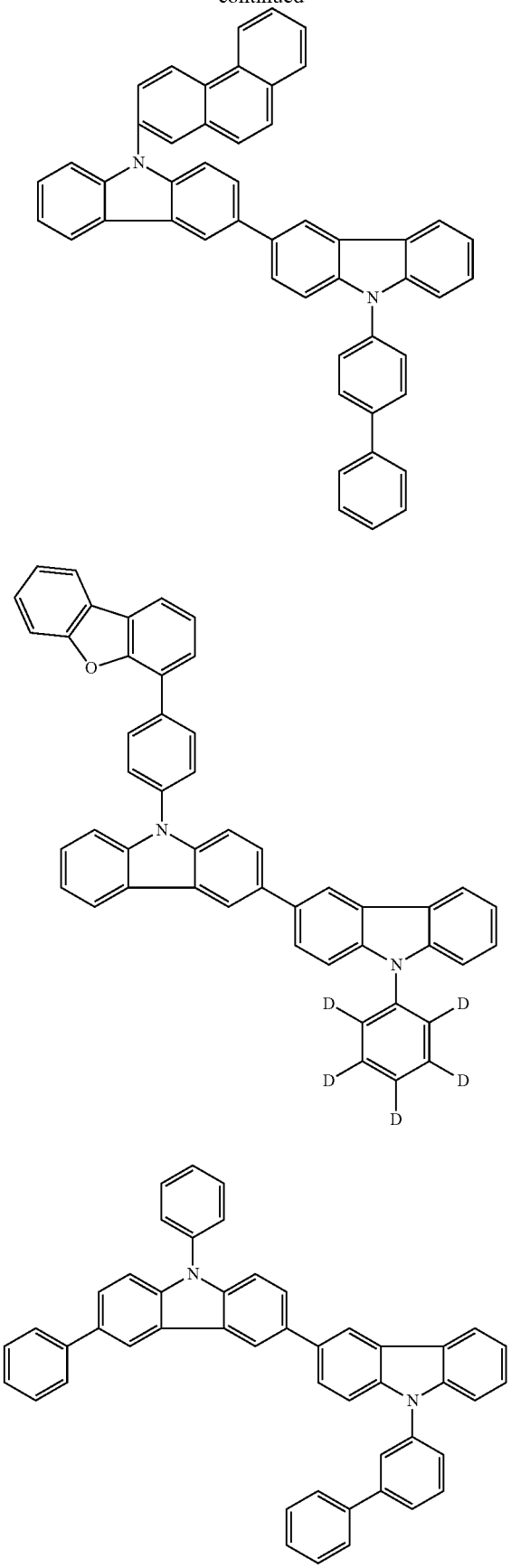
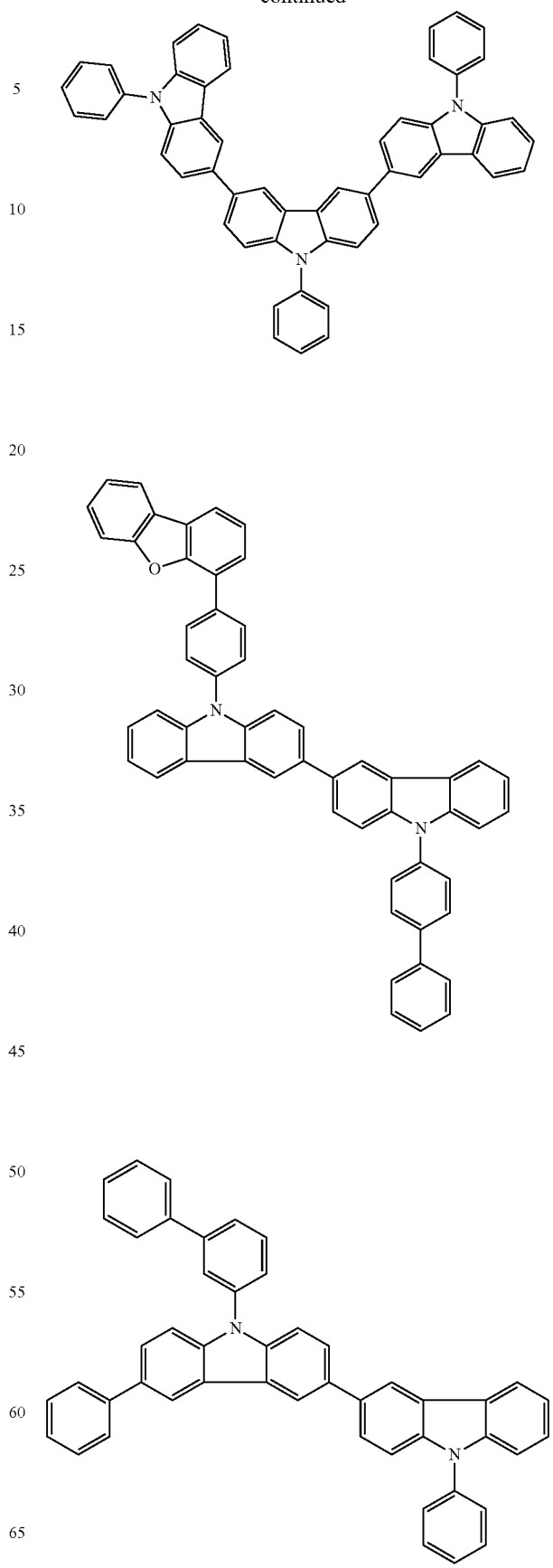

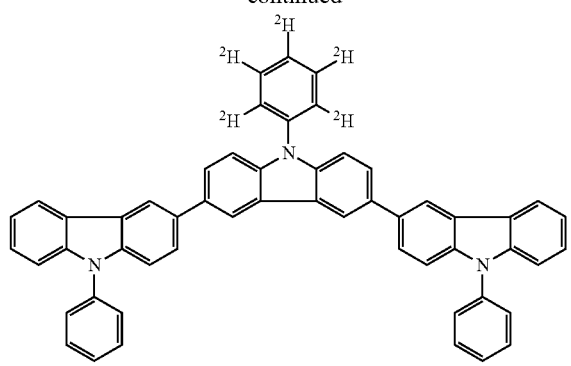
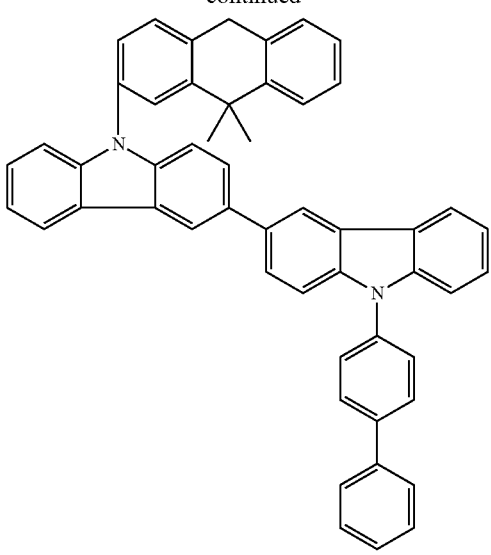
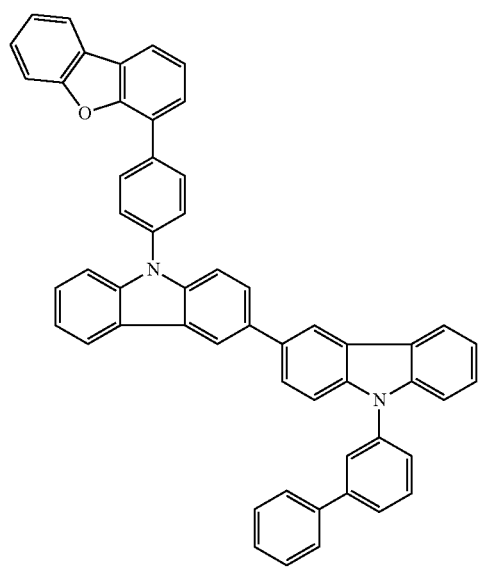
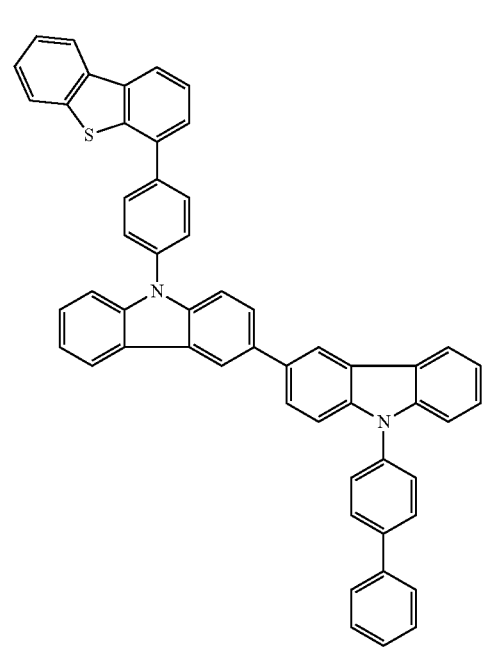
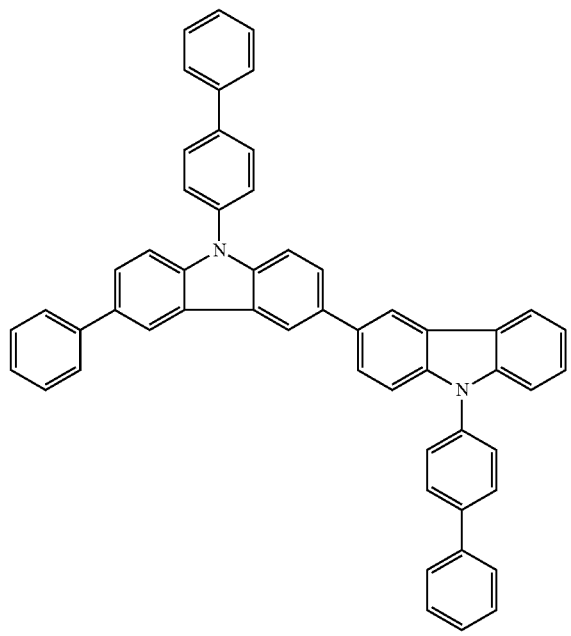
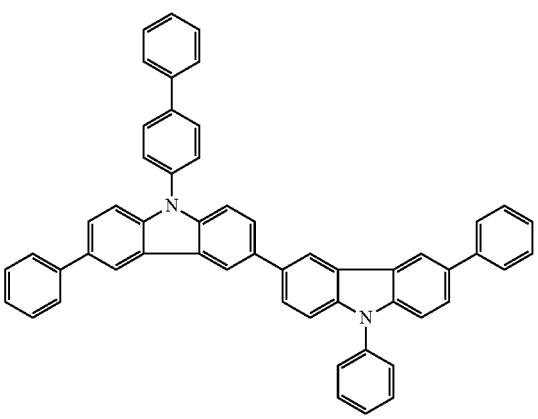

177
-continued
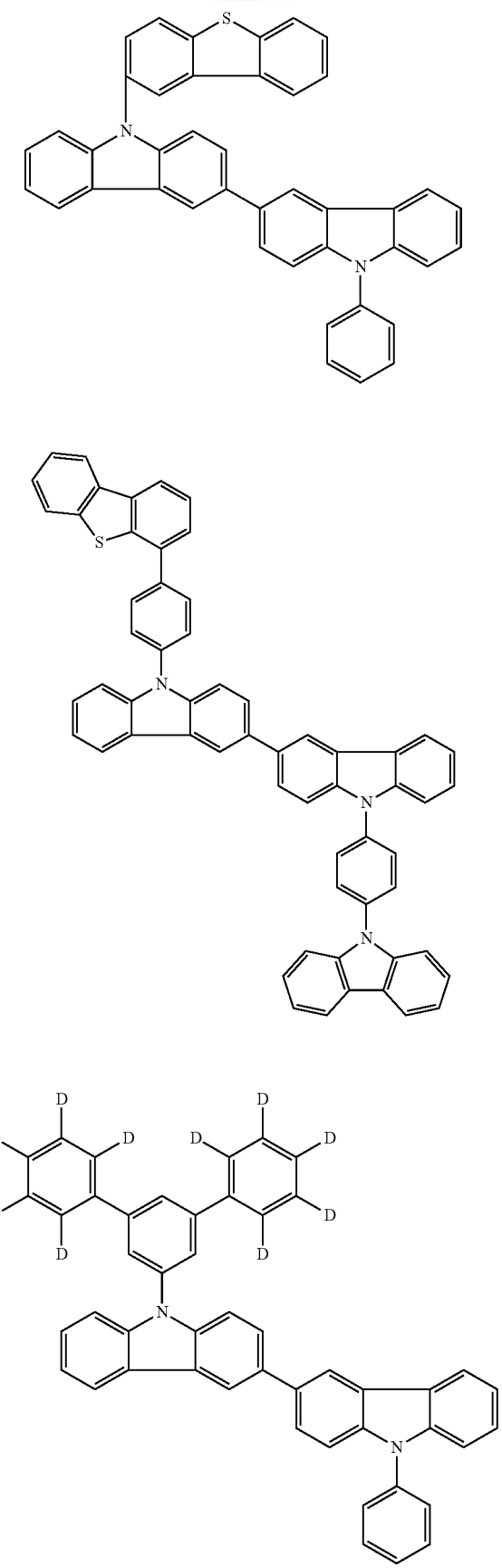
178
-continued
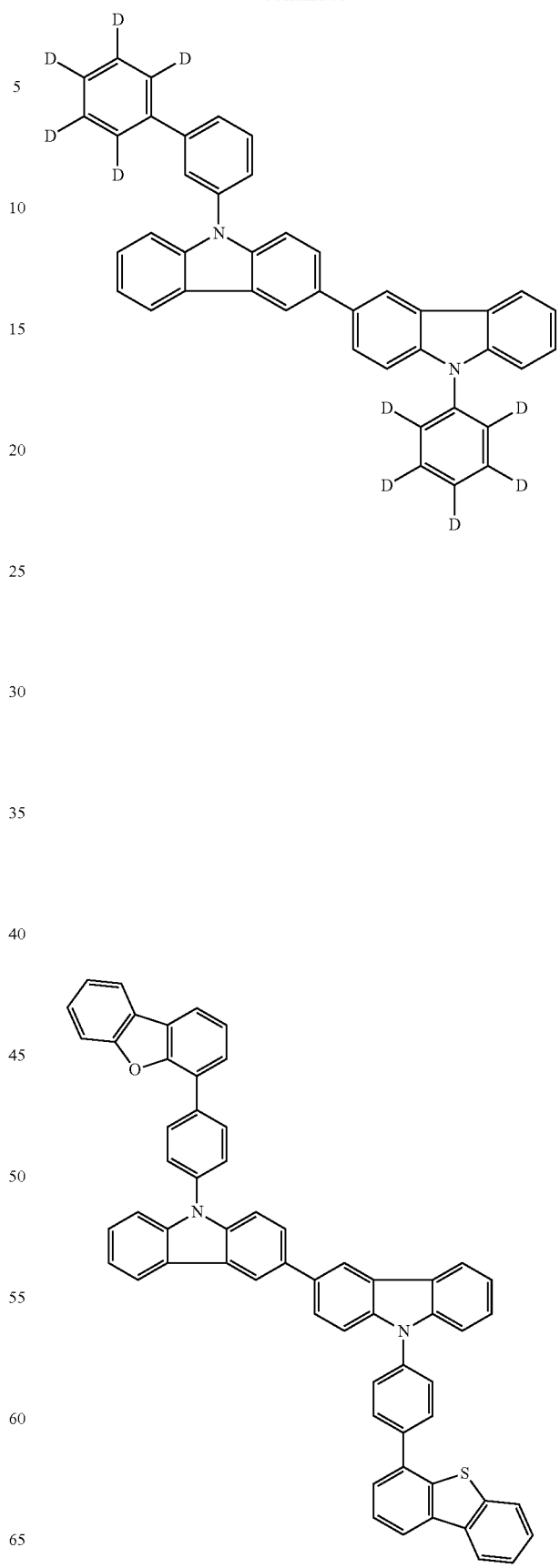

179
-continued
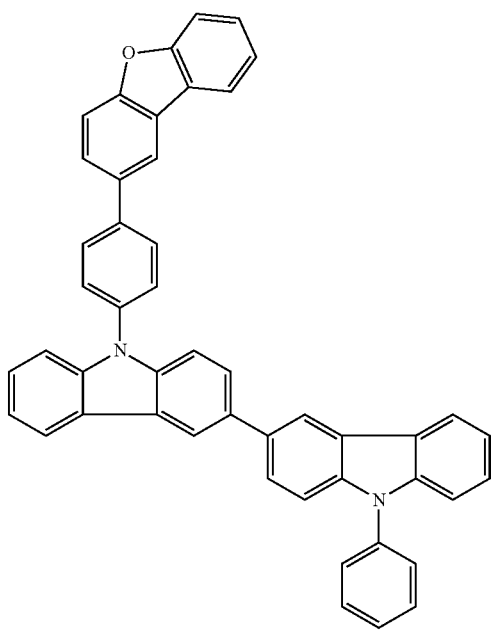
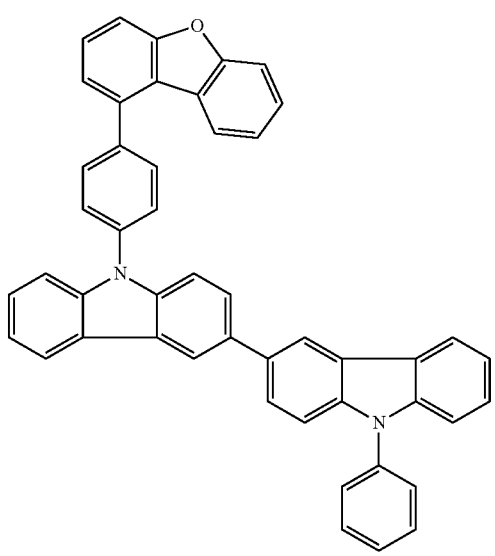
180
-continued
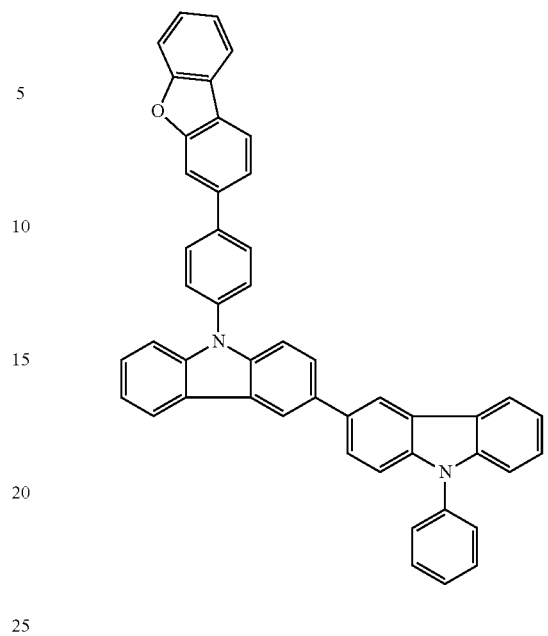
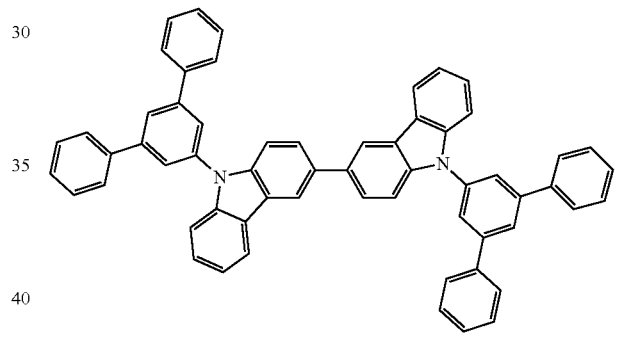
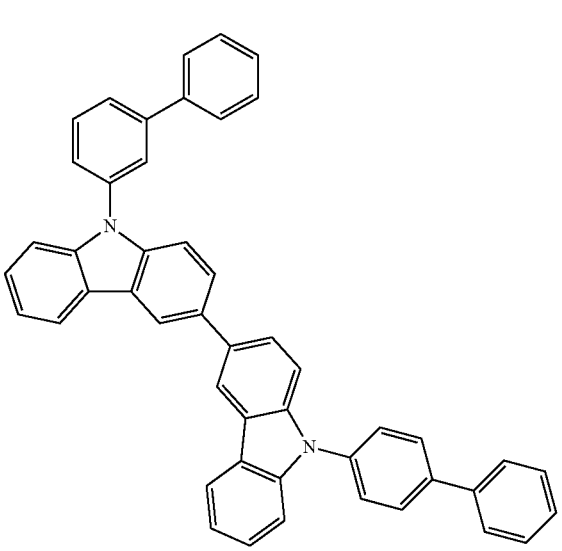

181
-continued
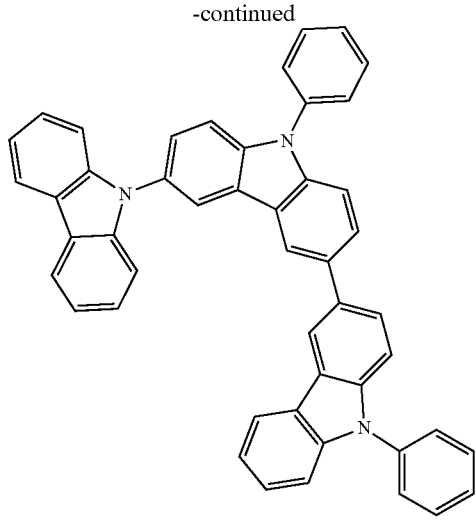
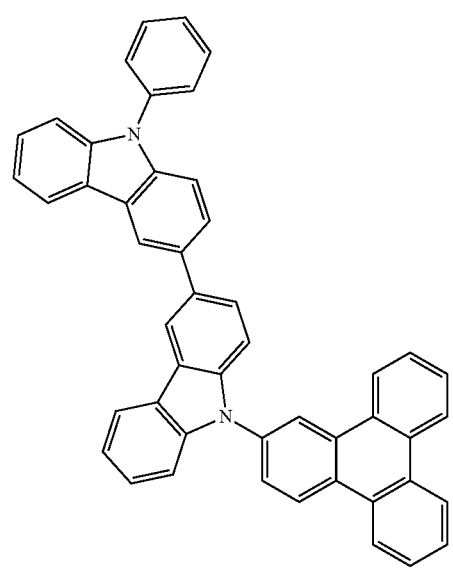
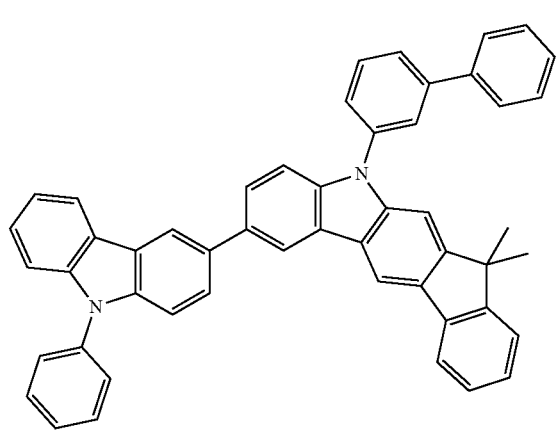
182
-continued
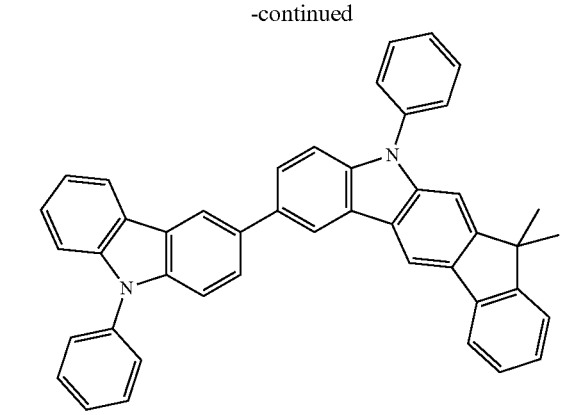
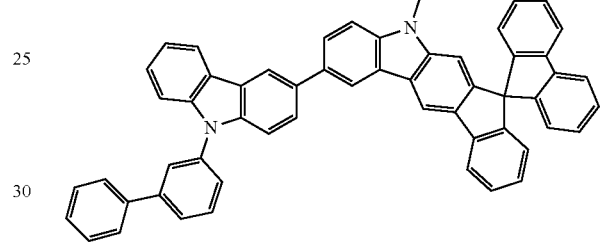
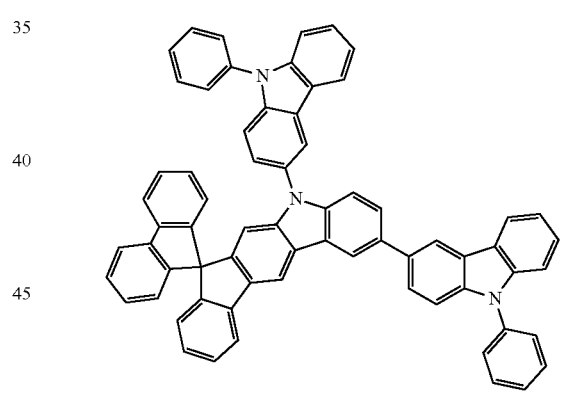
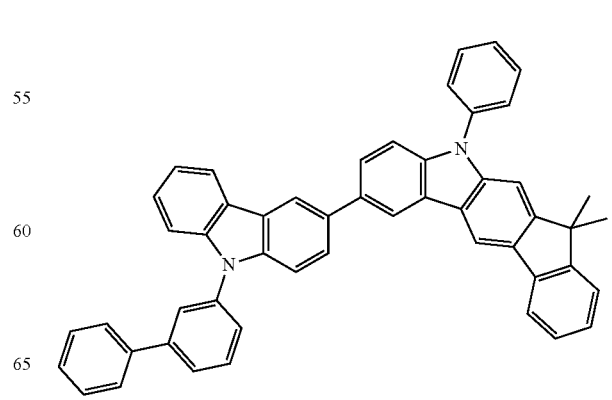

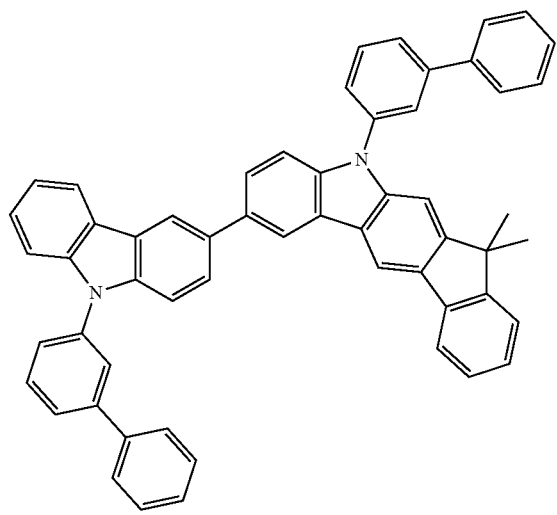

Preferred bridged carbazoles are the structures of the following formula (18):

Formula (18)
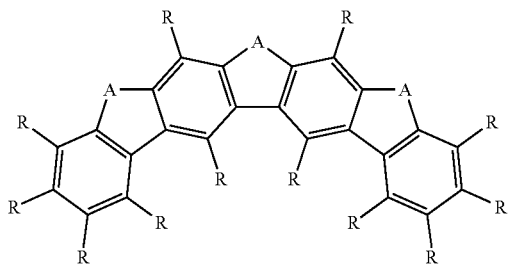

where A and R have the definitions given above and A is preferably the same or different at each instance and is selected from the group consisting of NAr and $CR_2$.

A preferred embodiment of the formula (18) is the compounds of the formula (18a), particular preference being given to the compounds of the formula (18b), and very particular preference to the compounds of the formula (18c)

Formula (18a)
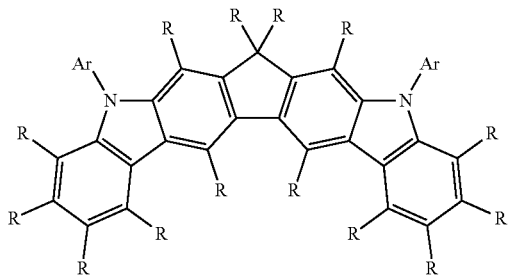

Formula (18b)
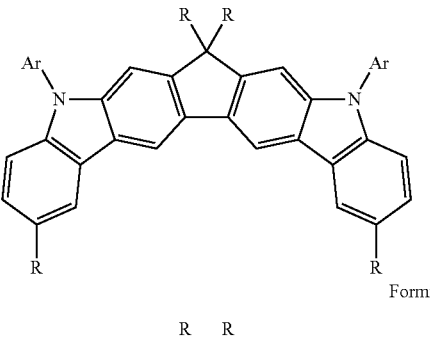

Formula (18c)
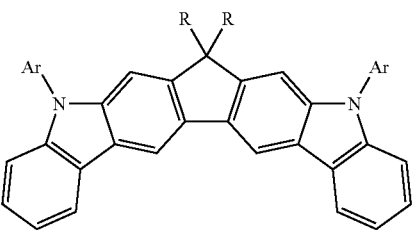

where Ar and R have the definitions given above. Ar here is preferably the same or different at each instance and is an aromatic ring system having 6 to 18 aromatic ring atoms, for example phenyl, ortho-, meta- or para-biphenyl or terphenyl. The R radical on the indene carbon atom is preferably the same or different at each instance and is an alkyl group having 1 to 5 carbon atoms, especially methyl, or an aromatic ring system having 6 to 18 aromatic ring atoms, especially phenyl.

Preferred triarylamines are the structures of the following formula (19):

Formula (19)
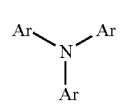

where Ar has the definitions given above.

Preferred dibenzofuran derivatives are the compounds of the following formula (20):

Formula (20)
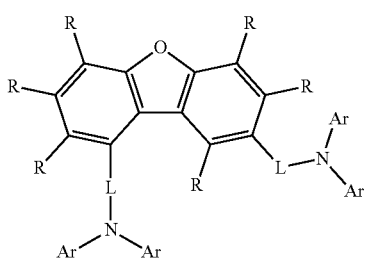

where the oxygen may also be replaced by sulfur so as to form a dibenzothiophene, L is a single bond or an aromatic or heteroaromatic ring system which has 5 to 30 aromatic ring atoms and may also be substituted by one or more R radicals, and R and Ar have the definitions given above. It is also possible here for the two Ar groups that bind to the same nitrogen atom, or for one Ar group and one L group that bind to the same nitrogen atom, to be bonded to one another, for example to give a carbazole.

Preferred embodiments of the compounds of the formula (20) are the compounds of the following formulae (20a) and (20b):

Formula (20a)

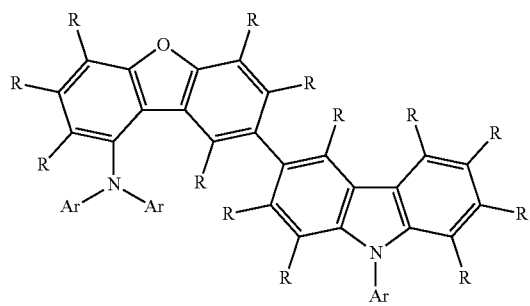

Formula (20b)

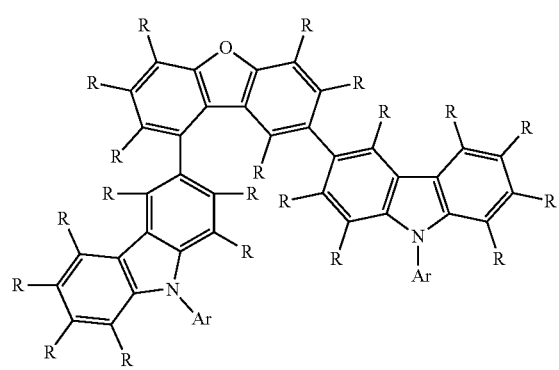

where the oxygen may also be replaced by sulfur so as to form a dibenzothiophene, and R and Ar have the definitions given above, where two adjacent R radicals, especially on the carbazole, here may also together form an aromatic or heteroaromatic ring system.

Particularly preferred embodiments are the compounds of the following formulae (20c) and (20d):

Formula (20c)

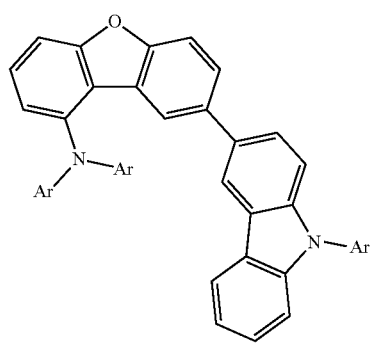

Formula (20d)

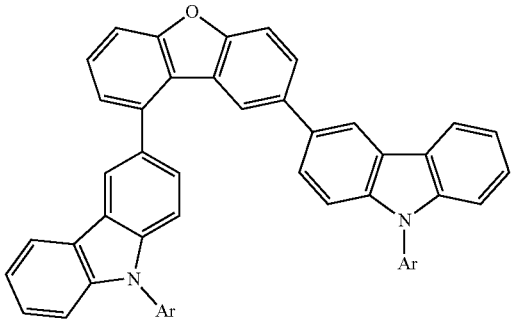

where the oxygen may also be replaced by sulfur so as to form a dibenzothiophene, and Ar has the definitions given above, where two adjacent R radicals, especially on the carbazole, here may also together form an aromatic or heteroaromatic ring system.

Examples of suitable dibenzofuran derivatives are the compounds depicted below.

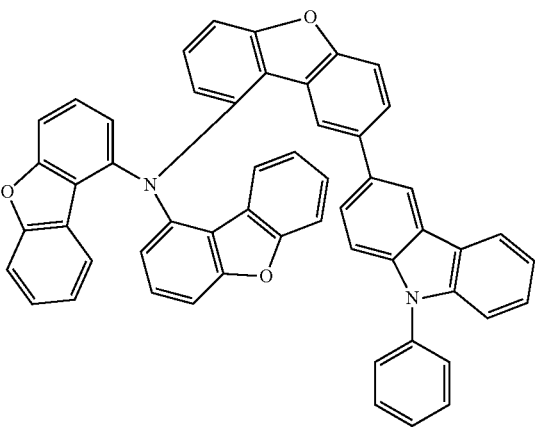

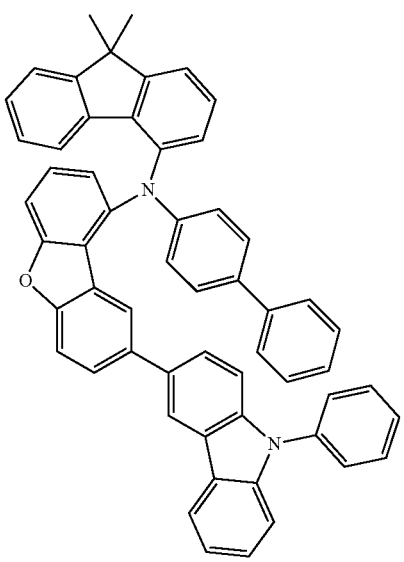

187
-continued
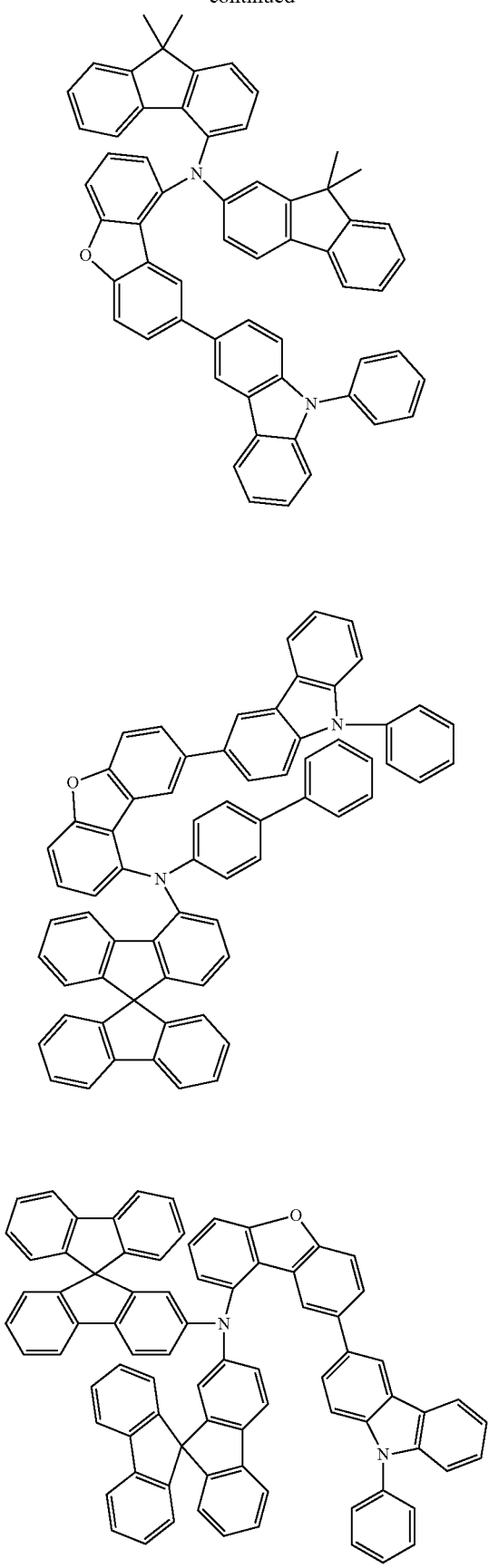
188
-continued
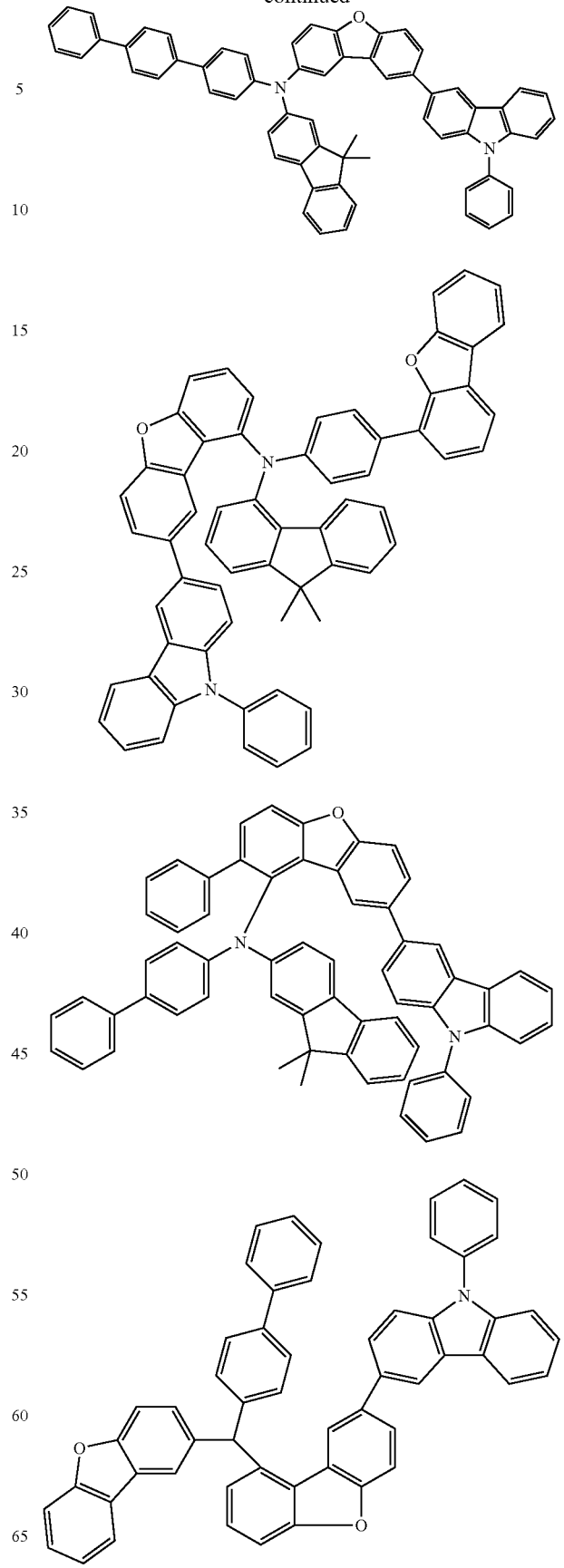

189
-continued
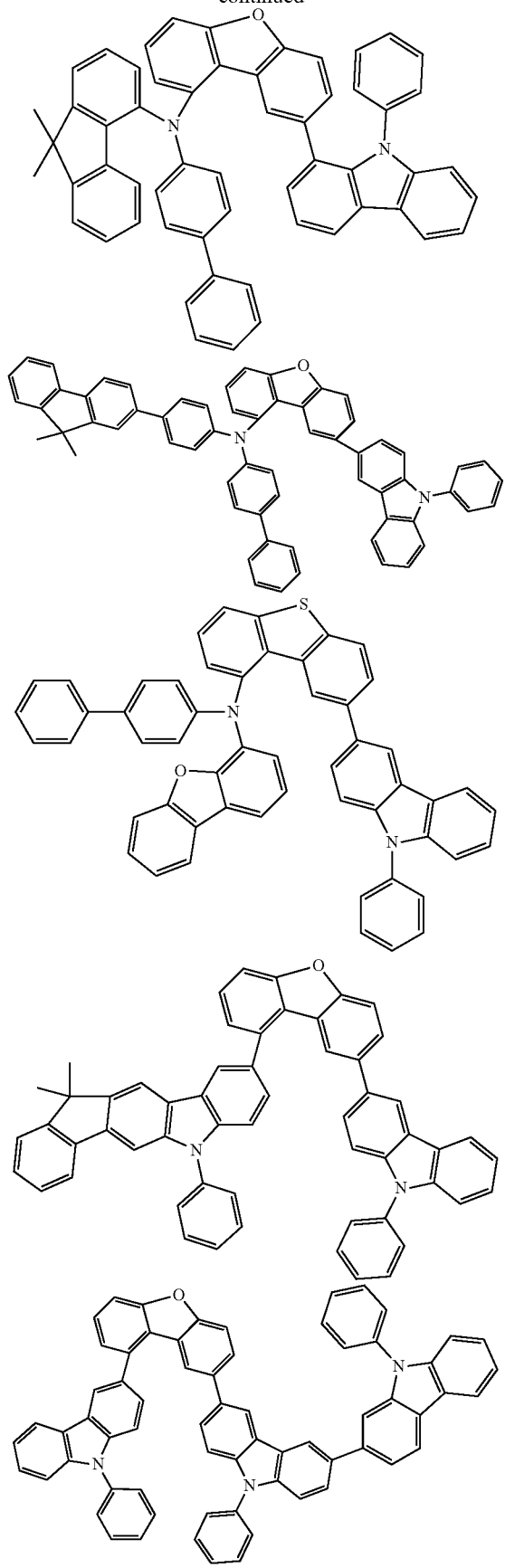
190
-continued
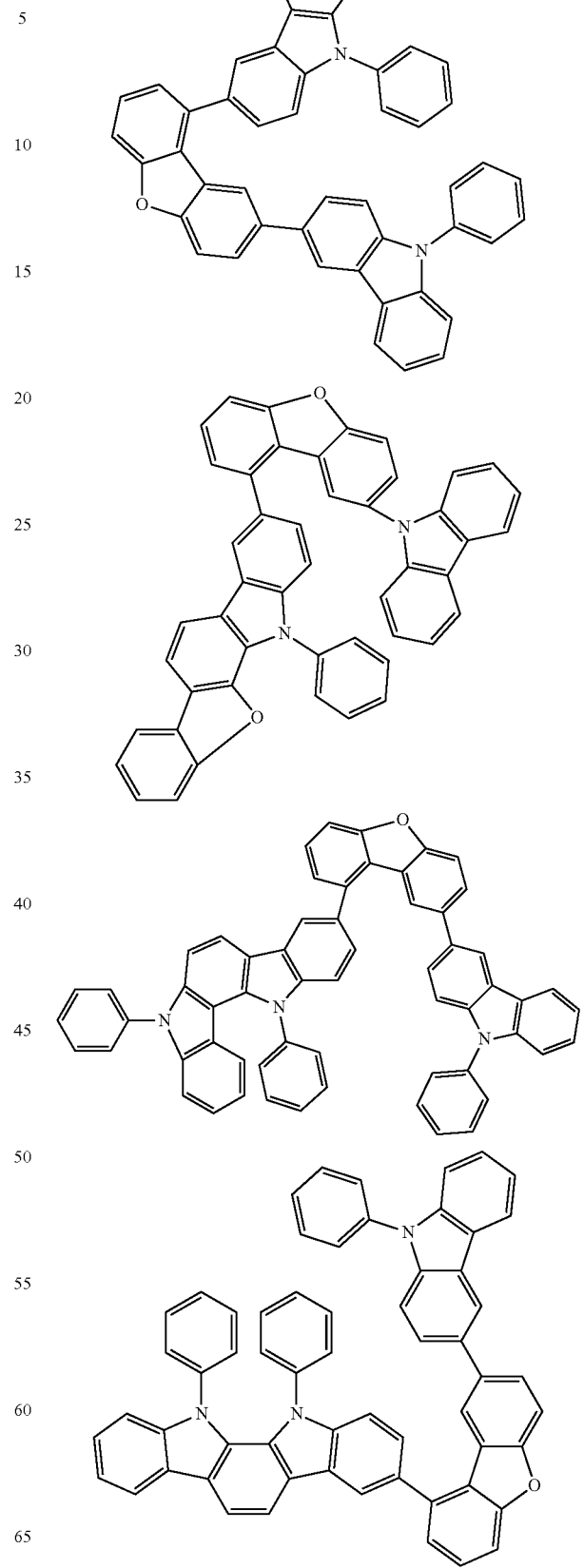

-continued

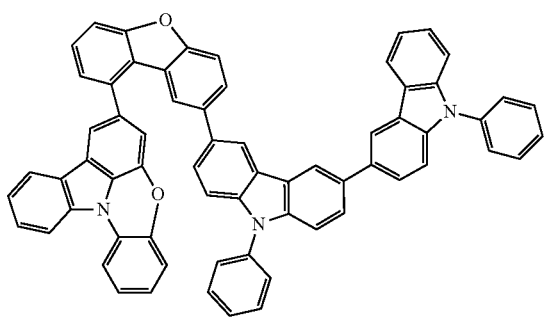

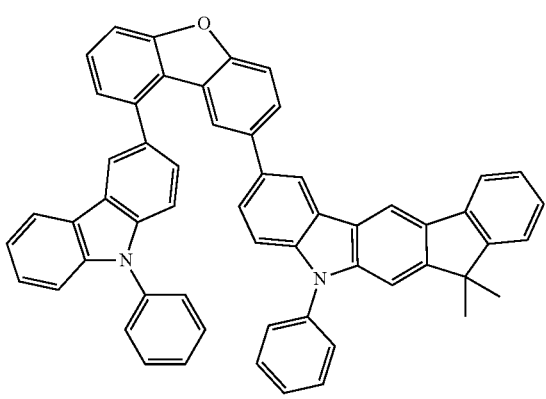

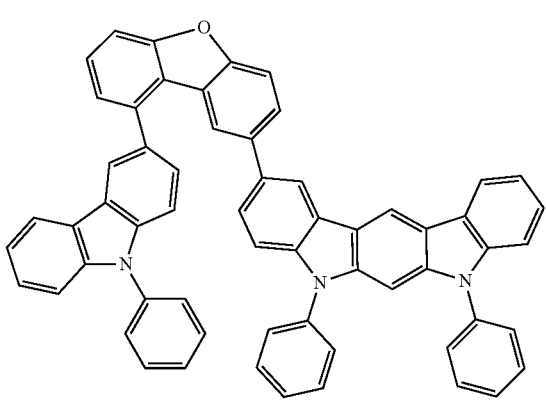

Preferred carbazoleamines are the structures of the following formulae (21), (22) and (23):

Formula (21)

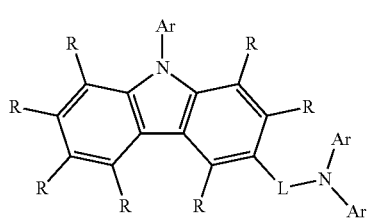

-continued

Formula (22)

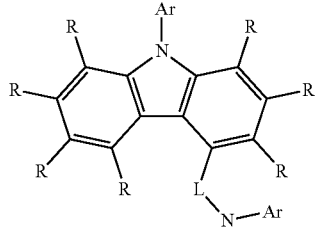

Formula (23)

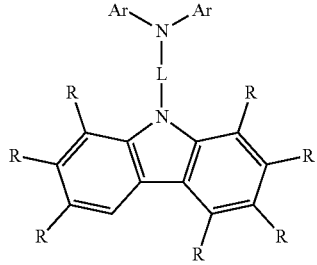

where L is an aromatic or heteroaromatic ring system which has 5 to 30 aromatic ring atoms and may be substituted by one or more R radicals, and R and Ar have the definitions given above, where two adjacent R radicals here too may form an aromatic ring system.

Examples of suitable carbazoleamine derivatives are the compounds depicted below.

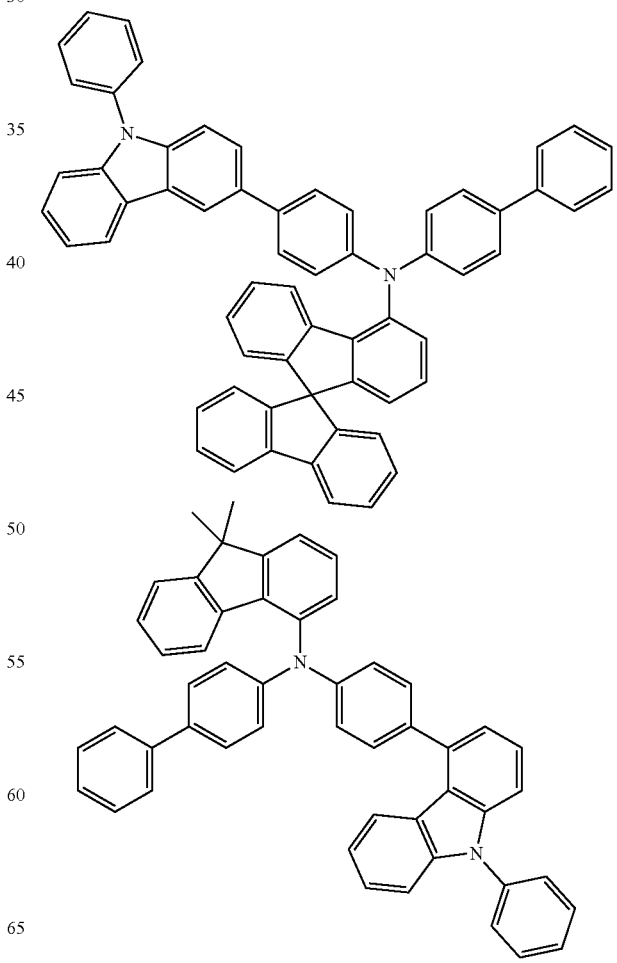

193
-continued
194
-continued
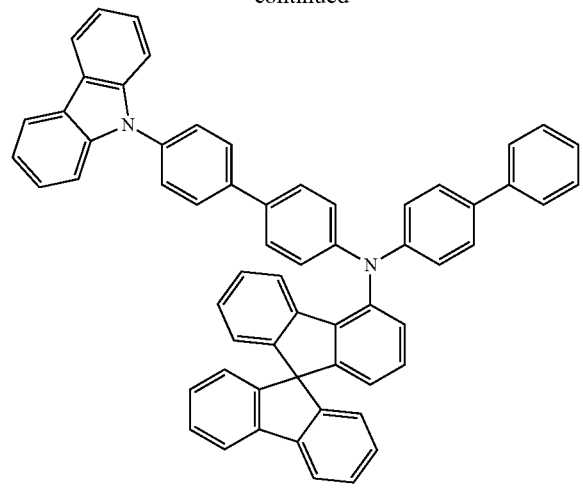
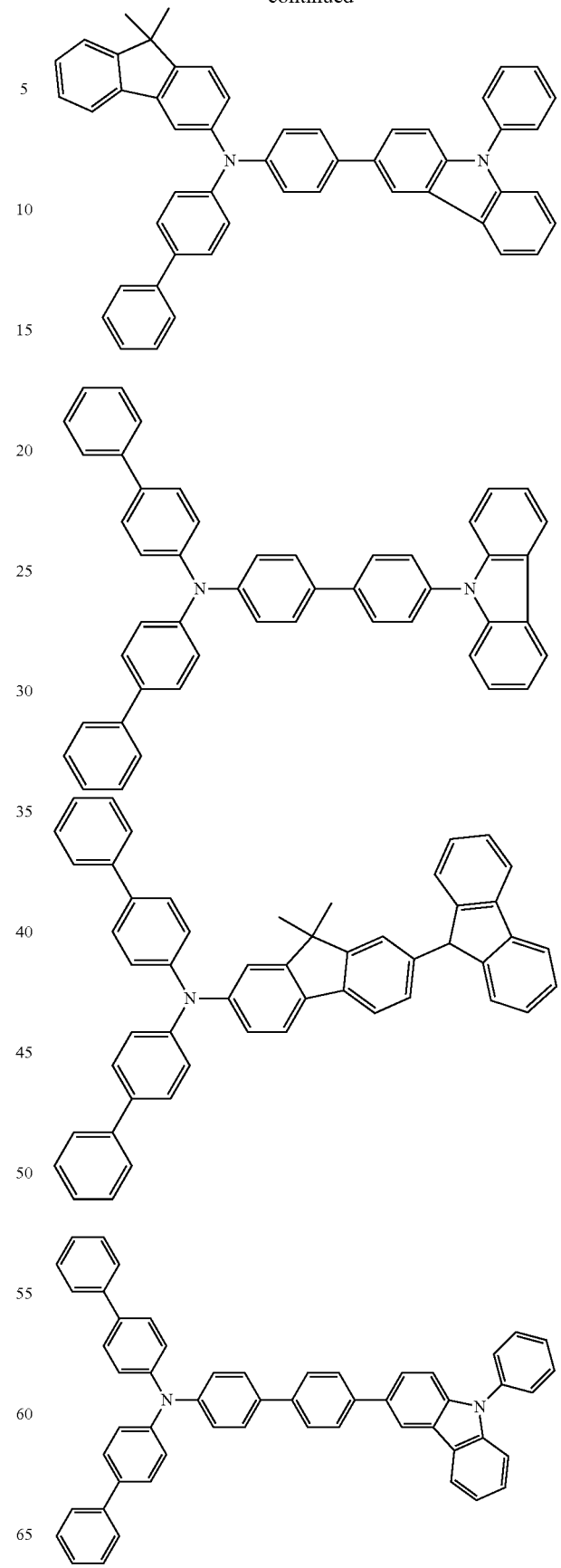

195
-continued
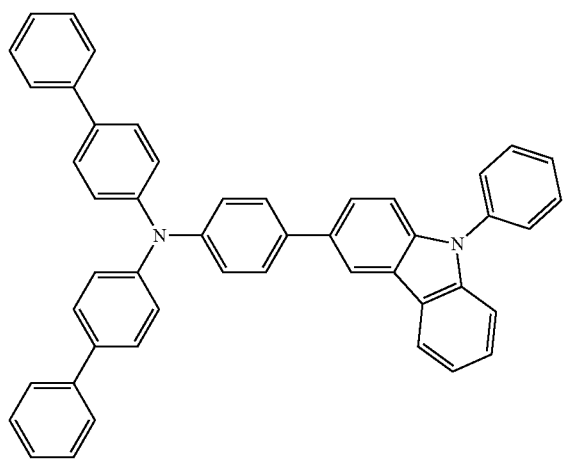
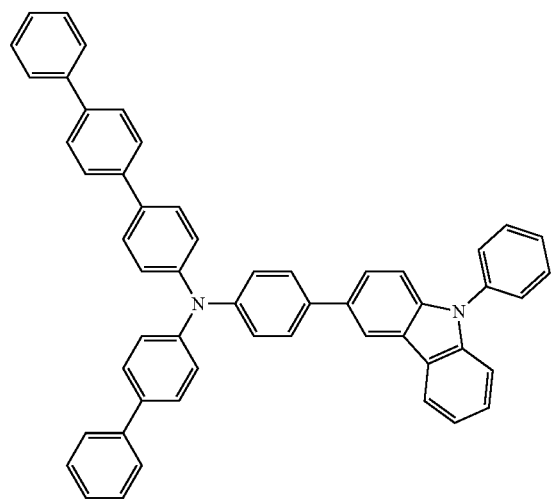
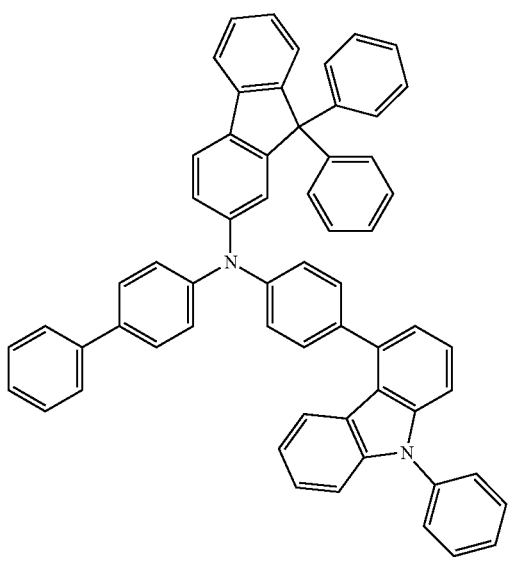
196
-continued
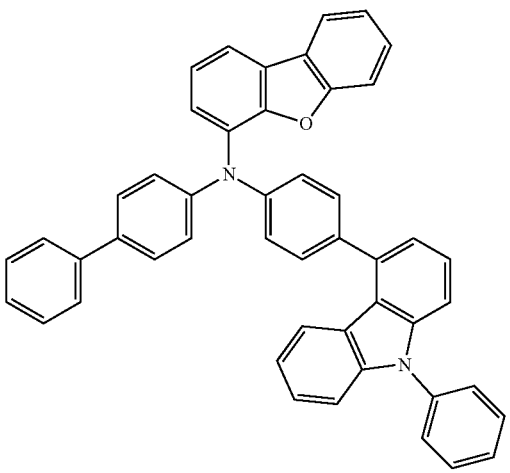
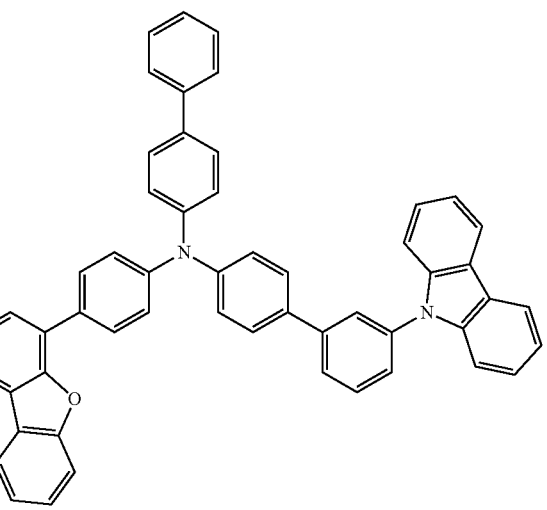

197
-continued
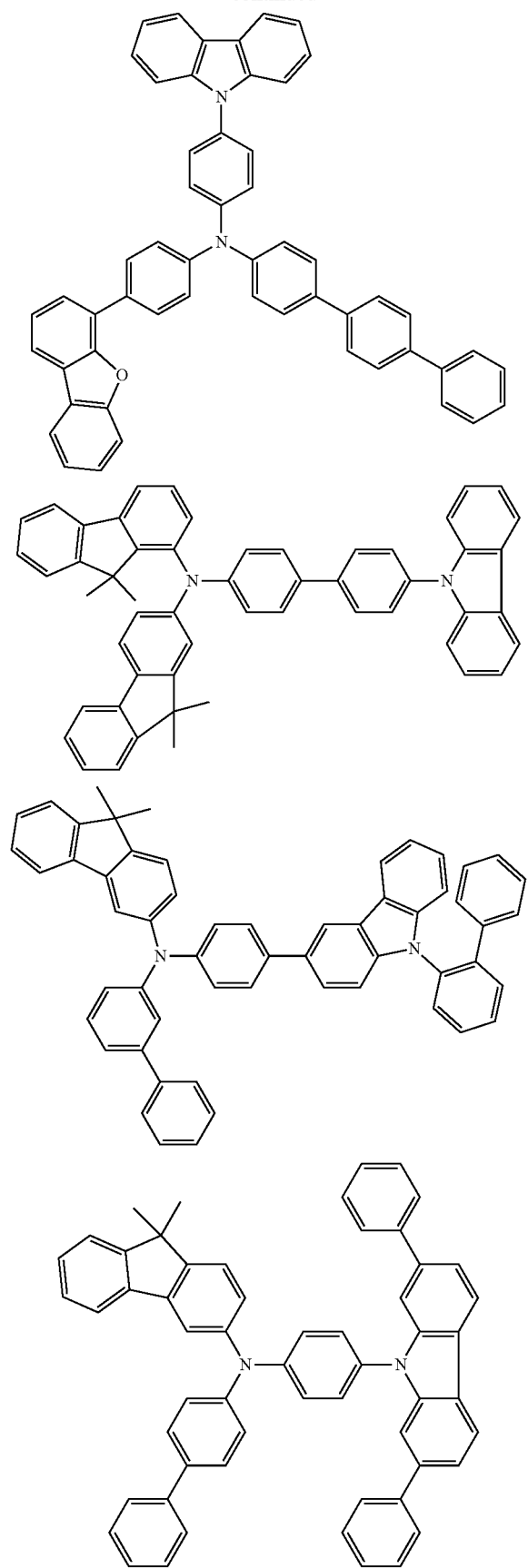
198
-continued
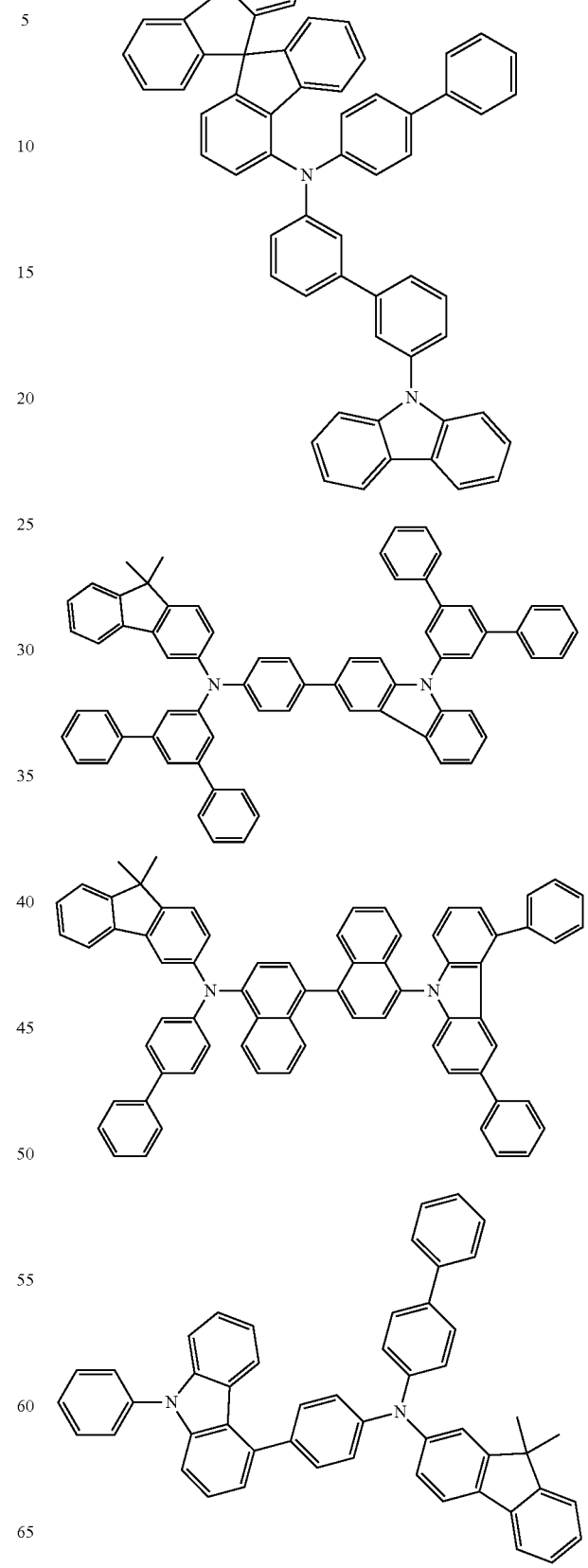

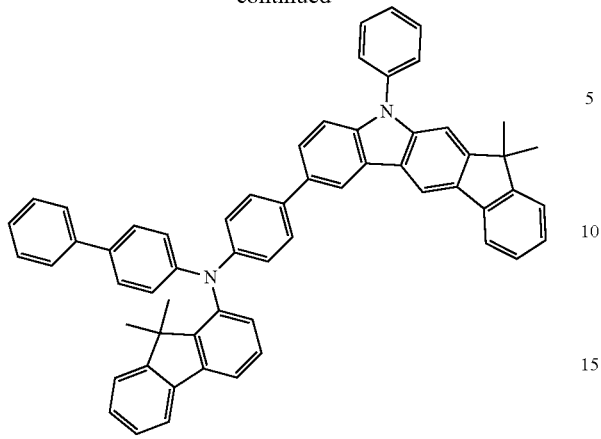

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538 and WO 2018/178001, and as yet unpublished patent applications EP 17206950.2 and EP 18156388.3. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

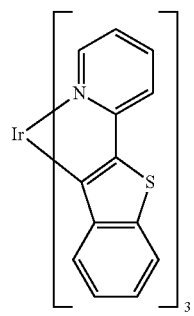

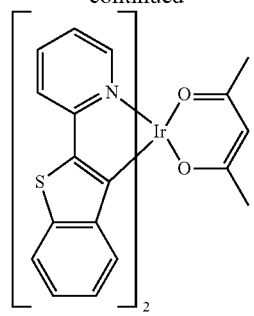

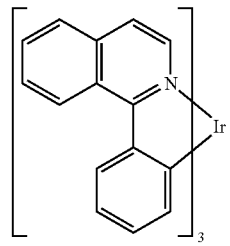

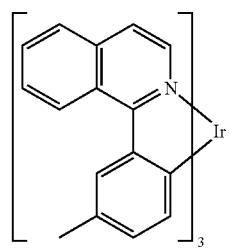

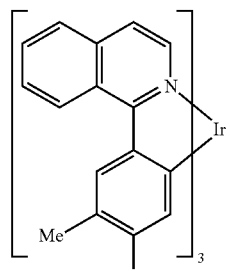

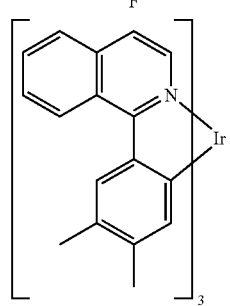

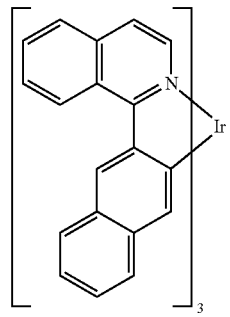

201
-continued
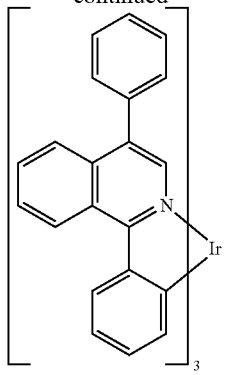
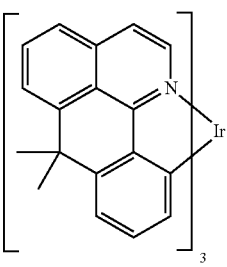
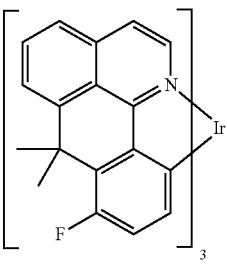
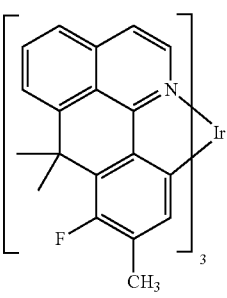
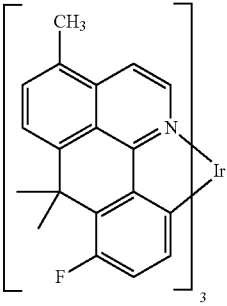
202
-continued
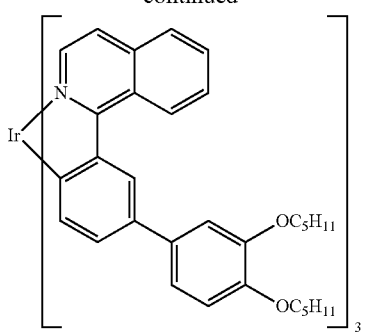
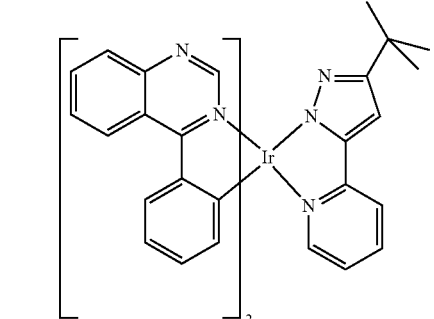
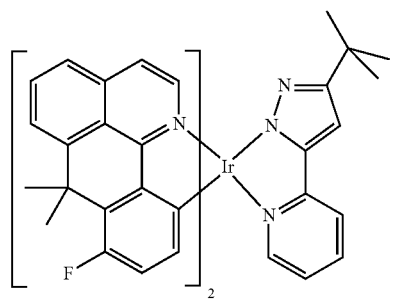

-continued
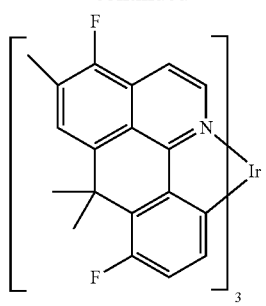
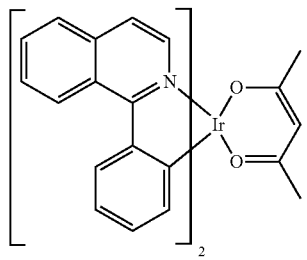
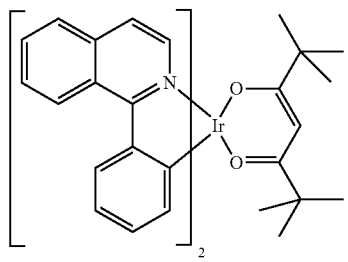
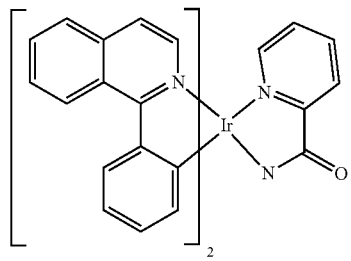
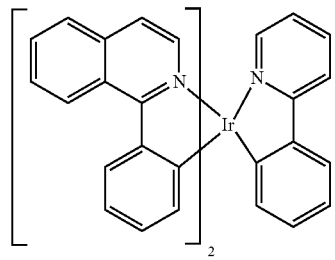
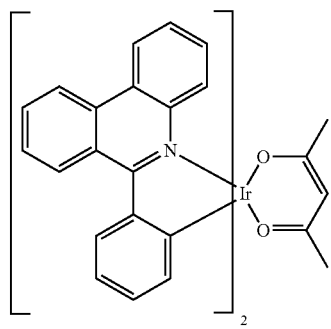
-continued
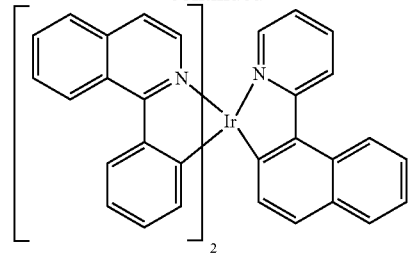
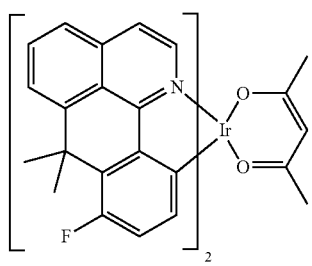
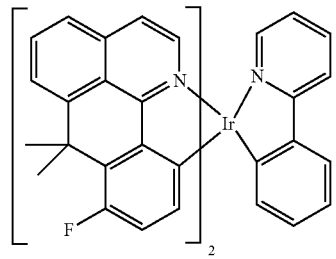
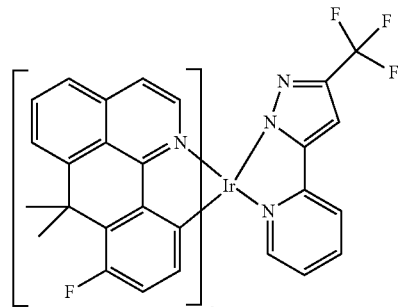
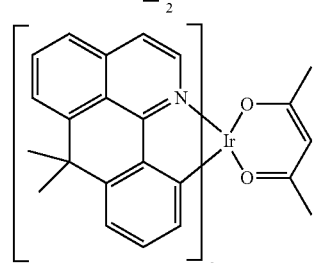
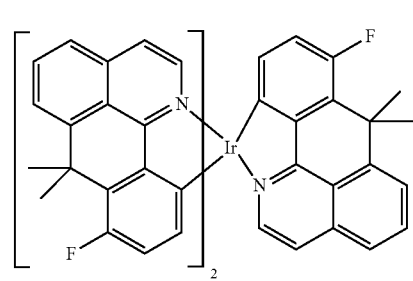

205
-continued
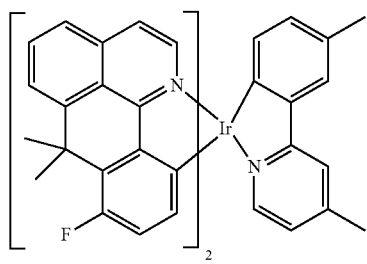
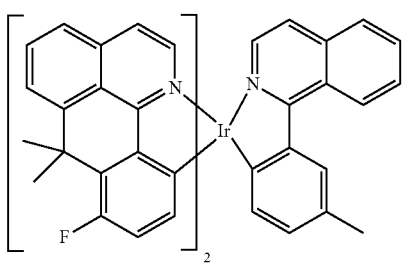
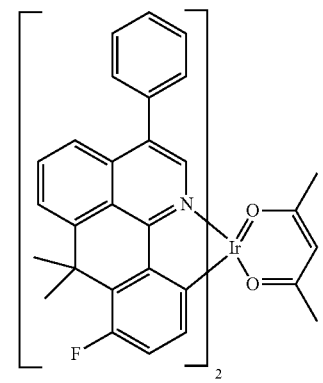
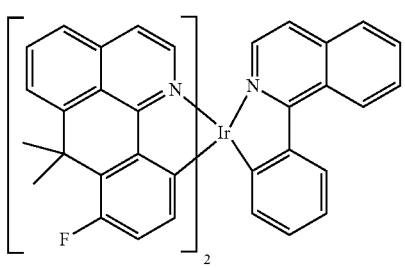
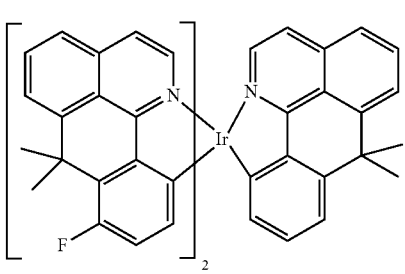
206
-continued
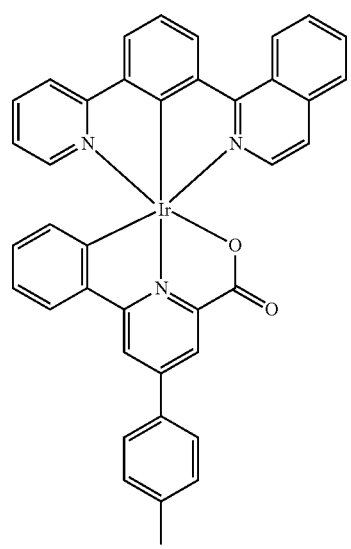
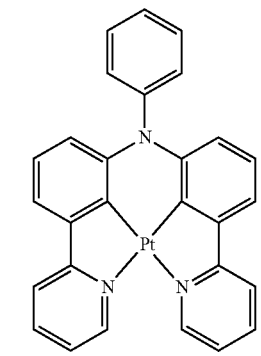
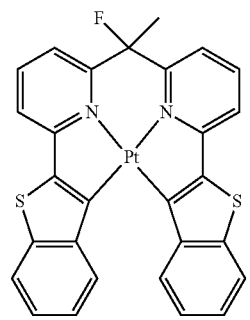

207
-continued
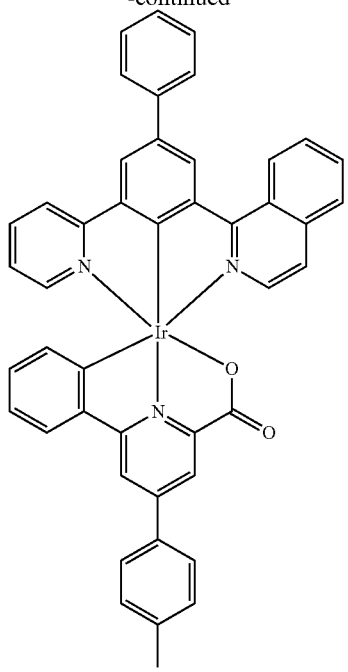
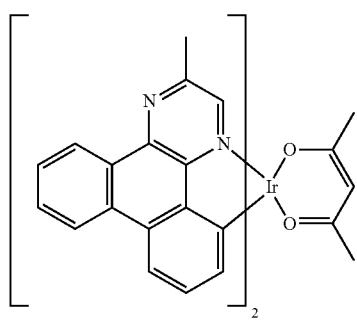
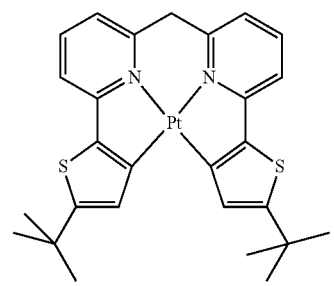
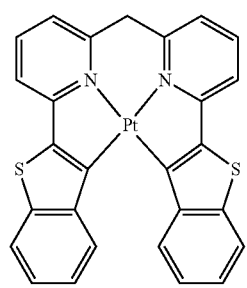
208
-continued
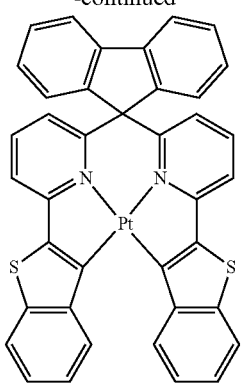
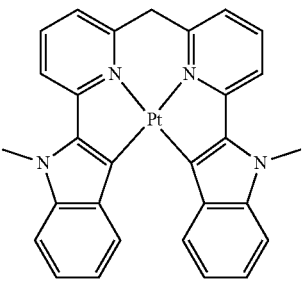
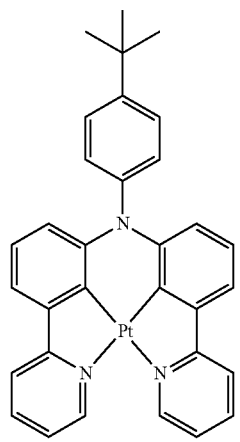

209
-continued
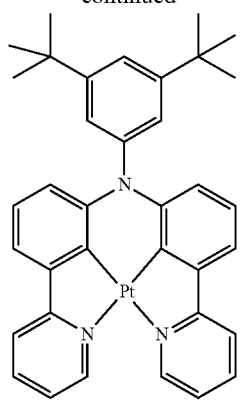
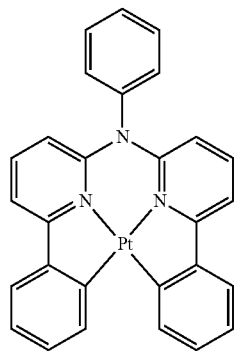
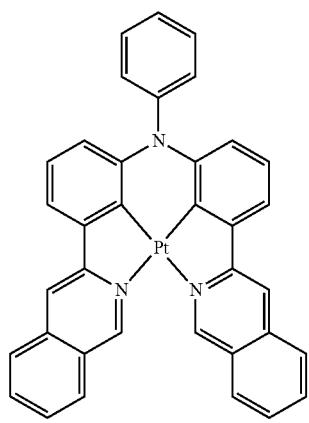
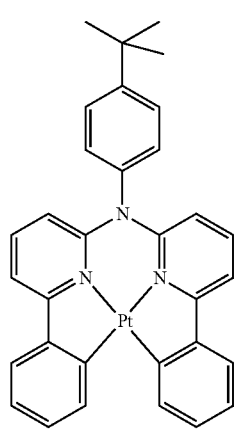
210
-continued
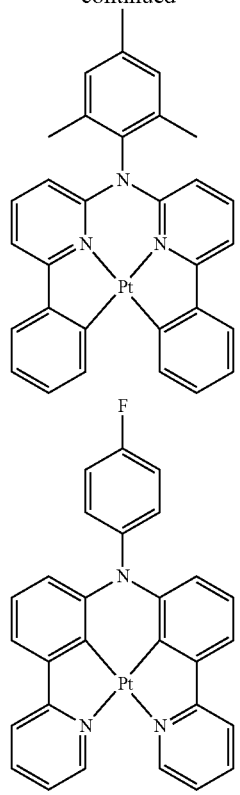
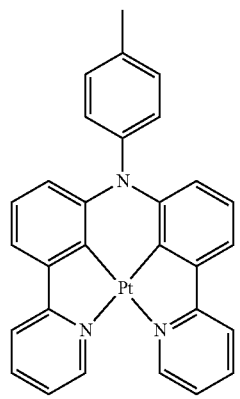
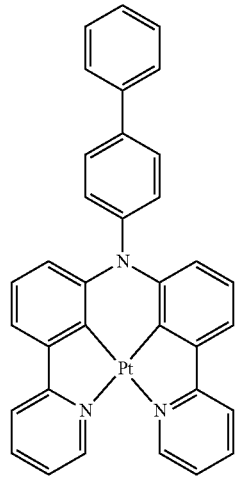

211
-continued
212
-continued
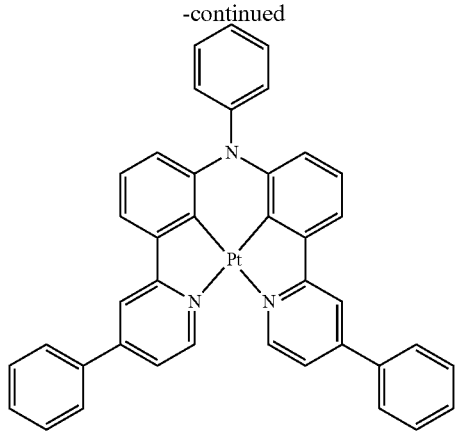
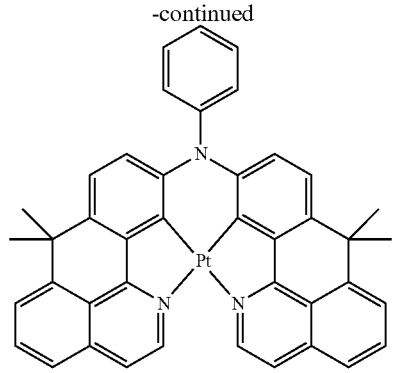
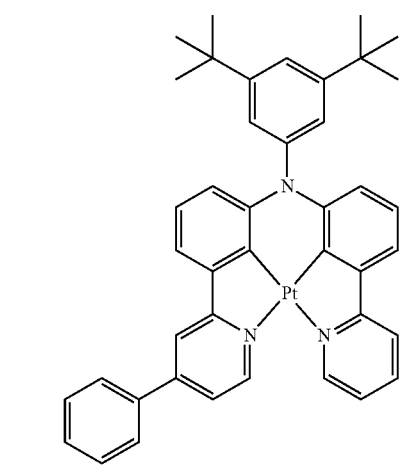
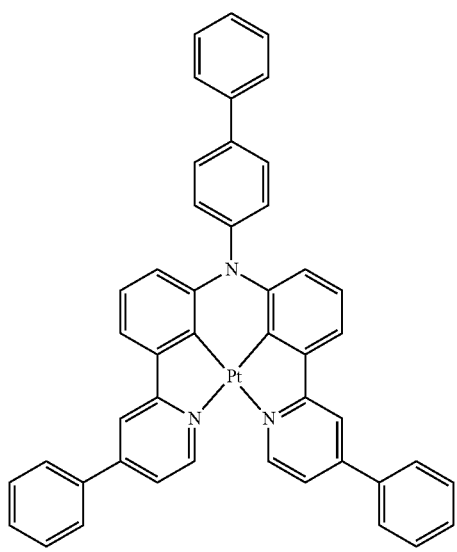

213
-continued
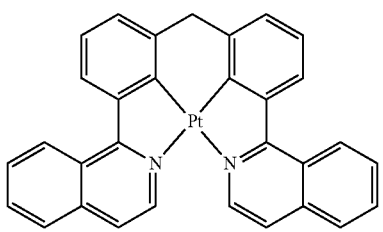
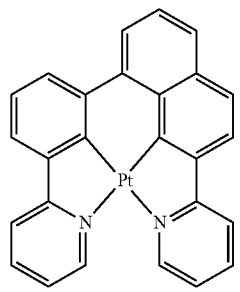
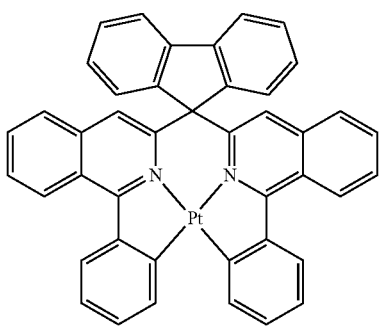
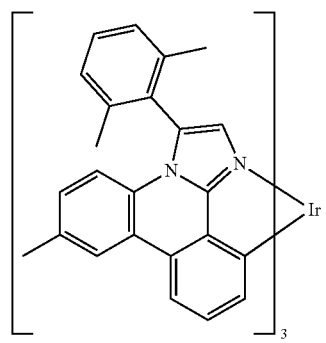
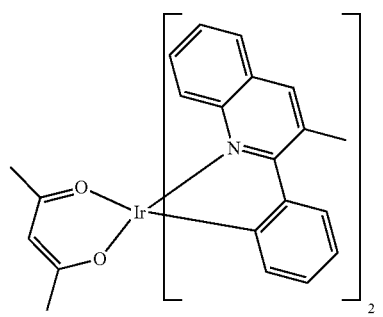
214
-continued
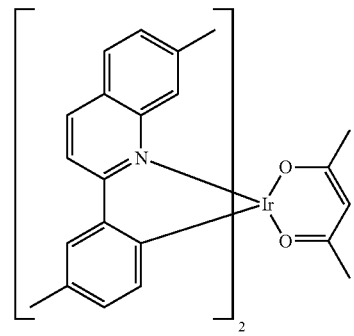
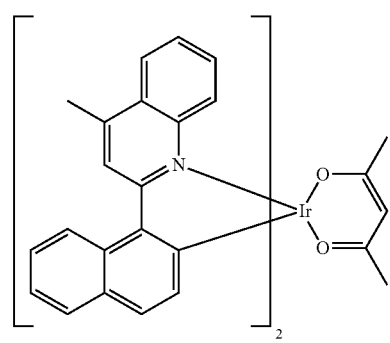
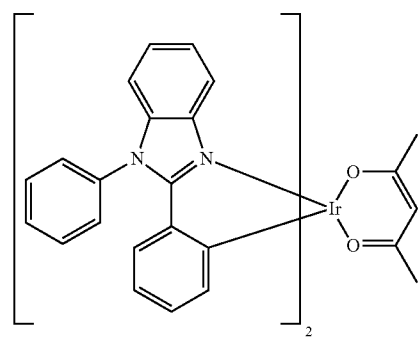
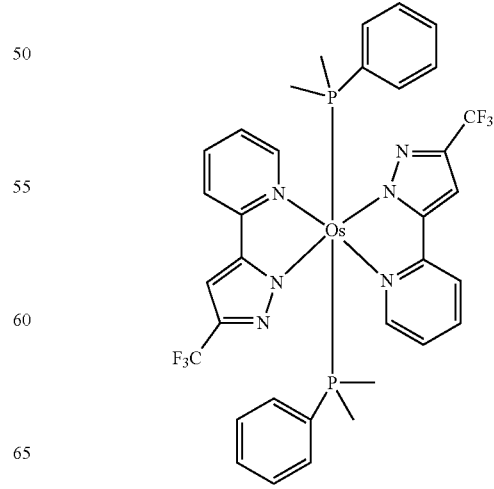

215
-continued
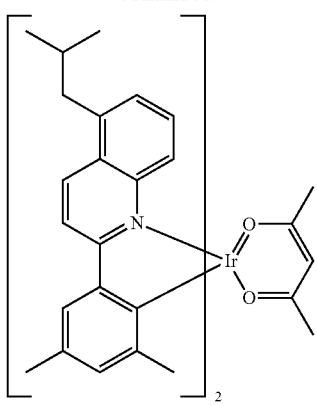
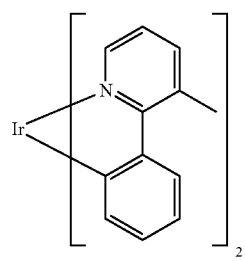
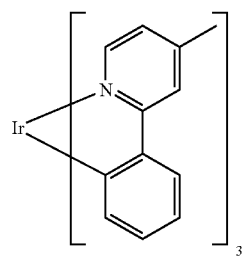
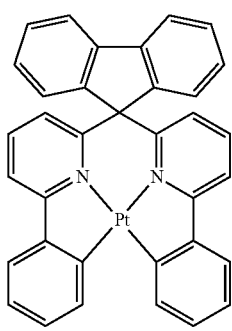
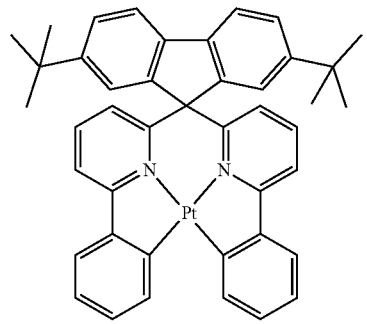
216
-continued
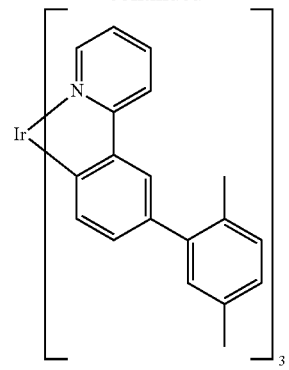
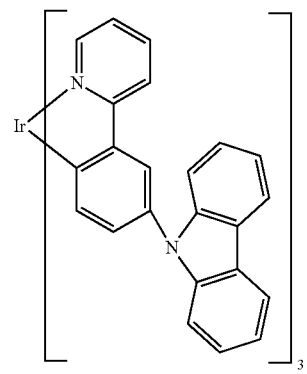
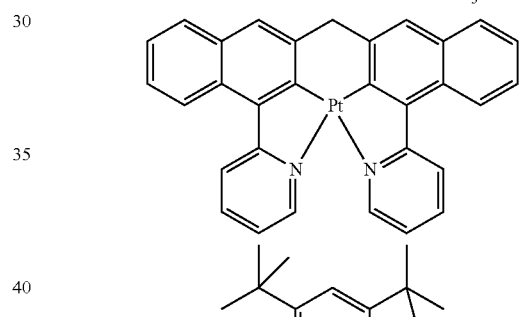
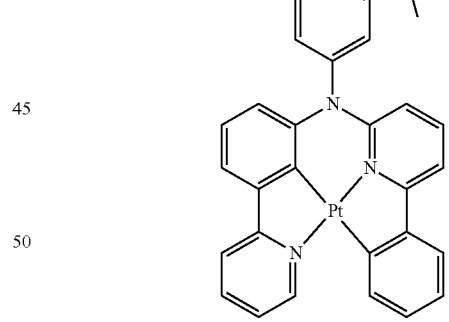
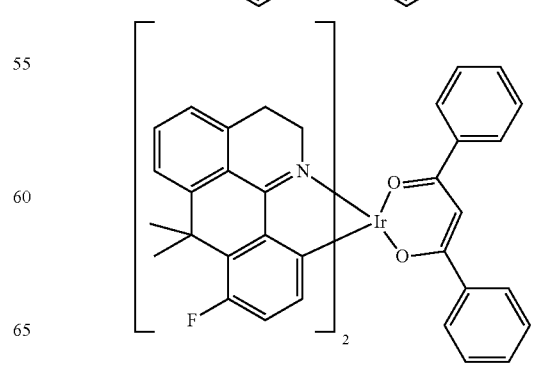

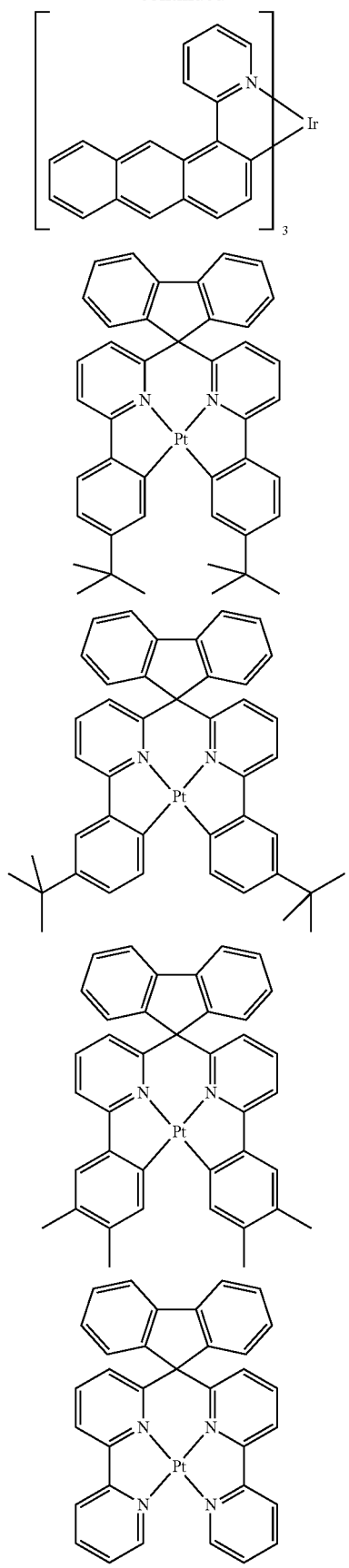
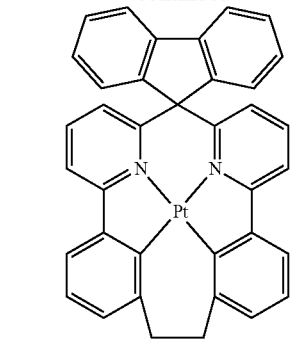
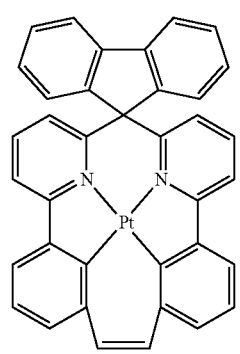
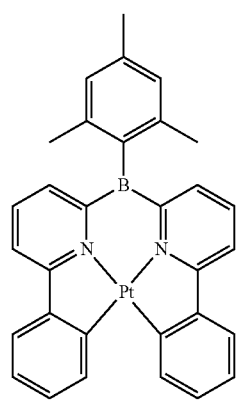
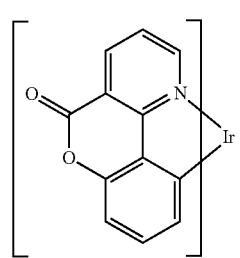
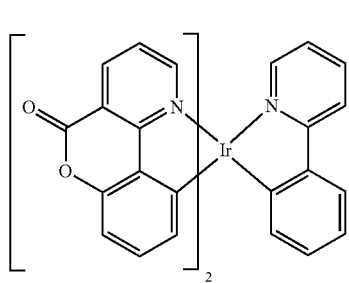

219
-continued
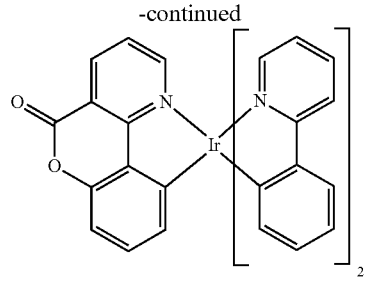
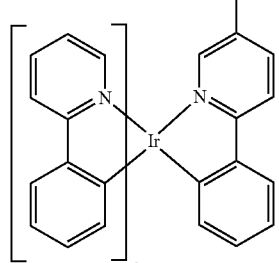
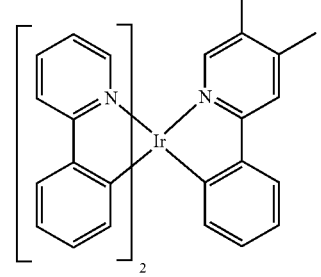
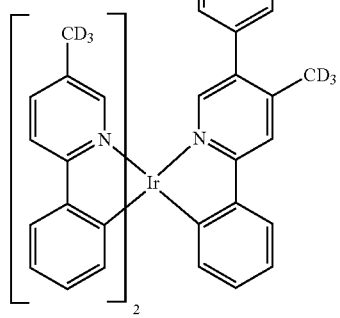
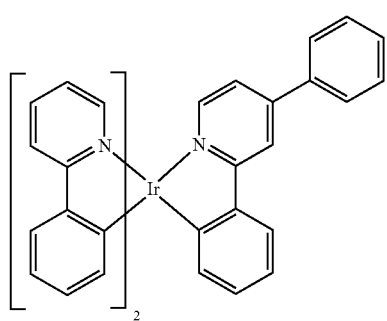
220
-continued
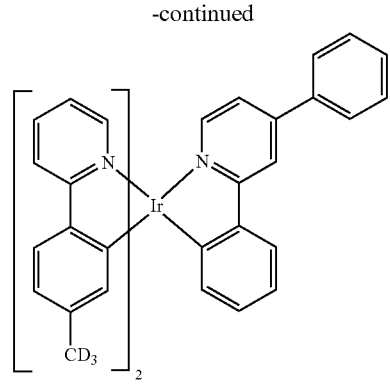
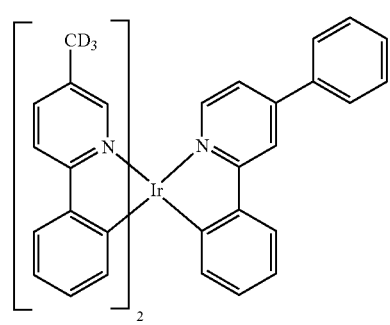
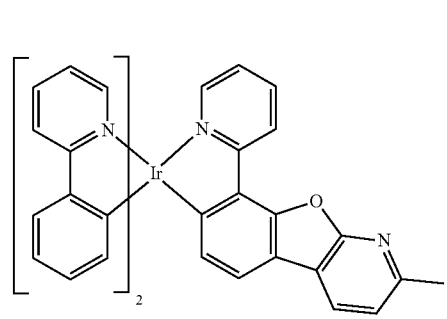
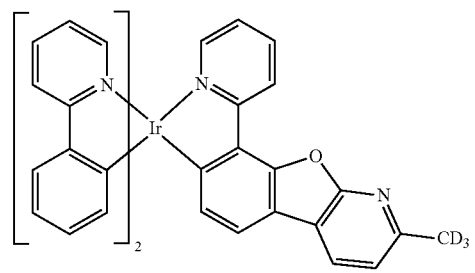
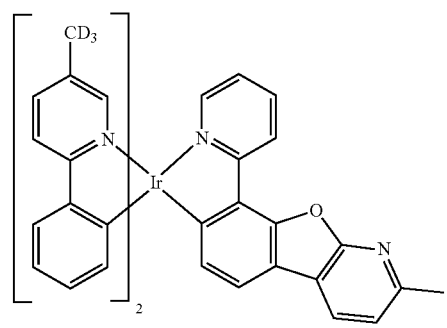

221
-continued
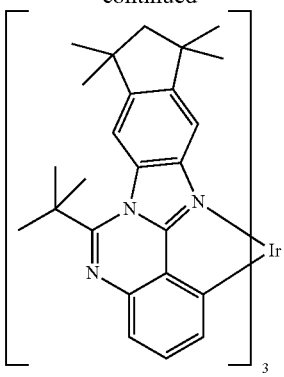
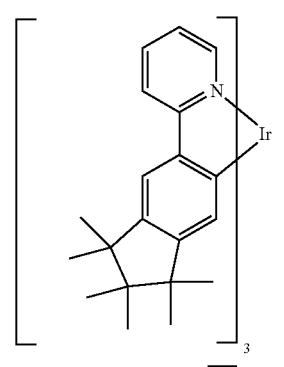
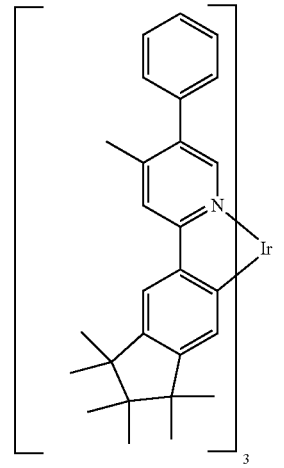
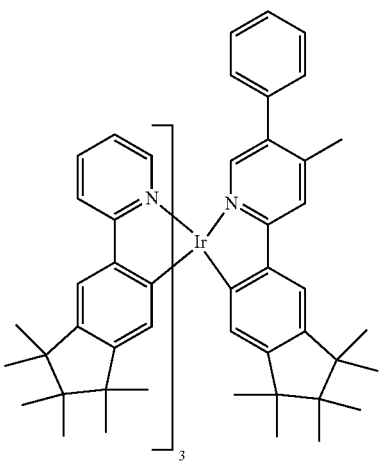
222
-continued
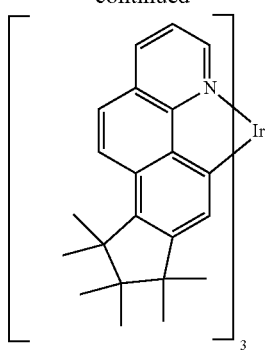
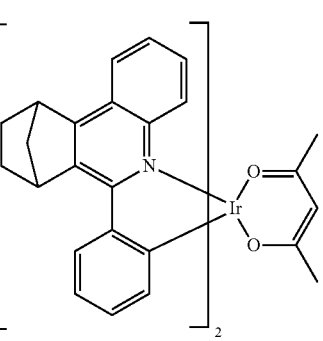
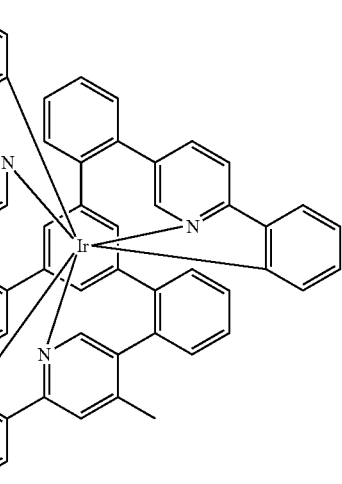
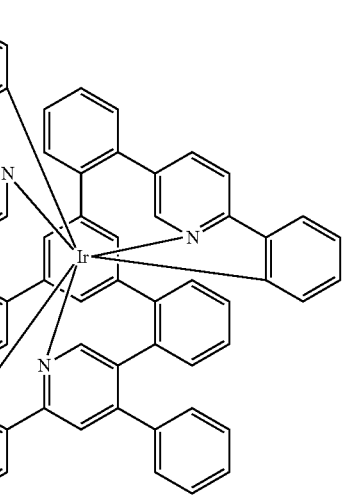

223
-continued
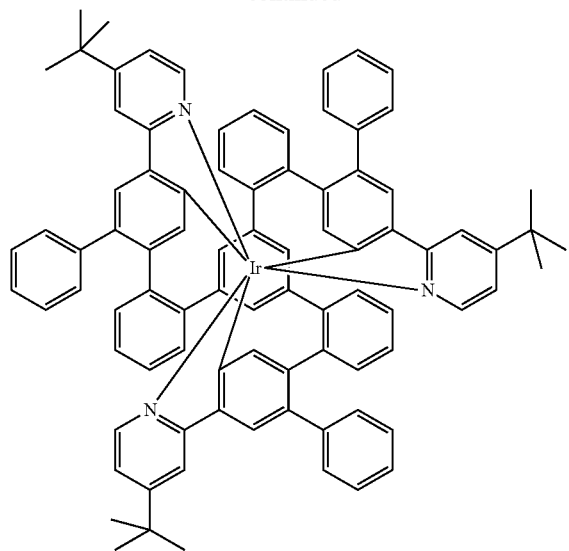
224
-continued
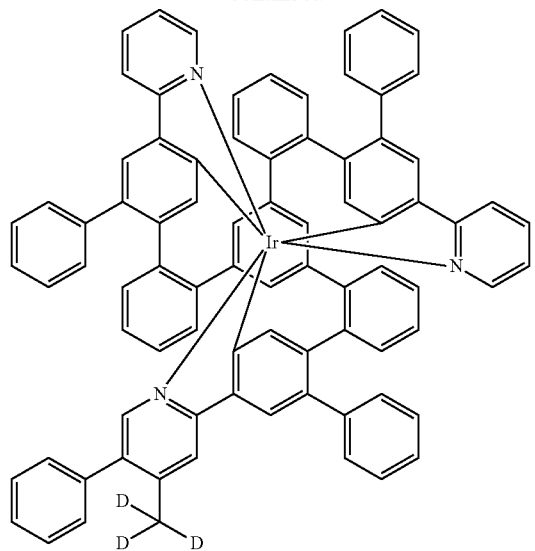
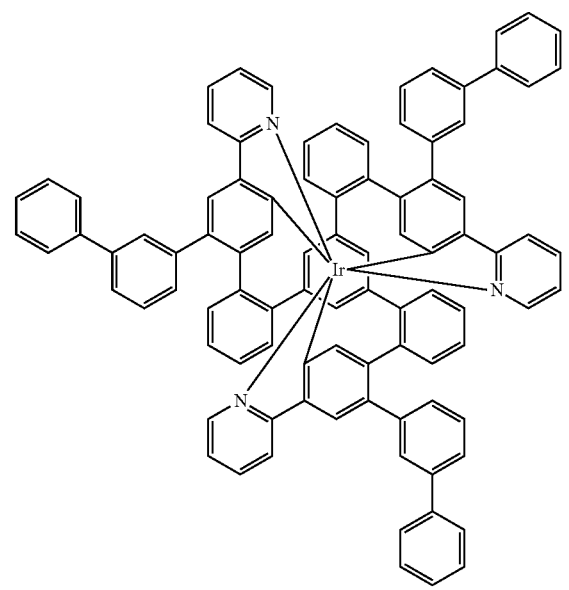
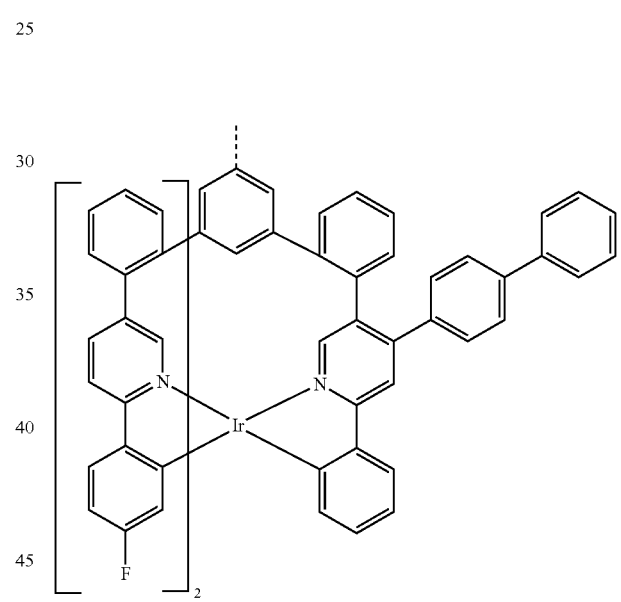
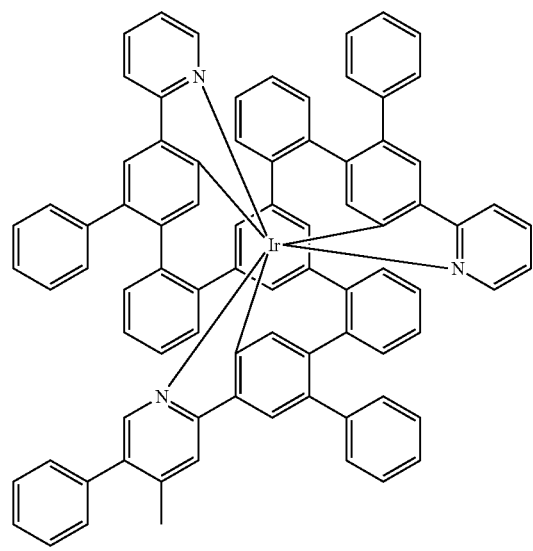
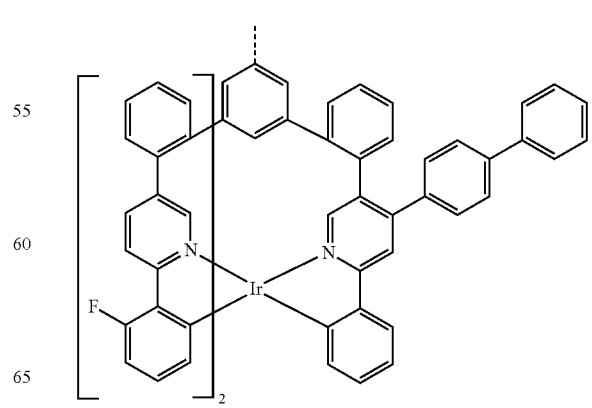

225
-continued
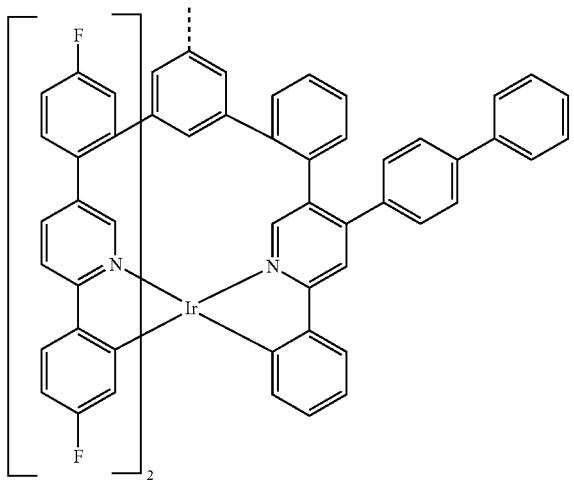
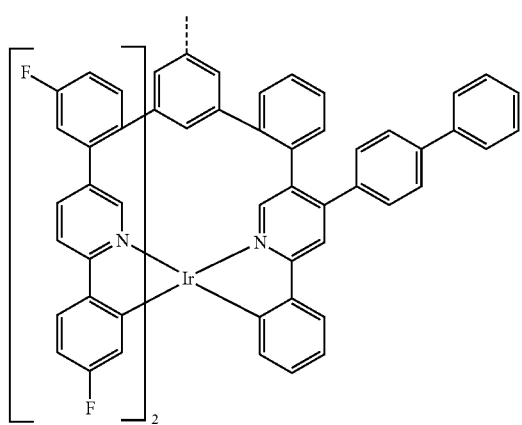
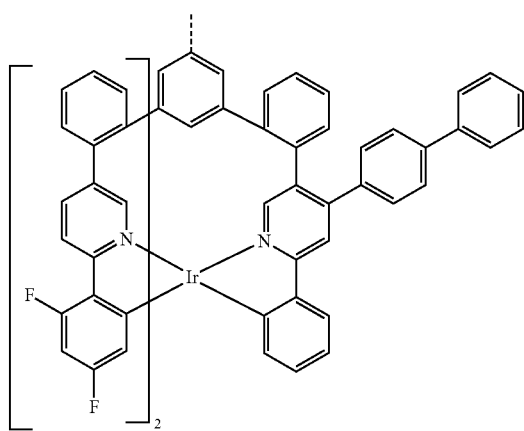
226
-continued
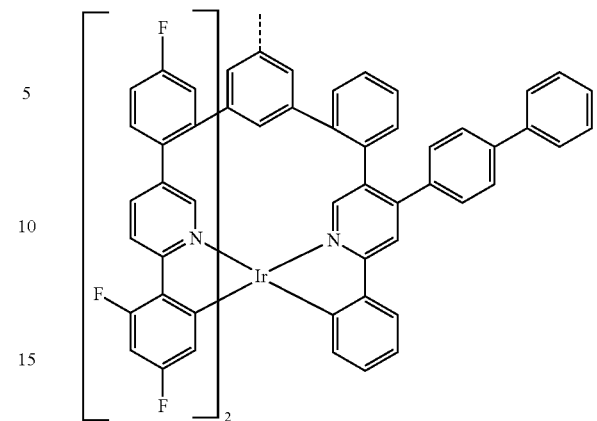
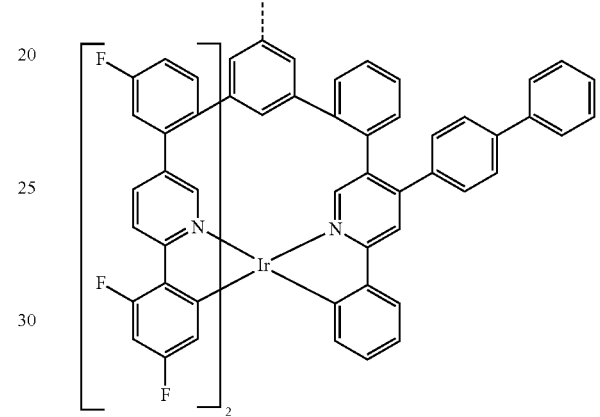
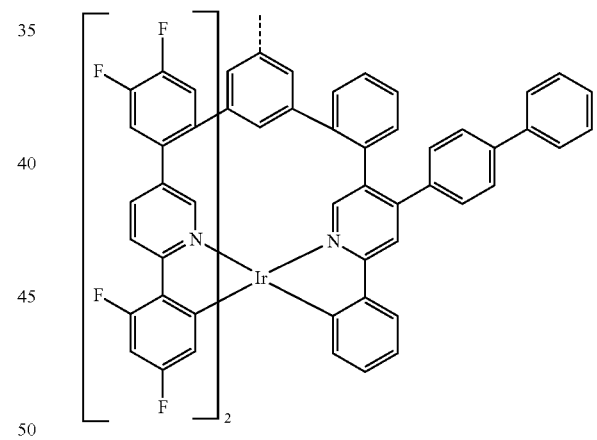
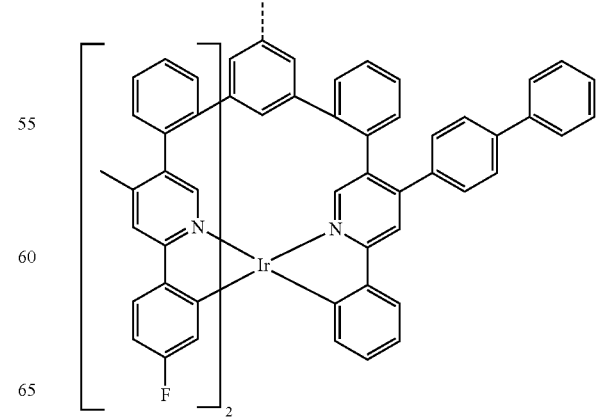

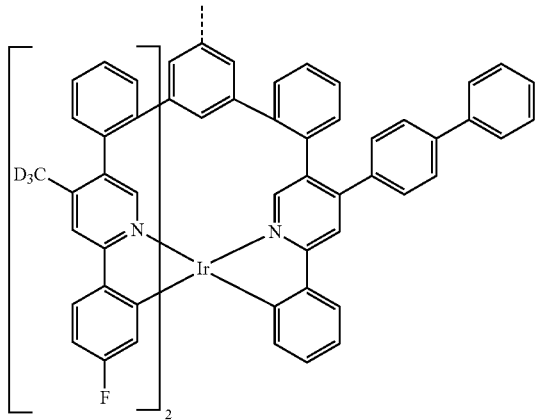
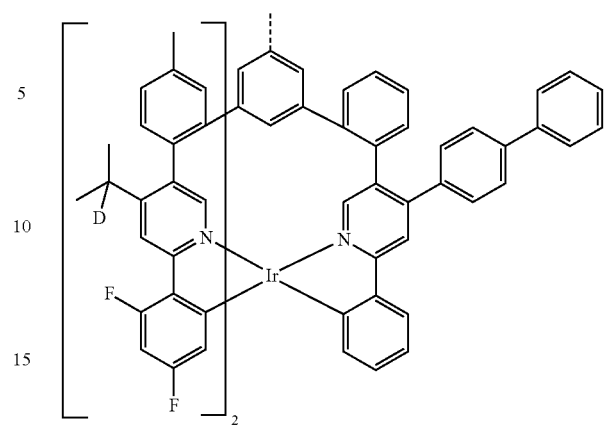
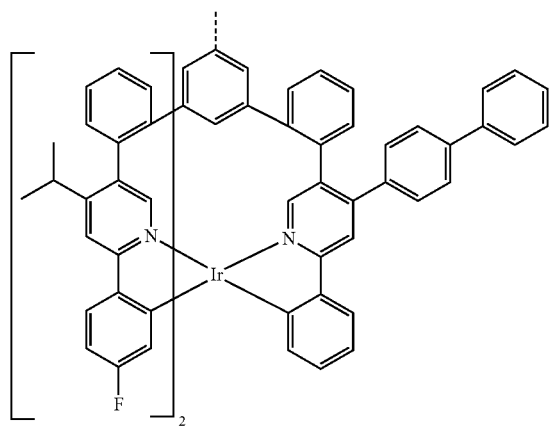
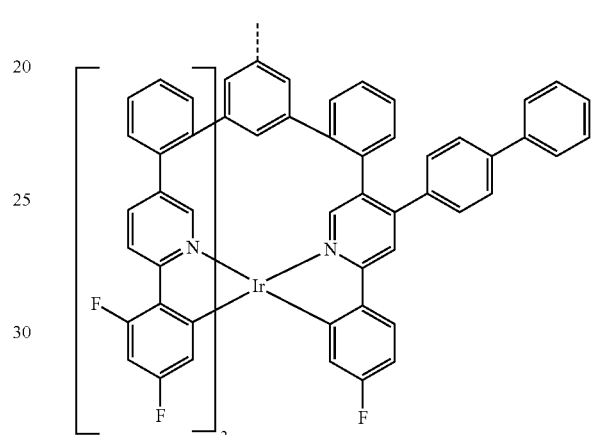
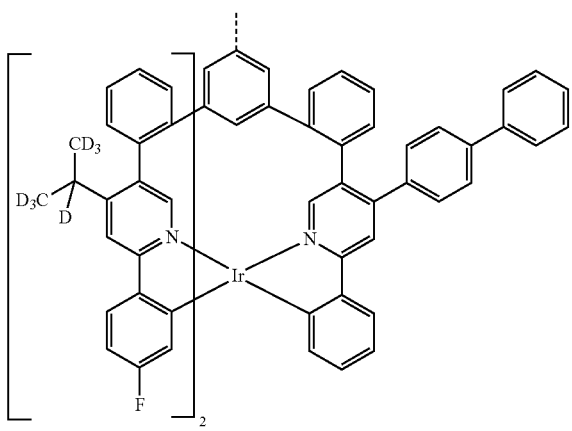
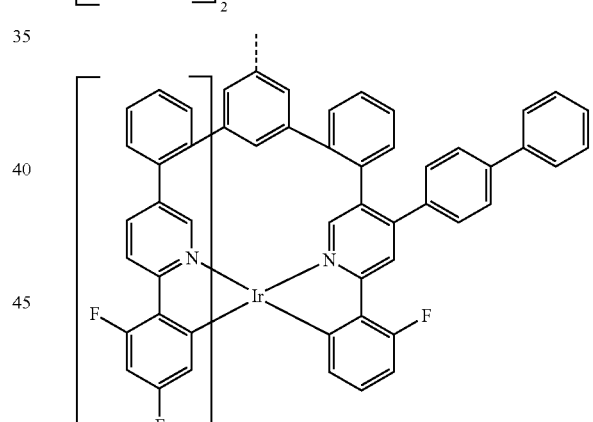
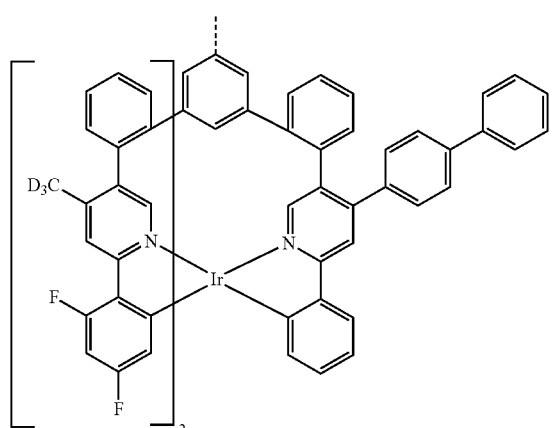
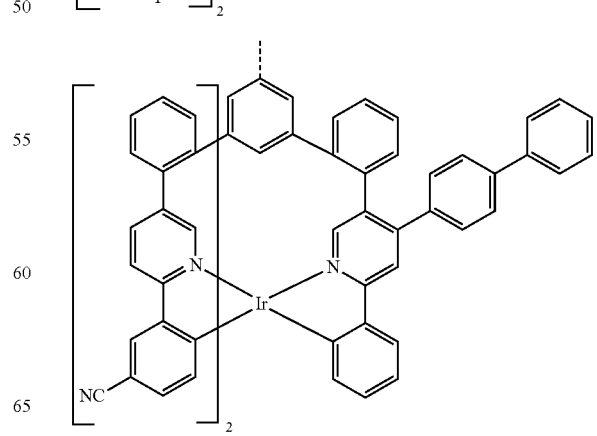

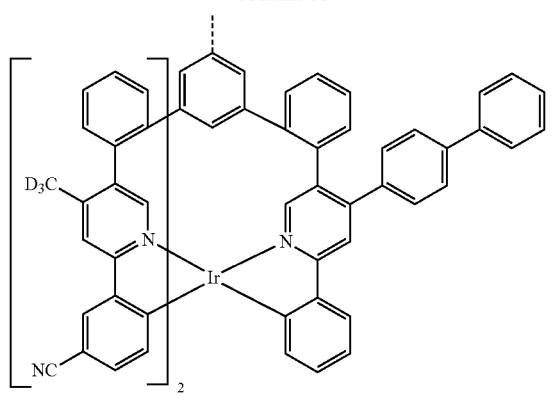
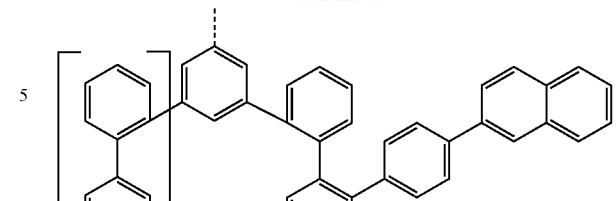
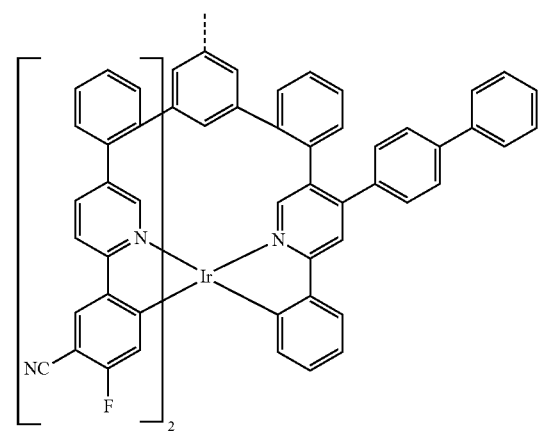
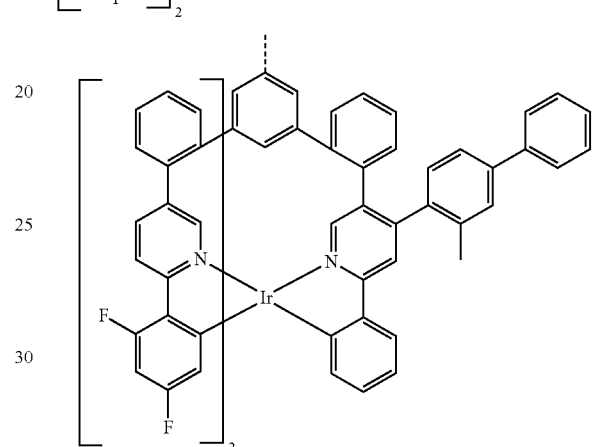
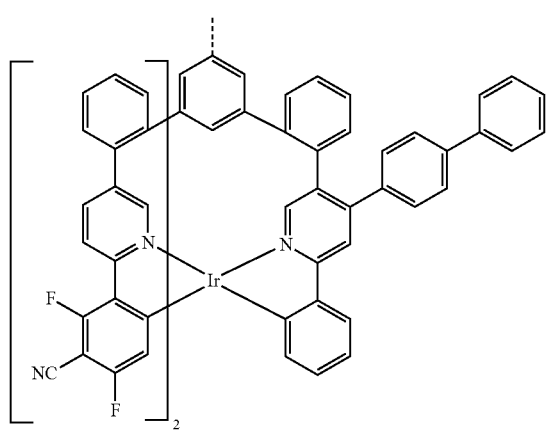
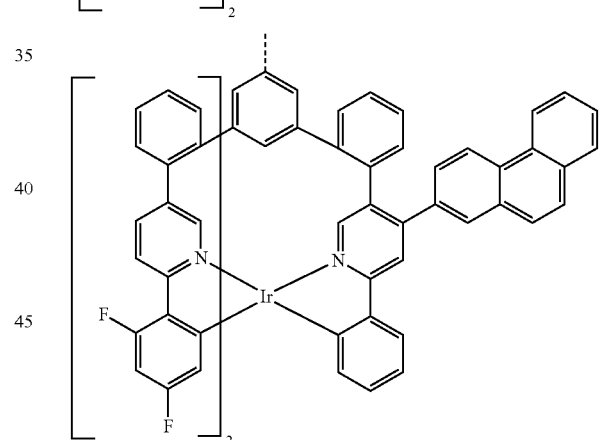
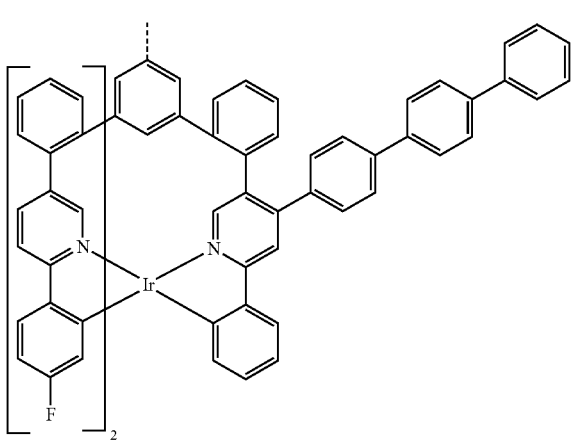
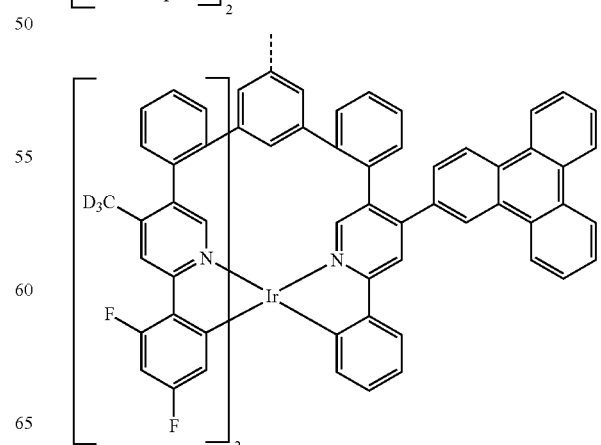

231
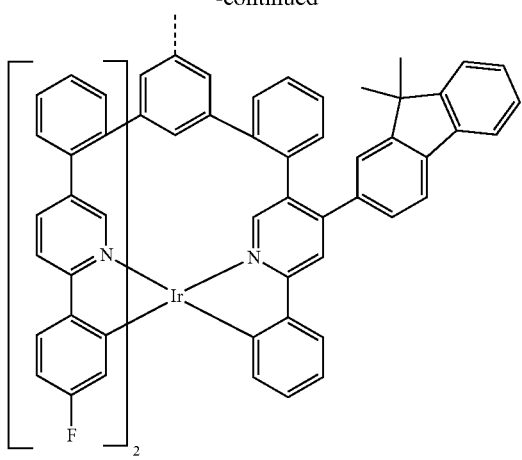
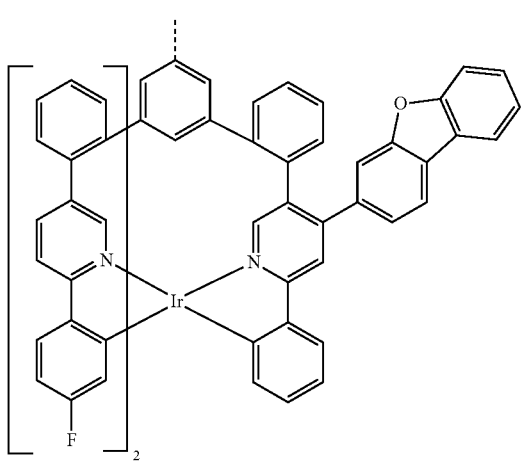
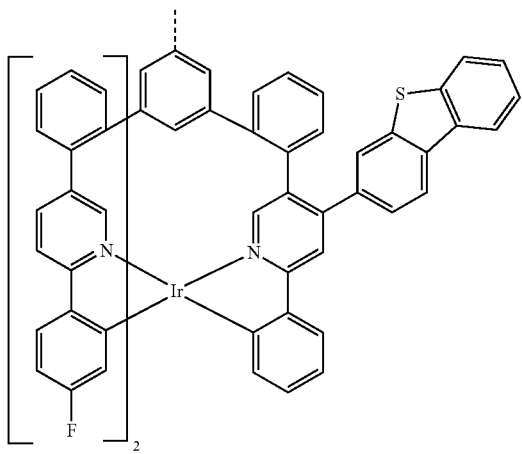
232
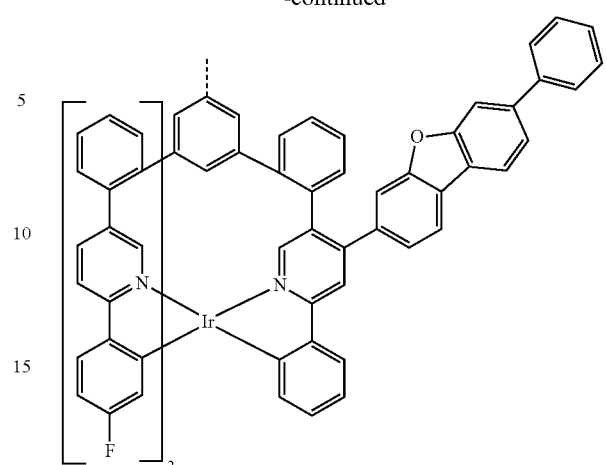
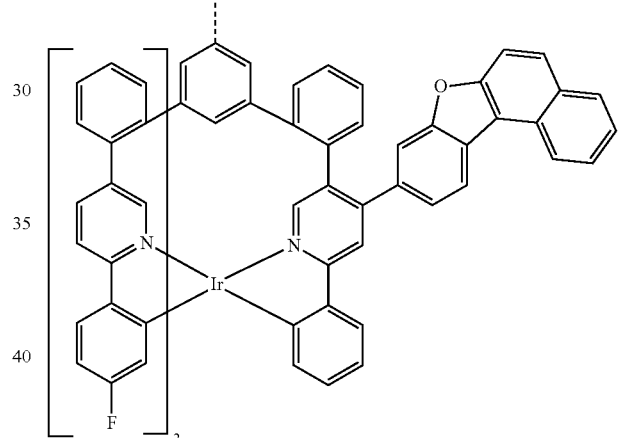
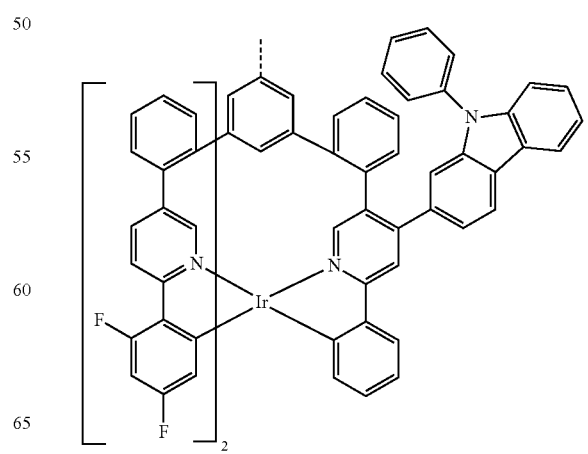

233
-continued
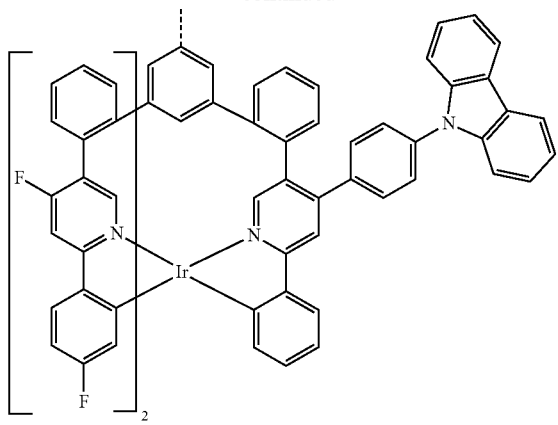
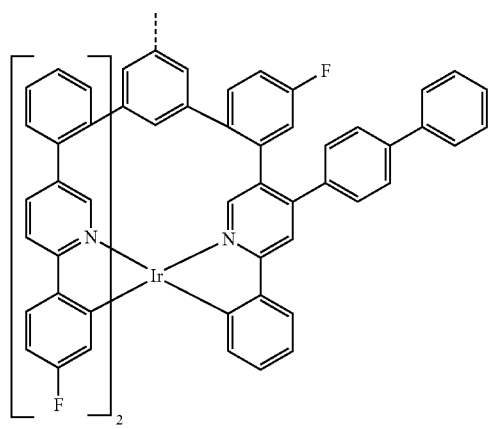
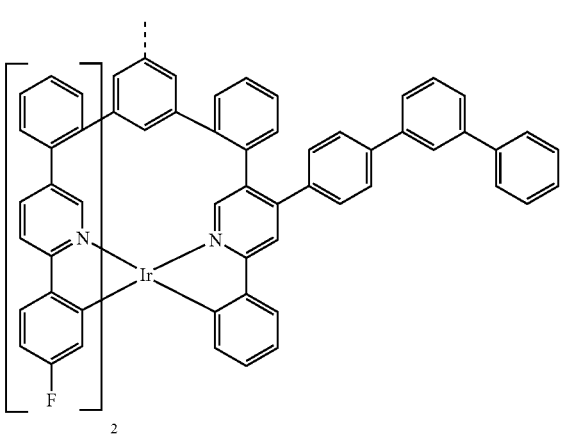
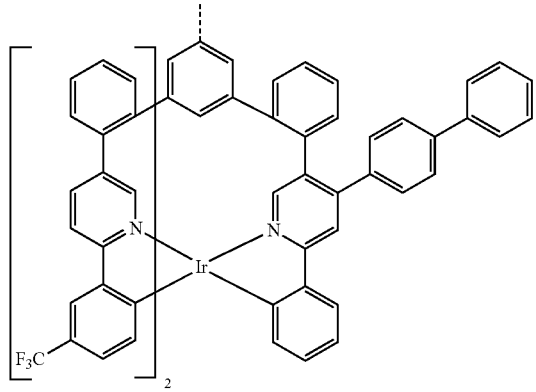
234
-continued
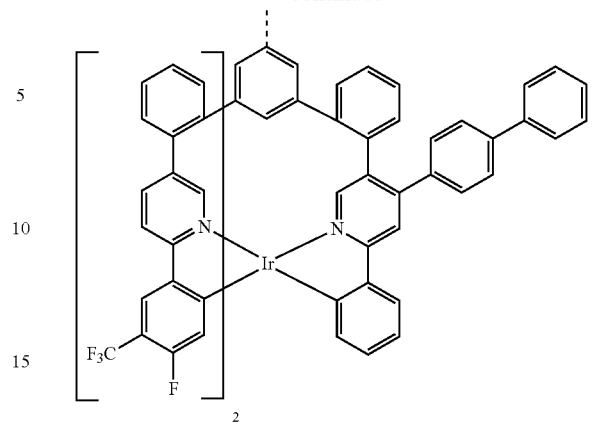
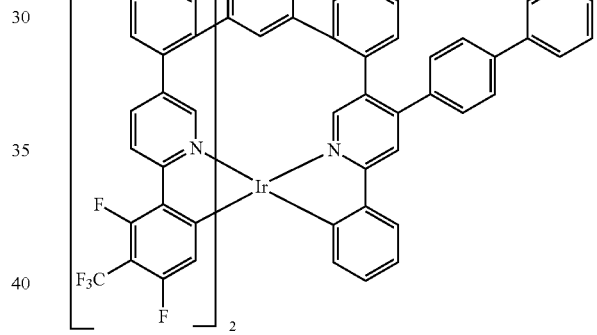
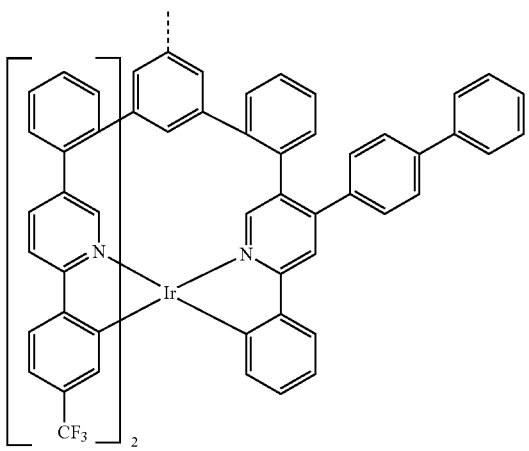

235
-continued

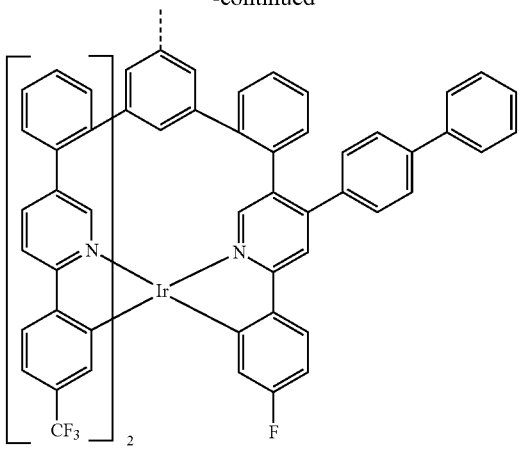

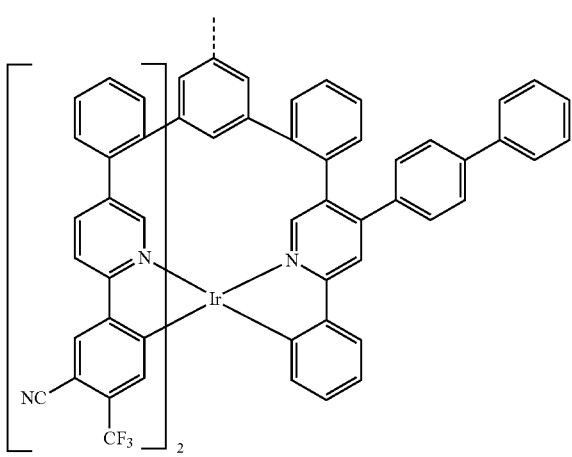

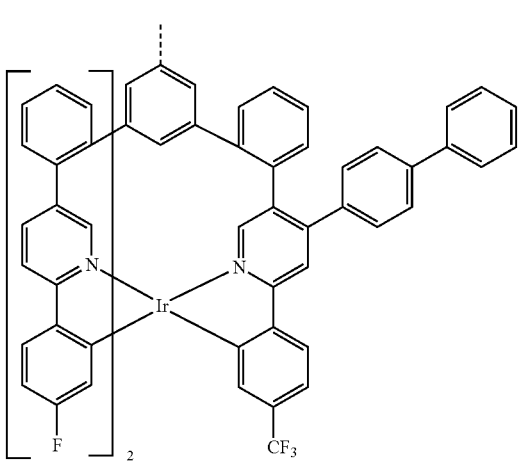

236
-continued

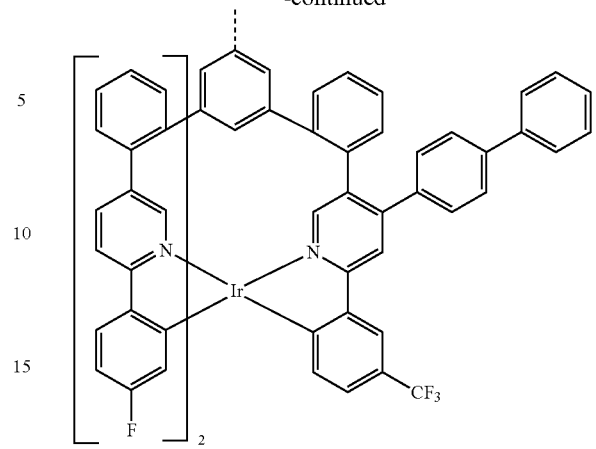

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixels, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition)

method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:
1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

Synthesis Examples

The syntheses which follow, unless stated otherwise, are conducted under protective gas atmosphere in dried solvents. The solvents and reagents can be purchased from ALDRICH or ABCR. The numbers given for the reactants that are not commercially available are the corresponding CAS numbers.

a) N-(2-Chlorophenyl)pyrido[1,2-a]benzimidazole-8-amine

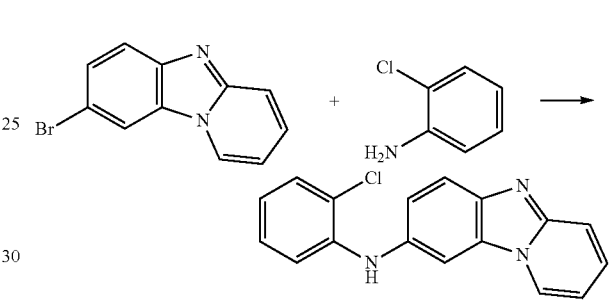

33 g (135 mmol) of 8-bromopyrido[1,2-a]benzimidazole, 68.2 g (710 mmol) of sodium tert-butoxide, 613 mg (3 mmol) of palladium(II) acetate and 3.03 g (5 mmol) of dppf are dissolved in 1.3 l of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 32 g (112 mmol); 82% of theory.

The following compounds can be prepared in an analogous manner:

| | Reactant 1 | Reactant 2 | Product | Yield |
|---|---|---|---|---|
| 1a | [2001623-01-2] | | | 77% |
| 2a | [2001622-99-5] | | | 79% |

-continued

| | Reactant 1 | Reactant 2 | Product | Yield |
|---|---|---|---|---|
| 3a | [2001623-04-5] | 2-chloroaniline | | 80% |
| 4a | [1821216-31-2] | 2-chloroaniline | | 75% |
| 5a | [1638528-29-6] | 2-chloroaniline | | 69% |
| 6a | [1445436-62-3] | 2-chloroaniline | | 88% |
| 7a | [136343-76-5] | 2-chloroaniline | | 83% |
| 8a | [1642587-46-9] | 2-chloroaniline | | 82% |

| | Reactant 1 | Reactant 2 | Product | Yield |
|---|---|---|---|---|
| 9a | [1445436-16-7] | | | 77% |
| 10a | [1445436-36-1] | | | 73% |
| 11a | [1368129-53-6] | | | 84% |
| 12a | [1821216-31-2] | | | 85% |
| 13a | [1821216-31-2] | 7285-66-7 | | 69% |
b) Cyclization
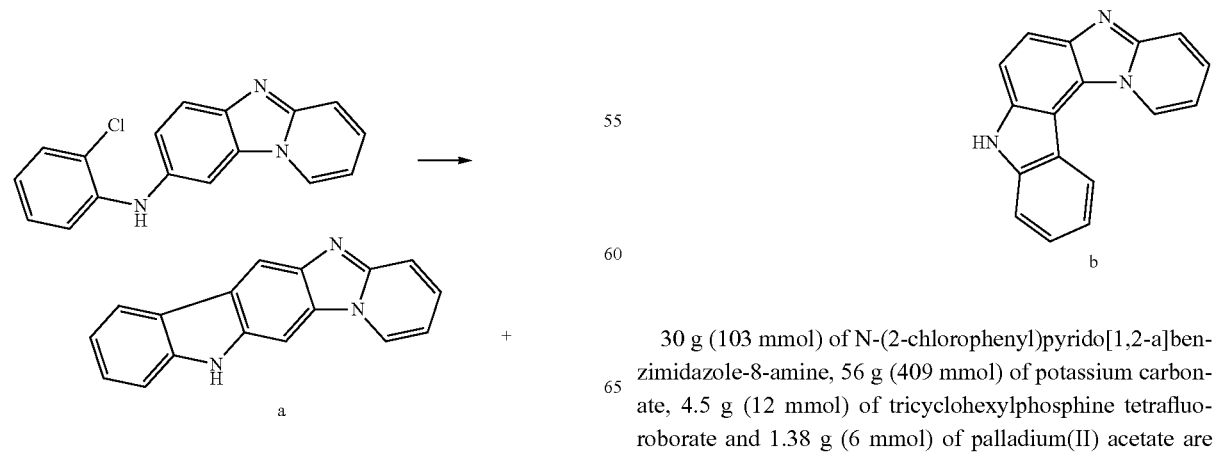
30 g (103 mmol) of N-(2-chlorophenyl)pyrido[1,2-a]benzimidazole-8-amine, 56 g (409 mmol) of potassium carbonate, 4.5 g (12 mmol) of tricyclohexylphosphine tetrafluoroborate and 1.38 g (6 mmol) of palladium(II) acetate are suspended in 500 ml of dimethylacetamide and stirred under reflux for 6 h. After cooling, the reaction mixture is stirred with 300 ml of water and 400 ml. The organic phase is separated off and filtered through a short Celite bed, and then the solvent is removed under reduced pressure. The crude product is subjected to hot extraction with toluene and recrystallized from toluene. Yield: 22.8 g (88 mmol) of the a+b mixture; 87% of theory; purity: 98.0% by HPLC. After recrystallization from EA/toluene (1:3) and subsequent workup, 60% a and 20% b are obtained.

The following compounds can be prepared in an analogous manner:

| | Reactant | Product a | Product b | Yield a, b |
|---|---|---|---|---|
| 1b | | | | 58%, 18% |
| 2b | | | | 65%, 13% |
| 3b | | | | 78% |
| 4b | | | | 61%, 19% |
| 5b | | | | 57%, 12% |
| 6b | | | | 80% |

-continued

| Reactant | Product a | Product b | Yield a, b |
|---|---|---|---|
| 7b | | | 64%, 11% |
| 8b | | | 63%, 13% |
| 9b | | | 60%, 15% |
| 10b | | | 81% |
| 11b | | | 57%, 16% |

-continued

| Reactant | Product a | Product b | Yield a, b |
|---|---|---|---|
| 12b | | | 50% 18% | c) Buchwald Coupling

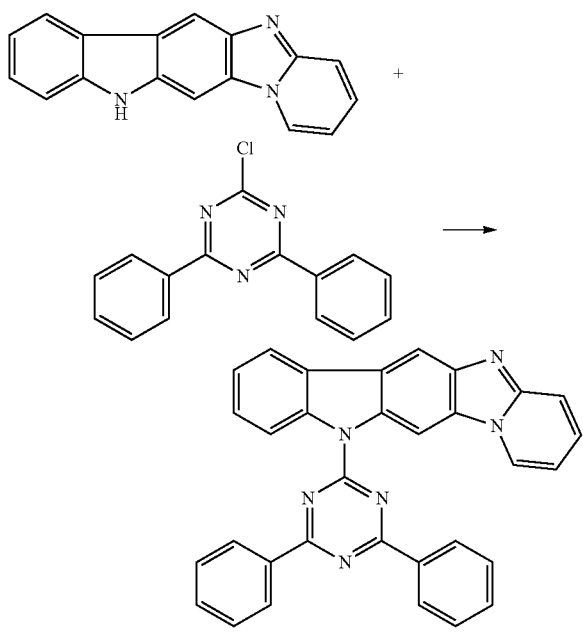

4.2 g (106 mmol) of 60% NaH in mineral oil is dissolved in 300 ml of dimethylformamide under protective atmosphere. 279 g (106 mmol) of compound (b a) is dissolved in 250 ml of DMF and added dropwise to the reaction mixture. After 1 h at room temperature, a solution of 2-chloro-4,6-diphenyl-[1,3,5]-triazine (34.5 g, 0.122 mol) in 200 ml of THF is added dropwise. The reaction mixture is stirred at room temperature for 12 h and then poured onto ice. After warming to room temperature, the solids that precipitate out are filtered and washed with ethanol and heptane. The residue is subjected to hot extraction with toluene, recrystallized from toluene/n-heptane and finally sublimed under high vacuum. The purity is 99.9%. The yield is 43 g (89 mmol), corresponding to 83% of theory.

The following compounds can be prepared in an analogous manner:

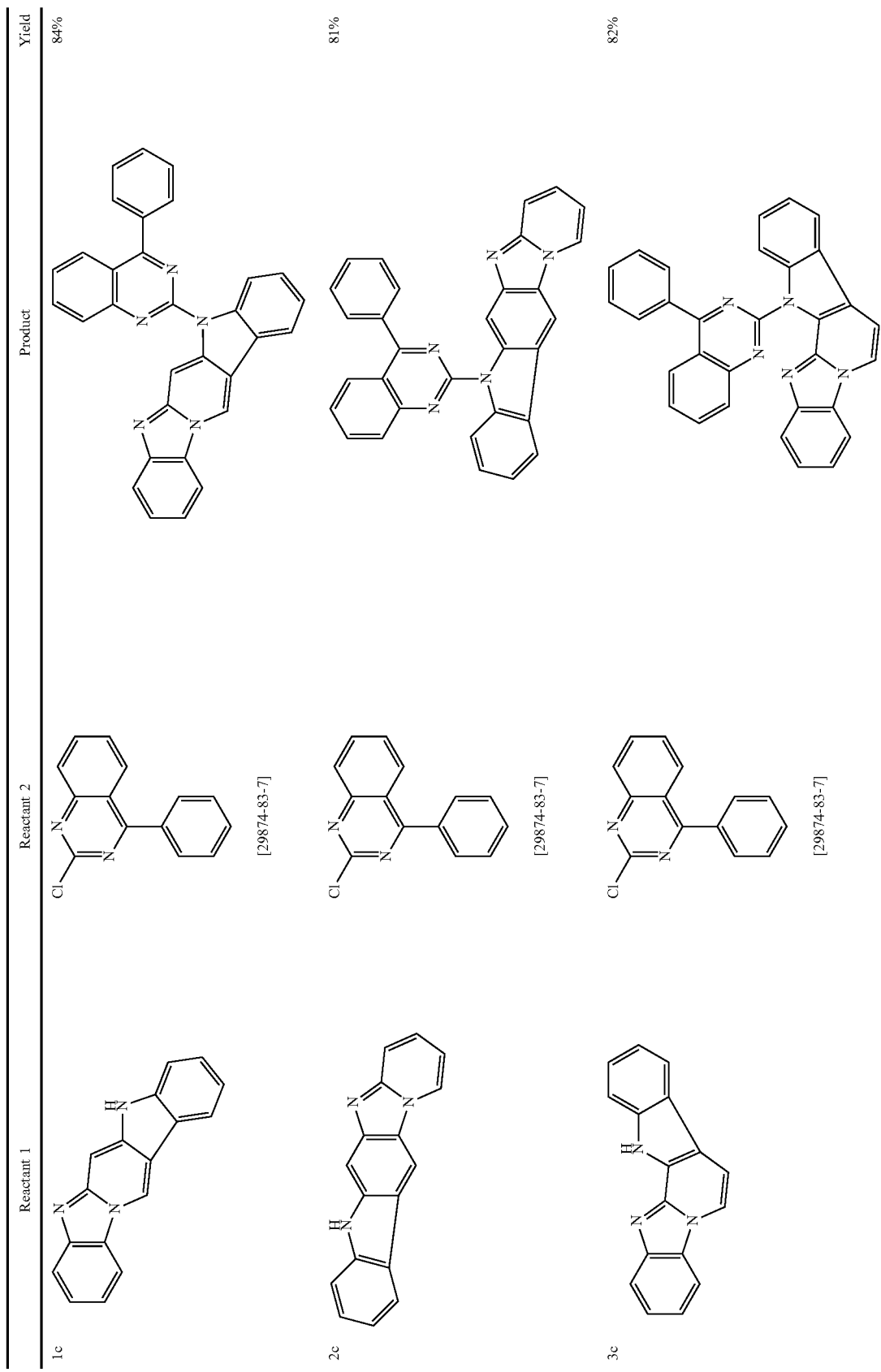

-continued

| | Reactant 1 | Reactant 2 | Product | Yield |
|---|---|---|---|---|
| 4c | | [29874-83-7] | | 82% |
| 5c | | [29874-83-7] | | 85% |

| | Reactant 1 | Reactant 2 | Product | Yield |
|---|---|---|---|---|
| 6c | | [29874-83-7] | | 75% |
| 7c | | [3842-55-5] | | 74% |

-continued

| | Reactant 1 | Reactant 2 | Product | Yield |
|---|---|---|---|---|
| 8c | | [760212-40-6] | | 73% |
| 9c | | [29874-83-7] | | 77% |

| | Reactant 1 | Reactant 2 | Product | Yield |
|---|---|---|---|---|
| 10c | | [29874-83-7] | | 76% |
| 11c | | [1373265-66-7] | | 68% |

| | Reactant 1 | Reactant 2 | Product | Yield |
|---|---|---|---|---|
| 12c | | [1373317-91-9] | | 75% |
| 13c | | [643017-61-2] | | 82% |

| | Reactant 1 | Reactant 2 | Product | Yield |
|---|---|---|---|---|
| 14c | 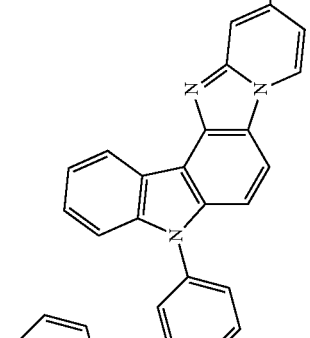 | 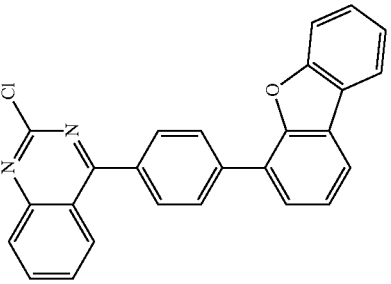 [1403252-58-3] | 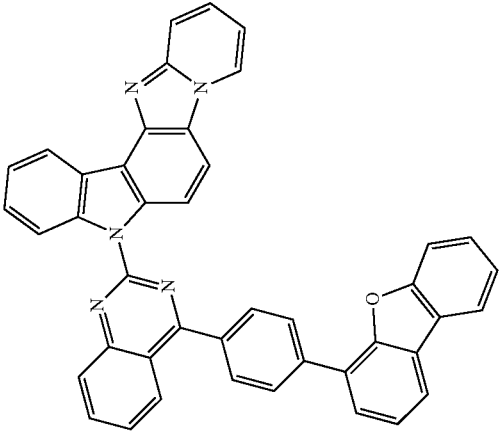 | 87% |
| 15c | 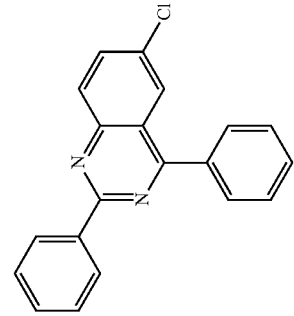 | 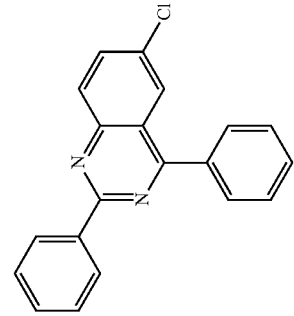 [30169-34-7] | 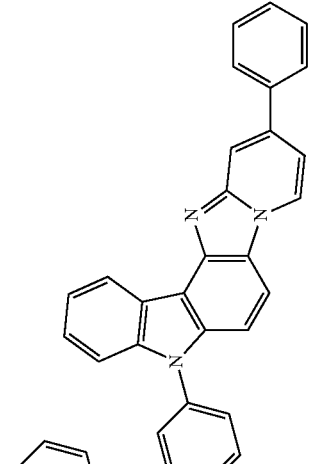 | 70% |

-continued

| | Reactant 1 | Reactant 2 | Product | Yield |
|---|---|---|---|---|
| 16c | | [1616499-38-7] | | 73% |
| 17c | | [3842-55-5] | | 79% |
| 18c | | [1292317-90-8] | | 71% |

| | Reactant 1 | Reactant 2 | Product | Yield |
|---|---|---|---|---|
| 19c | 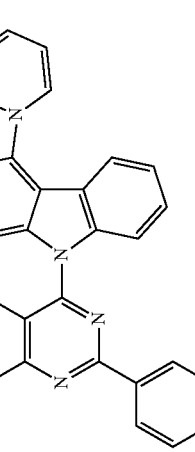 | 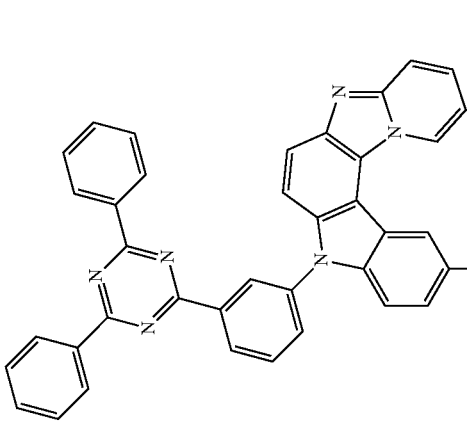 [6484-25-9] | 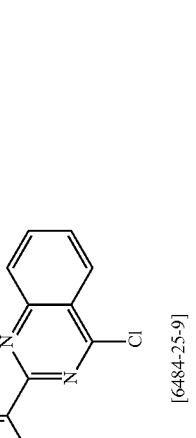 | 65% |
| 20c | 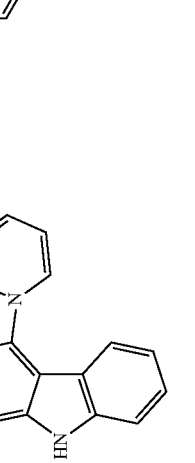 | 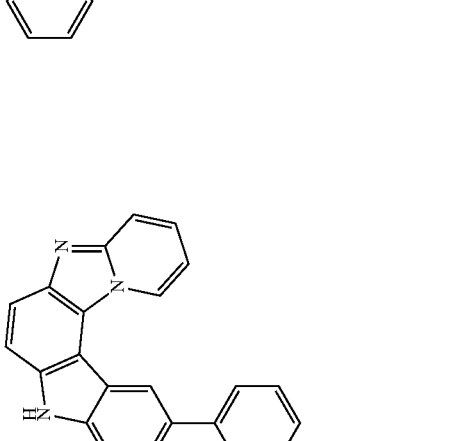 |  | 66% |

-continued

| | Reactant 1 | Reactant 2 | Product | Yield |
|---|---|---|---|---|
| 21c | [73157-31-0] | [1644054-73-8] | | 65% |
| 22c | [2202757-51-3] | 1384480-21-0 | | 62% |

| | Reactant 1 | Reactant 2 | Product | Yield |
|---|---|---|---|---|
| 23c | 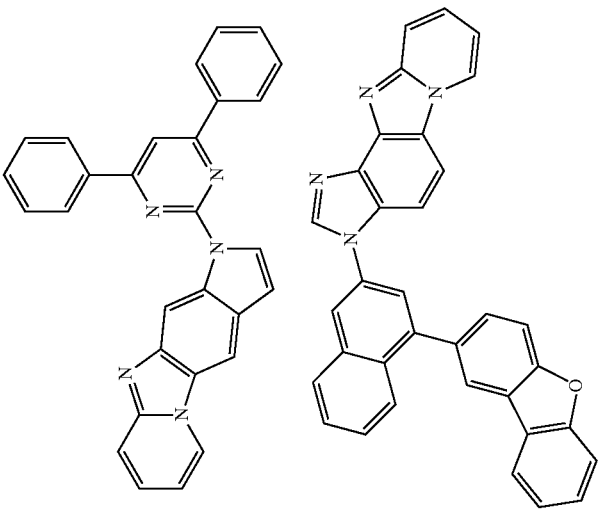 [879097-41-3] | 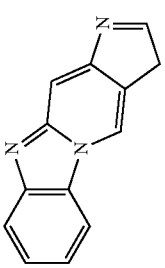 2915-16-4 | 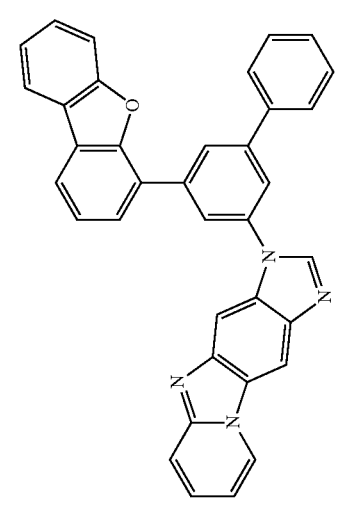 | 60% |
| 24c | 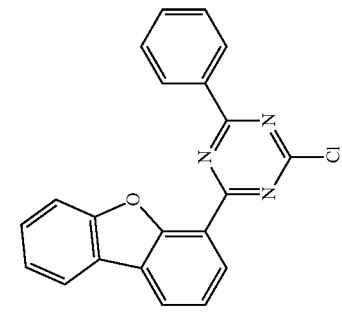 [73157-31-0] | 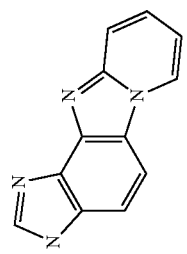 [1616499-38-7] | | 63% |
| 25c | 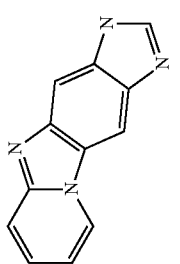 [73157-32-1] | | | 68% |

-continued

| | Reactant 1 | Reactant 2 | Product | Yield |
|---|---|---|---|---|
| 26c | | [29874-83-7] | | 76% |
| 27c | | 1404211-88-6 | | 70% |
| 28c | | 1404211-88-6 | | 72% | d) 2-[(Z)-(1-Phenylindolin-3-ylidene)methyl]-3-vinylimidazo[1,2-a]pyridine

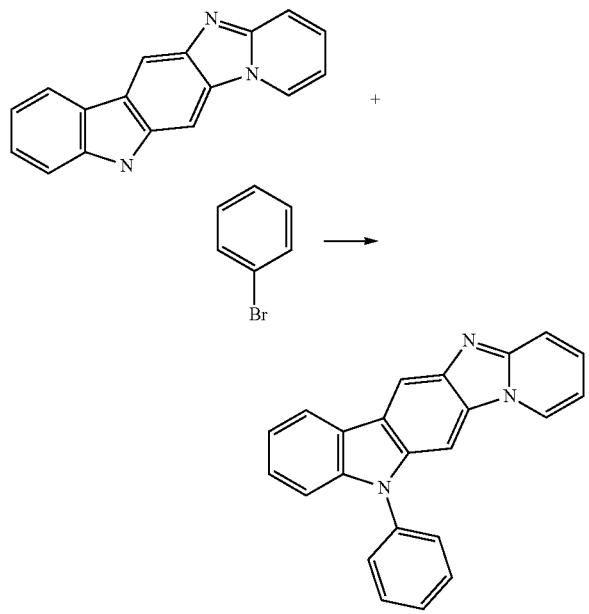

14 g (51 mmol) of 2-[(Z)-indolin-3-ylidenemethyl]-3-vinylimidazo[1,2-a]pyridine and 8.4 g (54 mmol) of bromobenzene are dissolved in 400 ml of toluene under an argon atmosphere. 1.0 g (5 mmol) of tri-tert-butylphosphine is added and the mixture is stirred under an argon atmosphere. 0.6 g (2 mmol) of Pd(OAc)$_2$ is added and the mixture is stirred under an argon atmosphere, and then 9.5 g (99 mmol) of sodium tert-butoxide are added. The reaction mixture is stirred under reflux for 24 h. After cooling, the organic phase is separated, washed three times with 200 ml of water, dried over MgSO$_4$ and filtered, and the solvent is removed under reduced pressure. The residue is purified by column chromatography using silica gel (eluent: DCM/heptane (1:3)). The residue is subjected to hot extraction with toluene, recrystallized from toluene/n-heptane and finally sublimed under high vacuum. The yield is 16.1 g (46 mmol), corresponding to 90% of theory.

The following compounds are obtained in an analogous manner:

| | Reactant 1 | Reactant 2 | Product | Yield |
|---|---|---|---|---|
| 1d | | [1505512-86-6] | | 75% |
| 2d | | CAS 1153-85-1 | | 80% |

-continued

| | Reactant 1 | Reactant 2 | Product | Yield |
|---|---|---|---|---|
| 3d | | [1225053-54-2] | | 81% |
| 4d | | CAS 212385-73-4 | | 76% |
| 5d | | | | 83% |

-continued

| | Reactant 1 | Reactant 2 | Product | Yield |
|---|---|---|---|---|
| 6d | 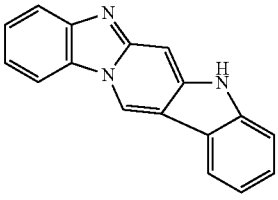 [SMILES: c1ccc2c(c1)nc1cc3[nH]c4ccccc4c3cn12] | 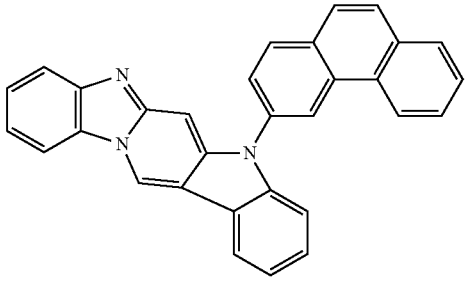 [SMILES: c1ccc2c(c1)ccc1ccc(-n3c4ccccc4c4cn5c(cc43)nc3ccccc35)cc12]\n[715-50-4] | 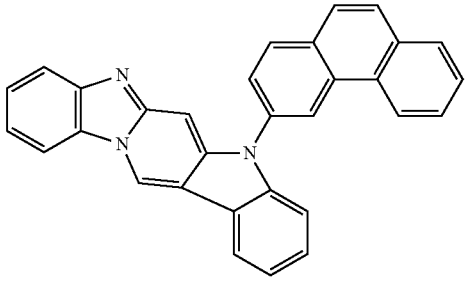 [SMILES: c1ccc2c(c1)ccc1ccc(-n3c4ccccc4c4cn5c(cc43)nc3ccccc35)cc12] | 78% |
| 7d | 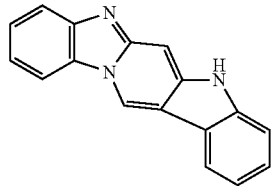 [SMILES: c1ccc2c(c1)nc1cc3[nH]c4ccccc4c3cn12] | 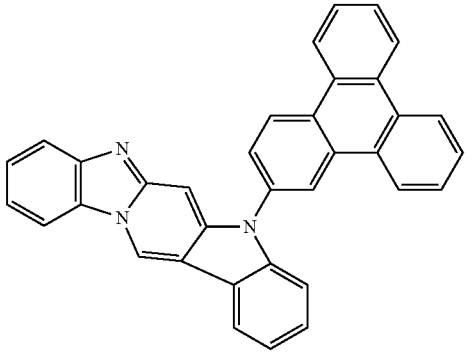 [SMILES: c1ccc2c(c1)nc1cc3c(cn12)c1ccccc1n3-c1ccc2c3ccccc3c3ccccc3c2c1]\n[19111-87-6] | 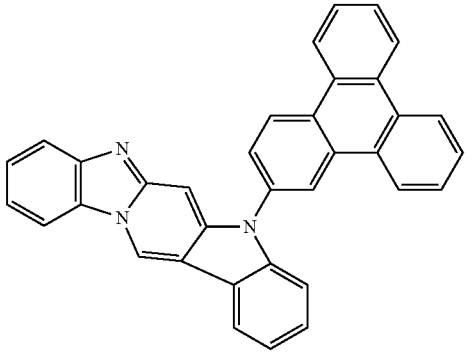 [SMILES: c1ccc2c(c1)nc1cc3c(cn12)c1ccccc1n3-c1ccc2c3ccccc3c3ccccc3c2c1] | 79% | e) Bromination

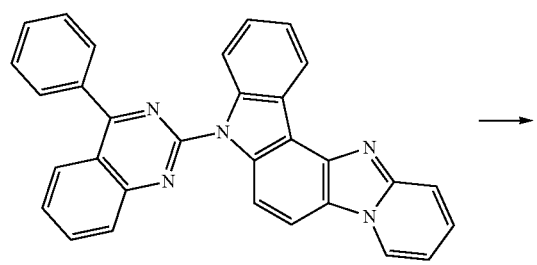

↓

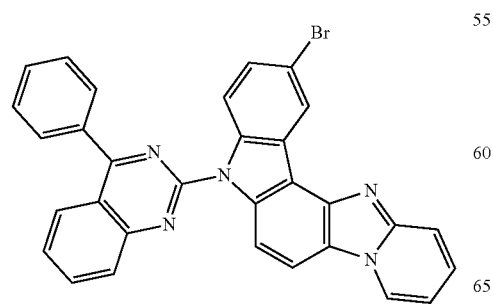

739 g (190 mmol) of compound 25c is suspended in 1800 ml of DMF. 34 g (190 mmol) of NBS is added to this suspension in portions and the mixture is stirred in the dark for 2 h. Thereafter, water/ice is added and the solids are removed and washed with ethanol. The isomers are separated by recrystallization. The yield is 60 g (129 mmol), corresponding to 70% of theory.

The following compounds are prepared in an analogous manner:

| Reactant | Product | Yield |
|---|---|---|
| 1e | | 59% |
| 2e | | 56% |
| 3e | | 57% |
| 4e | | 55% | f) Suzuki Reaction

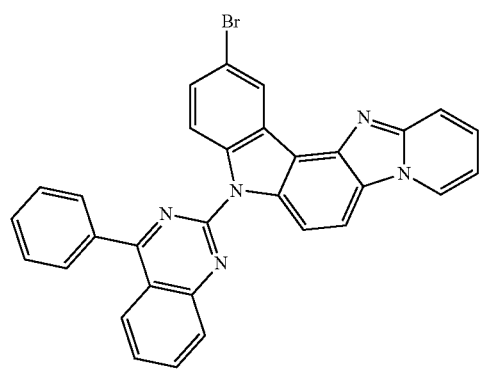

+

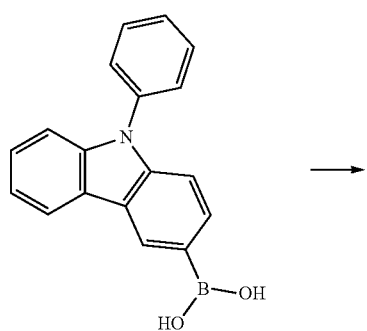

→

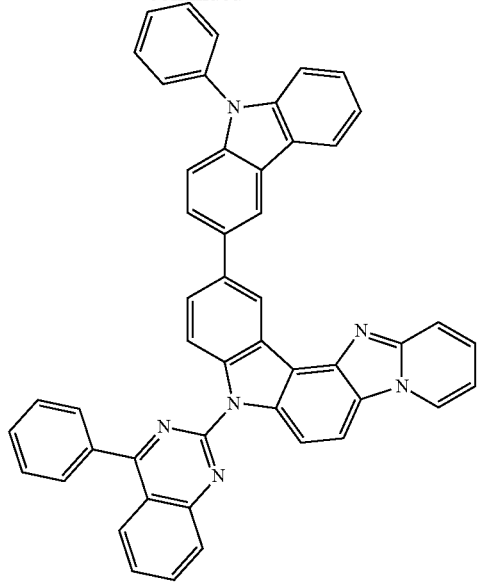

71 g (154 mmol) of compound e, 50 g (172 mmol) of N-phenylcarbazole-3-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The yield is 73 g (104 mmol), corresponding to 68% of theory.

The following compounds are prepared in an analogous manner:

| | Reactant 1 | Reactant 2 | Product | Yield |
|---|---|---|---|---|
| 1j | | | | 57% |
| 2j | | | | 60% |

| Reactant 1 | Reactant 2 | Product | Yield |
|---|---|---|---|
| 3j | [1001911-63-2] | | 64% |
| 4j | [1642121-58-1] | | 59% |
| 5j | [1572537-61-1] | | 78% |

| Reactant 1 | Reactant 2 | Product | Yield |
|---|---|---|---|
| 6j 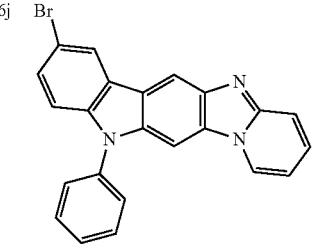 | 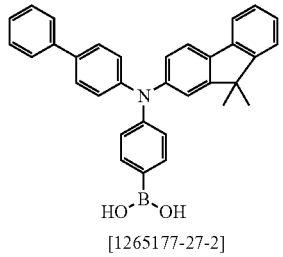 [SMILES: CC1(C)c2ccccc2-c2ccc(N(c3ccc(B(O)O)cc3)c3ccc(-c4ccccc4)cc3)cc21] [1265177-27-2] | 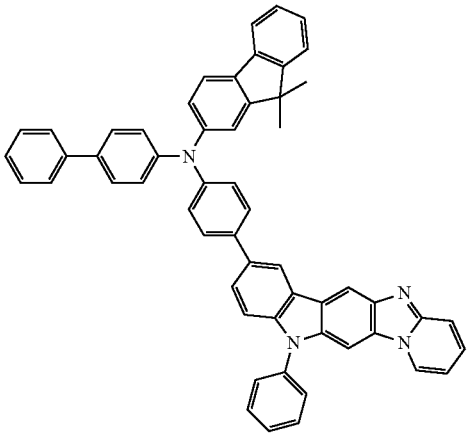 [SMILES: CC1(C)c2ccccc2-c2ccc(N(c3ccc(-c4ccccc4)cc3)c3ccc(-c4ccc5c(c4)c4cc6nc7ccccn7c6cc4n5-c4ccccc4)cc3)cc21] | 56% |

Production of the OLEDs

Examples E1 to E6 which follow (see table 1) present the use of the materials of the invention in OLEDs.

Pretreatment for examples E1-E6: Glass plaques coated with structured ITO (indium tin oxide) of thickness 50 nm are treated prior to coating with an oxygen plasma, followed by an argon plasma. These plasma-treated glass plaques form the substrates to which the OLEDs are applied. The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC2:TER5 (55%:35%:10%) mean here that the material IC1 is present in the layer in a proportion by volume of 55%, IC2 in a proportion by volume of 35% and TER5 in a proportion by volume of 10%. Analogously, the electron transport layer may also consist of a mixture of two materials.

The OLEDs are characterized in a standard manner. The electroluminescence spectra are determined at a luminance of 1000 cd/m$^2$, and the CIE 1931 x and y color coordinates are calculated therefrom.

Use of Materials of the Invention in OLEDs

The materials of the invention can be used in the emission layer in phosphorescent red OLEDs. The inventive compounds EG1 to EG6 can be used in examples E1 to E6 as matrix material in the emission layer. The color coordinates of the electroluminescence spectra of the OLEDs from these experiments are CIEx=0.67 and CIEy=0.33. The materials are thus suitable for use in the emission layer of red OLEDs.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| E1 | HATCN 5 nm | SpMA1 125 nm | SpMA3 10 nm | EG1:TER5 (95%:5%) 40 nm | — | ST2:LiQ (50%:50%) 35 nm | — |
| E2 | HATCN 5 nm | SpMA1 125 nm | SpMA3 10 nm | EG2:TER5 (95%:5%) 40 nm | — | ST2:LiQ (50%:50%) 35 nm | — |
| E3 | HATCN 5 nm | SpMA1 125 nm | SpMA3 10 nm | EG3:IC2:TER5 (60%:35%:5%) 40 nm | — | ST2:LiQ (50%:50%) 35 nm | — |
| E4 | HATCN 5 nm | SpMA1 125 nm | SpMA3 10 nm | EG4:TER5 (95%:5%) 40 nm | — | ST2:LiQ (50%:50%) 35 nm | — |
| E5 | HATCN 5 nm | SpMA1 125 nm | SpMA3 10 nm | IC1:EG5:TER5 (25%:70%:5%) 40 nm | — | ST2:LiQ (50%:50%) 35 nm | — |
| E6 | HATCN 5 nm | SpMA1 125 nm | SpMA3 10 nm | IC3:EG6:TER5 (47%:48%:5%) 40 nm | ST2 5 nm | ST2:LiQ (50%:50%) 30 nm | — |

TABLE 2
Structural formulae of the materials for the OLEDs
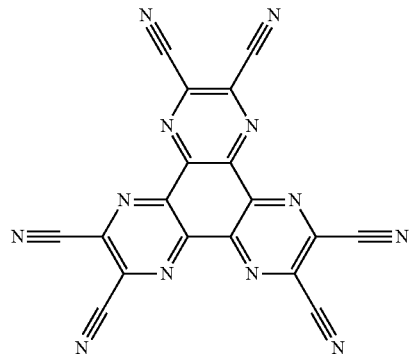
HATCN
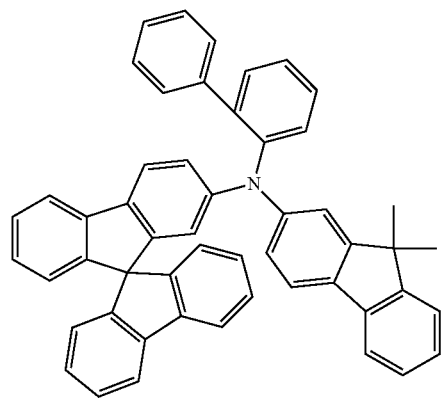
SpMA1
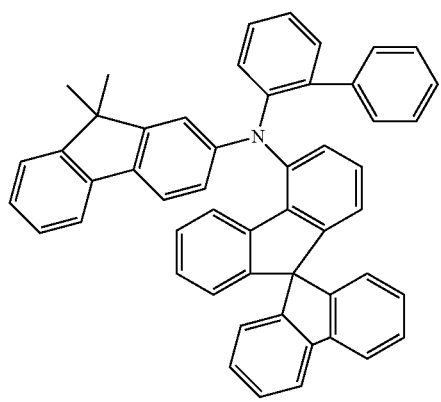
SpMA3
TABLE 2-continued
Structural formulae of the materials for the OLEDs
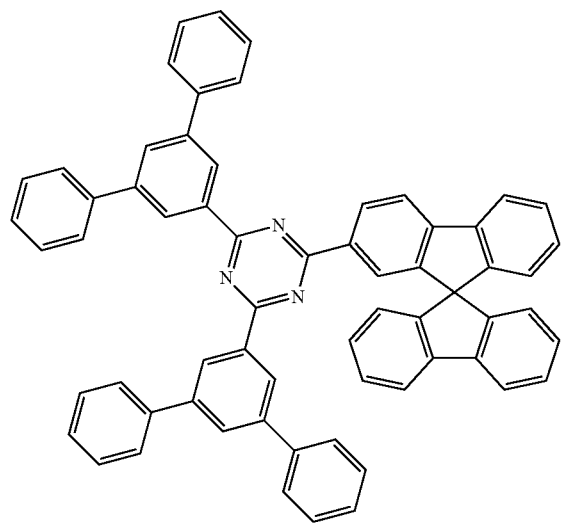
ST2
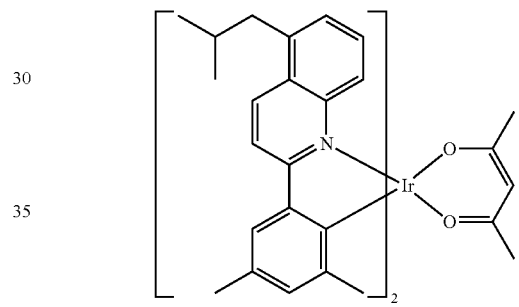
TER5
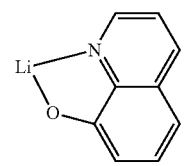
LiQ
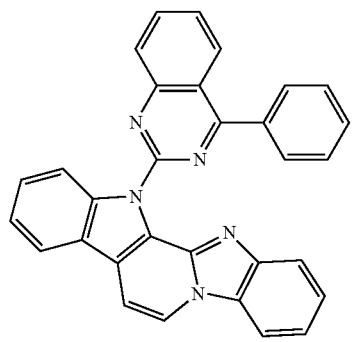
EG1

TABLE 2-continued
Structural formulae of the materials for the OLEDs
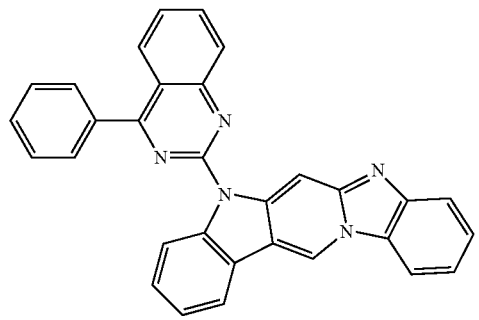
EG2
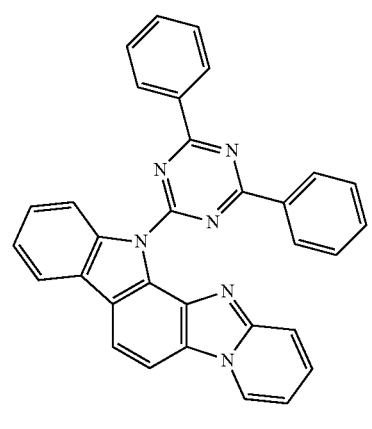
EG3
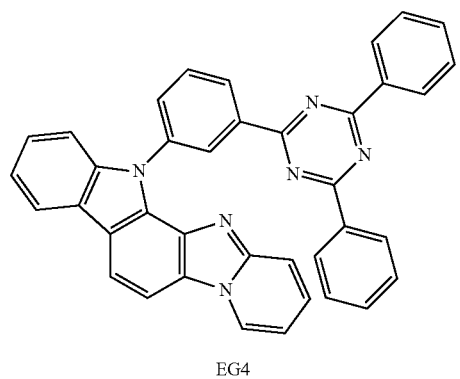 [SMILES: c1ccc(-c2nc(-c3ccccc3)nc(-c3cccc(-n4c5ccccc5c5ccc6c(nc7ccccn76)c54)c3)n2)cc1]
EG4
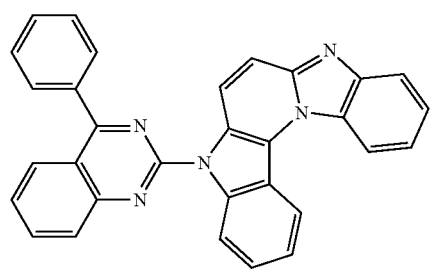
EG5
TABLE 2-continued
Structural formulae of the materials for the OLEDs
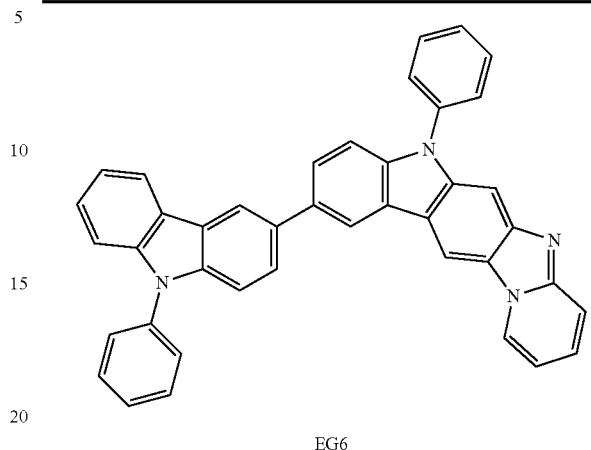
EG6
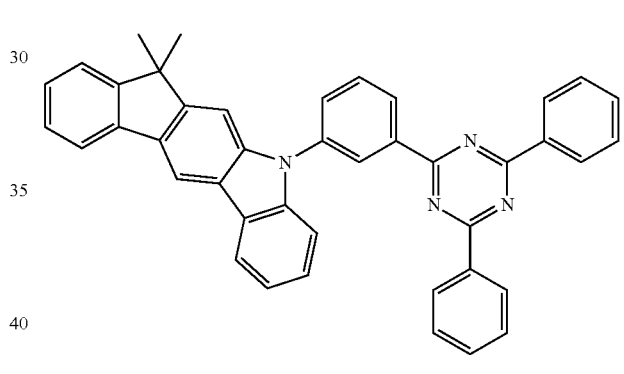
IC1
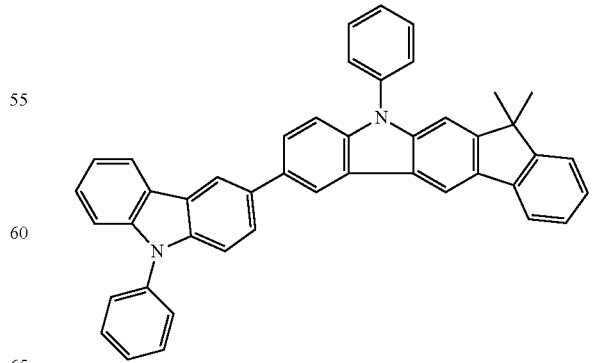
IC2

TABLE 2-continued

Structural formulae of the materials for the OLEDs

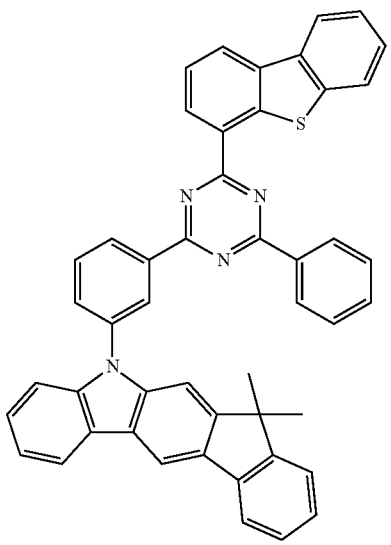

IC3

The invention claimed is:

1. A compound of formula (1):

Formula (1)

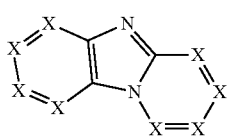

where the symbols used are as follows:

X two adjacent X are a group of the following formula (2) or (3), and the remaining X are the same or different at each instance and are CR or N;

Formula (2)

Formula (3)

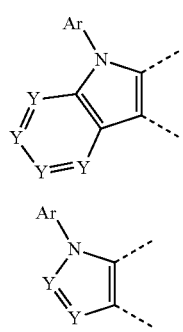

where the dotted bonds indicate the linkage of this group in the formula (1);

Y is the same or different at each instance and is CR' or N;

Ar is the same or different at each instance and is an aromatic or heteroaromatic ring system which has 5 to 40 aromatic ring atoms and may be substituted by one or more R radicals;

R, R' is the same or different at each instance and is H, D, F, Cl, Br, I, $N(Ar')_2$, $N(R^1)_2$, OAr', SAr', CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, and may be substituted in each case by one or more $R^1$ radicals; at the same time, two R radicals together may also form an aliphatic or heteroaliphatic ring system; in addition, two R' radicals together may also form an aliphatic, heteroaliphatic, aromatic or heteroaromatic ring system;

Ar' is the same or different at each instance and is an aromatic or heteroaromatic ring system which has 5 to 40 aromatic ring atoms and may be substituted by one or more $R^1$ radicals;

$R^1$ the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more non-adjacent $CH_2$ groups may be replaced by $Si(R^2)_2$, C=O, $NR^2$, O, S or $CONR^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form an aliphatic ring system;

$R^2$ is the same or different at each instance and is H, D, F, CN or an aliphatic, aromatic or heteroaromatic organic radical.

2. The compound as claimed in claim 1, selected from the structures of the formulae (4) to (15):

Formula (4)

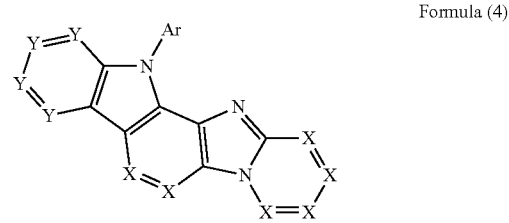

Formula (5)

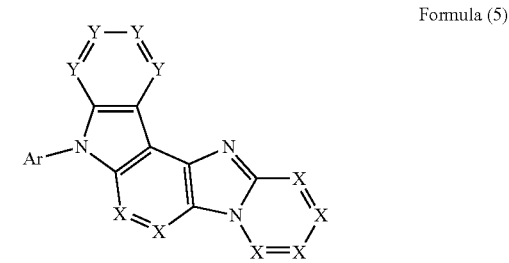

-continued

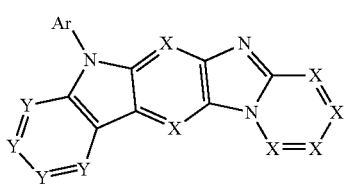
Formula (6)

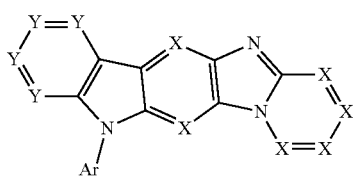
Formula (7)

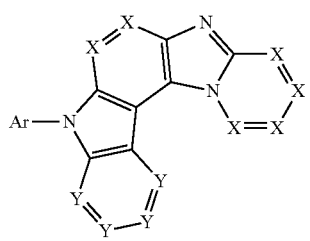
Formula (8)

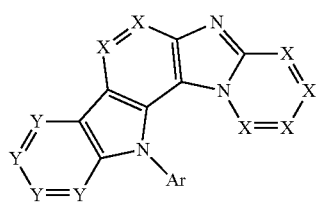
Formula (9)

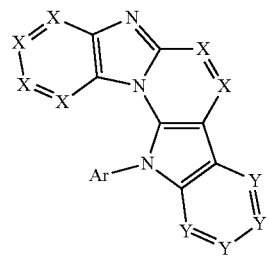
Formula (10)

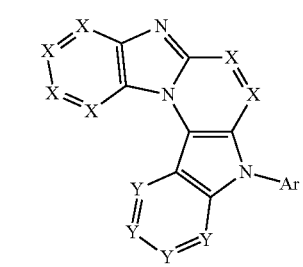
Formula (11)

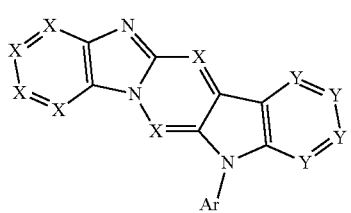
Formula (12)

-continued

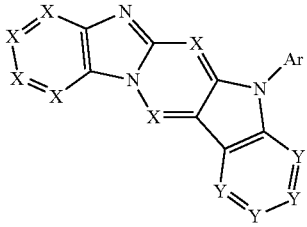
Formula (13)

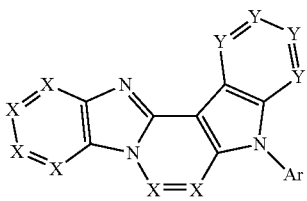
Formula (14)

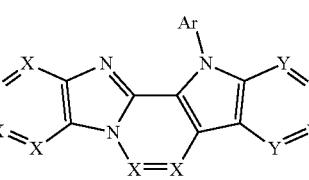
Formula (15)

where the symbols used have the definitions given in claim 1.

3. The compound as claimed in claim 1, characterized in that the group of the formula (2) is selected from the formulae (2a) to (2e) and in that the group of the formula (3) is selected from the formula (3a):

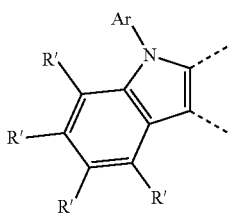
Formula (2a)

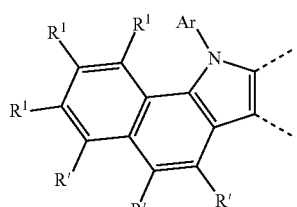
Formula (2b)

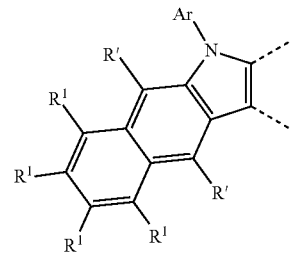
Formula (2c)

Formula (2d)

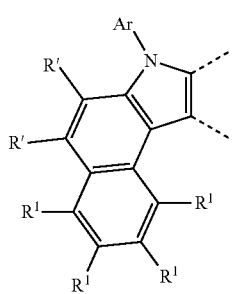

Formula (2e)

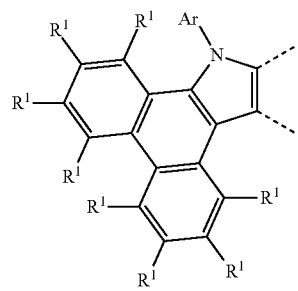

Formula (3a)

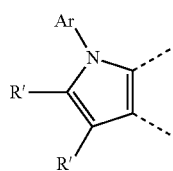

where the symbols used have the definitions given in claim 1 and the R' radicals do not form an aromatic or heteroaromatic ring system with one another.

4. The compound as claimed in claim 1, characterized in that not more than one of the symbols X and Y is N in total.

5. The compound as claimed in claim 1, selected from the structures of the formulae (4a) to (15a):

Formula (4a)

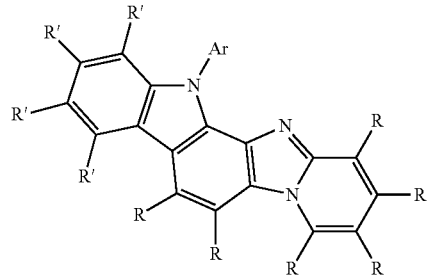

Formula (5a)

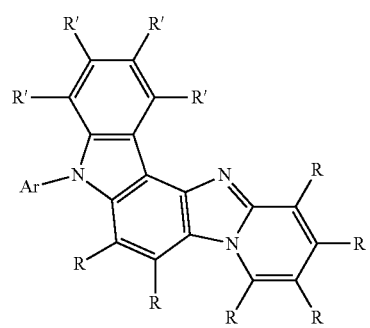

Formula (6a)

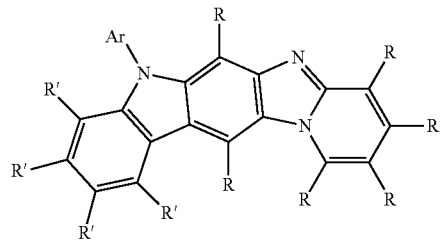

Formula (7a)

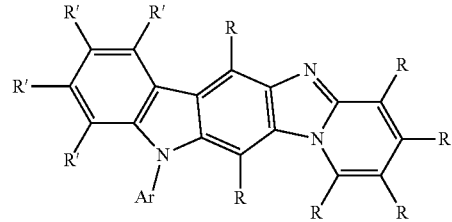

Formula (8a)

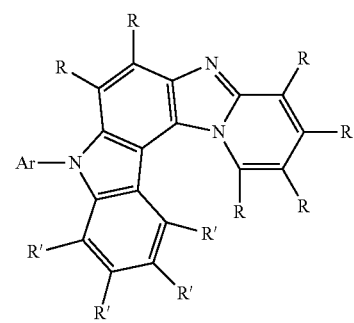

Formula (9a)

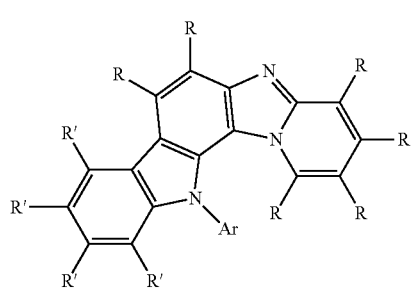

Formula (10a)

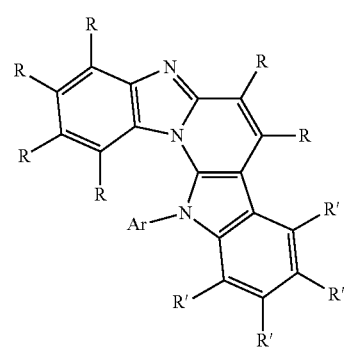

-continued
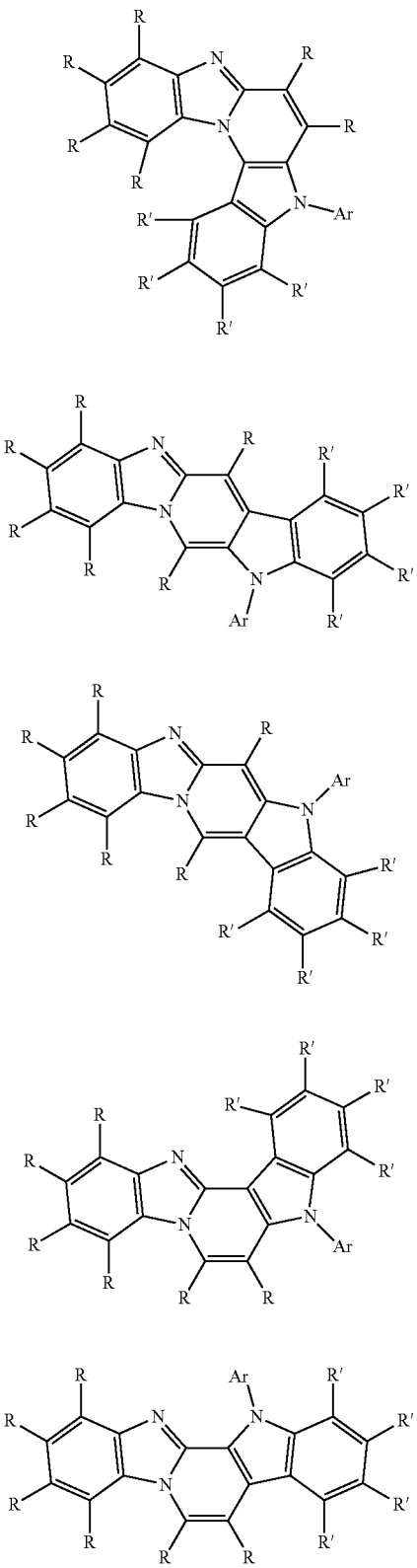
Formula (11a)
Formula (12a)
Formula (13a)
Formula (14a)
Formula (15a)
where the symbols used have the definitions given in claim 1.
6. The compound as claimed in claim 1, selected from the structures of the formulae (4b) to (15c):
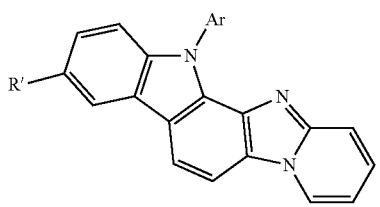
Formula (4b)
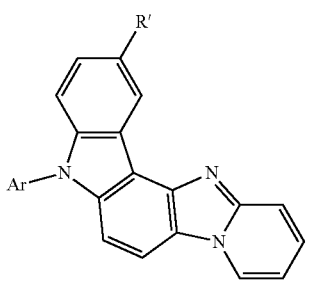
Formula (5b)
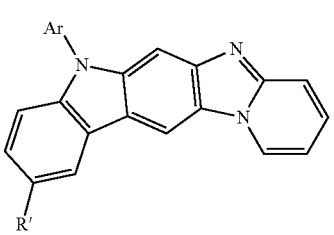
Formula (6b)
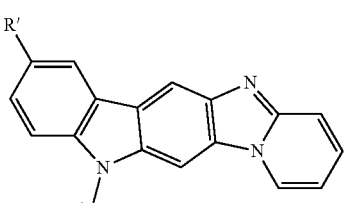
Formula (7b)
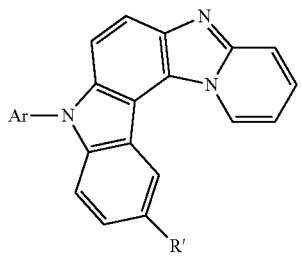
Formula (8b)
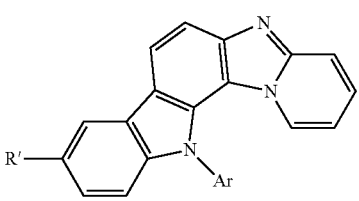
Formula (9b)
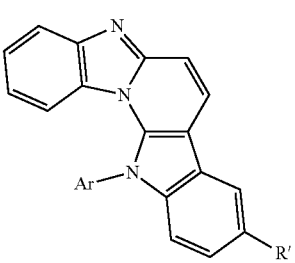
Formula (10b)

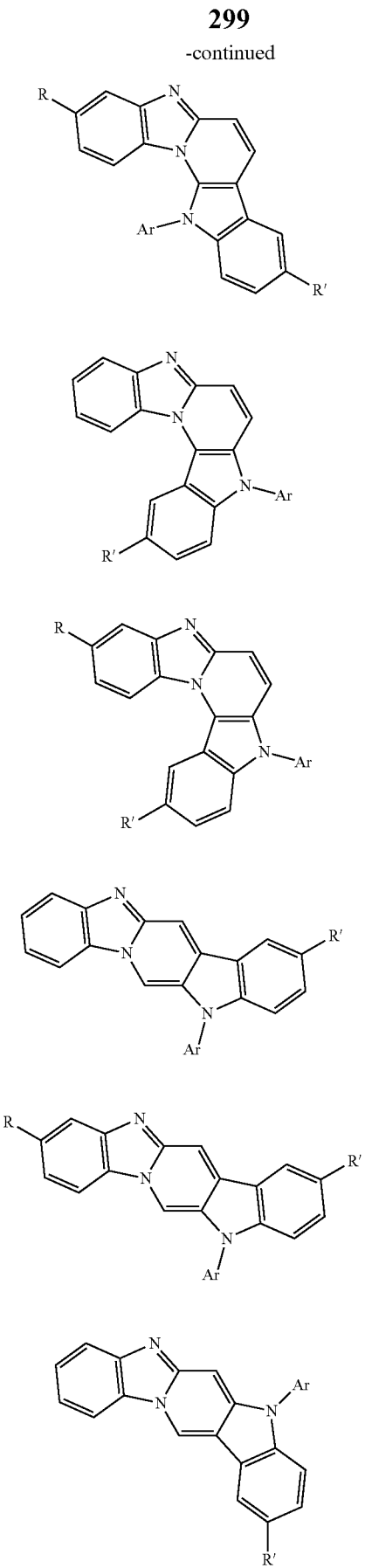
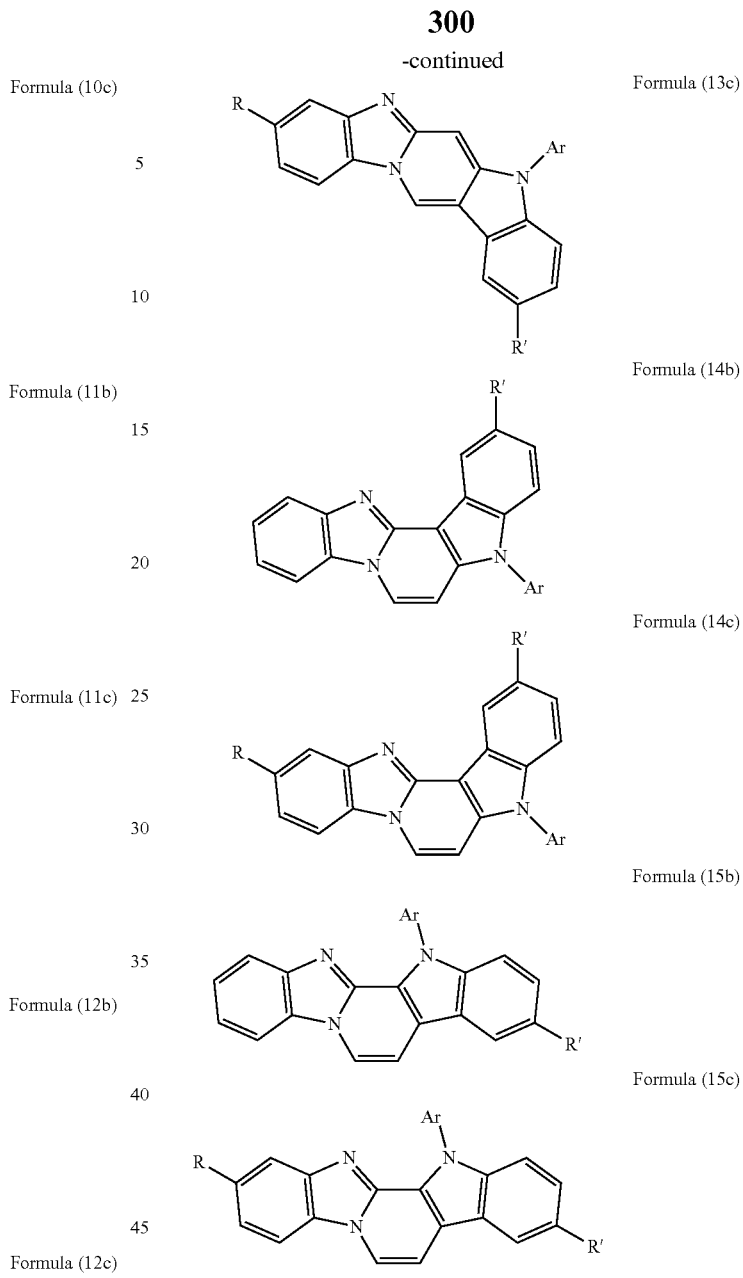

where the symbols used have the definitions given in claim 1.

7. The compound as claimed in claim 1, characterized in that Ar is an aromatic or heteroaromatic ring system which has 6 to 24 aromatic ring atoms and may be substituted by one or more R radicals.

8. The compound as claimed in claim 1, characterized in that Ar is selected from the group consisting of phenyl, biphenyl, terphenyl, quaterphenyl, fluorenyl, spirobifluorenyl, naphthyl, indolyl, benzofuranyl, benzothienyl, carbazolyl, dibenzofuranyl, dibenzothienyl, indenocarbazolyl, indolocarbazolyl, pyridyl, pyrimidinyl, pyrazinyl, pyridazinyl, triazinyl, quinolinyl, quinazolinyl, benzimidazolyl, phenanthryl, triphenylenyl or a combination of two or three of these groups, each of which may be substituted by one or more R radicals.

9. A process for preparing the compound as claimed in claim 1, characterized in that the base structure of the compound without the Ar group is first synthesized and, in a next step, the Ar group is introduced.

10. A formulation comprising at least one compound as claimed in claim 1 and at least one further compound.

11. An electronic device comprising at least one compound as claimed in claim 1.

12. An organic electroluminescent device, characterized in that the compound in claim 1 is used in an emitting layer as matrix material for phosphorescent or fluorescent emitters or for emitters that exhibit TADF, or in that the compound is used in an electron transport layer and/or in a hole blocker layer and/or in a hole transport layer and/or in an exciton blocker layer.

13. The electronic device as claimed in claim 12, characterized in that the compound is used as matrix material in an emitting layer in combination with a further matrix material selected from the group consisting of biscarbazoles, bridged carbazoles, triarylamines and carbazoleamines.

14. The compound as claimed in claim 1, wherein
R, R' is the same or different at each instance and is H, D, F, Cl, Br, I, $N(Ar')_2$, $N(R^1)_2$, $OAr'$, $SAr'$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 40 aromatic ring atoms, and may be substituted in each case by one or more $R^1$ radicals; at the same time, two R radicals together may also form an aliphatic or heteroaliphatic ring system; in addition, two R' radicals together may also form an aliphatic, heteroaliphatic, aromatic or heteroaromatic ring system.

15. The compound as claimed in claim 1, wherein $R^2$ is the same or different at each instance and is H, D, F, CN or a hydrocarbyl radical, having 1 to 20 carbon atoms, in which one or more hydrogen atoms is optionally replaced by F.

16. The compound as claimed in claim 1, wherein $R^2$ is the same or different at each instance and is H, F, an alkyl group having 1 to 4 carbon atoms or an aryl group having 6 to 10 carbon atoms, which is optionally substituted by an alkyl group having 1 to 4 carbon atoms.

17. The compound as claimed in claim 1, wherein $R^2$ is the same or different at each instance and is H, F, an alkyl group having 1 to 4 carbon atoms or an unsubstituted aryl group having 6 to 10 carbon atoms.

* * * * *